(12) United States Patent
Abato et al.

(10) Patent No.: US 9,012,433 B2
(45) Date of Patent: Apr. 21, 2015

(54) SUBSTITUTED TETRACYCLINE COMPOUNDS

(71) Applicant: Paratek Pharmaceuticals, Inc., Boston, MA (US)

(72) Inventors: Paul Abato, Providence, RI (US); Todd Bowser, Charlton, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 13/686,639

(22) Filed: Nov. 27, 2012

(65) Prior Publication Data

US 2013/0102779 A1    Apr. 25, 2013

Related U.S. Application Data

(62) Division of application No. 11/963,540, filed on Dec. 21, 2007, now Pat. No. 8,318,706.

(60) Provisional application No. 60/943,003, filed on Jun. 8, 2007, provisional application No. 60/876,313, filed on Dec. 21, 2006.

(51) Int. Cl.
*C07C 237/26* (2006.01)
*C07D 207/20* (2006.01)
(Continued)

(52) U.S. Cl.
CPC ............ *C07C 237/26* (2013.01); *C07C 2103/46* (2013.01); *C07D 207/50* (2013.01);
(Continued)

(58) Field of Classification Search
USPC .................... 514/152; 552/205, 203; 548/528; 544/154, 294; 546/195
See application file for complete search history.

(56) References Cited

U.S. PATENT DOCUMENTS 2,980,584 A    4/1961    Hammer
2,990,331 A    6/1961    Neumann et al.
(Continued)

FOREIGN PATENT DOCUMENTS

DE    2346535 A1    4/1974
FR    2208885 A1    6/1974
(Continued)

OTHER PUBLICATIONS

Bartzatt et al. "Synthesis and Analysis of a Methyl Ether Derivative of Tetracycline Which Inhibits Growth of *Escherichia coli*." Physiol. Chem. Phys. & Med. NMR. 34(2002):71-81.
(Continued)

*Primary Examiner* — Sabiha N Qazi
(74) *Attorney, Agent, or Firm* — McCarter & English, LLP; Elizabeth A. Hanley

(57) ABSTRACT

The present invention pertains to tetracycline compounds of formula (VIIa):

$R^{5*}$, $R^{5*'}$, $R^{7r*}$, and $R^{9m*}$ are defined herein. These tetracycline compounds can be used to treat tetracycline compound-responsive states, such as multiple sclerosis and rheumatoid arthritis.

11 Claims, 1 Drawing Sheet

(51) Int. Cl.
  *C07D 211/14* (2006.01)
  *C07D 239/26* (2006.01)
  *C07D 265/30* (2006.01)
  *C07D 207/50* (2006.01)
  *C07D 231/12* (2006.01)
  *C07D 239/20* (2006.01)
  *C07D 241/12* (2006.01)
  *C07D 261/02* (2006.01)
  *C07D 261/04* (2006.01)
  *C07D 263/32* (2006.01)
  *C07D 265/02* (2006.01)

(52) U.S. Cl.
  CPC ............ *C07D231/12* (2013.01); *C07D 239/20* (2013.01); *C07D 241/12* (2013.01); *C07D 261/02* (2013.01); *C07D 261/04* (2013.01); *C07D 263/32* (2013.01); *C07D 265/02* (2013.01); *C07D 207/20* (2013.01); *C07D 211/14* (2013.01); *C07D 239/26* (2013.01); *C07D 265/30* (2013.01)

(56) References Cited

U.S. PATENT DOCUMENTS

| | | |
|---|---|---|
| 3,047,617 A | 7/1962 | Blackwood et al. |
| 3,062,717 A | 11/1962 | Hammer |
| 3,165,531 A | 1/1965 | Blackwood et al. |
| 3,304,227 A | 2/1967 | Loveless |
| 3,345,379 A | 10/1967 | Martell et al. |
| 3,454,697 A | 7/1969 | Joyner et al. |
| 3,557,280 A | 1/1971 | Weber et al. |
| 3,674,859 A | 7/1972 | Beutel et al. |
| 3,901,942 A | 8/1975 | Bernardi et al. |
| 3,957,980 A | 5/1976 | Noseworthy |
| 4,018,889 A | 4/1977 | Armstrong |
| 4,024,272 A | 5/1977 | Rogalski et al. |
| 4,126,680 A | 11/1978 | Armstrong |
| 4,666,897 A | 5/1987 | Golub et al. |
| 4,704,383 A | 11/1987 | McNamara et al. |
| 4,806,372 A | 2/1989 | Strumskis |
| 4,925,833 A | 5/1990 | McNamara et al. |
| 4,935,412 A | 6/1990 | McNamara et al. |
| 5,021,407 A | 6/1991 | Levy |
| 5,231,017 A | 7/1993 | Lantero et al. |
| 5,258,371 A | 11/1993 | Golub et al. |
| 5,258,372 A | 11/1993 | Levy |
| 5,308,839 A | 5/1994 | Golub et al. |
| 5,321,017 A | 6/1994 | Golub et al. |
| RE34,656 E | 7/1994 | Golub et al. |
| 5,459,135 A | 10/1995 | Golub et al. |
| 5,523,297 A | 6/1996 | Pruzanski et al. |
| 5,532,227 A | 7/1996 | Golub et al. |
| 5,589,470 A | 12/1996 | Levy |
| 5,668,122 A | 9/1997 | Fife et al. |
| 5,770,588 A | 6/1998 | McNamara et al. |
| 5,773,430 A | 6/1998 | Simon et al. |
| 5,789,395 A | 8/1998 | Amin et al. |
| 5,811,412 A | 9/1998 | Levy |
| 5,827,840 A | 10/1998 | Ramamurthy et al. |
| 5,834,449 A | 11/1998 | Thompson et al. |
| 5,834,450 A | 11/1998 | Su |
| 5,837,696 A | 11/1998 | Golub et al. |
| 5,843,925 A | 12/1998 | Backer et al. |
| 5,919,774 A | 7/1999 | Bach et al. |
| 5,919,775 A | 7/1999 | Amin et al. |
| 5,929,055 A | 7/1999 | Ryan et al. |
| 5,977,091 A | 11/1999 | Nieman et al. |
| 5,998,390 A | 12/1999 | Ramamurthy et al. |
| 6,015,804 A | 1/2000 | Golub et al. |
| 6,043,225 A | 3/2000 | Shor et al. |
| 6,043,231 A | 3/2000 | Pruzanski et al. |
| 6,100,248 A | 8/2000 | Golub et al. |
| 6,231,894 B1 | 5/2001 | Stamler et al. |
| 6,256,365 B1 | 7/2001 | Lai |
| 6,277,061 B1 | 8/2001 | Golub et al. |
| 6,500,812 B2 | 12/2002 | Nelson et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 * | 1/2005 | Nelson et al. .................. 552/205 |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson et al. |
| 7,202,235 B2 | 4/2007 | Levy et al. |
| 7,208,482 B2 | 4/2007 | Garcia-Luzon et al. |
| 7,323,492 B2 | 1/2008 | Huss et al. |
| 7,326,696 B2 | 2/2008 | Nelson et al. |
| 7,361,674 B2 | 4/2008 | Nelson et al. |
| 7,414,041 B2 | 8/2008 | Levy |
| 7,521,437 B2 | 4/2009 | Nelson et al. |
| 7,553,828 B2 | 6/2009 | Nelson et al. |
| 7,858,601 B2 | 12/2010 | Berniac et al. |
| 7,935,687 B2 | 5/2011 | Berniac et al. |
| 2003/0069721 A1 | 4/2003 | Podlogar |
| 2004/0138183 A1 | 7/2004 | Nelson et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2005/0020545 A1 | 1/2005 | Draper et al. |
| 2005/0038002 A1 | 2/2005 | Nelson et al. |
| 2005/0070510 A1 | 3/2005 | Draper et al. |
| 2005/0143352 A1 | 6/2005 | Nelson et al. |
| 2005/0250744 A1 | 11/2005 | Levy et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0166944 A1 | 7/2006 | Berniac et al. |
| 2006/0166945 A1 | 7/2006 | Abato et al. |
| 2006/0166946 A1 | 7/2006 | Nelson et al. |
| 2006/0194773 A1 | 8/2006 | Levy et al. |
| 2006/0281717 A1 | 12/2006 | Berniac et al. |
| 2006/0287283 A1 | 12/2006 | Amoo et al. |
| 2007/0072834 A1 | 3/2007 | Nelson et al. |
| 2007/0093455 A1 | 4/2007 | Abato et al. |
| 2007/0167415 A1 | 7/2007 | Levy et al. |
| 2007/0270389 A1 | 11/2007 | Garcia-Luzon et al. |
| 2008/0015169 A1 | 1/2008 | Nelson et al. |
| 2008/0070873 A1 | 3/2008 | Alekshun et al. |
| 2008/0118979 A1 | 5/2008 | Draper et al. |
| 2008/0167273 A1 | 7/2008 | Nelson et al. |
| 2008/0287401 A1 | 11/2008 | Johnston et al. |
| 2008/0300424 A1 | 12/2008 | Nelson et al. |
| 2008/0306032 A1 | 12/2008 | Nelson et al. |
| 2009/0054379 A1 | 2/2009 | Huss et al. |
| 2009/0118269 A1 | 5/2009 | Berniac et al. |
| 2009/0124583 A1 | 5/2009 | Nelson et al. |
| 2009/0131696 A1 | 5/2009 | Levy |
| 2009/0156842 A1 | 6/2009 | Seyedi et al. |

FOREIGN PATENT DOCUMENTS

| | | |
|---|---|---|
| GB | 921252 A | 3/1963 |
| GB | 1108310 A | 4/1968 |
| GB | 1469384 A | 4/1977 |
| WO | WO-9522529 A1 | 8/1995 |
| WO | WO-9634852 A1 | 11/1996 |
| WO | WO-0119784 A1 | 3/2001 |
| WO | WO-0204406 A2 | 1/2002 |
| WO | WO-0204407 A2 | 1/2002 |
| WO | WO-02072022 A2 | 9/2002 |
| WO | WO-02072506 A2 | 9/2002 |
| WO | WO-02072532 A1 | 9/2002 |

(56) References Cited

FOREIGN PATENT DOCUMENTS

| WO | WO-03005971 | 1/2003 |
|---|---|---|
| WO | WO-03057169 A2 | 7/2003 |
| WO | WO-03075857 A2 | 9/2003 |
| WO | WO-03079984 A2 | 10/2003 |
| WO | WO-03088906 A2 | 10/2003 |
| WO | WO-2004064728 A2 | 8/2004 |
| WO | WO-2004091513 A2 | 10/2004 |
| WO | WO-2005112945 A2 | 12/2005 |
| WO | WO-2007133798 A2 | 11/2007 |

OTHER PUBLICATIONS

Bartzatt et al. "Synthesis and Analysis of Ethylated Tetracycline, an Antibiotic Derivative that Inhibits the Growth of Tetracycline-Resistant XL I-Blue Bacteria." *Biotechnol. Appl. Biochem.* 33(2001):65-69.

Berens et al. "Subtype Selective Tetracycline Agonists and their Application for a Two-Stage Regulatory System." *Chem. Bio. Chem.* 7(2006):1320-1324.

Berge et al. "Pharmaceutical Salts." *J. Pharm. Sci.* 66.1(1977):1-19.

Boothe et al. "6-Deoxtetracyclines. I. Chemical Modifications by Electrophilic Substitution." *Am. Chem. Soc.* 82.5(1960):1253-1254.

Chandler et al. "Matrix Metalloproteinases, Tumor Necrosis Factor and Multiple Sclerosis: An Overview." *J. Neuroimmunol.* 72(1997):155-161.

Greenwald et al. "In Vitro Sensitivity of the Three Mammalian Collagenases to Tetracycline Inhibition: Relationship to Bone and Cartilage Degradation." *Bone.* 22.1(1998):33-38.

Jiang et al. "α-(Trifluoromethyl)ethenyl Boronic Acid as a Useful Trifluoromethyl Containing Building Block. Preparation and Palladium-Catalysed Coupling with Aryl Halides." *Tetrahed. Lett.* 42(2001):4083-4085.

Koza et al. "Palladium Catalyzed C—N Bond Formation in the Synthesis of 7-Amino-Substituted Tetracyclines." *J. Org. Chem.* 67(2002):5025-5027.

Koza et al. "Synthesis and Biological Evaluation of 9-Substituted Tetracycline Derivatives." *Bioorg. Med. Chem. Lett.* 12.16(2002):2163-2165.

Koza. "Synthesis of 7-Substituted Tetracycline Derivatives." *Org. Lett.* 2.6(2000):815-817.

Koza. "The Synthesis of 8-Substituted Tetracycline Derivatives, the First 8-Position Carbon—Carbon Bond." *Tetrahedron Lett.* 41(2000):5017-5020.

Lew et al. "Antifungal Activity of Four Tetracycline Analogues against *Candida albicans* in Vitro: Potentiation by Amphotericin B." *J. Infect. Dis.* 136.2(1977):263-270.

Li et al. "Immunological Characterization of Cell-Surface and Soluble Forms of Membrane Type 1 Matrix Metalloproteinase in Human Breast Cancer Cells and in Fibroblasts." *Mol. Carcinog.* 22(1998):84-89.

Liedtke et al. "Effective Treatment of Models of Multiple Sclerosis by Matrix Metalloproteinase Inhibitors." *Ann. Neurol.* 44(1998):35-46.

Martell et al. "The 6-Deoxytetracyclines. IX. Imidomethylation." *J. Med Chem.* 10.3(1967):359-363.

Nelson et al. "Inhibition of the Tetracycline Efflux Antiport Protein by 13-Thio-Substituted 5-Hydroxy-6-Deoxytetracyclines." *J. Med. Chem.* 36.3(1993):370-377.

Nilges et al. "Identification and Characterization of a Tetracycline Semiquinone Formed During the Oxidation of Minocycline." *J. Org. Chem.* 56(1991):5623-5630.

Paemen et al. "The Gelatinase Inhibitory Activity of Tetracyclines and Chemically Modified Tetracycline Analogues as Measured by a Novel Microtiter Assay for Inhibitors." *Biochem. Pharm.* 52(1996):105-111.

Petersen et al. "In Vitro and In Vivo Antibacterial Activities of a Novel Glyclycycline, the 9-*t*-Butylglycylamido Derivative of Minocycline (GAR-936)." *Antimicrob. Agents Chemo.* 43.4(1999):738-744.

Ryan et al. "Potential of Tetrazylines to Modify Cartilage Breakdown in Osteoarthritis." *Curr. Op. Rheumatol.* 8(1996):238-247.

Spencer et al. "6-Deoxytetracyclines. V. 7,9-Disubstituted Products." *J. Med. Chem.* 122(1963):405-407.

Stetler-Stevenson et al. "Tumor Cell Interactions with the Extracellular Matrix During Invasion and Metastasis." *Annu. Rev. Cell Biol.* 9(1993):541-573.

Sum et al. "Glycylcyclines. 1. A New Generation of Potent Antibacterial Agents Through Modification of 9-Aminotetracyclines." *J. Med. Chem.* 37.1(1994):184-188.

Sum et al. "Recent Developments in Tetracycline Antibiotics." *Curr. Pharm. Des.* 4.2(1998):119-132.

Sum et al. "Synthesis and Antibacterial Activity of 9-Substituted Minocycline Derivatives." *Bioorg. Med. Chem. Lett.* 16(2006):400-403.

Tally et al. "Glycylcyclines: a New Generation of Tetracyclines." *J. Antimicrobial Chem.* 35(1995):449-452.

Tryggvason et al. "Proteolytic Degradation of Extracellular Matrix in Tumor Invasion." *Biochim. Biophys. Acta.* 907(1987):191-217.

Van den Bogert et al. "Doxycycline in Combination Chemotherapy of a Rat Leukemia." *Cancer Res.* 48(1988):6686-6690.

Waitz. "Methods for Dilution Antimicrobial Susceptibility Test for Bacteria that Grow Aerobically." *CLSI*, Document M7-A2. 10.8(1990):13-20.

Xie et al. "Squaric Acids: A New Motif for Designing Inhibitors of Protein Tyrosine Phosphatases." *Org. Lett.* 6.1(2004):83-86.

* cited by examiner

SUBSTITUTED TETRACYCLINE COMPOUNDS

RELATED APPLICATIONS

This application is a divisional application of U.S. Ser. No. 11/963,540, filed on Dec. 21, 2007 and issued as U.S. Pat. No. 8,318,706 on Nov. 27, 2012, which claims priority to U.S. Provisional Patent Application No. 60/876,313, filed on Dec. 21, 2006 and U.S. Provisional Patent Application No. 60/943,003, filed Jun. 8, 2007. The contents of the foregoing applications are hereby incorporated in their entirety.

BACKGROUND OF THE INVENTION

The development of the tetracycline antibiotics was the direct result of a systematic screening of soil specimens collected from many parts of the world for evidence of microorganisms capable of producing bactericidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines as antibiotics of choice.

SUMMARY OF THE INVENTION

In one embodiment, the invention pertains, at least in part, to substituted tetracycline compounds of Formula I:

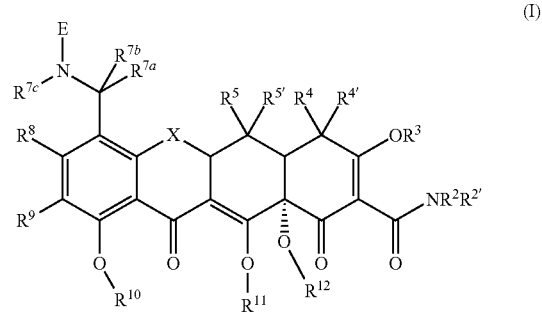

(I)

wherein
X is $CHC(R^{13}Y'Y)$, $CR^{6'}R^6$, $C=CR^{6'}R^6$, S, $NR^6$, or O;
E is $NR^{7d}R^{7e}$, $OR^{7f}$ or $(CH_2)_{0-1}C(=W')WR^{7g}$;
W is O, S, $NR^{7h}$ or $CR^{7i}R^{7j}$;
W' is O, S or $NR^{7k}$;
$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^3$, $R^{10}$, $R^{11}$ and $R^{12}$ are each hydrogen or a pro-drug moiety;
$R^4$ is $NR^{4a}R^{4b}$, alkyl, alkenyl, alkynyl, hydroxyl, halogen, or hydrogen;
$R^5$ and $R^{5'}$ are each hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^{7a}$, $R^{7b}$, $R^{7c}$, $R^{7d}$, $R^{7e}$, $R^{7f}$, $R^{7g}$, $R^{7h}$, $R^{7i}$, $R^{7j}$ and $R^{7k}$ are each independently hydrogen, allyl, alkyl, alkenyl, alkynyl, hydroxyl, alkoxy, alkylthio, alkylsulfinyl, alkylsulfonyl, amino, alkylamino, aminoalkyl, acyl, aryl, arylalkyl, alkylcarbonyloxy, alkylcarbonyloxyalkyl or arylcarbonyloxy, or $R^{7c}$ and $R^{7d}$ or $R^{7e}$ and $R^{7f}$ are linked to form a ring;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkynyl, arylalkynyl, thionitroso, or $-(CH_2)_{0-3}(NR^{9c})_{0-1}C(=Z')ZR^{9a}$;
Z is $CR^{9d}R^{9e}$, S, $NR^{9b}$ or O;
Z' is O, S, or $NR^{9f}$;
$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In another embodiment, the invention pertains, at least in part, to substituted tetracycline compounds of Formula II:

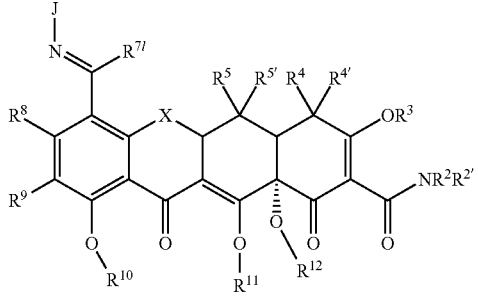

(II)

wherein
X is CHC(R$^{13'}$Y), CR$^{6'}$R$^6$, C=CR$^{6'}$R$^6$, S, NR$^6$, or O;
J is NR$^{7m}$R$^{7n}$, OR$^{7o}$ or heteroaryl;
R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^3$, R$^{10}$, R$^{11}$ and R$^{12}$ are each hydrogen or a prodrug moiety;
R$^4$ is NR$^{4a}$R$^{4b}$, alkyl, alkenyl, alkynyl, hydroxyl, halogen, or hydrogen;
R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^{7l}$, R$^{7m}$, R$^{7n}$ and R$^{7o}$ are each independently hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;
R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(=Z')ZR$^{9a}$;
Z is CR$^{9d}$R$^{9e}$, S, NR$^{9b}$ or O;
Z' is O, S, or NR$^{9f}$;
R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In yet another embodiment, the present invention pertains, at least in part, to substituted tetracycline compounds of Formula III:

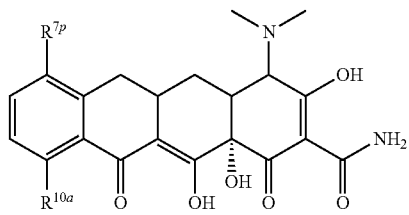

(III)

wherein
R$^{7p}$ is acyl, alkylamino, or heteroaryl;
R$^{10a}$ is hydrogen, aryl, carboxylate or alkoxycarbonyl;
R$^{13}$ is hydrogen, hydroxy, alkyl, alkenyl, alkynyl, alkoxy, alkylthio, alkylsulfinyl, alkylsulfonyl, alkylamino, or an arylalkyl; and pharmaceutically acceptable salts thereof.

In another embodiment, the present invention pertains, at least in part, to substituted tetracycline compounds of Formula IIIa:

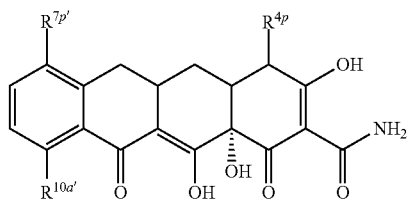

(IIIa)

wherein
R$^{4p}$ is —N(CH$_3$)$_2$ or hydrogen;
R$^{7p'}$ is hydrogen, amino, acyl, heteroaryl, aminoalkyl;
R$^{10a'}$ is hydrogen, heteroaryl, alkoxycarbonyl, carboxylate, cyano, alkyl or alkoxy; and pharmaceutically acceptable salts thereof.

The present invention also pertains, at least in part, to substituted tetracycline compounds of Formula IV:

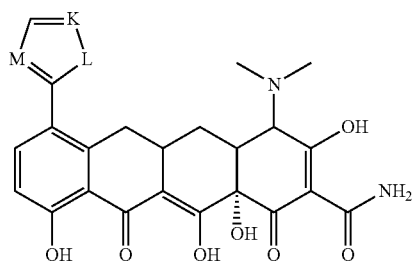

(IV)

wherein
L is O, NH or SH;
K is N or CR$^{7p'}$;
M is N or CR$^{7p''}$;
R$^{7p'}$ is hydrogen;
R$^{7p''}$ is hydrogen, aminoalkyl or alkoxycarbonylaminoalkyl, and pharmaceutically acceptable salts thereof.

In yet another embodiment, the present invention pertains, at least in part, to substituted tetracycline compounds of Formula IVa:

(IVa)

wherein
L* is O, NH or S;
*M is N, CH or CR$^{7ps''}$;
R$^{7ps''}$ is aminoalkyl; and pharmaceutically acceptable salts thereof.

In another embodiment, the present invention pertains, at least in part, to substituted tetracycline compounds of Formula V:

(V)

wherein
R$^4$ is hydrogen;
R$^{4'}$ is hydrogen or alkylamino;
R$^{9f}$ is CR$^{9g}$NR$^{9h}$ or CR$^{9i}$R$^{9j}$NR$^{9k}$R$^{9l}$;
R$^{9g}$, R$^{9h}$, R$^{9i}$, R$^{9j}$, R$^{9k}$ and R$^{9l}$ are each independently hydrogen, alkyl, hydroxyl, amino, urea or alkoxy, or R$^{9k}$ and R$^{9l}$ are joined to form a ring; and pharmaceutically acceptable salts thereof.

In another embodiment, the present invention pertains, at least in part, to substituted tetracycline compounds of Formula Va:

(Va)

wherein
Q is —CH$_2$ or —C═CH$_2$;
R$^4$ is hydrogen;
R$^{4'}$ is hydrogen or alkylamino;
R$^{5a'}$ is hydrogen or hydroxyl;
R$^{7qa}$ is —N(CH$_3$)$_2$ or hydrogen;
R$^{9q}$ is CR$^{9g'}$NR$^{9h'}$ or CR$^{9i'}$R$^{9j'}$NR$^{9k'}$R$^{9l'}$;
R$^{9g'}$, R$^{9h'}$, R$^{9i'}$, R$^{9j'}$, R$^{9k'}$ and R$^{9l'}$ are each independently hydrogen, alkyl, hydroxyl, amino, urea or alkoxy, or R$^{9k'}$ and R$^{9l'}$ are joined to form a ring; and pharmaceutically acceptable salts thereof.

In one embodiment, the present invention pertains, at least in part, to substituted tetracycline compounds of Formula VI:

(VI)

wherein
X is CHC(R$^{13Y13Y'}$Y), CR$^6$R$^6$, C═CR$^6$R$^6$, S, NR$^6$, or O;
p is a single bond or a double bond;
Q is CR$^{7s}$ when p is a double bond or Q is CR$^{7s'}$R$^{7s''}$ when p is a single bond;
R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^3$, R$^{10}$, R$^{11}$ and R$^{12}$ are each hydrogen or a pro-drug moiety;
R$^4$ is NR$^{4a}$R$^{4b}$, alkyl, alkenyl, alkynyl, hydroxyl, halogen, or hydrogen;
R$^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^{7s}$, R$^{7s'}$ and R$^{7s''}$ are each hydrogen, alkyl, alkenyl, alkynyl, hydroxyl, alkoxy, alkylthio, alkylsulfinyl, alkylsulfonyl, amino, aminoalkyl, alkylamino, aryl, acyl, arylalkyl, alkyl carbonyloxy, or arylcarbonyloxy;
R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —(CH$_2$)$_{0-3}$(NR$^{9c}$)$_{0-1}$C(═Z')ZR$^{9a}$;
Z is CR$^{9d}$R$^{9e}$, S, NR$^{9b}$ or O;
Z' is O, S, or NR$^{9f}$;
R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In a further embodiment, the present invention pertains, at least in part, to substituted tetracycline compounds of Formula VII:

(VII)

wherein

X is $CR^{6'}R^6$;

$R^5$ is hydroxyl or hydrogen;

$R^{5'}$ is hydrogen;

$R^{6'}$ hydrogen or alkyl;

$R^6$ is hydrogen;

$R^{7r}$ is hydrogen or alkylamino;

$R^{9m}$ is heteroaryl, aminocarbonyl, hydroxyaminocarbonyl, alkoxyaminocarbonyl or —$CR^{9m'}NR^{9m''}$;

$R^{9m'}$ and $R^{9m''}$ are each hydrogen, hydroxy, alkyl, alkenyl, alkynyl, alkoxy, alkylthio, alkylsulfinyl, alkylsulfonyl, alkylamino, or an arylalkyl; and pharmaceutically acceptable salts thereof.

In yet another embodiment, the present invention pertains, at least in part, to substituted tetracycline compounds of Formula VIIa:

(VIIa)

wherein

X is $CR^{6*'}R^{6*}$;

$R^{5*}$ is hydrogen;

$R^{5*'}$ is hydrogen hydroxyl;

$R^{6*'}$ is hydrogen or alkyl;

$R^{6*}$ is hydrogen;

$R^{7r*}$ is hydrogen, alkyl, heteroaryl, acyl or alkylamino;

$R^{9m*}$ is aminoalkyl, heterocyclic, aryl, —$CONR^{9ma}R^{9mb}$; —$COR^{9m*'}$; —$COOR^{9m*''}$, alkyl, cycloalkyl or hydrogen;

$R^{9m*'}$ is aminoalkyl, aryl or alkyl;

$R^{9m*''}$ is alkyl, alkoxyalkyl or hydroxyalkyl;

$R^{9ma}$ and $R^{9mb}$ are each hydrogen, hydroxyl, alkyl, hydroxyalkyl, aryl or alkoxy or are linked to form a ring; and pharmaceutically acceptable salts thereof.

The present invention also pertains, at least in part, to substituted tetracycline compounds of Formula VIII:

(VIII)

wherein:

T is N or $CR^{7td}$;

$R^4$ is alkylamino or hydrogen;

$R^{4'}$ is hydrogen;

$R^{7te}$ is hydrogen.

$R^{7ta}$, $R^{7tb}$, $R^{7tc}$ and $R^{7td}$ are each independently hydrogen, halogen, hydroxyalkyl, hydroxyalkylaminocarbonyl, alkylaminoalkyloxy, aminocarbonyl, alkylaminoalkylaminocarbonyl, aminoalkylaminocarbonyl, methylpiperazinylcarbonyl, alkylaminocarbonyl, heteroarylalkylaminocarbonyl, alkoxycarbonylalkylaminocarbonyl, acylaminoalkylaminocarbonyl, alkoxyaminocarbonyl, alkoxyalkylaminocarbonyl or alkylaminoalkylcarbonylamino, or $R^{7tb}$ and $R^{7tc}$ are linked to form a ring; and pharmaceutically acceptable salts thereof.

In another embodiment, the invention pertains, at least in part, to substituted tetracycline compounds of Formula VIIIa:

(VIIIa)

wherein:

T* is N or CH;

$R^{4*}$ is hydrogen or alkylamino.

$R^{7ta*}$ is hydrogen or halogen;

$R^{7tb*}$ is hydrogen, —CH=CHCN, hydroxyalkyl, —$CONR^{7tba}R^{7tbb}$; —$NHCOR^{7tbd}$;

$R^{7tba}$ and $R^{7tbb}$ are linked to form a ring; or $R^{7tba}$ is hydrogen or alkyl and $R^{7tbb}$ is hydrogen, alkoxy, alkyl or —$(CH_2)_x R^{7tbc}$;

$R^{7tbc}$ is amino, alkyl, alkoxycarbonyl, alkoxy, hydroxyl, aryl, a heterocyclic moiety or alkoxycarbonylamino;

$R^{7tbd}$ is —$(CH_2)_y R^{7tbe}$, wherein $R^{7tbe}$ is amino;

$R^{7tc*}$ is hydrogen, —$O(CH_2)_z R^{tca}$; —$CONHR^{tcb}$ or —$NHCOR^{7td}$; wherein $R^{tcb}$ is —$(CH_2)_w R^{tcc}$ and $R^{tca}$ and $R^{tcc}$ are each amino;

$R^{7td}$ is alkoxy; or $R^{7tb*}$ and $R^{7tc*}$ are linked to join a ring;

w, x, y and z are each, independently, an integer of between 0 and 5; and pharmaceutically acceptable salts thereof.

In one embodiment, the present invention also pertains to substituted tetracycline compounds of Formula IX:

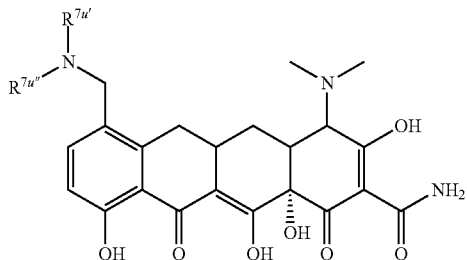

(IX)

wherein:
$R^{7u'}$ is hydrogen or cycloalkyl;
$R^{7u''}$ is alkyl, alkylcarbonyloxyalkyloxycarbonyl, or aminoalkyl, or $R^{7u'}$ and $R^{7u''}$ are linked to form a ring; and pharmaceutically acceptable salts thereof.

In yet another embodiment, the invention pertains, at least in part, to substituted tetracycline compounds of Formula (IXa):

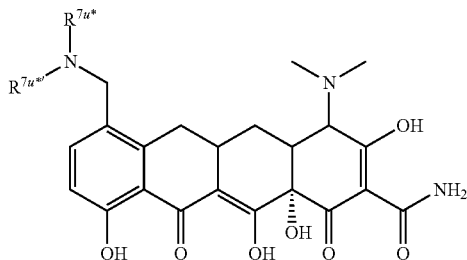

(IXa)

wherein
$R^{7u*}$ is hydrogen;
$R^{7u*'}$ is alkyl or —$(CH_2)_d R^{7ua}$, wherein d is an integer from between 0 and 5 and $R^{7ua}$ is amino; or
$R^{7u*}$ and $R^{7u*'}$ are linked to form a ring; and pharmaceutically acceptable salts thereof.

In another embodiment, the present invention also pertains, at least in part, to substituted tetracycline compounds of Formula X:

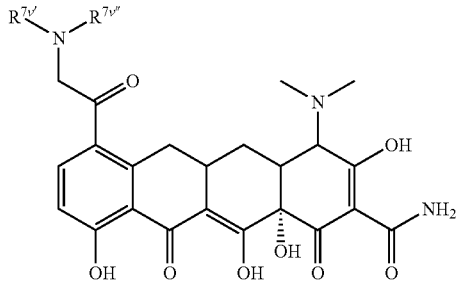

(X)

wherein
$R^{7v'}$ is alkyl, hydrogen or allyl;
$R^{7v''}$ is arylalkyl or alkylcarbonyloxyalkyloxycarbonyl; or
$R^{7v'}$ and $R^{7v''}$ are linked to form a ring; and pharmaceutically acceptable salts thereof.

In yet another embodiment, the invention pertains, at least in part, to substituted tetracycline compounds of Formula Xa:

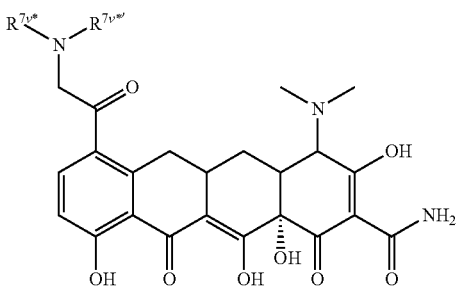

(Xa)

wherein
$R^{7v*}$ is alkyl, hydrogen or allyl;
$R^{7v*'}$ is arylalkyl or —$COO(CH_2)_f R^{7va}$; or
$R^{7v*}$ and $R^{7v*'}$ are linked to form a ring;
f is an integer from between 0 and 5;
$R^{7va}$ is alkylcarbonyloxy; and pharmaceutically acceptable salts thereof.

In yet another embodiment, the present invention pertains, at least in part, to a substituted tetracycline compound of the formula:

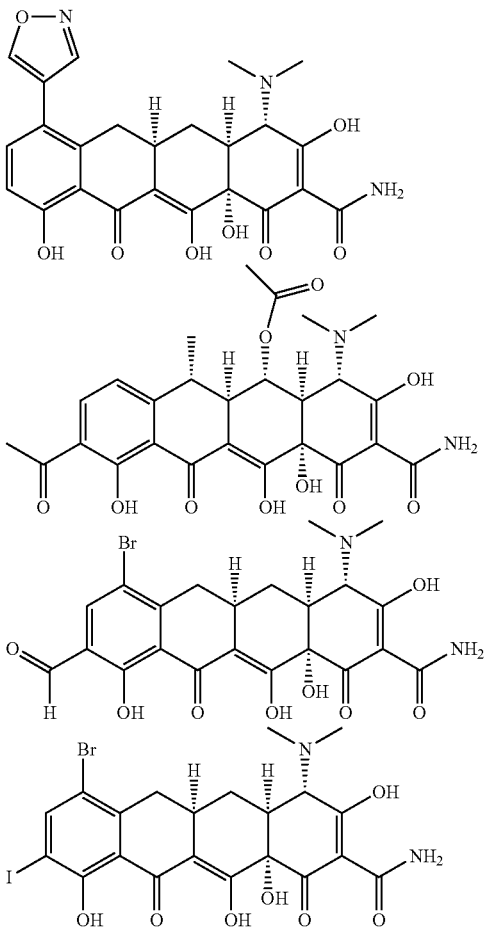

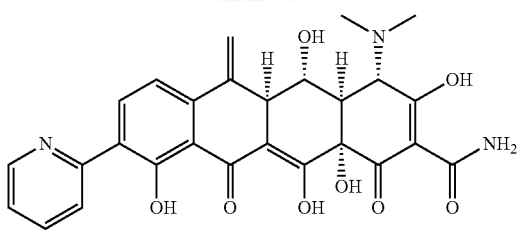

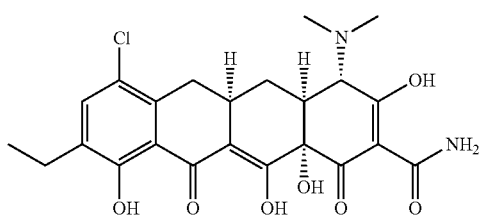

and pharmaceutically acceptable salts thereof.

In another embodiment, the invention pertains, at least in part to substituted tetracycline compounds of Formula XI:

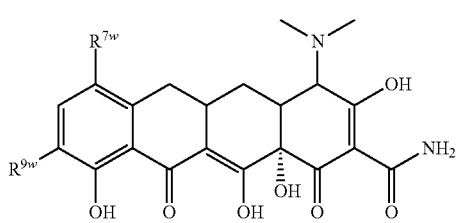

wherein $R^{7w}$ is cycloalkyl;

$R^{9w}$ is hydrogen or aminoalkyl, and pharmaceutically acceptable salts thereof.

In yet another embodiment, the invention pertains, at least in part, to substituted tetracycline compounds of Formula XIa:

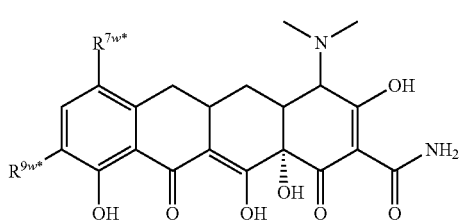

wherein $R^{7w*}$ is cycloalkyl;

$R^{9w*}$ is hydrogen or —CH$_2$NR$^{9wa}$R$^{9wb}$;

$R^{9wa}$ is alkyl and $R^{9wb}$ is allyl; and pharmaceutically acceptable salts thereof.

In one embodiment, the invention pertains, at least in part, to substituted tetracycline compounds of Formula XII:

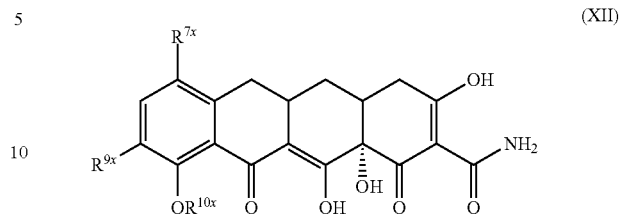

wherein $R^{7x}$ is isopropyl, dimethylamino, or hydrogen;

$R^{9x}$ is methyl, ethyl, furanyl, isopropyl, cyclopropyl, 2-dimethyl-propyl, C(=O)NR$^{9x'}$R$^{9x''}$, C(=O)OR$^{9x'}$, C(=O)R$^{9x'}$, thioazolyl, oxadiazolyl, hydrogen, phenyl, benzamidyl, dihydropyran, pyrazolyl, imidazolyl, or pyrrolyl;

$R^{9x'}$ and $R^{9x''}$ are each independently hydrogen, t-butyl, phenyl, hydroxyethyl, ethyl, 2-dimethylpropyl, or alkoxyethyl;

$R^{10x}$ is hydrogen or alkyl; and pharmaceutically acceptable salts thereof, provided that $R^{7x}$ is not hydrogen or dimethylamino when $R^{9x}$ and $R^{10x}$ are both hydrogen.

In one embodiment, the invention pertains, at least in part, to substituted tetracycline compounds of Formula XIII:

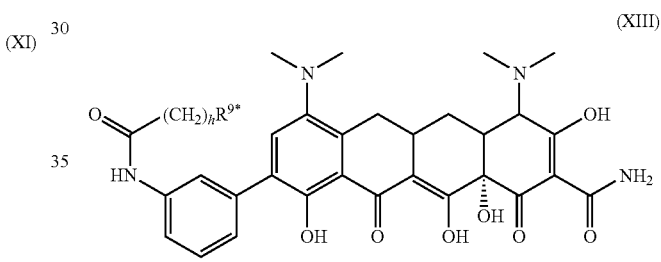

wherein h is an integer from between 0 and 5;

$R^{9*}$ is hydrogen, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, alkylcarbonyl, arylcarbonyl, carboxylate, alkoxycarbonyl, aryloxycarbonyl or aminocarbonyl; and pharmaceutically acceptable salts thereof.

In yet another embodiment, the invention pertains, at least in part, to substituted tetracycline compounds of Formula XIV:

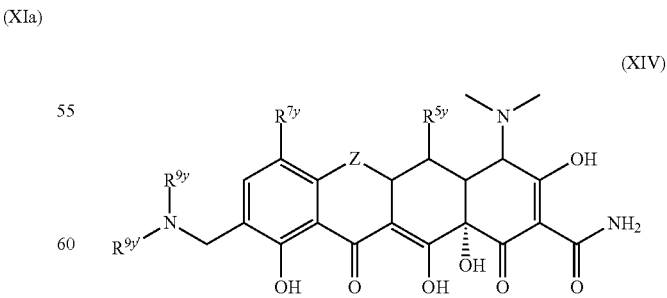

wherein

Z is —C—CH$_2$ or —CH$_2$;

$R^{5y}$ is hydrogen or hydroxyl;

$R^{7y}$ is hydrogen or dimethylamino;

$R^{9y}$ is hydrogen;
$R^{9y'}$ is —CH$_2$-cycloalkyl or —CH$_2$-substituted aryl; or
$R^{9y}$ and $R^{9y'}$ are linked to join a substituted piperidinyl ring or a tetracyclopyridinyl ring; and pharmaceutically acceptable salts thereof.

In yet another embodiment, the invention pertains, at least in part, to substituted tetracycline compounds of Formula XV:

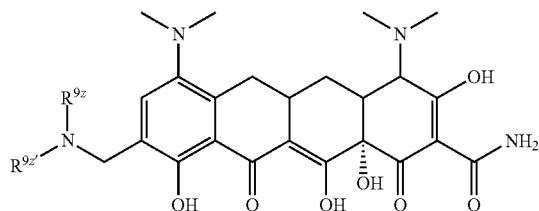

(XV)

wherein
$R^{9z}$ is hydrogen;
$R^{9z'}$ is halogen substituted alkyl; or
$R^{9z}$ and $R^{9z'}$ are linked to form a substituted piperidinyl ring; and pharmaceutically acceptable salts thereof.

In yet another embodiment, the invention pertains, at least in part, to substituted tetracycline compounds of Formula XVI:

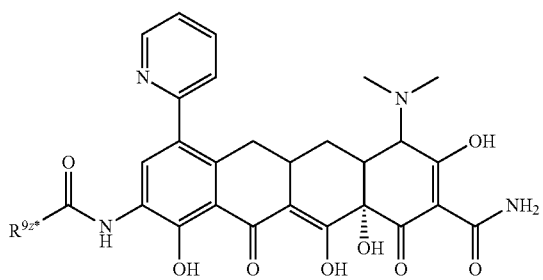

(XVI)

wherein
$R^{9z*}$ is —(CH$_2$)$_t$R$^{9za}$;
t is an integer from 0-1;
$R^{9za}$ is hydrogen, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, alkylcarbonyl, arylcarbonyl, carboxylate, alkoxycarbonyl, aryloxycarbonyl or aminocarbonyl; and pharmaceutically acceptable salts thereof.

In one embodiment, the invention pertains, at least in part, to a pharmaceutical composition comprising a therapeutically effective amount of a tetracycline compound of the invention, e.g., a compound of Formula I, II, III, IIIa, IV, IVa, V, Va, VI, VII, VIIa, VIII, VIIIa, IX, IXa, X, Xa, XI, XIa, XII, XIII, XIV, XV or XVI or a compound listed in Table 2, and a pharmaceutically acceptable carrier.

In another further embodiment, the invention pertains, at least in part, to methods for treating subjects for tetracycline responsive states by administering to them an effective amount of a tetracycline compound of the invention, e.g., a compound of Formula I, II, III, IIIa, IV, IVa, V, Va, VI, VII, VIIa, VIII, VIIIa, IX, IXa, X, Xa, XI, XIa, XII, XIII, XIV, XV or XVI or a compound listed in Table 2 or a tetracycline compound otherwise described herein.

DETAILED DESCRIPTION OF THE INVENTION

Figure 2:
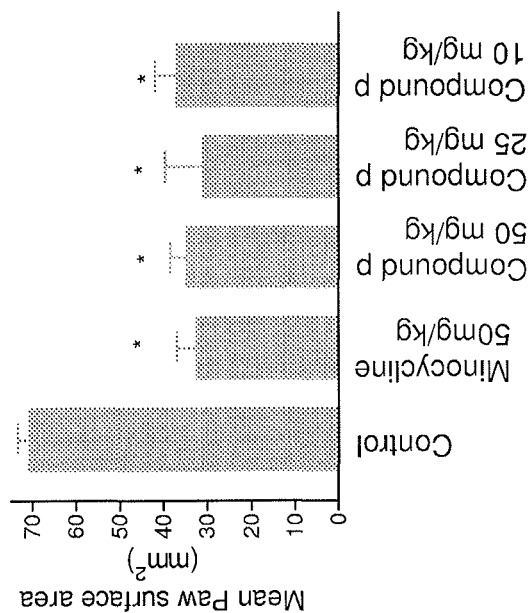
FIG. 2 is a graphical comparison of the modulation of carregeenan induced inflammation in the rat paw edema model between minocycline and compound P.

The present invention pertains, at least in part, to novel substituted tetracycline compounds. These tetracycline compounds can be used to treat numerous tetracycline compound-responsive states, such as bacterial infections, inflammation, and neoplasms, as well as other known applications for minocycline and tetracycline compounds in general, such as blocking tetracycline efflux and modulation of gene expression. The term "tetracycline compound" includes many compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

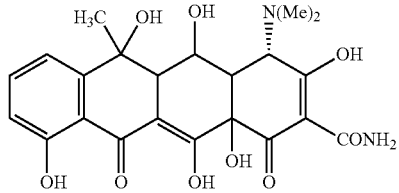

Oxytetracycline

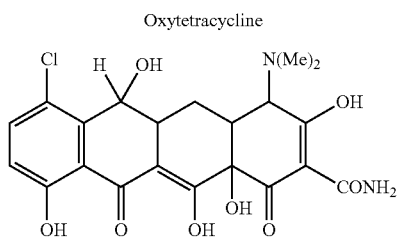

Demeclocycline

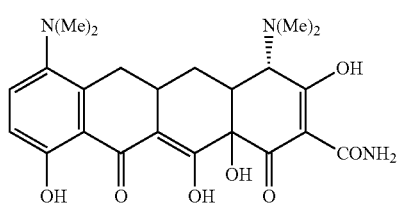

Minocycline

TABLE 1-continued

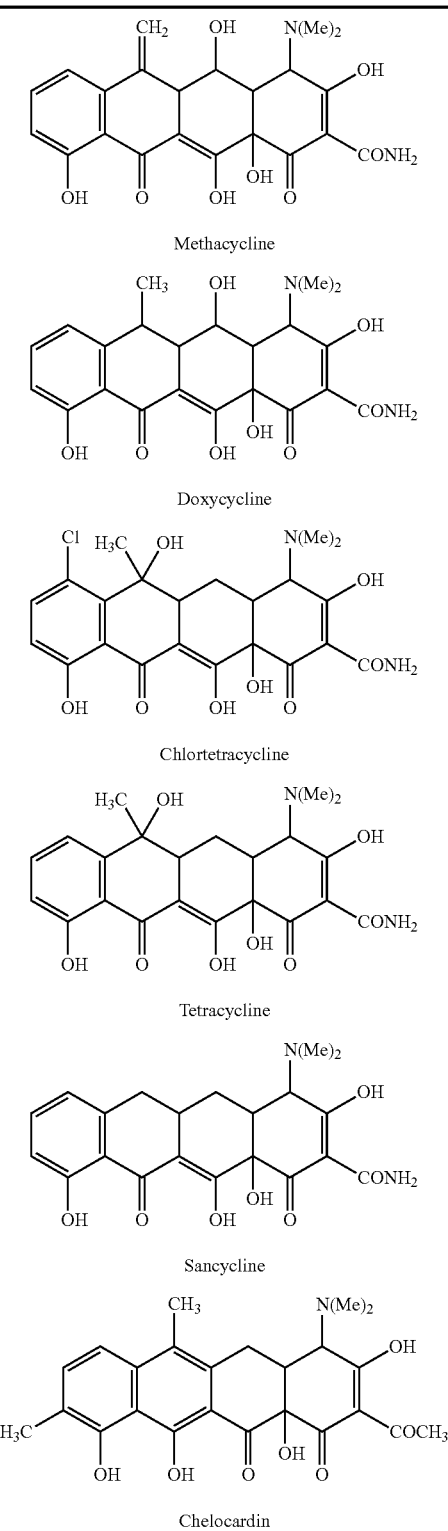

Methacycline

Doxycycline

Chlortetracycline

Tetracycline

Sancycline

Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a C1-6, 12 hemiketal tetracyclines; 11a C1-6-methylene tetracyclines; 6,13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxyanhydro tetracyclines; 6-demethyl-12α-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

In one embodiment, the invention pertains includes substituted tetracycline compound of Formula I:

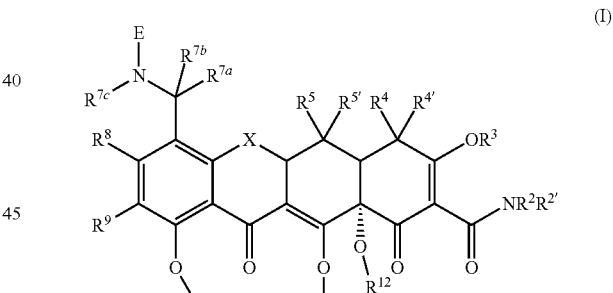

(I)

wherein

X is CHC($R^{13}Y^{13}Y'$Y), $CR^6R^6$, C=$CR^6R^6$, S, $NR^6$, or O;

E is $NR^{7d}R^{7e}$, $OR^f$ or $(CH_2)_{0-1}C(=W')WR^{7g}$;

W is O, S, $NR^{7h}$ or $CR^{7i}R^{7j}$;

W' is O, S or $NR^{7k}$;

$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a pro-drug moiety;

$R^4$ is $NR^{4a}R^{4b}$, alkyl, alkenyl, alkynyl, hydroxyl, halogen, or hydrogen;

$R^5$ and $R^{5'}$ are each hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R⁶ and R⁶' are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7a}$, $R^{7b}$, $R^{7c}$, $R^{7d}$, $R^7e$, $R^{7f}$, $R^{7g}$, $R^{7h}$, $R^{7i}$, $R^{7j}$ and $R^{7k}$ are each independently hydrogen, allyl, alkyl, alkenyl, alkynyl, hydroxyl, alkoxy, alkylthio, alkylsulfinyl, alkylsulfonyl, amino, alkylamino, aminoalkyl, acyl, aryl, arylalkyl, alkylcarbonyloxy, alkylcarbonyloxyalkyl or arylcarbonyloxy, or $R^{7c}$ and $R^{7d}$ or $R^{7e}$ and $R^{7f}$ are linked to form a ring;

R⁸ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R⁹ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, or $-(CH_2)_{0-3}(NR^{9c})_{0-1}C(=Z')ZR^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R¹³ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is $CR^{6'}R^6$, $RR^4$ is $NR^{4a}R^{4b}$ and $R^{4b}$ are each alkyl, and $R^2$, $R^{2'}$, $R^3$, $R^5$, $R^{5'}$ $R^6$, $R^{6'}$, $R^8$, $R^9$, $R^{10}$, $R^{11}$ and $R^{12}$ are each hydrogen and $R^{7a}$ and $R^{7b}$ are hydrogen. In a further embodiment, E is $OR^{7f}$, $R^{7c}$ is hydrogen, and $R^{7f}$ is alkyl (e.g., methyl, ethyl or t-butyl) or allyl.

In another embodiment, $R^{7c}$ is alkyl (e.g., methyl or ethyl) and $R^{7f}$ is alkyl (e.g., methyl, ethyl, isopropyl or t-butyl), which may be substituted with a halogen (e.g., fluorine).

In yet another embodiment, $R^{7c}$ and $R^{7f}$ are linked to join a ring.

In one embodiment, E is $NR^{7d}R^{7e}$, $R^{7c}$ is alkyl (e.g., ethyl), $R^{7d}$ is hydrogen and $R^{7e}$ is alkyl (e.g., ethyl).

In a further embodiment, E is $(CH_2)_{0-1}C(=W')WR^{7g}$, such as E is $C(=W')WR^{7g}$. Accordingly, $R^{7c}$ is alkyl (e.g., methyl), W and W' are each O and $R^{7g}$ is alkyl (e.g., methyl). Alternatively, E is $CH_2C(=W')WR^{7g}$, $R^{7c}$ is alkyl (e.g., methyl), W is $CR^{7i}R^{7j}$ and $R^{7g}$, $R^{7i}$ and $R^{7j}$ are each hydrogen. In a further embodiment, W' is $NR^{7h}$ and $R^{7h}$ is alkoxy (e.g., ethoxy).

In one embodiment, X is $CR^{6'}R^6$, $R^4$ is $NR^{4a}R^{4b}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$, $R^{7c}$, $R^8$, $R^9$, $R^{10}$, $R^{11}$ and $R^{12}$ are each hydrogen; E is $OR^{7f}$; $R^{7f}$ is allyl (e.g., $CH_2=CHCH_2-$) or alkyl (e.g., ethyl; isopropyl; t-butyl; alkoxy substituted alkyl (e.g., methoxyethyl); halogen substituted alkyl (e.g., alkyl substituted with fluorine, for example, $FCH_2CH_2-$; $F_2CHCH_2-$; $CF_3CH_2-$ or $CF_2H-$); alkylcarbonylalkyl (e.g., $CH_3CO(CH_2)_n-$, in which n is an integer from 0-6, for example 1); alkoxycarbonylalkyl (e.g., $CH_3OCO(CH_2)_m-$, in which m is an integer from 0-6, for example 1) or carboxylatealkyl ($HOOC(CH_2)_q-$, in which q is an integer from 0-6, for example 1).

In one embodiment, X is $CR^{6'}R^6$, $R^4$ is $NR^{4a}R^{4b}$, $R^{4a}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$, $R^8$, $R^9$, $R^{10}$, $R^{11}$ and $R^{12}$ are each hydrogen; E is $OR^{7f}$ and $R^{7c}$ and $R^{7f}$ are linked to join a ring, for example, a 5- or 6-membered ring (e.g.,

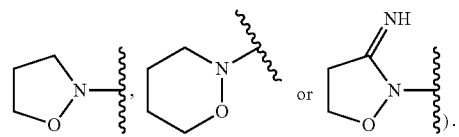

).

In another embodiment, X is $CR^{6'}R^6$, $R^4$ is $NR^{4a}R^{4b}$, $R^{4a}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$ $R^8$, $R^9$, $R^{10}$, $R^{11}$ and $R^{12}$ are each hydrogen; E is $OR^{7f}$; $R^{7c}$ and $R^{7f}$ may be each independently alkyl (e.g., methyl or ethyl).

In yet another embodiment, X is $CR^{6'}R^6$, $R^4$ is $NR^{4a}R^{4b}$, $R^{4a}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$, $R^{7c}$, $R^8$, $R^9$, $R^{10}$, $R^{11}$ and $R^{12}$ are each hydrogen; E is $NR^{7d}R^{7e}$; $R^{7c}$ is alkyl (e.g., ethyl); $R^{7d}$ is hydrogen and $R^{7e}$ is alkyl (e.g., ethyl).

In another embodiment, X is $CR^{6'}R^6$, $R^4$ is $NR^{4a}R^{4b}$, $R^{4a}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$, $R^{7c}$, $R^8$, $R^9$, $R^{10}$, $R^{11}$ and $R^{12}$ are each hydrogen; E is $-C(=W')WR^{7g}$; W and W' are each oxygen; $R^{7c}$ is allyl (e.g., $CH_2=CHCH_2-$) and $R^{7g}$ is alkoxy (e.g., methoxy).

In one embodiment, X is $CR^{6'}R^6$, $R^4$ is $NR^{4a}R^{4b}$, $R^{4a}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$, $R^{7c}$, $R^8$, $R^9$, $R^{10}$, $R^{11}$ and $R^{12}$ are each hydrogen; E is $-CH_2(C=W')WR^{7g}$; $R^{7c}$ is alkyl (e.g., methyl); W is $CR^{7i}R^{7j}$; $R^{7i}$, $R^{7j}$ and $R^{7g}$ are each hydrogen; W' is $NR^{7k}$ and $R^{7k}$ is alkoxy (e.g., ethoxy).

In a further embodiment, In one embodiment, X is $CR^{6'}R^6$, $R^4$ is $NR^{4a}R^{4b}$, $R^{4a}$ and $R^{4b}$ are each alkyl (e.g., methyl); $R^2$, $R^{2'}$, $R^3$, $R^{4'}$ $R^5$, $R^{5'}$ $R^6$, $R^{6'}$, $R^{7a}$, $R^{7b}$, $R^{7c}$, $R^8$, $R^9$, $R^{10}$, $R^{11}$ and $R^{12}$ are each hydrogen; E is $-C(=W')WR^{7g}$; W and W' are each oxygen; $R^{7g}$ is alkylcarbonyloxyalkyl (e.g., $R^{7ga}R^{7gb}R^{7gc}COO(CH_2)_r-$ in which r is an integer between 1 and 5 and $R^{7ga}R^{7gb}R^{7gc}$ are each independently alkyl or hydrogen). In one embodiment, wherein $R^{7ga}R^{7gb}R^{7gc}$ are each alkyl (e.g., methyl); r is 1 and $R^{7C}$ is hydrogen or alkyl (e.g., cycloalkyl, for example, cyclopropyl).

Examples of substituted tetracycline compounds of Formula (I) include:

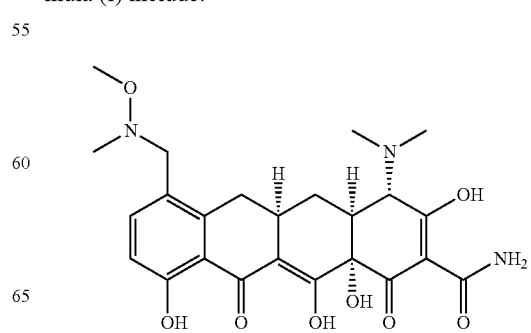

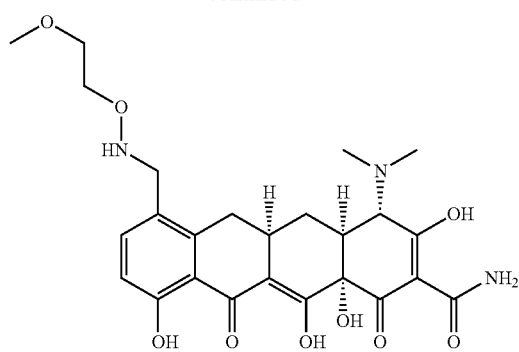
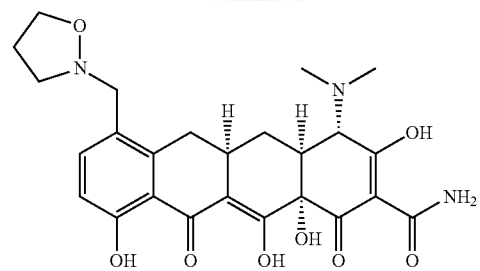
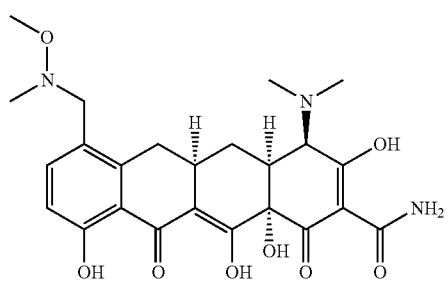
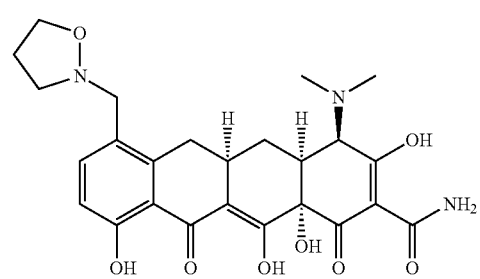
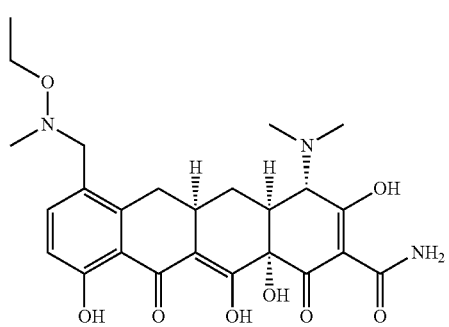
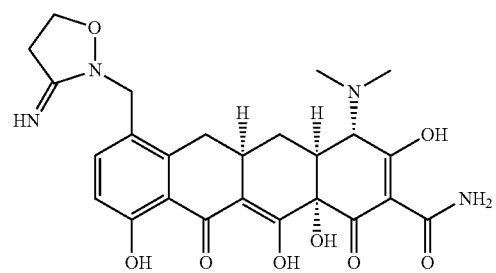
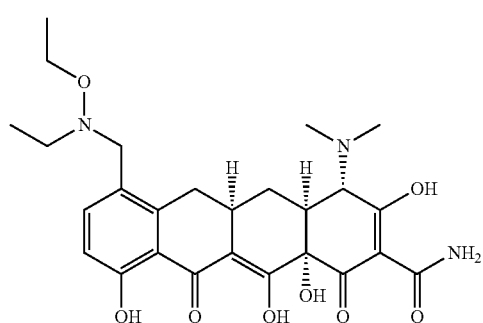
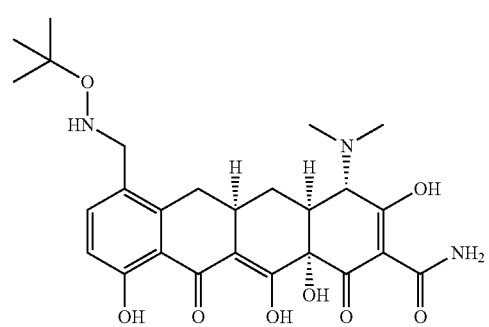
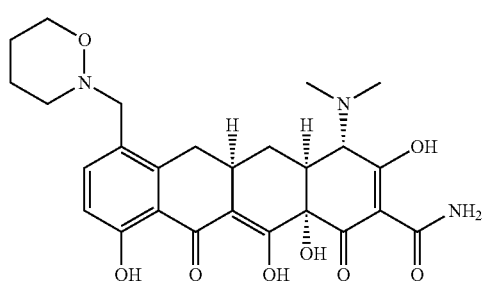
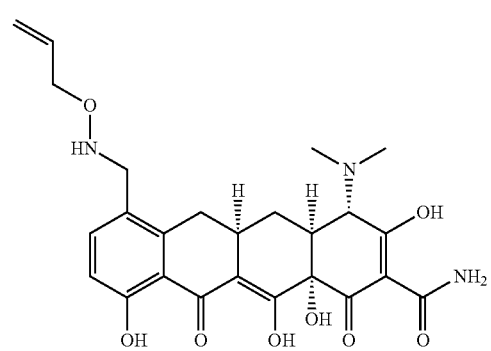

-continued
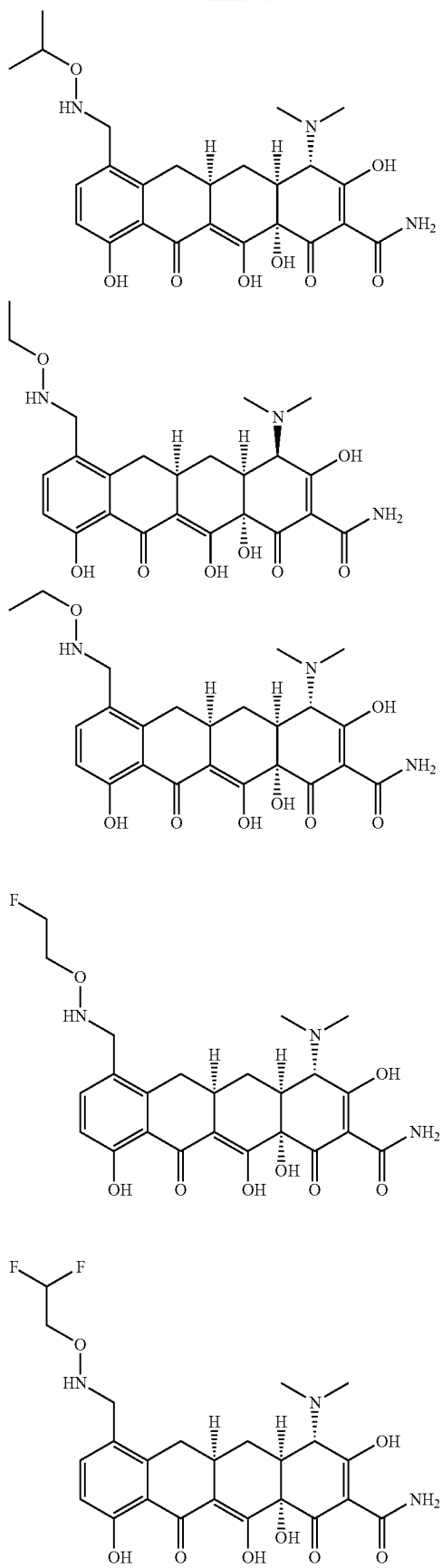
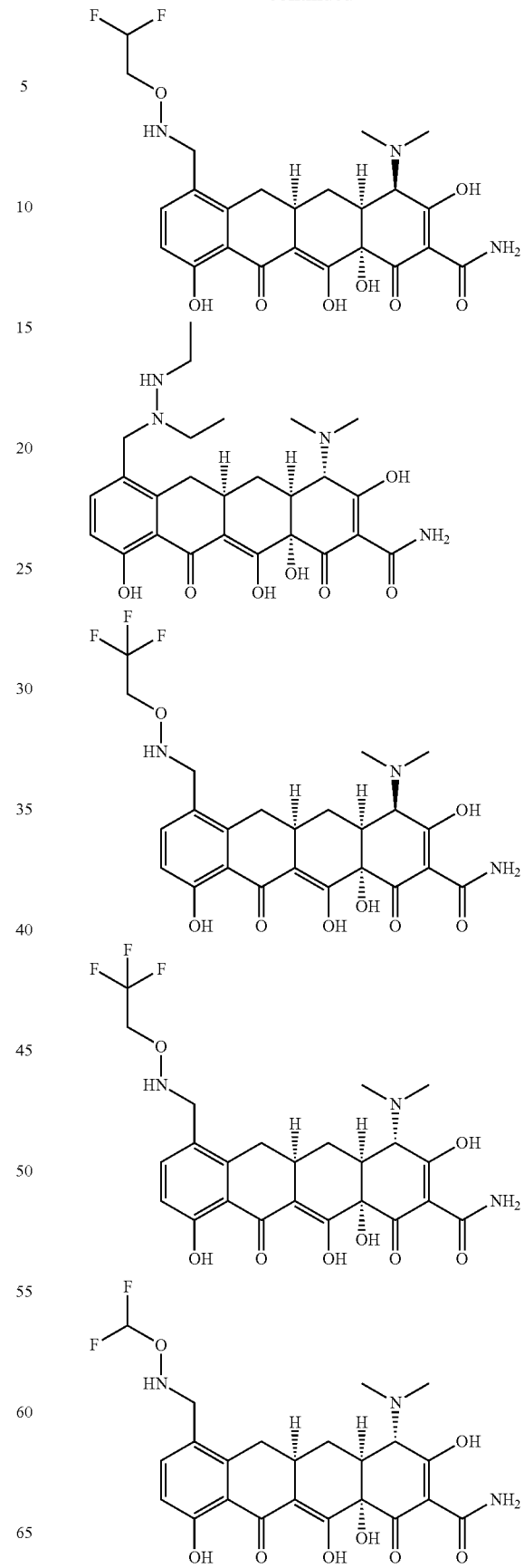

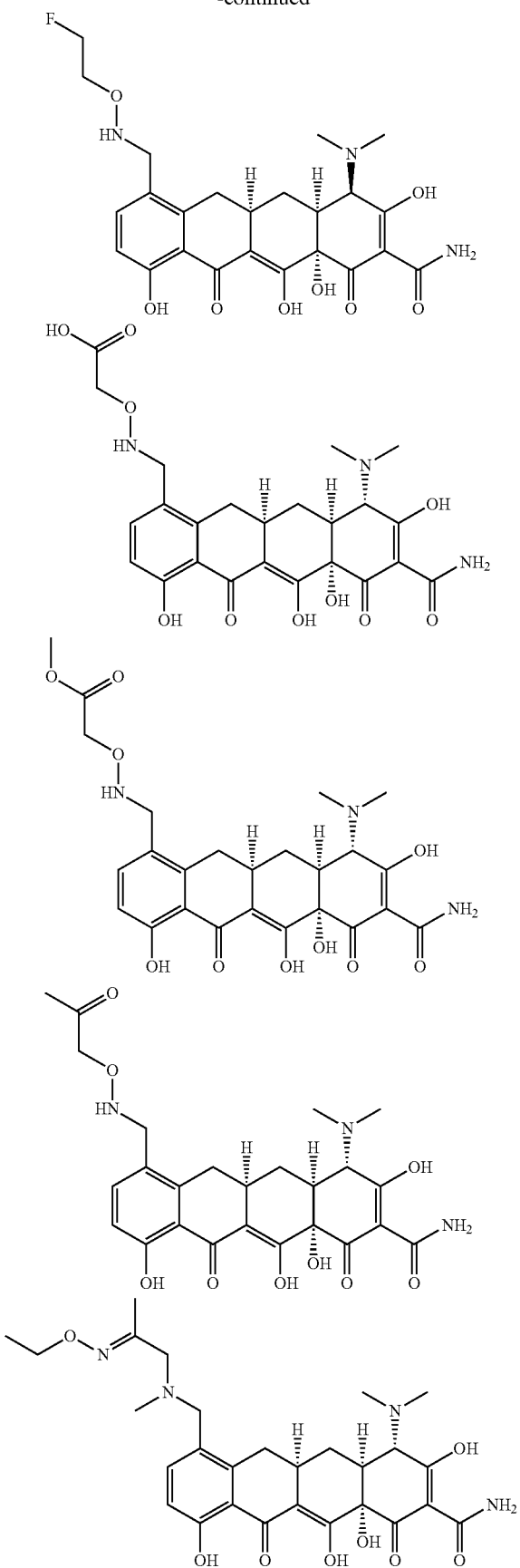
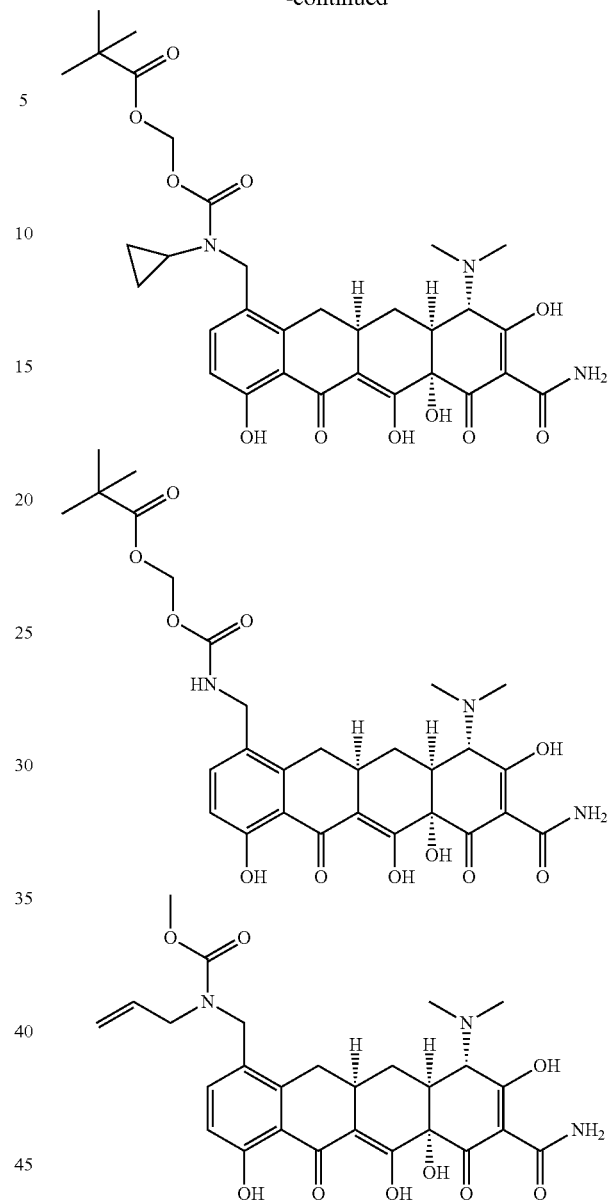
and pharmaceutically acceptable salts thereof.
In another embodiment, the invention includes substituted tetracycline compounds of Formula II:
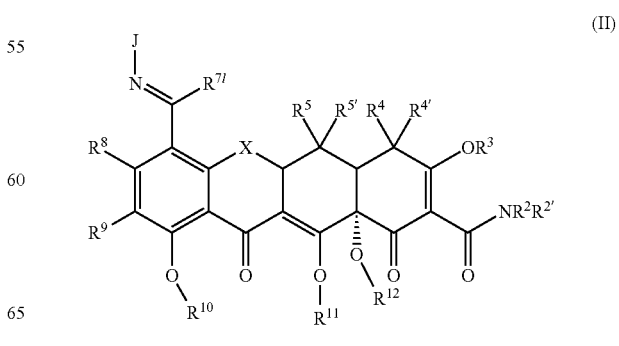

wherein

X is CHC($R^{13\prime}$Y), $CR^{6\prime}R^6$, C=$CR^{6\prime}R^6$, S, $NR^6$, or O;

J is $NR^{7m}R^{7n}$, $OR^{7o}$ or heteroaryl;

$R^2$, $R^{2\prime}$, $R^{4\prime}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a prodrug moiety;

$R^4$ is $NR^{4a}R^{4b}$, alkyl, alkenyl, alkynyl, hydroxyl, halogen, or hydrogen;

$R^5$ and $R^{5\prime}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6\prime}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7l}$, $R^{7m}$, $R^{7n}$ and $R^{7o}$ are each independently hydrogen, alkyl, alkenyl, alkynyl, hydroxyl, alkoxy, amino, alkylamino, aminoalkyl, acyl, alkylthio, alkylsulfinyl, alkylsulfonyl, aryl, arylalkyl, alkylcarbonyloxy, or arylcarbonyloxy;

$R^8$ is hydrogen, hydroxyl, halogen, thiol, alkyl, alkenyl, alkynyl, aryl, alkoxy, alkylthio, alkylsulfinyl alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or —$(CH_2)_{0-3}(NR^{9c})_{0-1}C(=Z\prime)ZR^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is $CR^{6\prime}R^6$, $R^4$ is $NR^{4a}R^{4b}$, $R^{4a}$ and $R^{4b}$ are each alkyl (e.g., methyl), $R^2$, $R^{2\prime}$, $R^3$, $R^{4\prime}$, $R^5$, $R^{5\prime}$, $R^6$, $R^{6\prime}$, $R^8$, $R^9$, $R^{10}$, $R^{11}$ and $R^{12}$ are each hydrogen; J is $OR^{7o}$; $R^{7o}$ is alkyl (e.g., ethyl or t-butyl) and $R^{7l}$ is alkyl (e.g., methyl) or aminoalkyl (e.g., dialkylaminoalkyl, such as dimethylaminoethyl).

In one embodiment, X is $CR^{6\prime}R^6$, $R^4$ is $NR^{4a}R^{4b}$, $R^{4a}$ and $R^{4b}$ are each alkyl (e.g., $R^2$, $R^{2\prime}$, $R^3$, $R^{4\prime}$, $R^5$, $R^{5\prime}$, $R^6$, $R^{6\prime}$, $R^8$, $R^{10}$, $R^{11}$ and $R^{12}$ are each hydrogen; $R^9$ is amino; $R^{7l}$ is alkyl (e.g., methyl); J is $OR^{7o}$; $R^{7o}$ is alkyl (e.g., halogen substituted alkyl; such as fluorine substituted alkyl, for example, $CF_3CH_2$—; ethyl or t-butyl).

In another embodiment, X is $CR^{6\prime}R^6$, $R^4$ is $NR^{4a}R^{4b}$, $R^{4a}$ and $R^{4b}$ are each alkyl (e.g., methyl), $R^2$, $R^{2\prime}$, $R^3$, $R^{4\prime}$, $R^5$, $R^{5\prime}$, $R^6$, $R^{6\prime}$, $R^8$, $R^{10}$, $R^{11}$ and $R^{12}$ are each hydrogen; $R^9$ is aminoalkyl (e.g., t-butylaminomethyl); $R^{7o}$ is alkyl (e.g., ethyl); and $R^{7l}$ is alkyl (e.g., methyl).

In yet another embodiment, X is $CR^{6\prime}R^6$, $R^4$ is $NR^{4a}R^{4b}$, $R^{4a}$ and $R^{4b}$ are each alkyl (e.g., methyl), $R^2$, $R^{2\prime}$, $R^3$, $R^{4\prime}$, $R^5$, $R^{5\prime}$, $R^6$, $R^{6\prime}$, $R^8$, $R^9$, $R^{10}$, $R^{11}$ and $R^{12}$ are each hydrogen; J is $NR^{7m}R^{7n}$; $R^{7l}$ and $R^{7m}$ are each hydrogen and $R^{7n}$ is alkyl (e.g., t-butyl).

In a further embodiment, X is $CR^{6\prime}R^6$, $R^4$ is $NR^{4a}R^{4b}$, $R^{4a}$ and $R^{4b}$ are each alkyl (e.g., methyl), $R^2$, $R^{2\prime}$, $R^3$, $R^{4\prime}$, $R^5$, $R^{5\prime}$, $R^6$, $R^{6\prime}$, $R^{7l}$, $R^8$, $R^9$, $R^{10}$, $R^{11}$ and $R^{12}$ are each hydrogen; J is heteroaryl (e.g., pyrrolyl).

In one embodiment, X is $CR^{6\prime}R^6$, $R^4$ is $NR^{4a}R^{4b}$, $R^{4a}$ and $R^{4b}$ are each alkyl, and $R^2$, $R^{2\prime}$, $R^3$, $R^{4a}$, $R^{4b}$, $R^5$, $R^{5\prime}$ $R^6$, $R^{6\prime}$, $R^8$, $R^{10}$, $R^{11}$ and $R^{12}$ are each hydrogen, and J is $OR^{7o}$ Accordingly, $R^9$ is hydrogen and $R^{7o}$ is alkyl (e.g., methyl, ethyl or t-butyl).

In another embodiment, $R^{7l}$ is alkyl (e.g., methyl). Alternatively, $R^{7l}$ is aminoalkyl, $R^9$ is amino and $R^{7o}$ is alkyl (e.g., ethyl or t-butyl).

In a further embodiment, $R^{7l}$ is alkyl (e.g., methyl), $R^9$ is aminoalkyl and $R^{7o}$ is alkyl (e.g., ethyl). In yet another embodiment, $R^{7l}$ is alkyl (e.g., methyl).

In one embodiment, J is $NR^{7m}R^{7n}$, $R^{9m}$, $R^{7l}$ and $R^{7m}$ are each hydrogen and $R^{7n}$ is alkyl (e.g., t-butyl).

In another embodiment, J is heteroaryl (e.g., pyrrolyl) and $R^9$ and $R^{7l}$ are each hydrogen.

Examples of substituted tetracycline compounds of Formula II include:

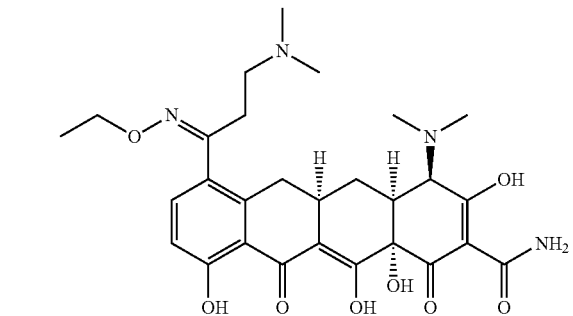 [SMILES: CCO/N=C(/CCN(C)C)c1ccc(O)c2c1C[C@H]1C[C@H]3[C@H](N(C)C)C(O)=C(C(N)=O)C(=O)[C@@]3(O)C(O)=C1C2=O]

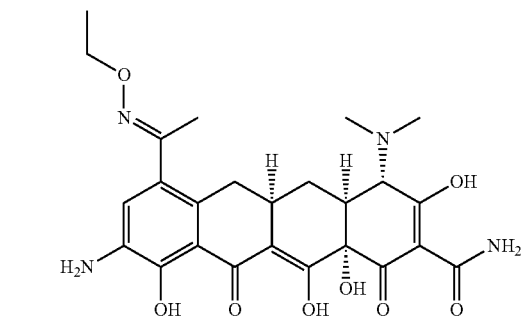 [SMILES: CCO/N=C(\C)c1cc(N)c(O)c2c1C[C@H]1C[C@H]3[C@H](N(C)C)C(O)=C(C(N)=O)C(=O)[C@@]3(O)C(O)=C1C2=O]

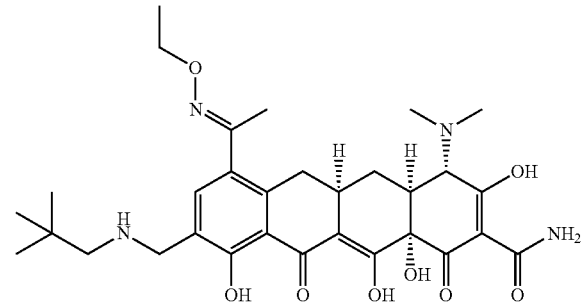 [SMILES: CCO/N=C(\C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O]

27
-continued
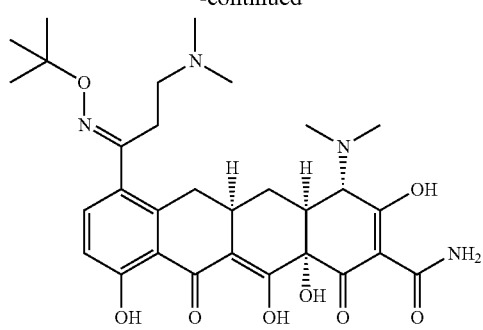
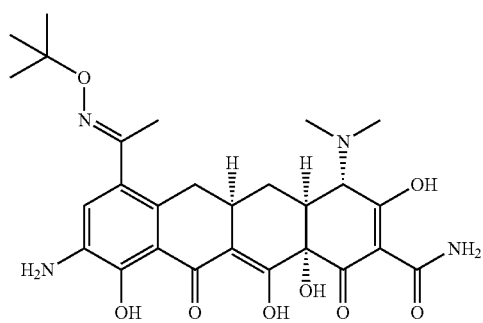 [SMILES: C/C(=N\OC(C)(C)C)c1cc(N)c(O)c2c1C[C@H]1C[C@H]3[C@H](N(C)C)C(O)=C(C(N)=O)C(=O)[C@@]3(O)C(O)=C1C2=O]
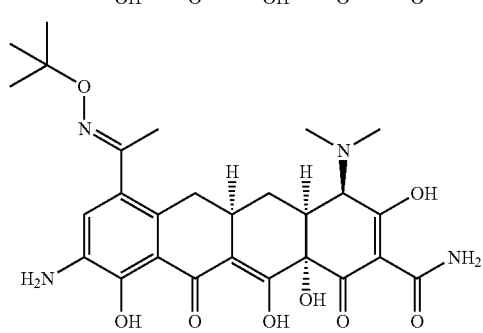
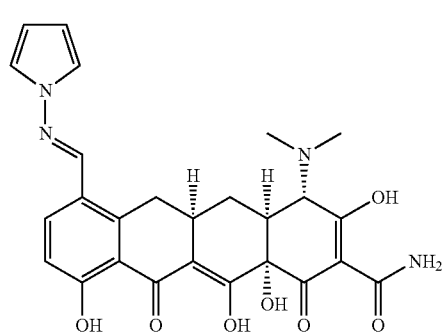 [SMILES: CN(C)[C@@H]1C(O)=C(C(N)=O)C(=O)[C@@]2(O)C(O)=C3C(=O)c4c(O)ccc(/C=N/n5cccc5)c4C[C@H]3C[C@@H]12]
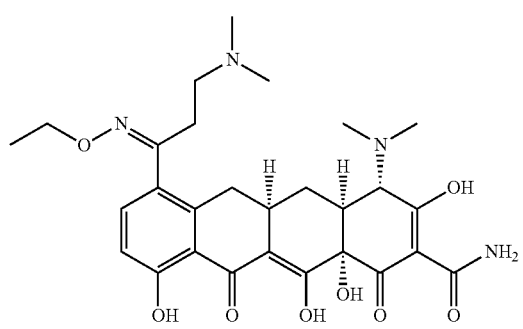
28
-continued
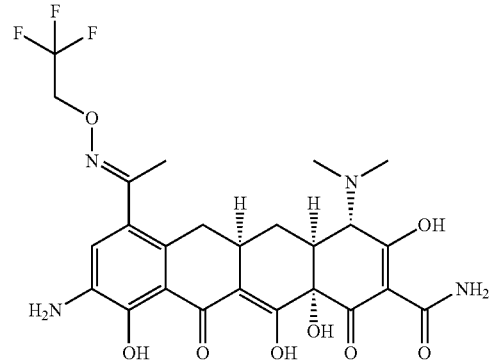
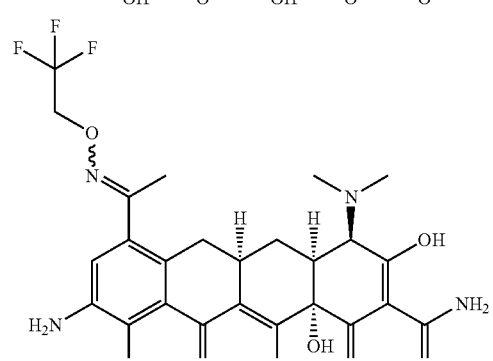
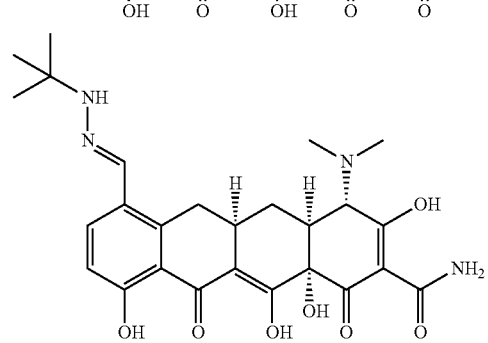
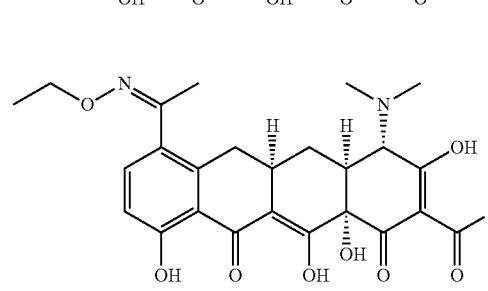
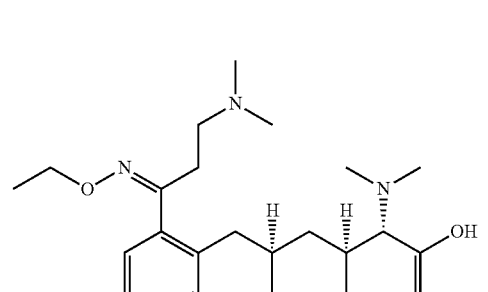

-continued

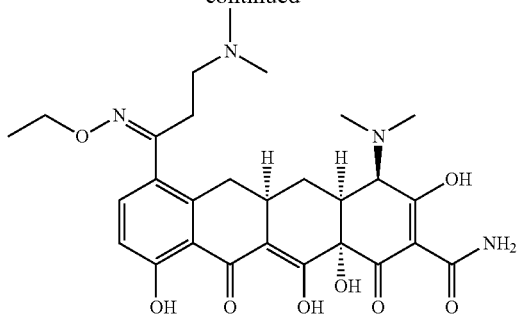

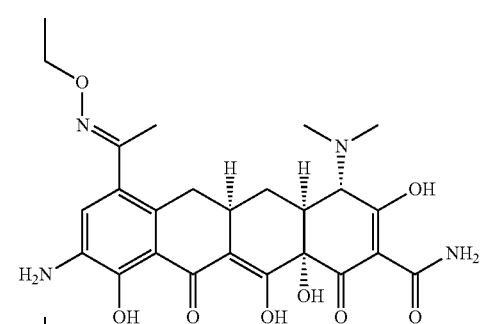

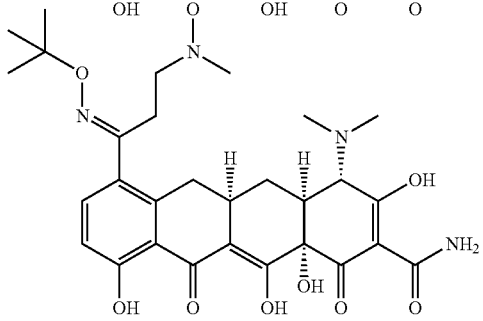

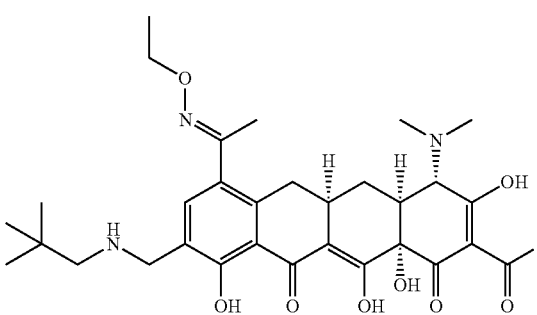

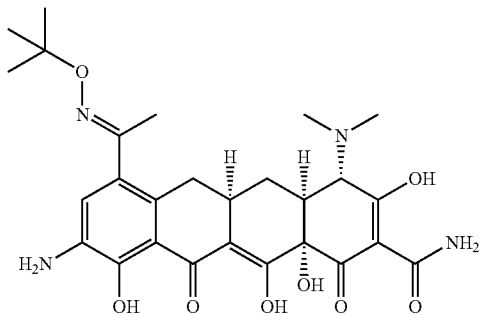

-continued

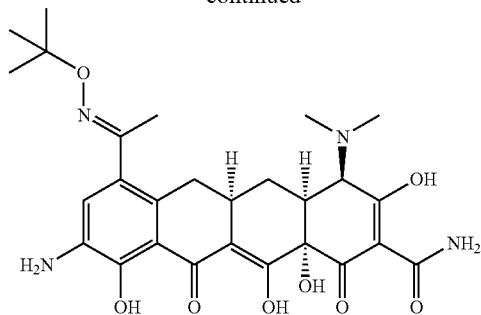

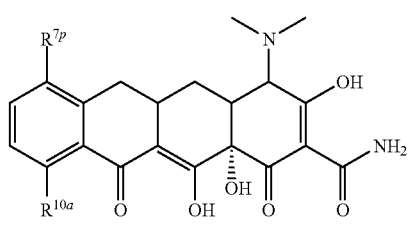

and pharmaceutically acceptable salts thereof.

In another embodiment, the invention pertains to substituted tetracycline compounds of Formula III:

$$\text{(III)}$$

wherein
R$^{7p}$ is acyl, alkylamino, or heteroaryl;
R$^{10a}$ is hydrogen, aryl, carboxylate or alkoxycarbonyl;
R$^{13}$ is hydrogen, hydroxy, alkyl, alkenyl, alkynyl, alkoxy, alkylthio, alkylsulfinyl, alkylsulfonyl, alkylamino, or an arylalkyl; and pharmaceutically acceptable salts thereof.

In one embodiment, R$^{7p}$ is alkylamino (e.g., dialkylamino, such as dimethylamino or substituted piperidinyl), acyl or heteroaryl (e.g., pyrimidine or pyrazine).

In a further embodiment, R$^{10a}$ is heteroaryl (e.g., oxazolyl), carboxylate or is alkoxycarbonyl (e.g., methoxycarbonyl).

In yet another embodiment, the invention includes substituted tetracycline compounds of Formula IIIa:

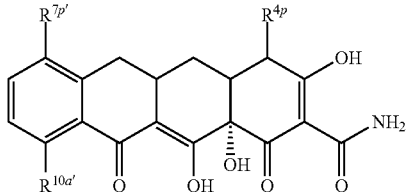

(IIIa)

wherein $R^{4p}$ is —N(CH$_3$)$_2$ or hydrogen;

$R^{7p'}$ is hydrogen, amino, acyl, heteroaryl, aminoalkyl;

$R^{10a'}$ is hydrogen, heteroaryl, alkoxycarbonyl, carboxylate, cyano, alkyl or alkoxy; and pharmaceutically acceptable salts thereof.

In one embodiment, $R^{4p}$ is —N(CH$_3$)$_2$; $R^{10a}$ is hydrogen and $R^{7p'}$ is acyl (e.g., CH$_3$CO—); heteroaryl (e.g., pyrimidinyl or pyrazinyl) or aminoalkyl (e.g., piperidinylalkyl, for example, 4-methylpiperidinylmethyl)

In another embodiment, $R^{4p}$ is —N(CH$_3$)$_2$; $R^{7p}$ is dimethylamino and $R^{10a'}$ is heteroaryl (e.g., oxazolyl or pyrazolyl), alkoxycarbonyl (e.g., methoxycarbonyl), carboxylate or cyano.

In yet another embodiment, $R^{4p}$ is —N(CH$_3$)$_2$; $R^{7p'}$ is hydrogen and $R^{10a'}$ is alkoxycarbonyl (e.g., methoxycarbonyl) or alkyl (e.g., methyl).

In another embodiment, $R^{4p}$ is hydrogen; $R^{7p'}$ is dimethylamino and $R^{10a'}$ is alkyl (e.g., methyl) or alkoxy (e.g., methoxy).

Examples of substituted tetracycline compounds of Formulae III and IIIa include:

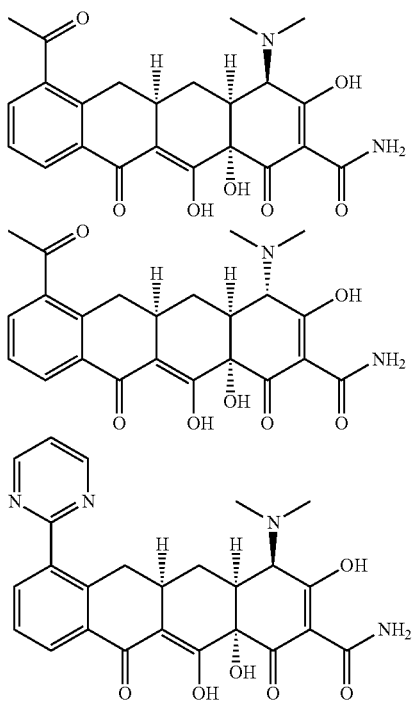

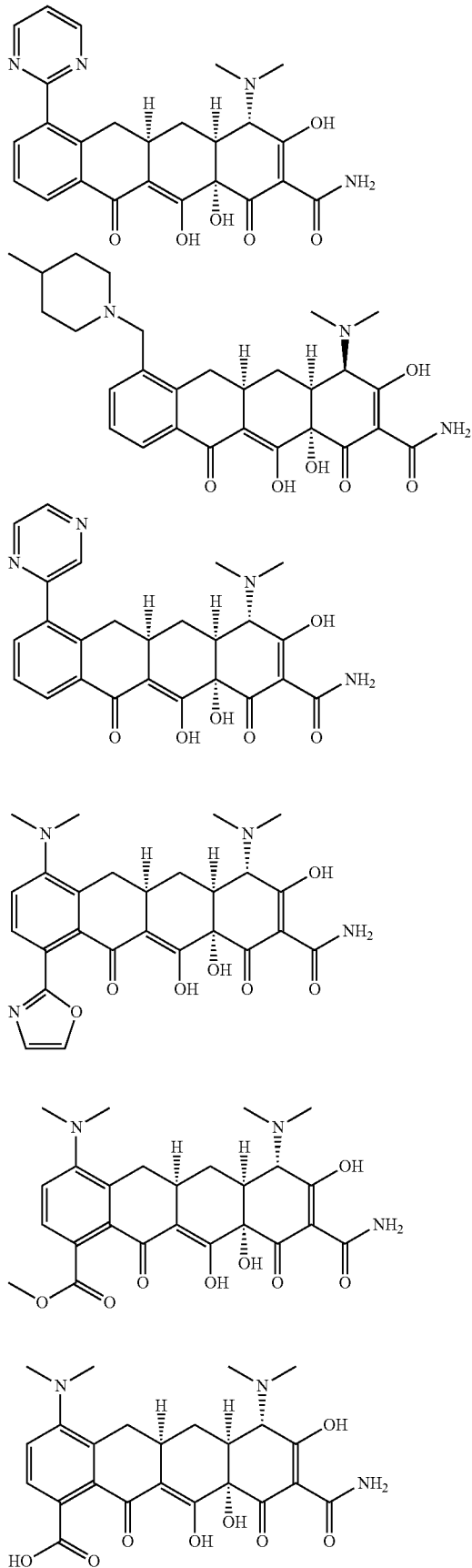

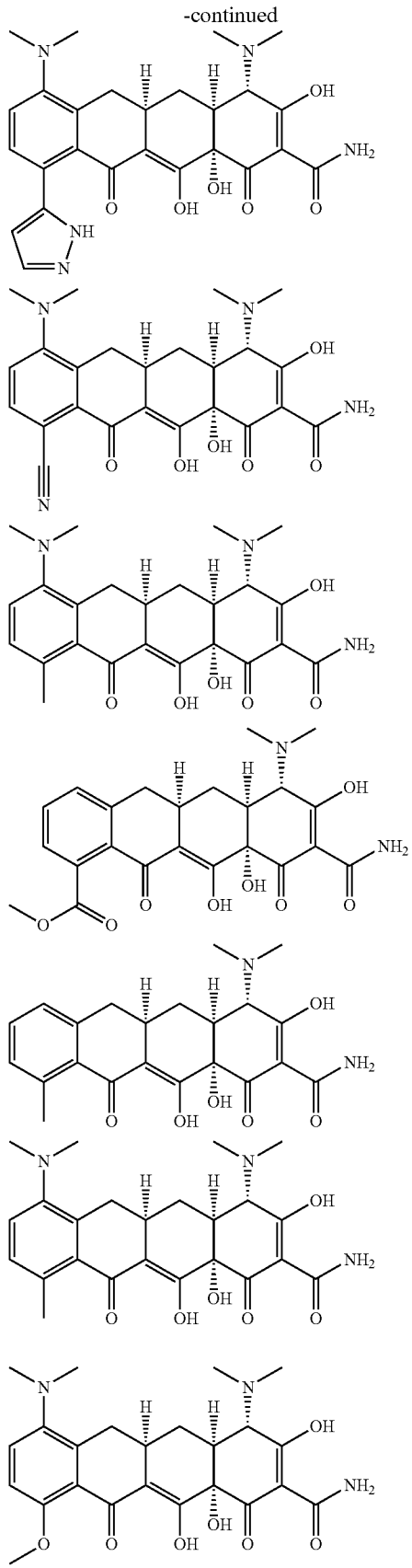

and pharmaceutically acceptable salts thereof.

In another embodiment, the invention includes substituted tetracycline compounds of Formula IV:

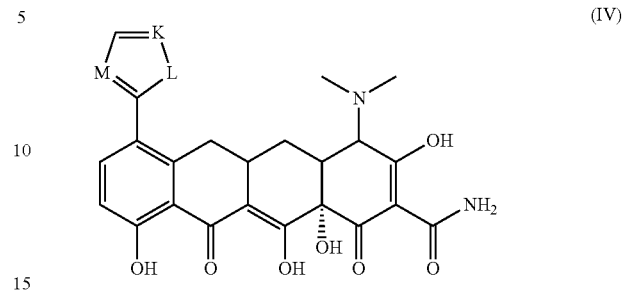

wherein

L is O, NH or SH;

K is N or $CR^{7p'}$;

M is N or $CR^{7p'}$;

$R^{7p'}$ is hydrogen;

$R^{7p''}$ is hydrogen, aminoalkyl or alkoxycarbonylaminoalkyl, and pharmaceutically acceptable salts thereof.

In one embodiment, L is O, K is N, M is $CR^{7p''}$ and $R^{7p''}$ is hydrogen.

In another embodiment, L is O, K is $CR^{7p'}$, $R^{7p'}$ is hydrogen and M is N. Alternatively, M is $R^{7p''}$ and $R^{7p''}$ is alkylamino (e.g., is methylaminoalkyl, isopropylaminoalkyl or t-butylaminoalkyl) or is alkoxycarbonylaminoalkyl.

In another embodiment, L is SH, K is $CR^{7p'}$, $R^{7p'}$ is hydrogen and M is N.

In yet another embodiment, L is NH, K is $CR^{7p'}$ and M is $CR^{7p''}$ and $R^{7p'}$ and $R^{7p''}$ are each hydrogen.

In another embodiment, includes substituted tetracycline compounds of Formula IVa:

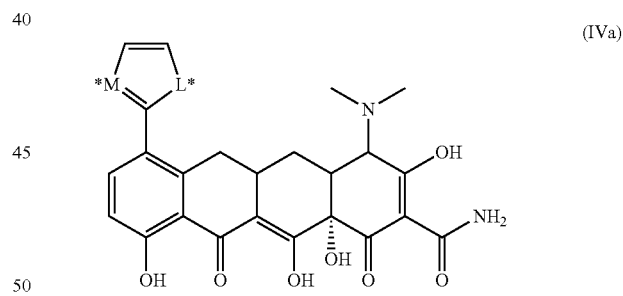

wherein

L* is O, NH or S;

*M is N, CH or $CR^{7ps''}$;

$R^{7ps''}$ is aminoalkyl; and pharmaceutically acceptable salts thereof.

In one embodiment, *M is N and L* is S or O.

In another embodiment, *M is CH and L* is NH or O.

In a further embodiment, M is $CR^{7ps''}$; $R^{7ps''}$ is aminoalkyl (e.g., $—(CH_2)_tNR^{7pa}R^{7pb}$ in which t is an integer from 0 to 5 and $R^{7pa}$ is hydrogen or alkyl and $R^{7pb}$ is alkyl or alkoxycarbonyl). In one embodiment, t is 1; $R^{7pa}$ is alkyl (e.g., methyl) and $R^{7pb}$ is alkyl (e.g., methyl) or alkoxycarbonyl (e.g., methoxycarbonyl). In another embodiment, $R^{7pa}$ is hydrogen and $R^{7pb}$ is alkyl (e.g., methyl, isopropyl or t-butyl).

Examples of substituted tetracycline compounds of Formulae IV and IVa include:

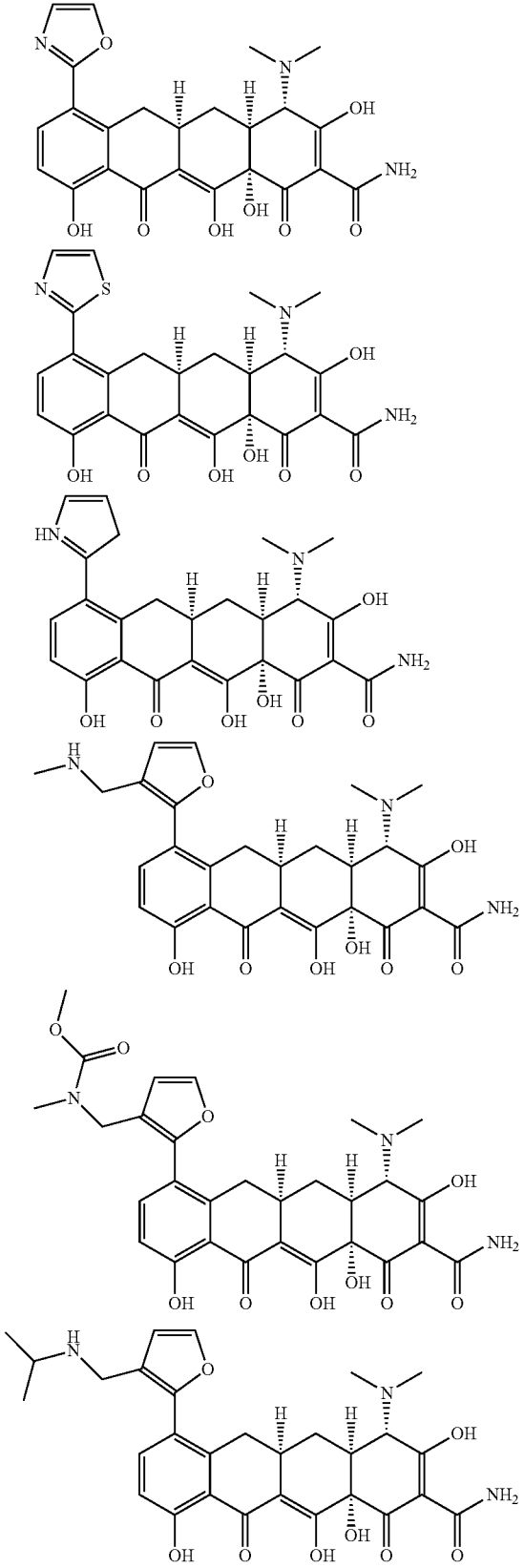

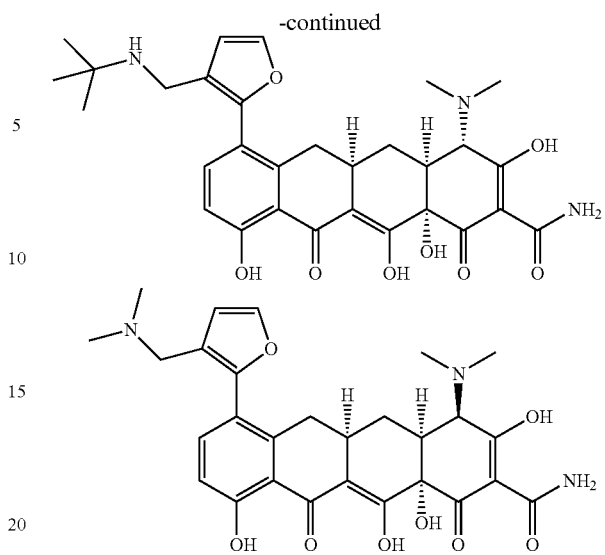

and pharmaceutically acceptable salts thereof.

The present invention also includes substituted tetracycline compounds of Formula V:

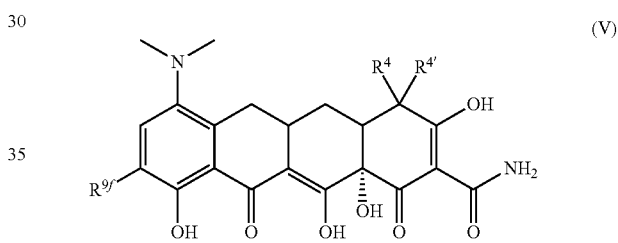

wherein

R$^4$ is hydrogen;

R$^{4'}$ is hydrogen or alkylamino;

R$^{9f}$ is CR$^{9g}$NR$^{9h}$ or CR$^{9i}$R$^{9j}$NR$^{9k}$R$^{9l}$;

R$^{9g}$, R$^{9h}$, R$^{9i}$, R$^{9j}$, R$^{9k}$ and R$^{9l}$ are each independently hydrogen, alkyl, hydroxyl, amino, urea or alkoxy, or R$^{9k}$ and R$^{9l}$ are joined to form a ring; and pharmaceutically acceptable salts thereof.

In one embodiment, R$^4$ is hydrogen and R$^{4'}$ is alkylamino (e.g., dialkylamino, such as dimethylamino), R$^{9f}$ is CR$^{9g}$NR$^{9h}$, R$^{9g}$ is hydrogen and R$^{9h}$ is alkoxy (e.g., methoxy). In another embodiment, R$^{9g}$ is alkyl (e.g., methyl) and R$^{9h}$ is alkoxy (e.g., ethoxy).

In another embodiment, R$^{9f}$ is CR$^{9i}$R$^{9j}$NR$^{9k}$R$^{9l}$, R$^{9i}$ and R$^{9j}$ are each hydrogen, R$^{9k}$ is alkyl (e.g., methyl) and R$^{9l}$ is alkoxy (e.g., methoxy or ethoxy). Alternatively, R$^{9k}$ and R$^{9l}$ are joined to form a ring (e.g., a six-membered ring). In another embodiment, R$^{9l}$ is amino, which may be substituted with an alkylcarbonyl, or a urea moiety, which may be substituted with alkyl (e.g., t-butyl).

In yet another embodiment, R$^{9k}$ is hydrogen, R$^{9l}$ is alkoxy (e.g., methoxy).

In a further embodiment, R$^4$ and R$^{4'}$ are each hydrogen, R$^{9f}$ is CR$^{9g}$NR$^{9h}$, R$^{9g}$ is alkyl (e.g., methyl) and R$^{9h}$ is alkoxy (e.g. methoxy).

In yet another embodiment, the invention includes substituted tetracycline compounds of Formula Va:

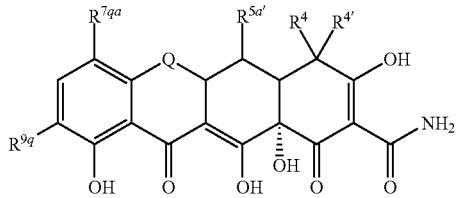

(Va)

wherein

Q is —CH$_2$ or —C=CH$_2$;

R$^4$ is hydrogen;

R$^{4'}$ is hydrogen or alkylamino;

R$^{5a'}$ is hydrogen or hydroxyl;

R$^{7qa}$ is —N(CH$_3$)$_2$ or hydrogen;

R$^{9q}$ is CR$^{9g'}$NR$^{9h'}$ or CR$^{9i'}$R$^{9j'}$NR$^{9k'}$R$^{9l'}$;

R$^{9g'}$, R$^{9h'}$, R$^{9i'}$, R$^{9j'}$, R$^{9k'}$ and R$^{9l'}$ are each independently hydrogen, alkyl, hydroxyl, amino, urea or alkoxy, or R$^{9k'}$ and R$^{9l'}$ are joined to form a ring; and pharmaceutically acceptable salts thereof.

In one embodiment, Q is —C=CH$_2$; R$^4$ is alkylamino; R$^{5a'}$ is hydroxyl and R$^{7qa}$ is hydrogen and R$^{9q}$ is CR$^{9i'}$R$^{9j'}$NR$^{9k'}$R$^{9l'}$. In a further embodiment, R$^{9i'}$ and R$^{9j'}$ are each hydrogen and R$^{9k'}$ is alkyl (e.g., methyl) and R$^{9l'}$ is alkoxy (e.g., methoxy).

In another embodiment, Q is —CH$_2$; R$^4$ and R$^{5a'}$ are each hydrogen; R$^{7qa}$ is N(CH$_3$)$_2$; R$^{9q}$ is CR$^{9g'}$NR$^{9h'}$; R$^{9g'}$ is alkyl (e.g., methyl) and R$^{9h'}$ is alkoxy (e.g., methoxy).

In a further embodiment, Q is —CH$_2$; R$^4$ is aminoalkyl; R$^{5a'}$ and R$^{7qa}$ are each hydrogen; R$^{9q}$ is CR$^{9i'}$R$^{9j'}$NR$^{9k'}$R$^{9l'}$; R$^{9i'}$, R$^{9j'}$ and R$^{9k'}$ are each hydrogen; R$^{9l'}$ is alkoxy (e.g., ethoxy).

In one embodiment, Q is —CH$_2$; R$^{4'}$ is aminoalkyl; R$^{5a'}$ and R$^{7qa}$ are each hydrogen; R$^{9q}$ is CR$^{9i'}$R$^{9j'}$NR$^{9k'}$R$^{9l'}$; R$^{9i'}$ and R$^{9j'}$ are each hydrogen; R$^{9k'}$ is alkyl (e.g., methyl) and wherein R$^{9l'}$ is alkoxy (e.g., methoxy).

In a yet another embodiment, Q is —CH$_2$; R$^{4'}$ is alkylamino, R$^{5a'}$ is hydrogen; R$^{7qa}$ is —N(CH$_3$)$_2$; R$^{9q}$ is CR$^{9g'}$NR$^{9h'}$; R$^{9g'}$ is hydrogen and R$^{9h'}$ is alkoxy (e.g., methoxy).

In a another embodiment, Q is —CH$_2$; R$^{4'}$ is alkylamino, R$^{5a'}$ is hydrogen; R$^{7qa}$ is —N(CH$_3$)$_2$; R$^{9q}$ is CR$^{9g'}$NR$^{9h'}$; R$^{9g'}$ is alkyl (e.g., methyl) and R$^{9l'}$ is alkoxy (e.g., methoxy).

In a further embodiment, Q is —CH$_2$; R$^{4'}$ is alkylamino, R$^{5a'}$ is hydrogen; R$^{7qa}$ is —N(CH$_3$)$_2$; R$^{9q}$ is CR$^{9i'}$R$^{9j'}$NR$^{9k'}$R$^{9l'}$; R$^{9i'}$, R$^{9j'}$ and R$^{9k'}$ are each hydrogen and R$^{9l'}$ is alkoxy (e.g., methoxy); alkylcarbonylamino (e.g., t-butylcarbonylamino) or alkylurea (e.g., t-butylurea).

In yet another embodiment, Q is —CH$_2$; R$^{4'}$ is alkylamino, R$^{5a'}$ is hydrogen; R$^{7qa}$ is —N(CH$_3$)$_2$; R$^{9q}$ is CR$^{9i'}$R$^{9j'}$NR$^{9k'}$R$^{9l'}$; R$^{9i'}$ and R$^{9j'}$ are each hydrogen; R$^{9k'}$ is alkyl (e.g., methyl) and R$^{9l'}$ is alkoxy (e.g., methoxy).

Examples of substituted tetracycline compounds of Formulae V and Va include:

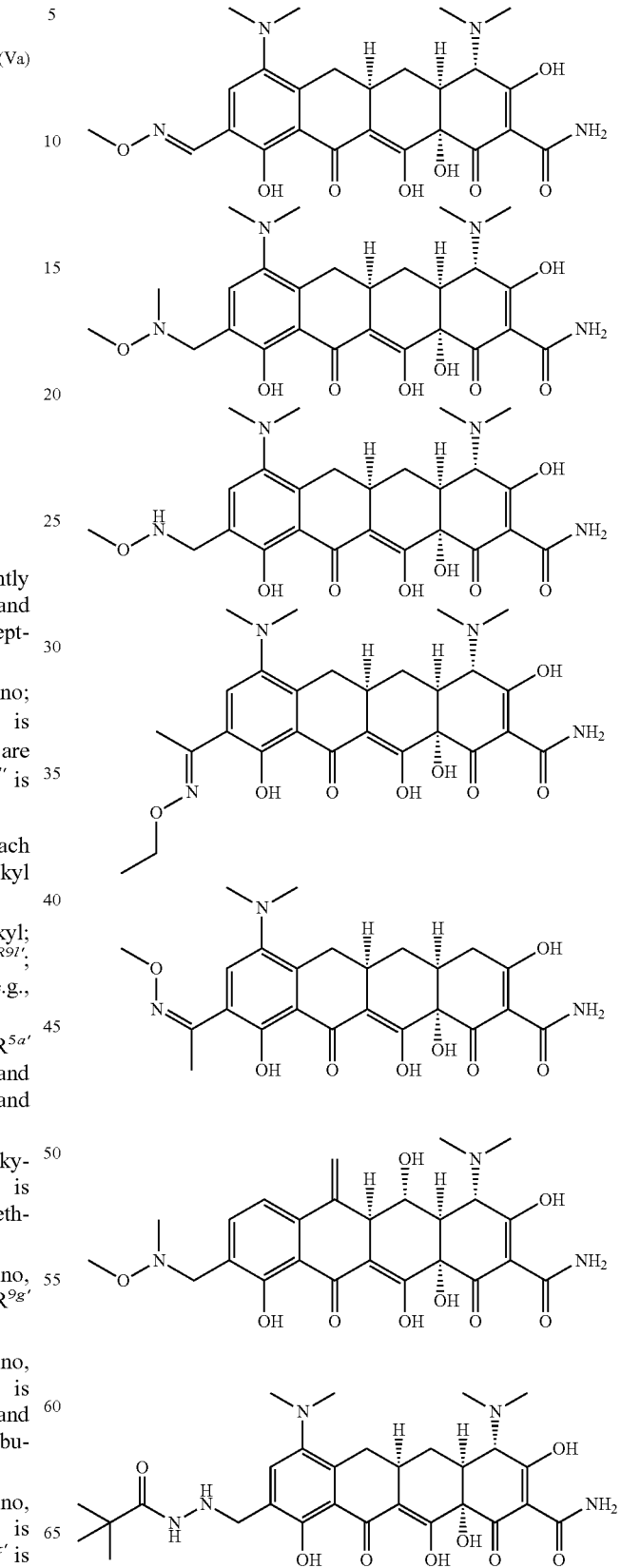

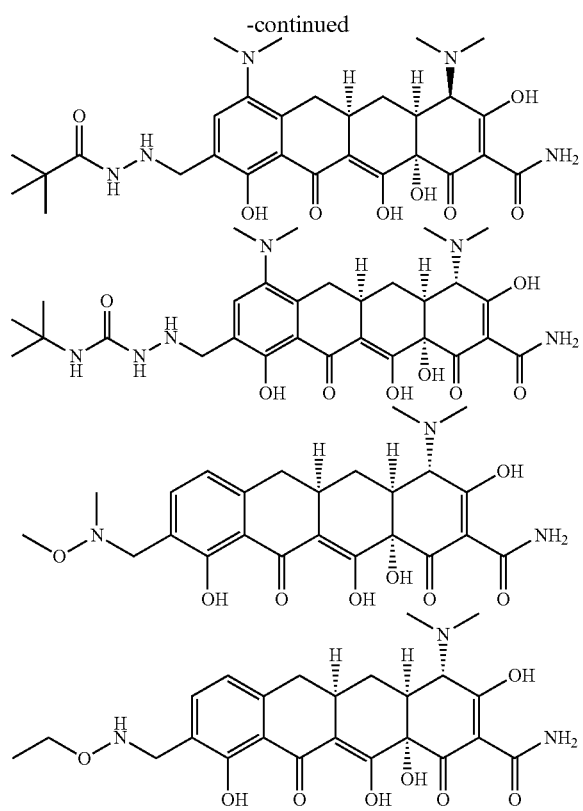

and pharmaceutically acceptable salts thereof.

In one embodiment, the invention also includes substituted tetracycline compounds

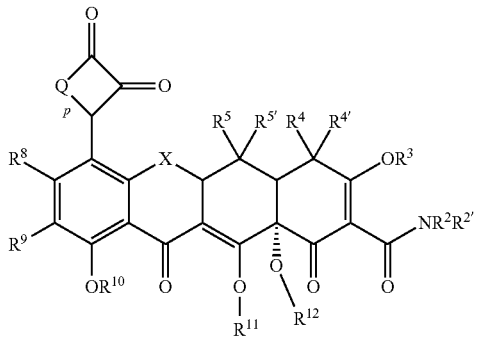

(VI)

wherein

X is CHC($R^{13}$'Y), $CR^{6'}R^6$, C=$CR^{6'}R^6$, S, $NR^6$, or O;

p is a single bond or a double bond;

Q is $CR^{7s}$ when p is a double bond or Q is $CR^{7s'}R^{7s''}$ when p is a single bond;

$R^2$, $R^{2'}$, $R^{4'}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each hydrogen or a prodrug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7s}$, $R^{7s'}$ and $R^{7s''}$ are each hydrogen, alkyl, alkenyl, alkynyl, hydroxyl, alkoxy, alkylthio, alkylsulfinyl, alkylsulfonyl, amino, aminoalkyl, alkylamino, aryl, acyl, arylalkyl, alkyl carbonyloxy, or arylcarbonyloxy;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso or $-(CH_2)_{0-3}(NR^{9c})_{0-1}C(=Z')ZR^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, and pharmaceutically acceptable salts thereof.

In one embodiment, X is $CR^{6'}R^6$, $R^4$ is $NR^{4a}R^{4b}$, $R^{4a}$ and $R^{4b}$ are each alkyl (e.g., methyl) and $R^2$, $R^{2'}$, $R^3$, $R^{4'}$, $R^5$, $R^{5'}$, $R^6$, $R^{6'}$, $R^8$, $R^9$, $R^{10}$, $R^{11}$ and $R^{12}$ are each hydrogen. In another embodiment, p is a double bond and Q is $CR^{7s}$. In a further embodiment, $R^{7s}$ is amino, alkylamino (e.g., methylamino) or dialkylamino (e.g., dimethylamino).

Examples of substituted tetracycline compounds of Formula VI include:

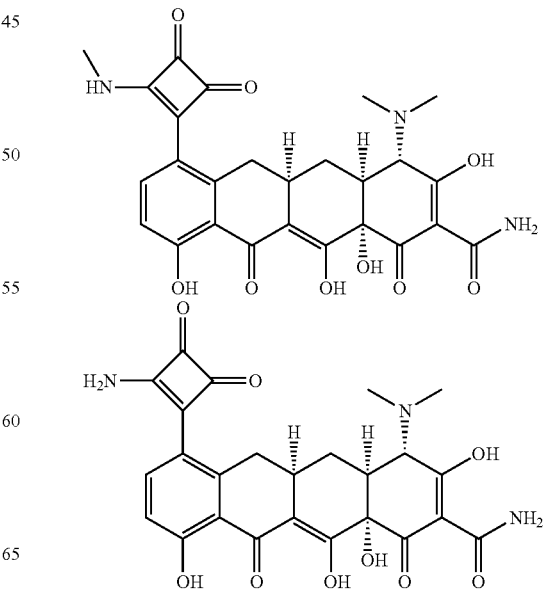

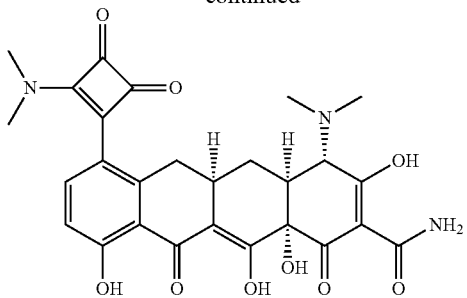

and pharmaceutically acceptable salts thereof.

In one embodiment, the substituted tetracycline compounds of the invention include compounds of Formula VII:

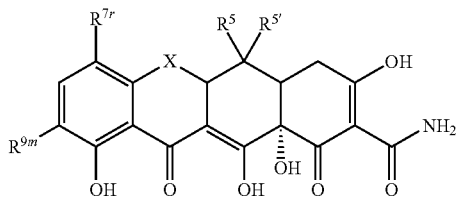

(VII)

wherein

X is $CR^{6'}R^6$;

$R^5$ is hydroxyl or hydrogen;

$R^{5'}$ is hydrogen;

$R^{6'}$ hydrogen or alkyl;

$R^6$ is hydrogen;

$R^{7r}$ is hydrogen or alkylamino;

$R^{9m}$ is heteroaryl, aminocarbonyl, hydroxyaminocarbonyl, alkoxyaminocarbonyl or $—CR^{9m'}NR^{9m''}$;

$R^{9m'}$ and $R^{9m''}$ are each hydrogen, hydroxy, alkyl, alkenyl, alkynyl, alkoxy, alkylthio, alkylsulfinyl, alkylsulfonyl, alkylamino, or an arylalkyl; and pharmaceutically acceptable salts thereof.

In one embodiment, X is $CR^{6'}R^6$; and $R^5$, $R^{5'}$, $R^6$ and $R^{6'}$ are each hydrogen, $R^7$ is alkylamino (e.g., dialkylamino such as dimethylamino) and $R^{9m''}$ is heteroaryl (e.g., oxazolyl, isoxazolyl, pyrazolyl or pyridinyl), aminocarbonyl (e.g., dialkylaminocarbonyl, such as diethylaminocarbonyl, dimethylaminocarbonyl, propylmethylaminocarbonyl, pyrrolidinyl or piperidinyl), hydroxyaminocarbonyl (e.g., hydroxyaminomethylcarbonyl), alkoxyaminocarbonyl (e.g., methoxyaminocarbonyl), alkoxycarbonyl (e.g., ethoxycarbonyl or methoxycarbonyl) or $—CR^{9m'}NR^{9m''}$. Accordingly, $R^{9m'}$ is alkyl (e.g., methyl) and $R^{9m''}$ is alkoxy (e.g., methoxy).

In another embodiment, X is $CR^{6'}R^6$; $R^6$ is alkyl, $R^5$ is hydroxyl and $R^{5'}$ and $R^{6'}$ are each hydrogen and $R^{9m}$ is heteroaryl.

In yet another embodiment, the substituted tetracycline compounds of the invention include compounds of Formula VIIIa:

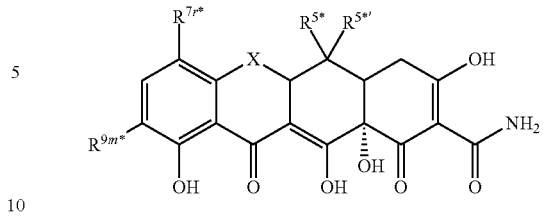

(VIIa)

wherein

X is $CR^{6*'}R^{6*}$;

$R^{5*}$ is hydrogen;

$R^{5*'}$ is hydrogen hydroxyl;

$R^{6*'}$ is hydrogen or alkyl;

$R^{6*}$ is hydrogen;

$R^{7r*}$ is hydrogen, alkyl, heteroaryl, acyl or alkylamino;

$R^{9m*}$ is aminoalkyl, a heterocyclic moiety, aryl, $—CONR^{9ma}R^{9mb}$; $—COR^{9m*'}$, $—COOR^{9m*''}$, alkyl, cycloalkyl or hydrogen;

$R^{9m*'}$ is aminoalkyl, aryl or alkyl;

$R^{9m*''}$ is alkyl, alkoxyalkyl or hydroxyalkyl;

$R^{9ma}$ and $R^{9mb}$ are each hydrogen, hydroxyl, alkyl, hydroxyalkyl, aryl or alkoxy or are linked to form a ring; and pharmaceutically acceptable salts thereof.

In one embodiment, $R^{5*'}$ is hydroxyl; $R^{6*'}$ is alkyl; $R^{7r*}$ is hydrogen; $R^{9m*}$ is aryl (e.g., heteroaryl, such as oxazolyl).

In yet another embodiment, $R^{5*'}$ and $R^{6*'}$ are each hydrogen; $R^{7r*}$ is alkylamino (e.g., dialkylamino, for example, dimethylamino); and $R^{9m*}$ is aminoalkyl (e.g., dimethylaminopropyl); a heterocyclic moiety (e.g., a dihydropyranyl moiety, for example,

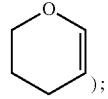

);

aryl (e.g., phenyl or benzamido; or a heteroaryl moiety such as oxazolyl, oxadiazolyl (e.g., alkyl substituted oxadiazolyl, such as methyl or isopropyl substituted oxazolyl), isoxazolyl, pyrazolyl, pyridinyl, thiazolyl, methylpyrazolyl, methylimidazolyl, oxadiazolyl, furanyl (e.g., carboxylate substituted furanyl) or pyrrolyl); alkyl (e.g., methyl, ethyl, isopropyl, neopentyl, or trifluoromethyl) or cycloalkyl (e.g., cyclopropyl).

In yet another embodiment, $R^{5*'}$ and $R^{6*'}$ are each hydrogen; $R^{7r*}$ is alkylamino (e.g., dialkylamino, for example, dimethylamino); and $R^{9m*}$ is $—CONR^{9ma}R^{9mb-}$; $R^{9ma}$ is hydrogen and $R^{9mb}$ is hydroxyl, hydroxyalkyl (e.g., hydroxyethyl), alkoxy (e.g., methoxy), aryl (e.g., phenyl) or alkyl (e.g., t-butyl). In a further embodiment, $R^{9ma}$ is alkyl (e.g., methyl, ethyl or propyl) and $R^{9mb}$ is alkyl (e.g., methyl, ethyl or propyl) or hydroxyl. In yet another embodiment, $R^{9ma}$ and $R^{9mb}$ are linked to form a ring (e.g., a 5- or 6-membered ring).

In one embodiment, $R^{5*'}$ and $R^{6*'}$ are each hydrogen; $R^{7r*}$ is alkylamino (e.g., dialkylamino, for example, dimethylamino); and $R^{9m*}$ is $—COR^{9m*'}$ and $R^{9m*'}$ is alkyl (e.g., methyl, ethyl or neopentyl), alkoxyalkyl (e.g., methoxyethyl) or hydroxyalkyl (e.g., hydroxyethyl).

In another embodiment, $R^{5*'}$ and $R^{6*'}$ are each hydrogen; $R^{7r*}$ is alkylamino (e.g., dialkylamino, for example, dimethylamino); $R^{9m*}$ is $—COR^{9m*'}$ and $R^{9m*'}$ is alkyl (e.g., ethyl or neopentyl), aminoalkyl (e.g., dimethylaminoethyl) or phenyl.

In one more embodiment, $R^{5*'}$ and $R^{6*'}$ are each hydrogen; $R^{9m*}$ is hydrogen and $R^{7r*}$ is alkyl (e.g., methyl or isopropyl), aryl (e.g., heteroaryl, for example oxazolyl) or acyl.
Examples of substituted tetracycline compounds of Formulae VII and VIIa include:
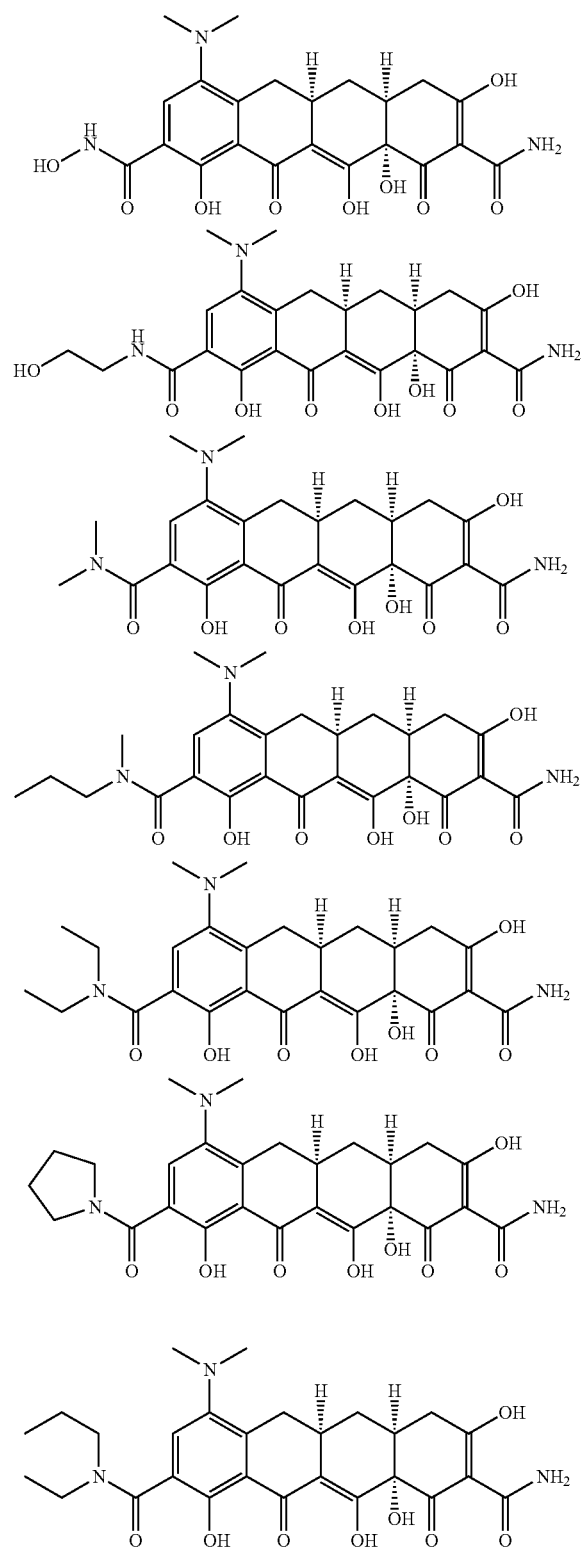
-continued
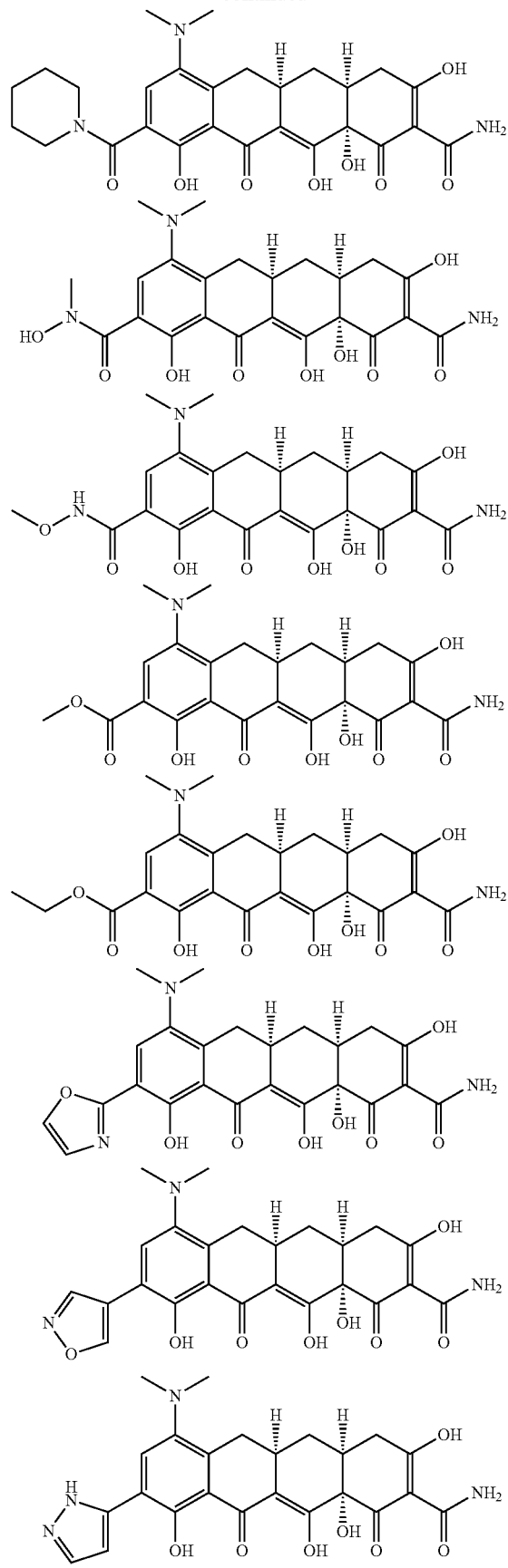

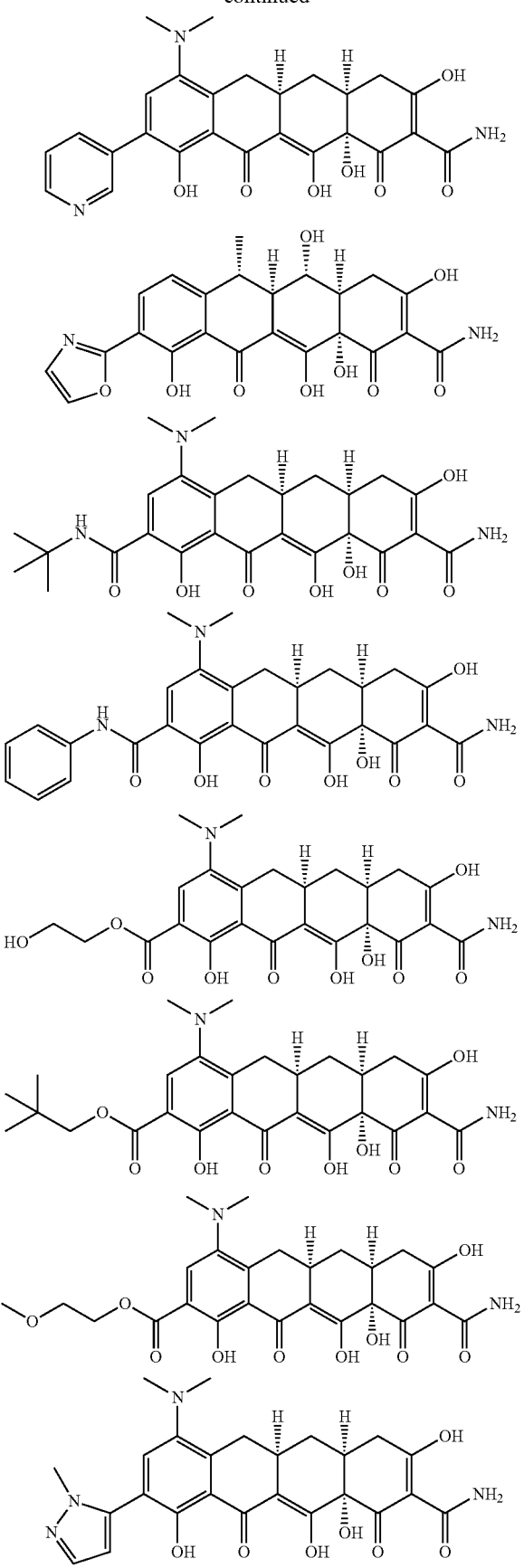
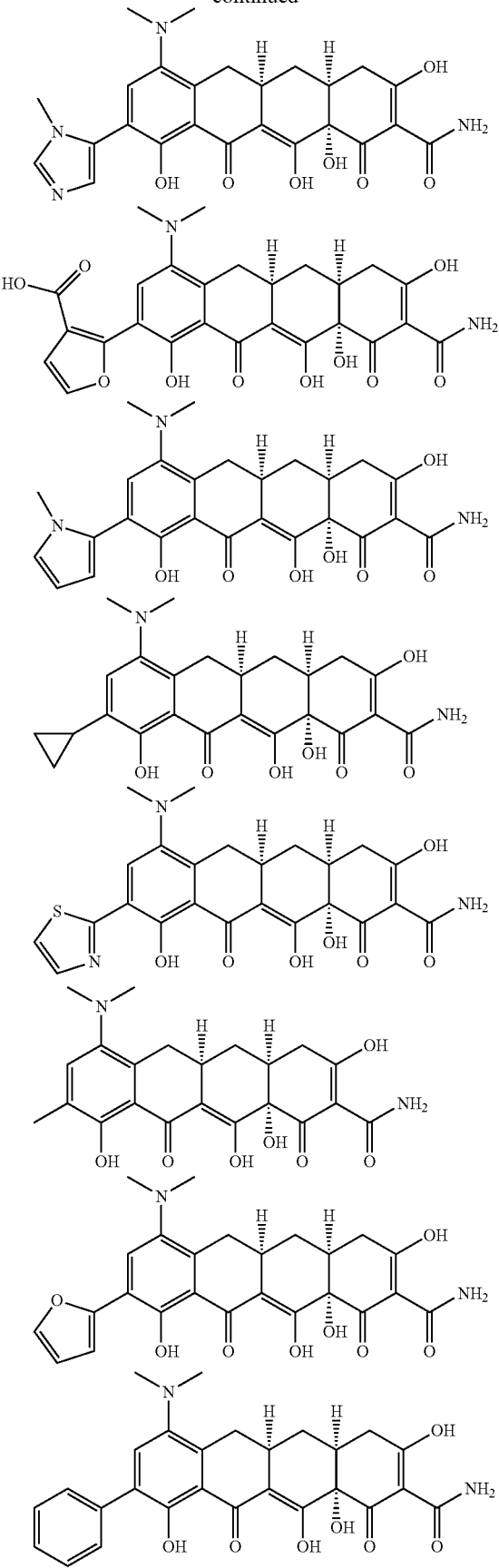

47
-continued
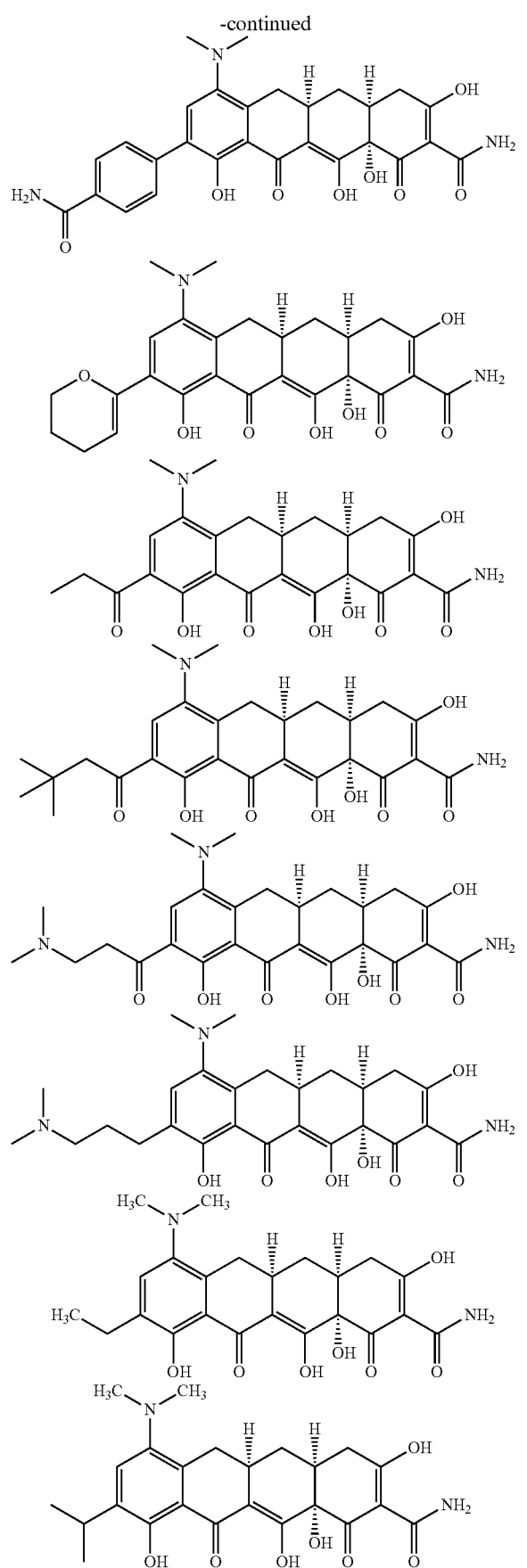
48
-continued
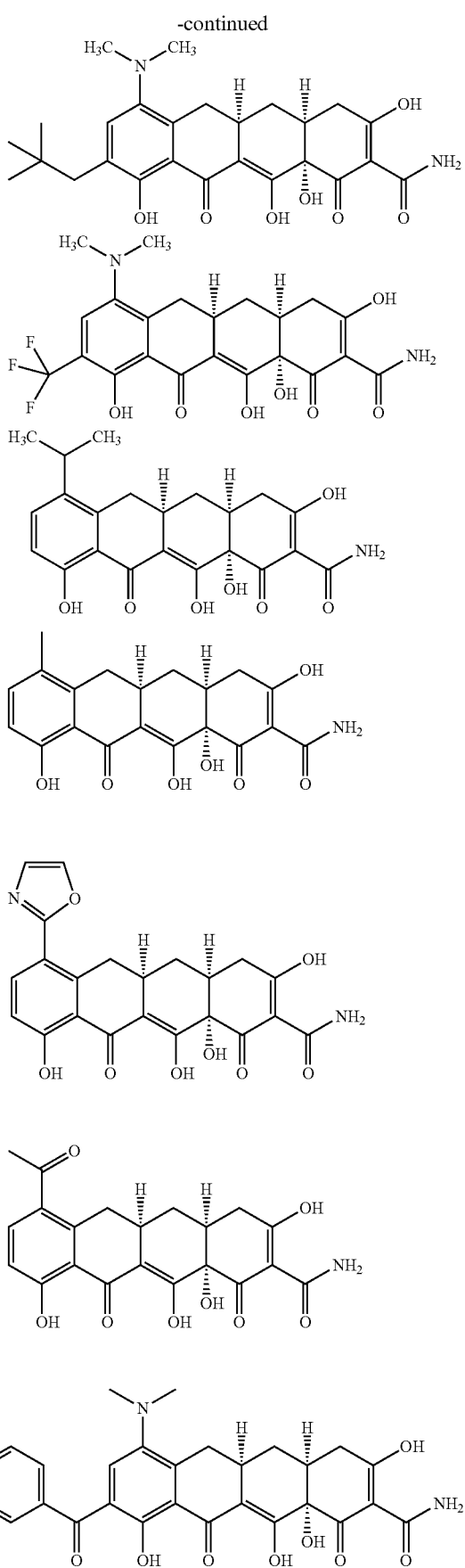

49

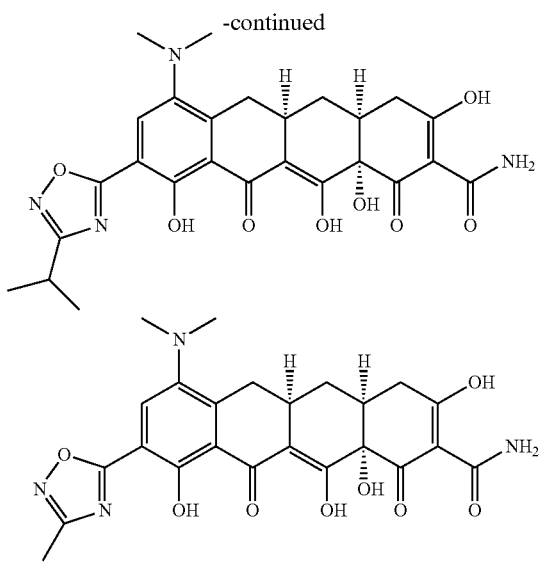

and pharmaceutically acceptable salts thereof.

In yet another embodiment, the substituted tetracycline compounds include compounds of Formula VIII:

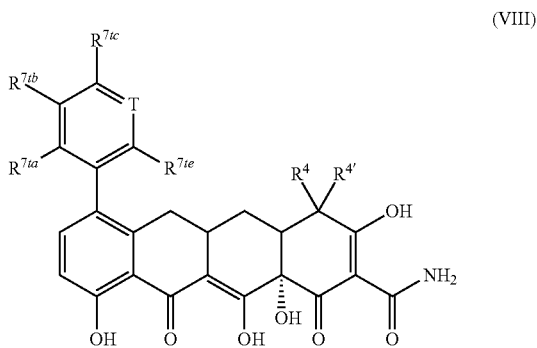

(VIII)

wherein:
T is N or $CR^{7td}$;
$R^4$ is alkylamino or hydrogen;
$R^{4'}$ is hydrogen;
$R^{7te}$ is hydrogen.
$R^{7ta}$, $R^{7tb}$, $R^{7tc}$ and $R^{7td}$ are each independently hydrogen, halogen, hydroxyalkyl, hydroxyalkylaminocarbonyl, alkylaminoalkyloxy, aminocarbonyl, alkylaminoalkylaminocarbonyl, aminoalkylaminocarbonyl, methylpiperazinylcarbonyl, alkylaminocarbonyl, heteroarylalkylaminocarbonyl, alkoxycarbonylalkylaminocarbonyl, acylaminoalkylaminocarbonyl, alkoxyaminocarbonyl, alkoxyalkylaminocarbonyl or alkylaminoalkylcarbonylamino, or $R^{7tb}$ and $R^{7tc}$ are linked to form a ring; and pharmaceutically acceptable salts thereof.

In one embodiment, $R^4$ is alkylamino (e.g., dialkylamino such as dimethylamino), $R^{4'}$ is hydrogen, T is N and $R^{7ta}$ and $R^{7td}$ are each hydrogen and $R^{7tb}$ and $R^{7tc}$ are linked to form a ring. In another embodiment, $R^{7tc}$ is alkylaminoalkyloxy (e.g., dialkylaminoalkyloxy such as dimethylaminoalkyloxy).

In a further embodiment, N is $CR^{7td}$ and $R^{7ta}$, $R^{7tc}$ and $R^{7td}$ are each hydrogen. In another embodiment, $R^{7td}$ is hydroxyalkyl, aminocarbonyl, alkylaminoalkylaminocarbonyl (e.g., methylaminoalkylaminocarbonyl), dialkylaminoalkylaminocarbonyl (e.g., dimethylaminoalkylaminocarbonyl, diethylaminoalkylaminocarbonyl, diisopropylaminoalkylaminocarbonyl, pyrrolidinylalkylaminocarbonyl or piperidinylalkylaminocarbonyl), hydroxyalkylaminocarbonyl, aminoalkylaminocarbonyl, methylpiperazinylcarbonyl, Alkylaminoalkylaminocarbonyl, heteroarylalkylaminocarbonyl (e.g., furanylalkylaminocarbonyl), alkoxycarbonylalkylaminocarbonyl (e.g., ethoxycarbonylalkylaminocarbonyl), acylaminoalkylaminocarbonyl, alkoxyaminocarbonyl (e.g., methoxyaminocarbonyl), alkoxyalkylaminocarbonyl (e.g., methoxyalkylaminocarbonyl) or alkylaminoalkylcarbonylamino (e.g., dialkylaminoalkylcarbonylamino such as dimethylaminoalkylcarbonylamino).

In another embodiment, $R^{7ta}$, $R^{7tb}$ and $R^{7td}$ are hydrogen and $R^{7tc}$ is alkylaminocarbonyl.

In yet another embodiment, $R^{7ta}$ is halogen (e.g., fluorine), $R^{7tc}$ and $R^{7td}$ are each hydrogen and $R^{7tb}$ is alkylaminoalkylaminocarbonyl (e.g., dialkylaminoalkylaminocarbonyl such as dimethylaminoalkylaminocarbonyl).

In one embodiment, $R^4$ and $R^{4'}$ are each hydrogen, $R^{7ta}$, $R^{7tc}$ and $R^{7td}$ are each hydrogen and $R^{7tb}$ is alkylaminoalkylaminocarbonyl (e.g., dialkylaminoalkylaminocarbonyl such as dimethylaminoalkylaminocarbonyl).

In a further embodiment, the substituted tetracycline compounds of the invention include compounds of Formula VIIIa:

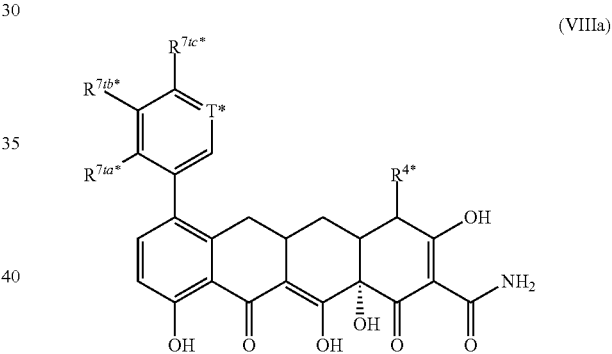

(VIIIa)

wherein:
$T^*$ is N or CH;
$R^{4*}$ is hydrogen or alkylamino.
$R^{7ta*}$ is hydrogen or halogen;
$R^{7tb*}$ is hydrogen, —CH=CHCN, hydroxyalkyl, —$CONR^{7tba}R^{7tbb}$; —$NHCOR^{7tbd}$;
$R^{7tba}$ and $R^{7tbb}$ are linked to form a ring; or $R^{7tba}$ is hydrogen or alkyl and $R^{7tbb}$ is hydrogen, alkoxy, alkyl or —$(CH_2)_xR^{7tbc}$;
$R^{7tbc}$ is amino, alkyl, alkoxycarbonyl, alkoxy, hydroxyl, aryl, a heterocyclic moiety or alkoxycarbonylamino;
$R^{7tbd}$ is —$(CH_2)_yR^{7tbe}$, wherein $R^{7tbe}$ is amino;
$R^{7tc*}$ is hydrogen, —$O(CH_2)_zR^{tca}$; —$CONHR^{tcb}$ or —$NHCOR^{7td}$; wherein $R^{tcb}$ is $(CH_2)_wR^{tcc}$ and $R^{tca}$ and $R^{tcc}$ are each amino;
$R^{7td}$ is alkoxy; or
$R^{7tb*}$ and $R^{7tc*}$ are linked to join a ring;
w, x, y and z are each, independently, an integer of between 0 and 5; and pharmaceutically acceptable salts thereof.

In one embodiment, $T^*$ is CH and $R^{4*}$ is alkylamino (e.g., dimethyamino); $R^{7ta*}$ and $R^{7tc*}$ are each hydrogen and $R^{7tb*}$ is —CH=CHCN, hydroxyalkyl (e.g., hydroxypropyl) or —$CONR^{7tba}R^{7tbb}$. In one embodiment, $R^{7tba}$ is hydrogen and $R^{7tbb}$ is hydrogen, alkoxy (e.g., methoxy), alkyl (e.g., butyl) or $R^{7tbb}$ is —$(C_2)_x R^{7tbc}$, in which, when x is 1, $R^{7tbc}$ may be aryl (e.g., heteroaryl, such as furanyl); when x is 2, $R^{7tbc}$ may be amino (e.g., —$NH_2$, methylamino, dimethylamino, diethylamino or diisopropylamino), alkoxycarbonyl (e.g., ethoxycarbonyl), hydroxyl, alkoxy (e.g., methoxy), alkylcarbonylamino (e.g., methylcarbonylamino) or a heterocyclic moiety (e.g., piperidinyl or morpholinyl); when x is 3, $R^{7tbc}$ may be amino (e.g., dimethylamino) or alkoxy (e.g., methoxy) or when x is 4, $R^{7tbc}$ may be amino (e.g., dimethylamino).

In another embodiment, $R^{7tba}$ is alkyl (e.g., methyl) and $R^{7tbb}$ is —$(CH_2)_x R^{tbc}$ in which, when x is 2, $R^{tbc}$ may be amino (e.g., dimethylamino).

In a further embodiment, $R^{7tba}$ and $R^{tbb}$ are linked to join a ring (e.g., a 5- or 6-membered ring, for example,

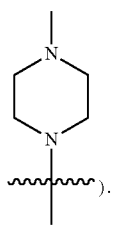

In one embodiment, T* is CH and $R^{4*}$ is alkylamino (e.g., dimethyamino); $R^{7ta*}$ and $R^{7tc*}$ are each hydrogen and $R^{7tb*}$ is —$NHCOR^{7tbd}$; $R^{7tbd}$ is $(CH_2)_y R^{7tbc}$, y is 2 or 4 and $R^{7tbc}$ is amino (e.g., dimethylamino).

In another embodiment, T* is CH and $R^{4*}$ is alkylamino (e.g., dimethyamino); $R^{7tc*}$ is hydrogen; $R^{7ta*}$ is a halogen (e.g., fluorine); $R^{7tb*}$ is —$CONR^{7tba}R^{7tbb}$ in which $R^{7tba}$ is hydrogen and $R^{7tbb}$ is —$(CH_2)_x R^{7tbc}$. In one embodiment, x is 2 and $R^{7tbc}$ is amino (e.g., dimethylamino).

In a further embodiment, T* is CH and $R^{4*}$ is hydrogen; $R^{7ta*}$ and $R^{7tc*}$ are each hydrogen; $R^{7tb*}$ is —$CONR^{7tba}R^{7tbb}$; $R^{7tba}$ is hydrogen; $R^{7bb}$ is —$(CH_2)_x R^{tbc}$ in which when x is 2, $R^{7tbc}$ may be amino (e.g., dimethylamino).

In yet another embodiment, T* is CH and $R^{4*}$ is alkylamino (e.g., dimethyamino); $R^{7ta*}$ and $R^{7tb*}$ are each hydrogen; $R^{7tc*}$ is —$CONHR—(CH_2)_w R^{tcc}$ in which when w is 2, $R^{7tc*}$ may be —$NHCOR^{7td}$ and $R^{7td}$ is alkoxy (e.g., halogen substituted alkoxy, for example, is —$CH_2CH_2F$).

In another embodiment, T* is N and $R^{4*}$ is alkylamino (e.g., dimethylamino); $R^{7ta*}$ is hydrogen and $R^{7b*}$ and $R^{7c*}$ are linked to form a ring (e.g.,

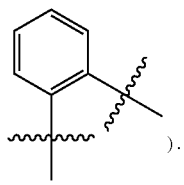

In one embodiment, T* is N and $R^{4*}$ is alkylamino (e.g., dimethylamino); $R^{7ta*}$ and $R^{7tb*}$ are each hydrogen and $R^{7tc*}$ is —$O(CH_2)_z R^{tca}$ in which z is 3.

Examples of substituted tetracycline compounds of Formulae VIII and VIIIa include:

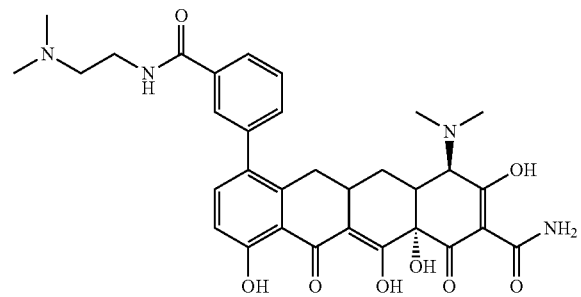 [SMILES: CN(C)CCNC(=O)c1cccc(-c2ccc(O)c3c2CC2CC4[C@@H](N(C)C)C(O)=C(C(N)=O)C(=O)[C@@]4(O)C(O)=C2C3=O)c1]

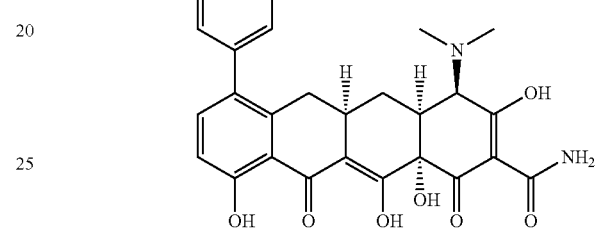

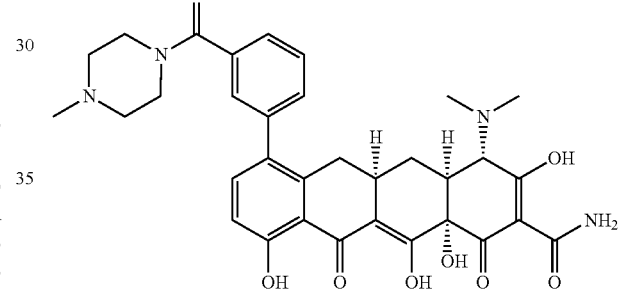

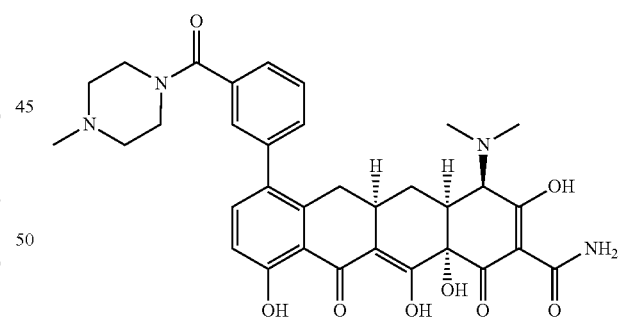

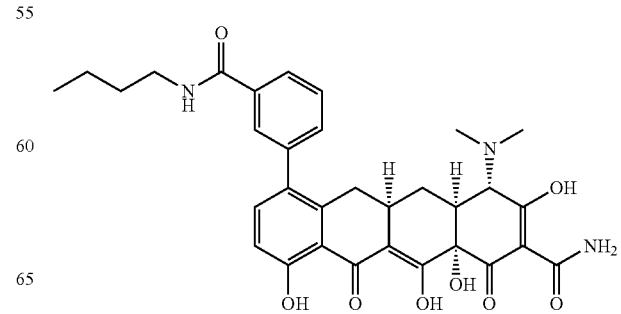

53
-continued
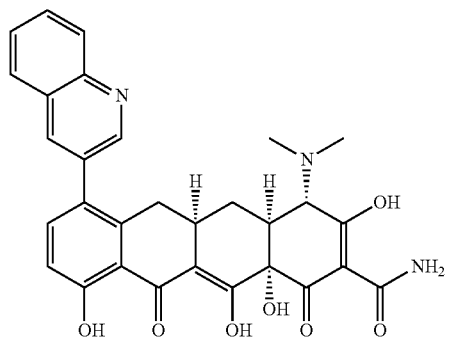
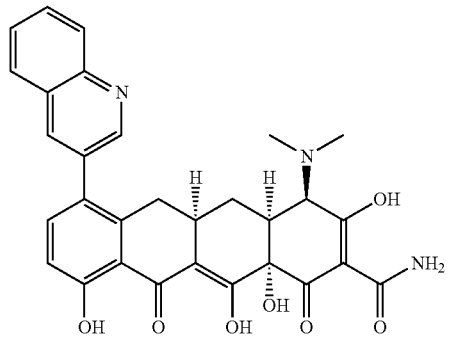
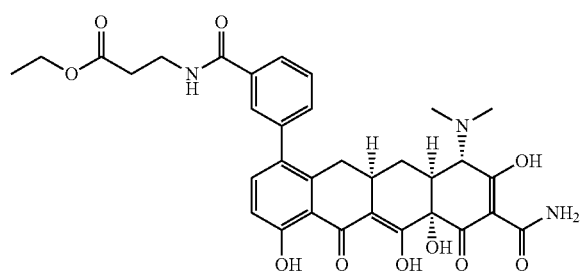
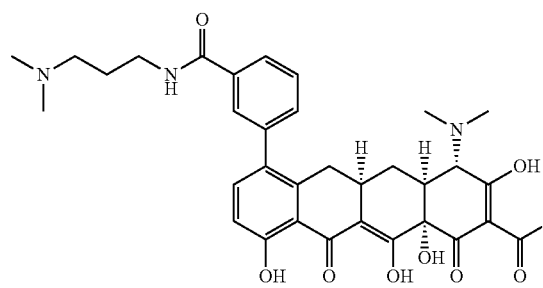
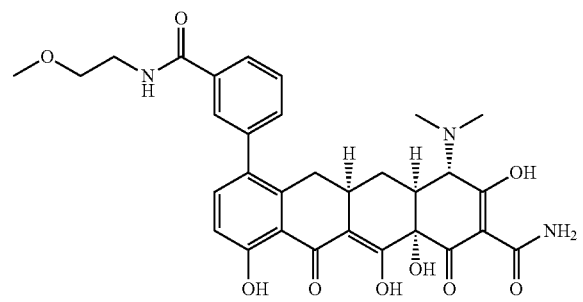
54
-continued
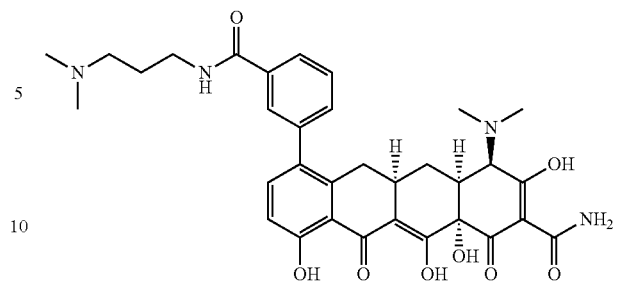
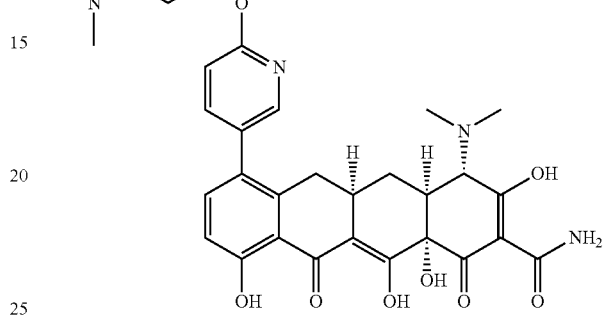
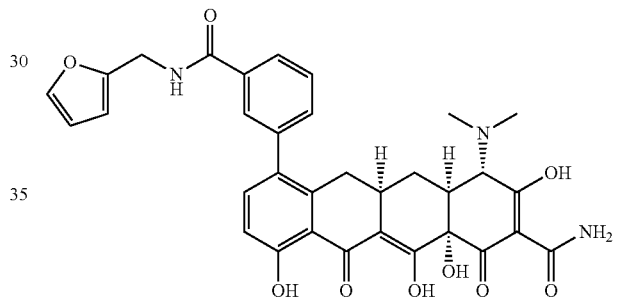
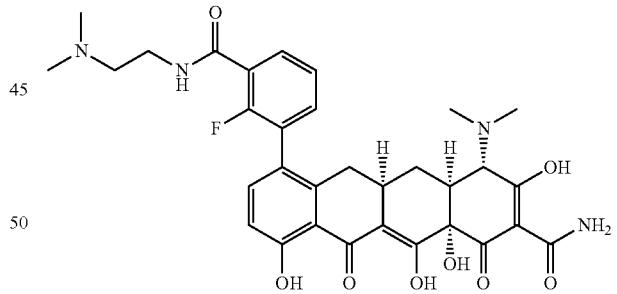
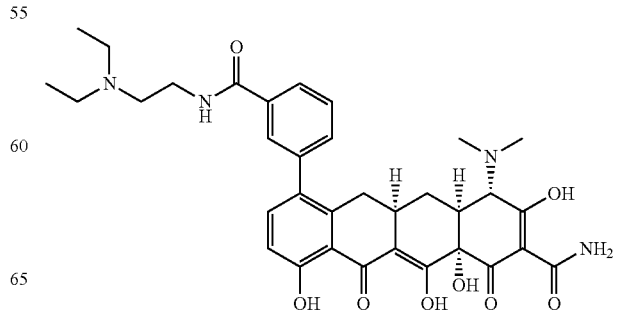

55
-continued
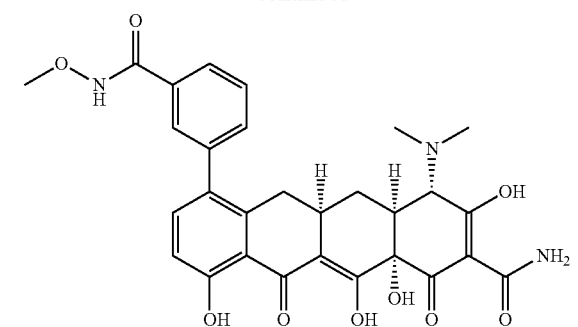
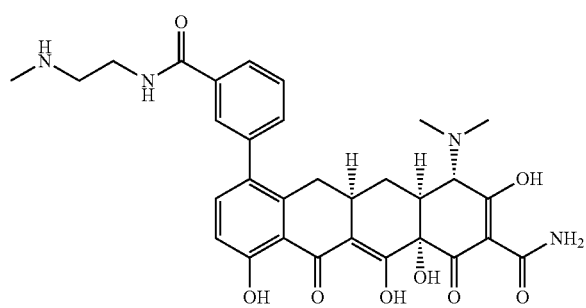
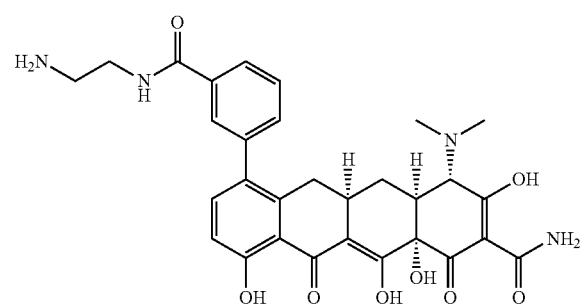
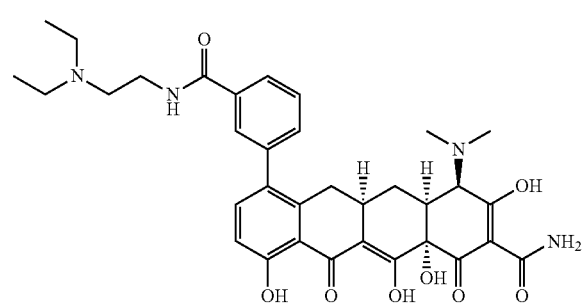
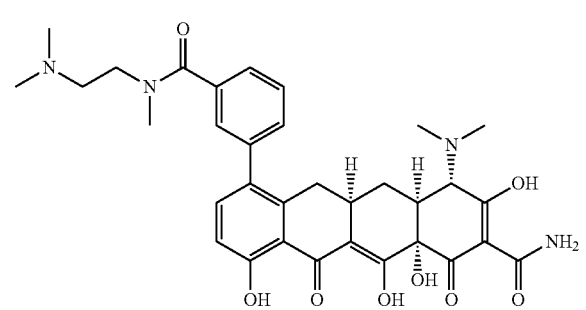
56
-continued
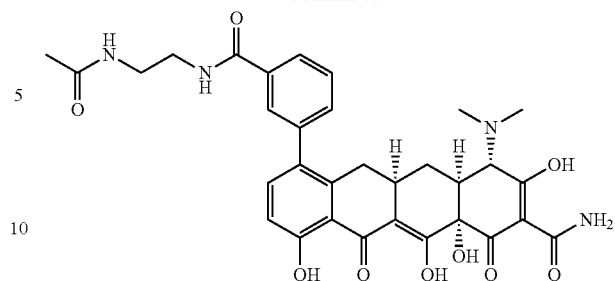
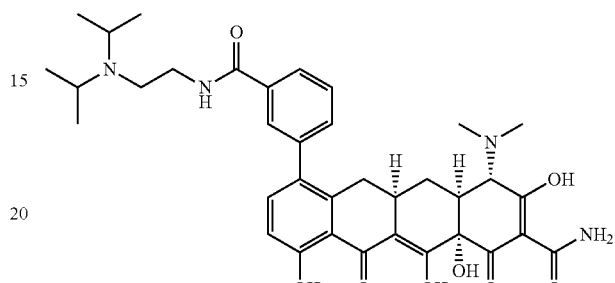
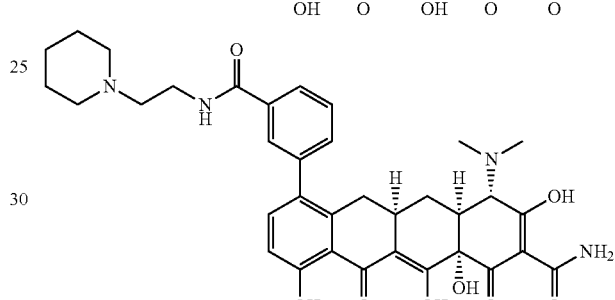
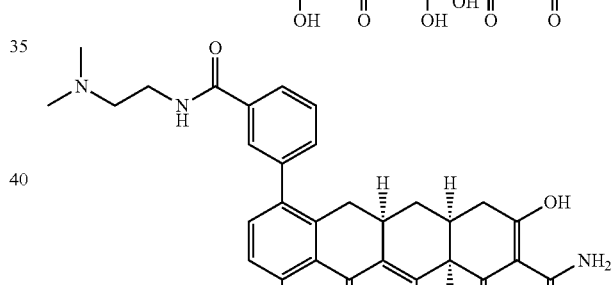
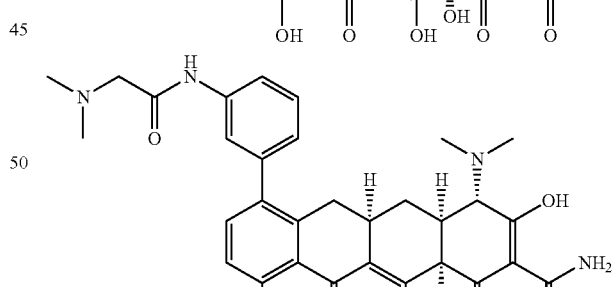
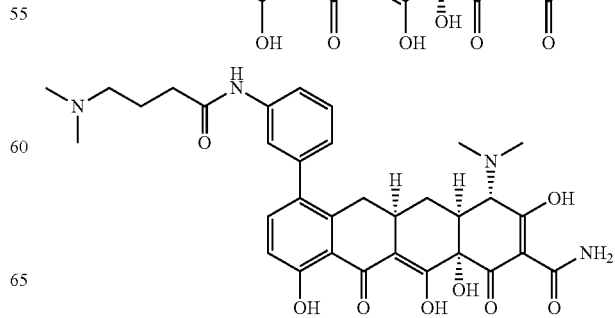

-continued

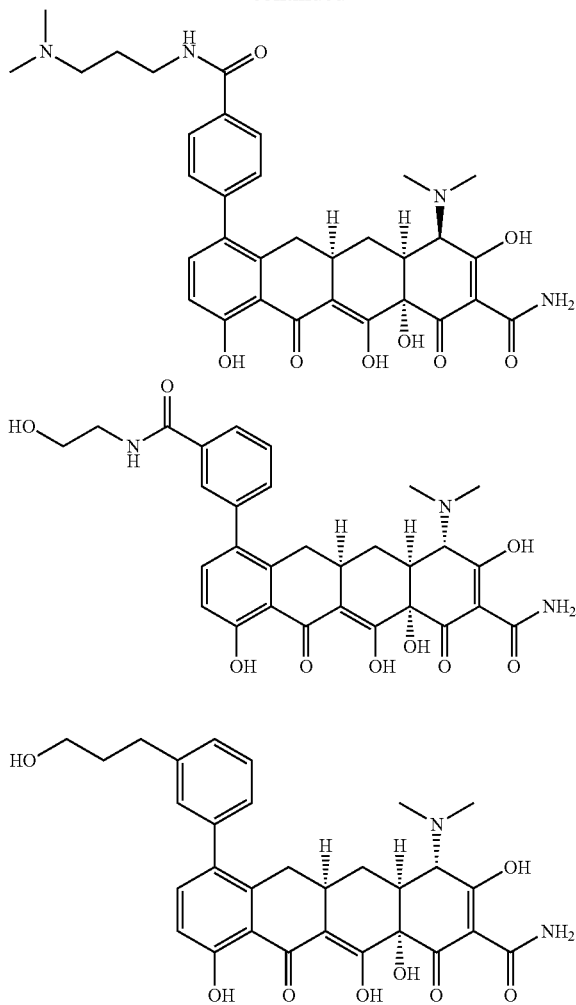

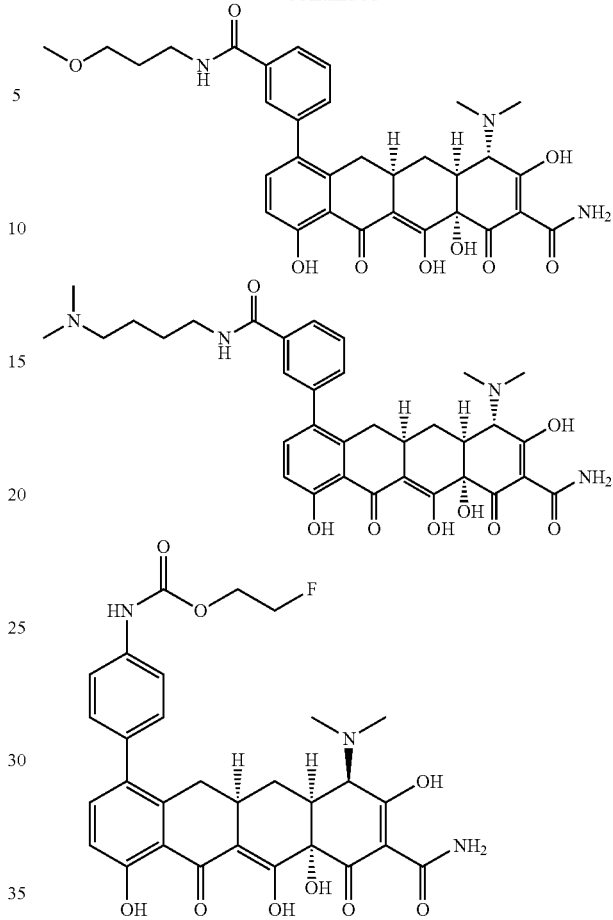

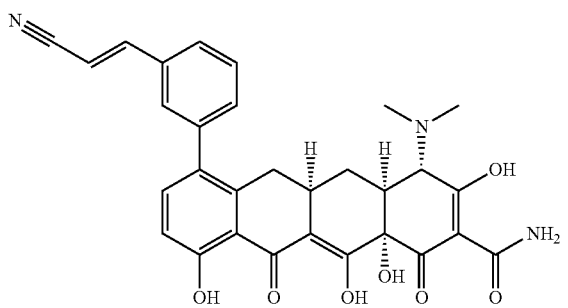

and pharmaceutically acceptable salts thereof.

The substituted tetracycline compounds of the invention also include compounds of Formula IX:

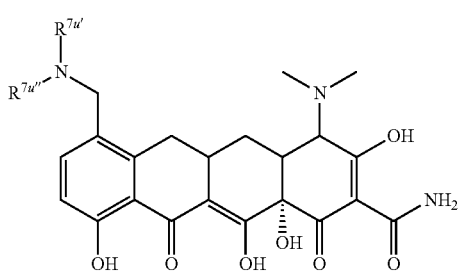

wherein:

$R^{7u'}$ is hydrogen or cycloalkyl;

$R^{7u''}$ is alkyl, alkylcarbonyloxyalkyloxycarbonyl, or aminoalkyl, or $R^{7u'}$ and $R^{7u''}$ are linked to form a ring; and pharmaceutically acceptable salts thereof.

In one embodiment, $R^{7u'}$ is hydrogen and $R^{7u''}$ is alkyl (e.g., t-butyl, isopropyl, cyclopropyl or cyclopentyl). Alternatively, $R^{7u''}$ is alkylcarbonyloxyalkyloxycarbonyl or aminoalkyl (e.g., dialkylaminoalkyl, such as dimethylaminoalkyl).

In another embodiment, $R^{7u'}$ and $R^{7u''}$ are linked to form a ring (e.g., a substituted piperidinyl ring). Examples of substituents on the ring include, for example, an alkyl substitu-

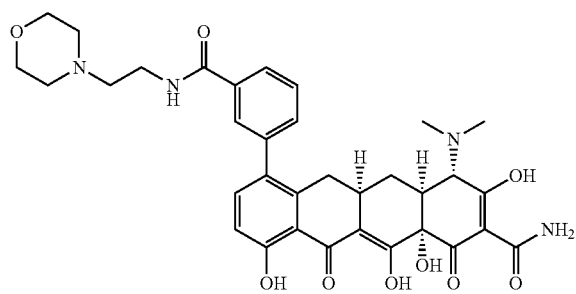

ent, which may or may not be substituted with one or more halogens (e.g., fluorine). In one embodiment, the ring is an indole ring.

In another embodiment, $R^{7u'}$ is cycloalkyl (e.g., cyclopropyl) and $R^{7u''}$ is alkylcarbonyloxyalkyloxycarbonyl.

In another embodiment, the substituted tetracycline compounds of the invention include compounds of Formula IXa:

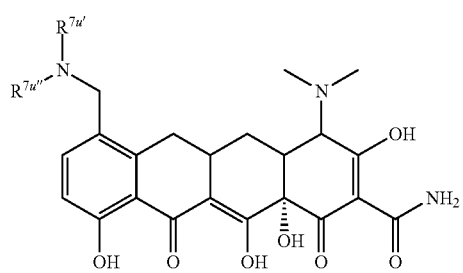

(IX)

wherein:

$R^{7u*}$ is hydrogen;

$R^{7u*'}$ is alkyl or —$(CH_2)_d R^{7ua}$, wherein d is an integer from between 0 and 5 and $R^{7ua}$ is amino; or $R^{7u*}$ and $R^{7u*'}$ are linked to form a ring; and pharmaceutically acceptable salts thereof.

In one embodiment, $R^{7u*}$ is hydrogen and $R^{7u*'}$ is alkyl (e.g., a cycloalkyl moiety, such as is cyclopropyl or cyclopentyl, or t-butyl or isopropyl)

In another embodiment, $R^{7u*}$ is hydrogen and $R^{7u*'}$ is —$(CH_2)_d R^{7ua}$, in which d may be 4 and $R^{7ua}$ may be amino (e.g., dimethylamino).

In a further embodiment, $R^{7u*}$ and $R^{7u*'}$ are linked to form a ring (e.g., a 5- or 6-membered ring, such as

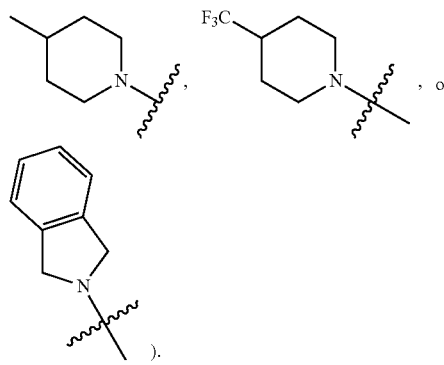

).

Examples of substituted tetracycline compounds of Formulae IX or IXa include:

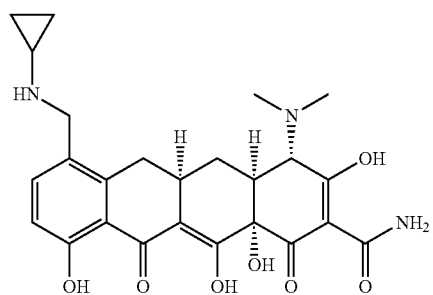

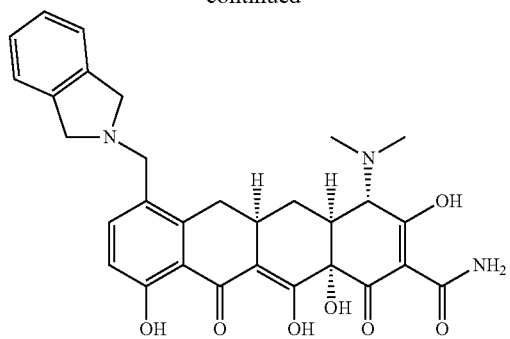

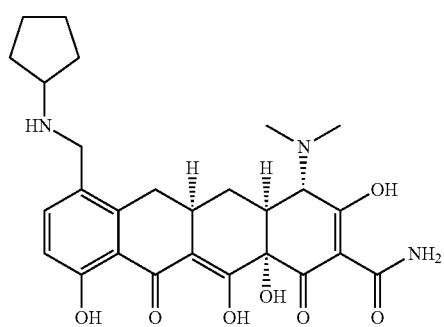

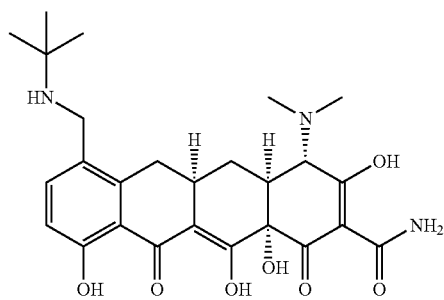

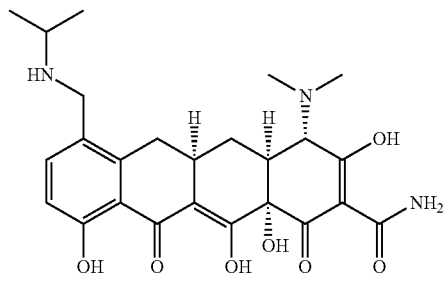

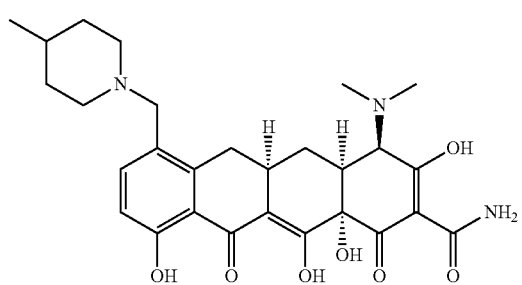

-continued

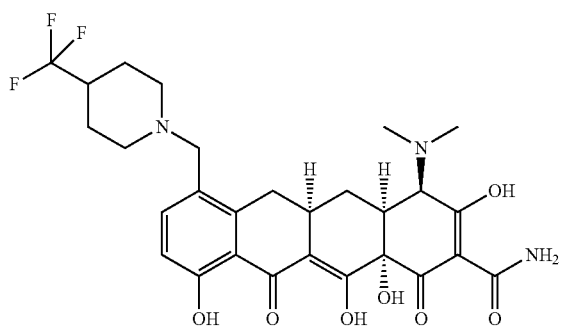

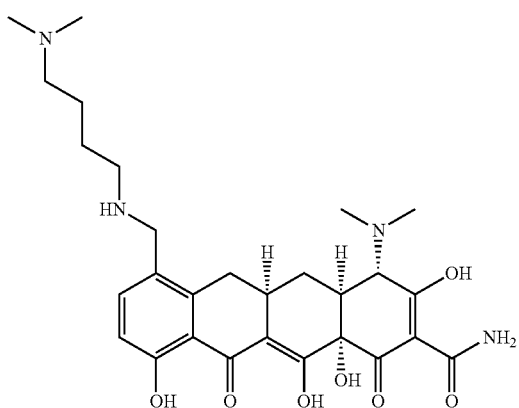

and pharmaceutically acceptable salts thereof.

The substituted tetracycline compounds of the invention include compounds of Formula X:

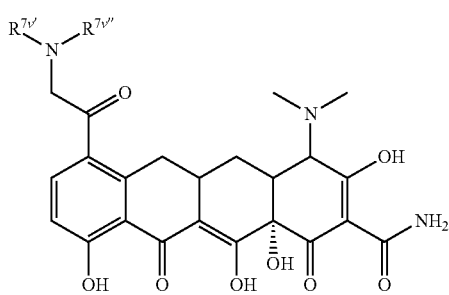

(X)

wherein

R$^{7v'}$ is alkyl, hydrogen or allyl;

R$^{7v''}$ is arylalkyl or alkylcarbonyloxyalkyloxycarbonyl; or

R$^{7v'}$ and R$^{7v''}$ are linked to form a ring; and pharmaceutically acceptable salts thereof.

In one embodiment, R$^{7v'}$ is alkyl or allyl and R$^{7v''}$ is alkylcarbonyloxyalkyloxycarbonyl.

In another embodiment, R$^{7v'}$ and R$^{7v''}$ are linked to form a ring.

In yet another embodiment, R$^{7v'}$ is hydrogen and R$^{7v''}$ is arylalky, such as for example, phenylalkyl, which may be substituted with one or more halogens (e.g., fluorine).

In one embodiment, the substituted tetracycline compounds of the invention include compounds of Formula Xa:

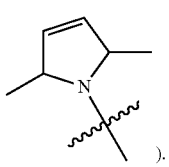

(Xa)

wherein

R$^{7v*}$ is alkyl, hydrogen or allyl;

R$^{7v*'}$ is arylalkyl or —COO(CH$_2$)$_f$R$^{7va}$; or

R$^{7v*}$ and R$^{7v*'}$ are linked to form a ring;

f is an integer from between 0 and 5;

R$^{7va}$ is alkylcarbonyloxy; and pharmaceutically acceptable salts thereof.

In one embodiment, R$^{7v*}$ is hydrogen and R$^{7v*'}$ is arylalkyl (e.g., benzyl, for example, 2,6-difluorobenzyl).

In another embodiment, R$^{7v*}$ is alkyl (e.g., methyl) or allyl and R$^{7v*'}$ is —COO(CH$_2$)$_f$R$^{7va}$, in which f may be 1 and R$^{7va}$ may be t-butylcarbonyloxy.

In a further embodiment, R$^{7v*}$ and R$^{7v*'}$ are linked to form a ring (e.g., a 5- or 6-membered aliphatic or aromatic ring, for example,

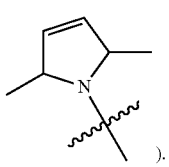

).

Examples of substituted tetracycline compounds of Formulae X and Xa include:

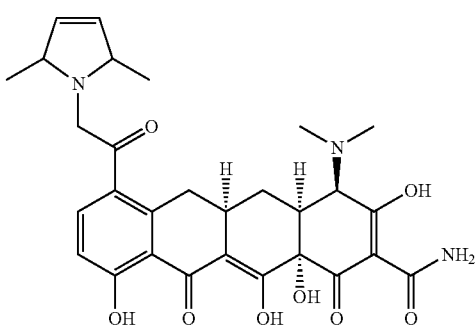

63

-continued

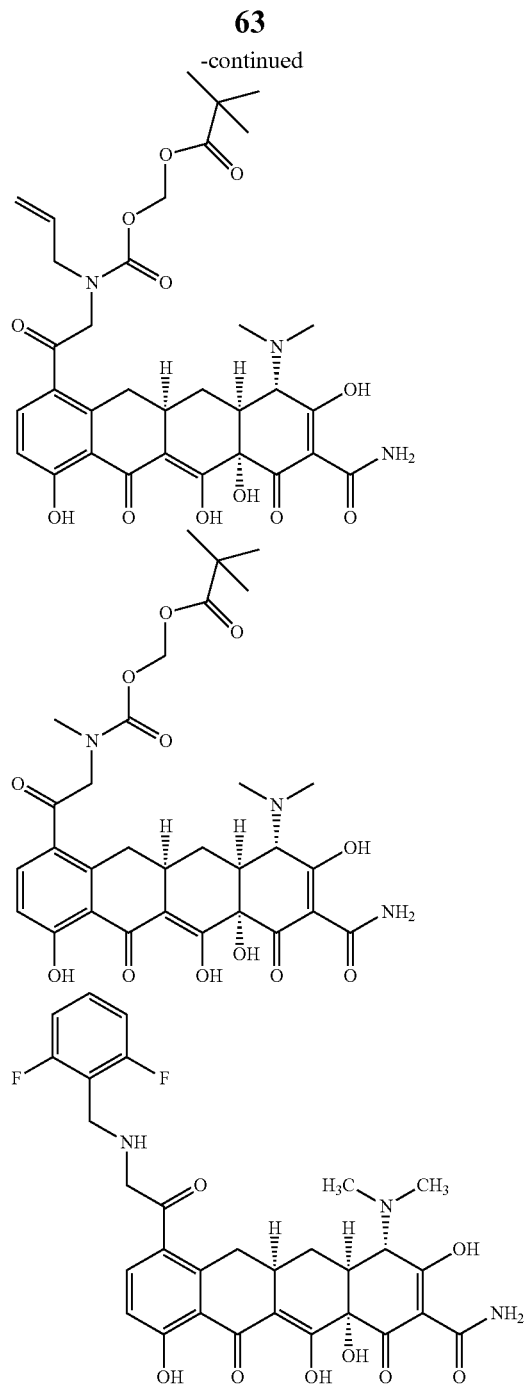

and pharmaceutically acceptable salts thereof.

In yet another embodiment, the substituted tetracycline compounds include compounds of the formula:

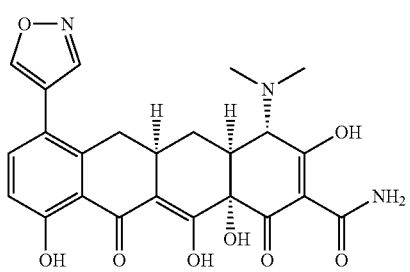

64

-continued

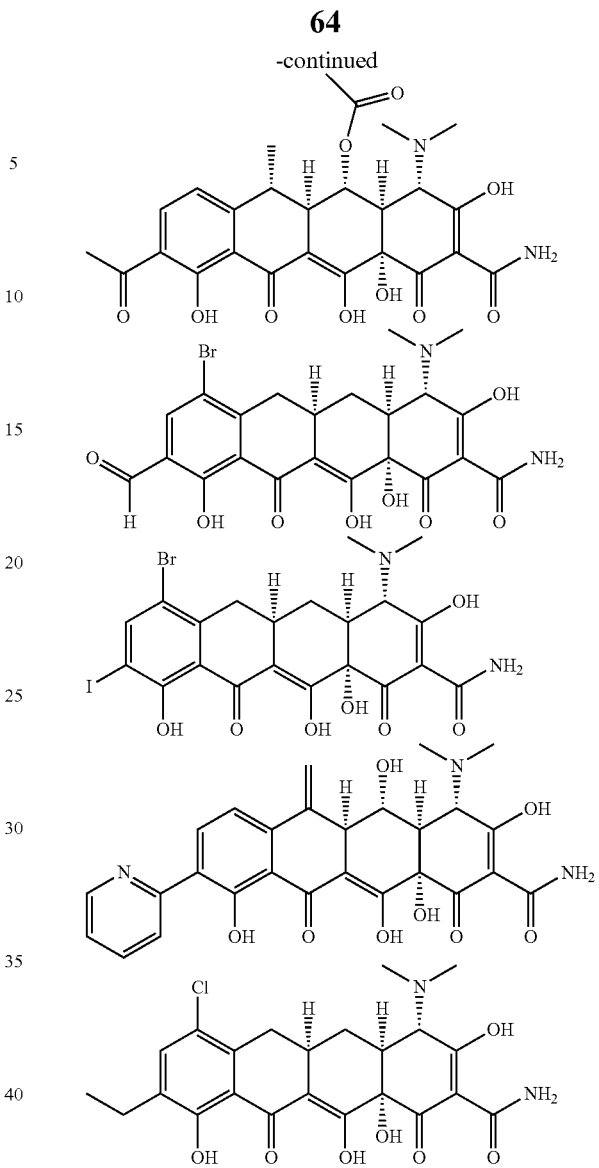

and pharmaceutically acceptable salts thereof.

In another embodiment, the substituted tetracycline compounds of the invention include compounds of Formula XI:

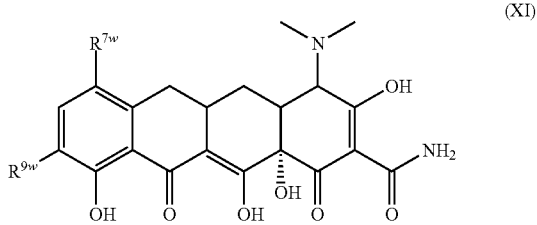

(XI)

wherein $R^{7w}$ is cycloalkyl;

$R^{9w}$ is hydrogen or aminoalkyl; and pharmaceutically acceptable salts thereof.

In one embodiment, the cycloalkyl is cyclopropyl. In another embodiment, $R^{9w}$ is hydrogen. In a further embodiment, $R^{9w}$ is aminoalkyl (e.g., dialkylamino).

In yet another embodiment, the substituted tetracycline compounds of the invention include compounds of Formula XIa:

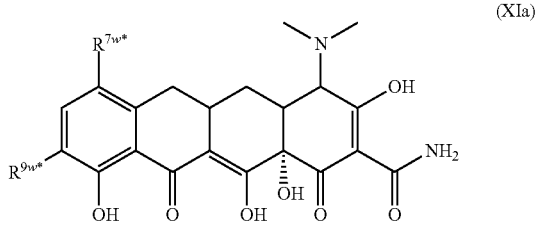

wherein $R^{7w*}$ is cycloalkyl;

$R^{9w*}$ is hydrogen or —$CH_2NR^{9wa}R^{9wb}$;

$R^{9wa}$ is alkyl and $R^{9wb}$ is allyl; and pharmaceutically acceptable salts thereof.

In one embodiment, the cycloalkyl is cyclopropyl and $R^{9w*}$ is hydrogen. In another embodiment, $R^{9w*}$ is —$CH_2NR^{9wa}R^{9wb}$, in which $R^{9wa}$ is methyl.

Examples of substituted tetracycline compound of Formulae XI and XIa include:

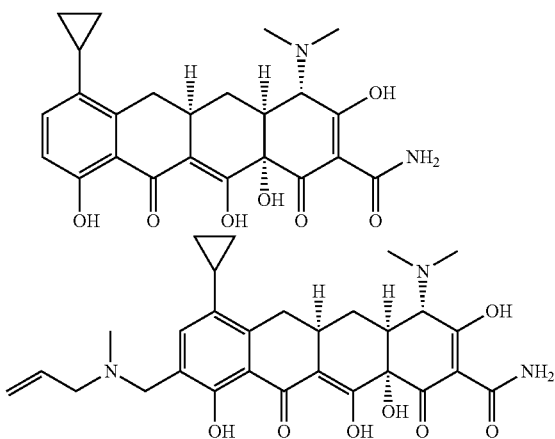

and pharmaceutically acceptable salts thereof.

In another embodiment, the tetracycline compounds of the invention include substituted tetracycline compounds of formula XII:

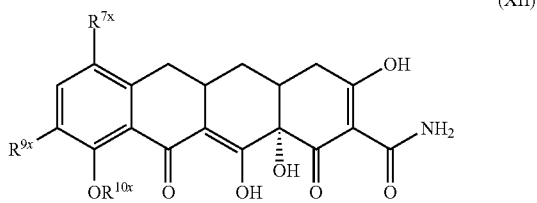

wherein $R^{7x}$ is isopropyl, dimethylamino, or hydrogen;

$R^{9x}$ is methyl, ethyl, furanyl, isopropyl, cyclopropyl, 2-dimethyl-propyl, $C(=O)NR^{9x'}R^{9x''}$, $C(=O)OR^{9x'}$, $C(=O)R^{9x'}$, thioazolyl, oxadiazolyl, hydrogen, phenyl, benzamidyl, dihydropyran, pyrazolyl, imidazolyl, or pyrrolyl;

$R^{9x'}$ and $R^{9x''}$ are each independently hydrogen, t-butyl, phenyl, hydroxyethyl, ethyl, 2-dimethylpropyl, or alkoxyethyl;

$R^{10x}$ is hydrogen or alkyl; and pharmaceutically acceptable salts thereof, provided that $R^{7x}$ is not hydrogen or dimethylamino when $R^{9x}$ and $R^{10x}$ are both hydrogen.

In a further embodiment, $R^{7x}$ is isopropyl and $R^{9x}$ and $R^{10x}$ are each hydrogen.

In another embodiment, $R^{7x}$ is dimethylamino. Examples of $R^{9x}$ groups include: ethyl, methyl, isopropyl, cyclopropyl, 2-dimethylpropyl, phenyl, 4-benzamidyl, 2-furanyl, 3,4-dihydropyranyl, and 2-thioazolyl. In certain cases, the $R^{9x}$ groups can be further substituted. For example, $R^{9x}$ furanyl groups may be substituted with substituents such as carboxylate (—COOH).

In another embodiment, $R^{9x}$ is $C(=O)NR^{9x'}R^{9x''}$ and $R^{9x'}$ is hydrogen. Examples of $R^{9x''}$ include phenyl and t-butyl. Other options for $R^{9x}$ include $C(=O)OR^{9x'}$, wherein $R^{9x'}$ may be 2-hydroxyethyl, 2-dimethylpropyl or 2-methyoxyethyl. $R^{9x}$ also may be $C(=O)R^{9x'}$, when $R^{9x'}$ is ethyl or 2-dimethylpropyl.

In another embodiment, $R^{9x}$ is substituted oxadiazolyl. Examples of substituents include those which allow the compound of the invention to perform its function, such as, but not limited to alkyl, e.g., methyl or isopropyl.

In yet another embodiment, $R^{9x}$ is substituted pyrazolyl, imidazolyl, or pyrrolyl. $R^{9x}$ may be substituted with one or more substituents. Examples of such substituents include alkyl, e.g., methyl, ethyl, etc. In another further embodiment, the pyrazolyl, imidazolyl, and/or pyrrolyl groups are N-substituted, e.g., N-methyl substituted.

In another further embodiment, $R^{9x}$ is hydrogen and $R^{9x}$ is methyl.

In another embodiment, the substituted tetracycline compounds of the invention include compounds of Formula XIII:

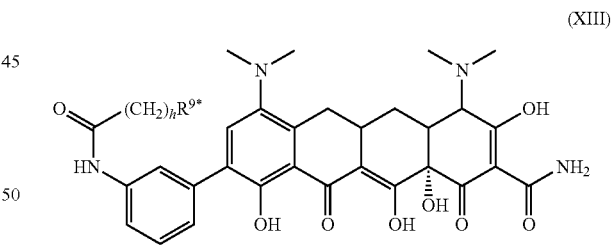

wherein h is an integer from between 0 and 5;

$R^{9*}$ is hydrogen, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, alkylcarbonyl, arylcarbonyl, carboxylate, alkoxycarbonyl, aryloxycarbonyl or aminocarbonyl; and pharmaceutically acceptable salts thereof.

In one embodiment, h is 2 or 3 and the amino is alkylamino (e.g., dimethylamino).

Examples of substituted tetracycline compounds of Formula XIII include:

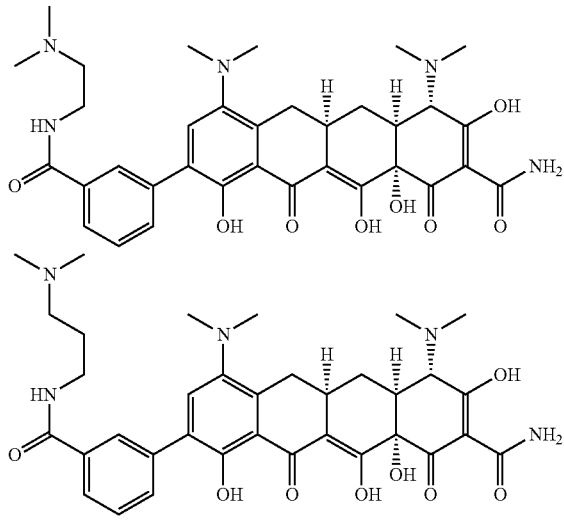

and pharmaceutically acceptable salts thereof.

The substituted tetracyclines of the invention also include compounds of Formula XIV:

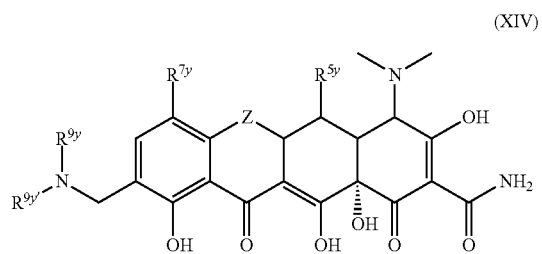

(XIV)

wherein
Z is —C=CH$_2$ or —CH$_2$;
R$^{5y}$ is hydrogen or hydroxyl;
R$^{7y}$ is hydrogen or dimethylamino;
R$^{9y}$ is hydrogen;
R$^{9y'}$ is —CH$_2$-cycloalkyl or —CH$_2$-substituted aryl; or
R$^{9y}$ and R$^{9y'}$ are linked to join a substituted piperidinyl ring or a tetracyclopyridinyl ring; and pharmaceutically acceptable salts thereof.

In one embodiment, Z is —C=CH$_2$, R$^{5y}$ is hydroxyl, R$^{7y}$ is hydrogen and R$^{9y}$ and R$^{9y'}$ are linked to join a substituted piperidinyl ring (e.g., a halogen substituted piperidinyl ring, such as a fluorine substituted piperidinyl ring, for example,

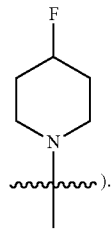

In another embodiment, Z is CH$_2$, R$^{5y}$ and R$^{7y}$ are each hydrogen and R$^{9y}$ and R$^{9y'}$ are linked to join a substituted piperidinyl ring (e.g., a halogen substituted piperidinyl ring, such as a fluorine substituted piperidinyl ring, for example,

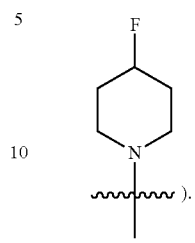

In yet another embodiment, Z is CH$_2$, R$^{5y}$ is hydrogen; R$^{7y}$ is dimethylamino; R$^{9y}$ is hydrogen and R$^{9y'}$ is —CH$_2$-cycloalkyl (e.g., —CH$_2$-cyclopropyl); —CH$_2$-substituted aryl (e.g., hydroxyl substituted phenyl such as 2,3-diphenolyl); or R$^{9y}$ and R$^{9y'}$ are linked to form a substituted piperidinyl ring (e.g.,

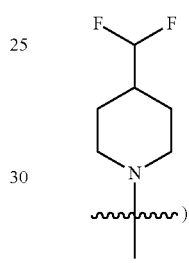

or a tetrahydropyridinyl ring (e.g.,

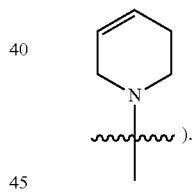

Examples of substituted tetracycline compounds of Formula XIV include:

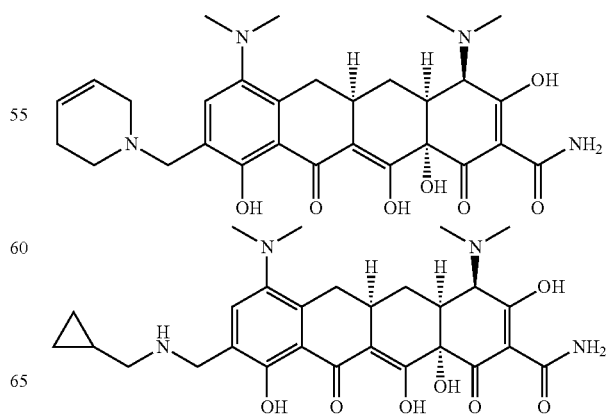

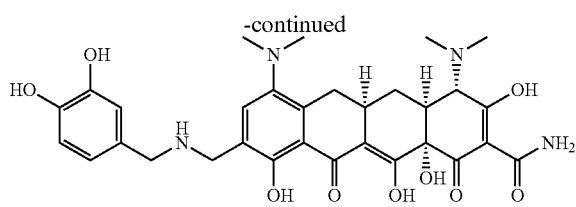

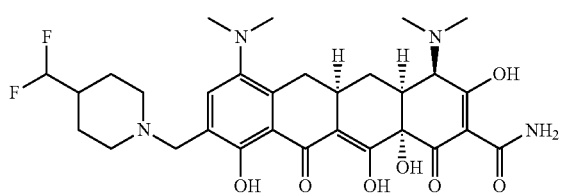

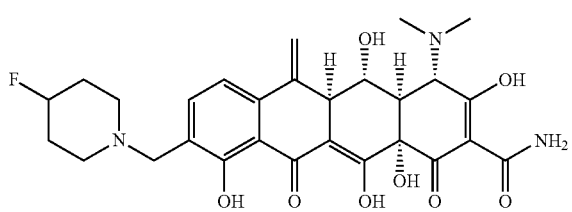

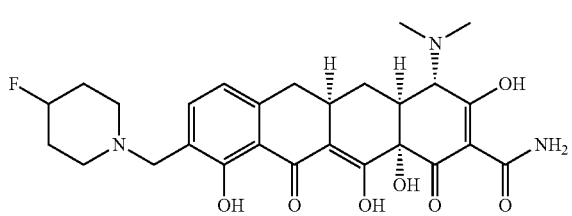

and pharmaceutically acceptable salts thereof.

The substituted tetracycline compounds of the invention also include compounds of

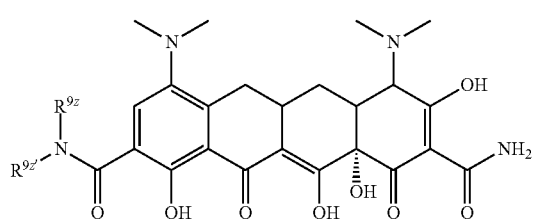

(XV)

wherein $R^{9z}$ is hydrogen;

$R^{9z'}$ is halogen substituted alkyl; or $R^{9z}$ and $R^{9z'}$ are linked to form a substituted piperidinyl ring; and pharmaceutically acceptable salts thereof.

In one embodiment, $R^{9z}$ is hydrogen and $R^{9z'}$ is halogen substituted alkyl, such as $CF_3(CH_2)_p$—, wherein p is an integer from 0 to 5 (e.g., 1).

In another embodiment, $R^{9z}$ and $R^{9z'}$ are linked to form a substituted piperidinyl ring (e.g., an alkyl substituted piperidinyl ring, such as, methyl substituted piperidinyl or trifluoromethyl substituted piperidinyl, for example,

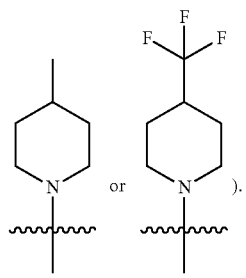

or

).

Examples of substituted tetracycline compounds of Formula XV include:

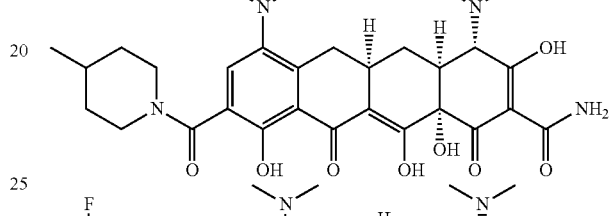

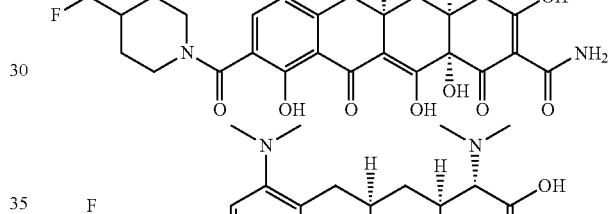

and pharmaceutically acceptable salts thereof.

In another embodiment, the substituted tetracycline compounds include compounds of Formula XVI:

(XVI)

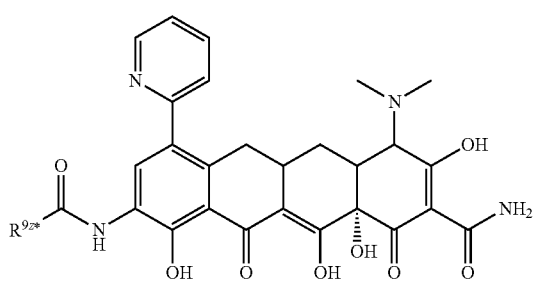

wherein

R$^{9z*}$ is —(CH$_2$)$_t$R$^{9za}$;

t is an integer from 0-1;

R$^{9za}$ is hydrogen, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, alkylcarbonyl, arylcarbonyl, carboxylate, alkoxycarbonyl, aryloxycarbonyl or aminocarbonyl; and pharmaceutically acceptable salts thereof.

In one embodiment, t is 1 and R$^{9za}$ is amino (e.g., dimethylamino or trimethylammonium).

Examples of substituted tetracycline compounds of Formula XVI include:

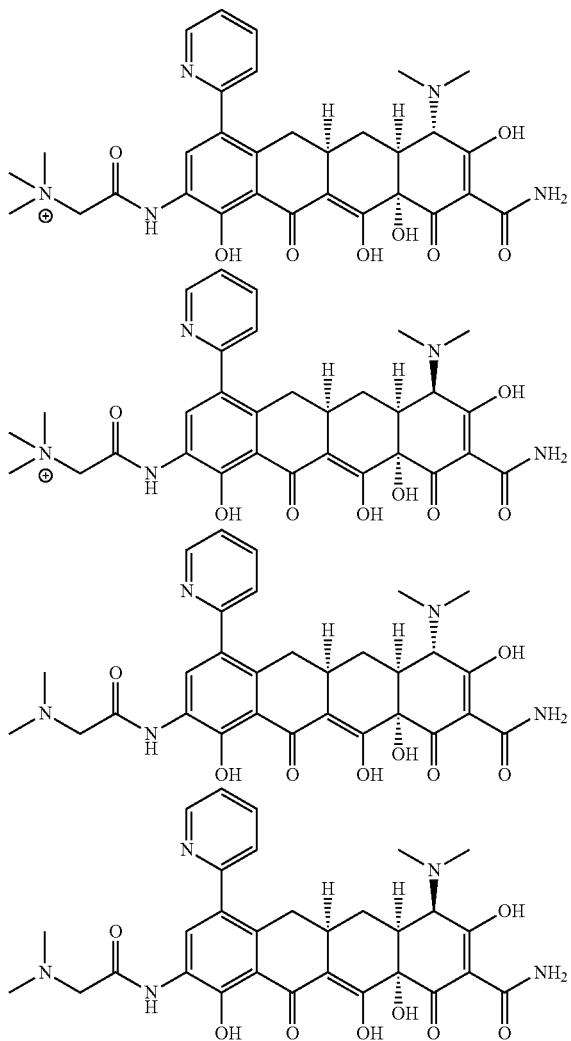

and pharmaceutically acceptable salts thereof.

METHODS FOR SYNTHESIZING TETRACYCLINE COMPOUNDS OF THE INVENTION

The substituted tetracycline compounds of the invention can be synthesized using the methods described in the following schemes and by using art recognized techniques. All novel substituted tetracycline compounds described herein are included in the invention as compounds.

In Scheme 1, a general synthetic scheme for synthesizing 7-substituted In Scheme 1, a general synthetic scheme for synthesizing 7-substituted tetracyclines is shown. A palladium catalyzed coupling of an iodosancycline (1) is performed to form a 7-substituted aldehyde intermediate (2). The aldehyde intermediate is reduced in the presence of a hydroxylamine to give the desired product (3). Compounds P, Y, U, DR and DS may be synthesized as described in Scheme 1.

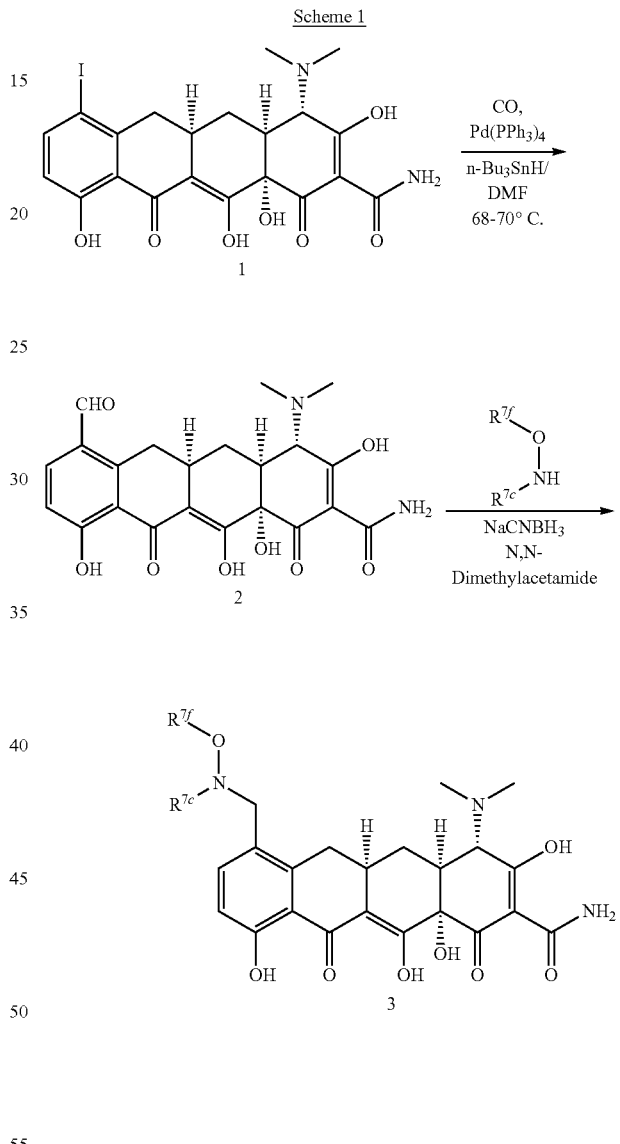

7- and 9-substituted tetracycline compounds may be synthesized by reacting the 7-iodo-9-aminoalkyl sancycline derivative (4) with trimethylsilylethyne in the presence of a palladium catalyst to yield a 7-substituted alkynyl intermediate. Subsequent acid hydrolysis yields the 7-acyl intermediate (5). Further derivitization of the 9-position may be accomplished by reductive alkylation of the amino group with t-butyl aldehyde, hydrogen and palladium on carbon to form compound 6, which can then be reacted with a primary hydroxylamine to form the oxime 7. Compound N may be synthesized as described in Scheme 2.

Scheme 2

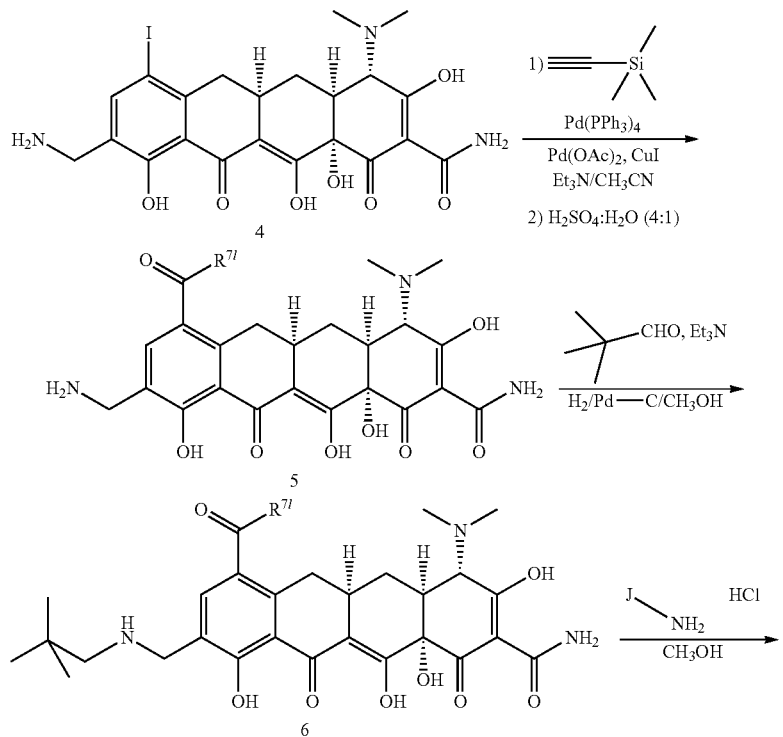

7- and 9-substituted tetracycline compounds may also be prepared as shown in Scheme 3. Beginning with a 7-iodo-9-nitro substituted sancycline derivative (8), a Hiyama coupling followed by acid hydrolysis yields a 7-acyl-9-nitro intermediate (9). The nitro moiety may then be reduced to the amino group by hydrogen gas in the presence of a palladium catalyst (10). Reaction of the acyl group with a primary hydroxylamine provides the product 11. Compounds M, Q, R, DT and DU may be synthesized as shown in Scheme

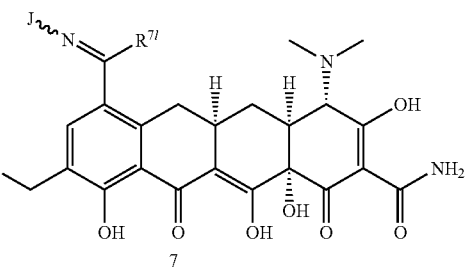

-continued

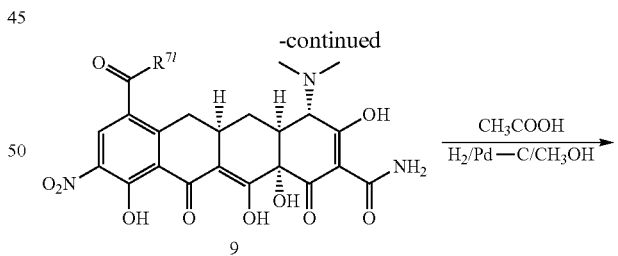

Scheme 3

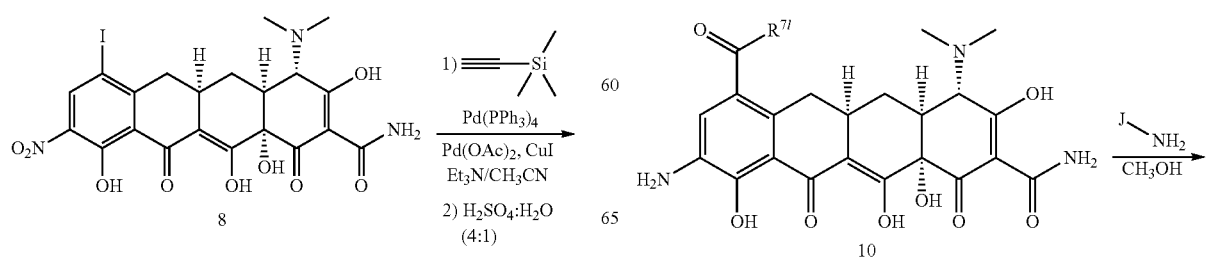

-continued

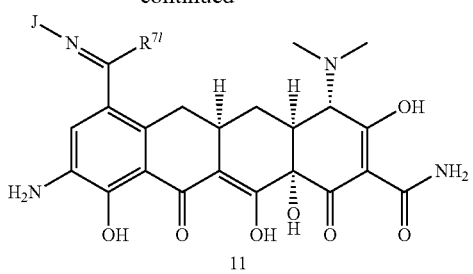

11

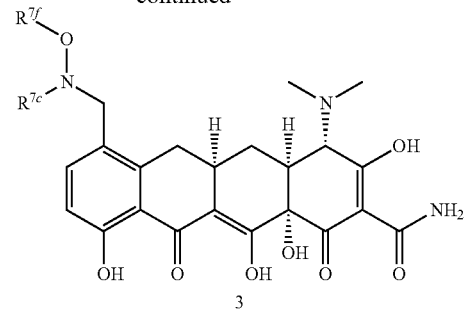

3

Scheme 4 also provides a method for synthesizing 7-substituted tetracyclines. As described above, a palladium catalyzed carbonylation of an iodosancycline (1) is performed to form a 7-substituted aldehyde intermediate (2). The aldehyde intermediate is reduced in the presence of a hydroxylamine to give compound 12, which may then be reacted with formaldehyde and triethylamine, followed by reduction to give the desired product (3). Compounds AA, AM, AB, AE, AF, AG, DV, DW, DX, DY, DZ, EA, EB, EC, ED, EE, EF, EG and EH may be synthesized as illustrated in Scheme 4.

Scheme 5 details the synthesis of substituted tetracyclines with hydroxy in the 10-position. A 7-substituted tetracycline compound may be reacted with N-(5-chloro-2-pyridyl)bis(trifluoromethanesulfonimide) to form a trifluoromethane substituted intermediate (14), which can then be reacted with ammonium formate in the presence of a palladium catalyst to form the desired product (15). Compounds D, E, G, H, S and W may be synthesized as shown in Scheme 5.

Scheme 4

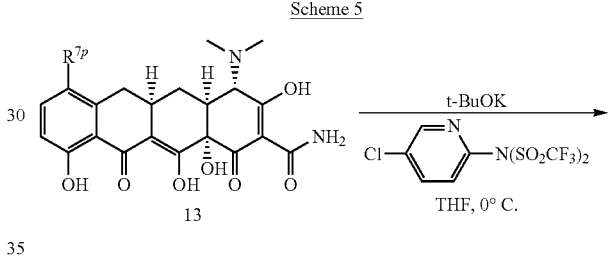

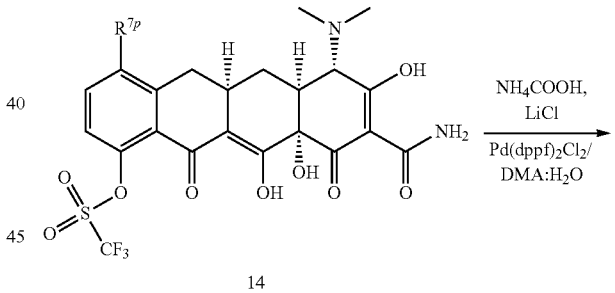

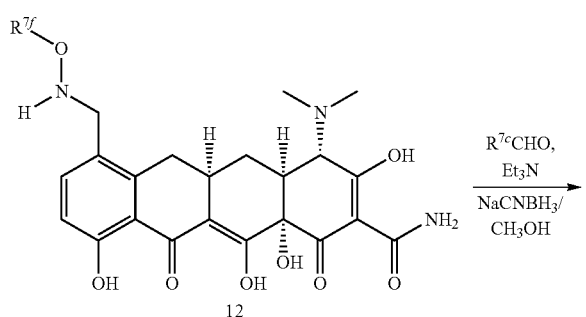

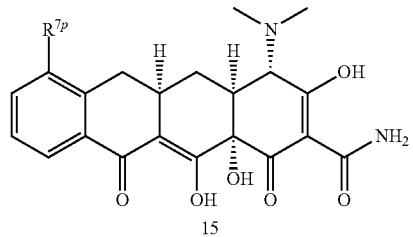

Scheme 6 outlines the general synthesis of 7-substituted tetracyclines. A 7-iodo sancycline derivative (1) may undergo a Stille coupling or a Suzuki coupling by reacting with an alkyl tin derivative or a boronic acid derivative in the presence of a palladium catalyst to form the desired product (16). Compounds J, K, L and T may be synthesized as illustrated in Scheme 6.

Scheme 6

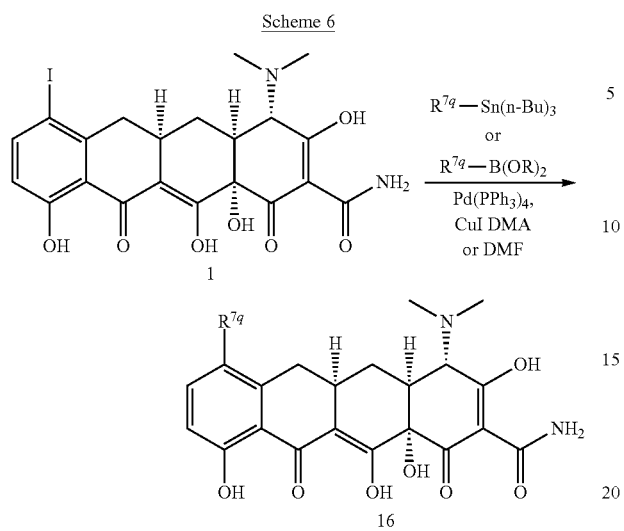

The 7-substituted oxime derivatives may also be prepared as shown in Scheme 7. An 7-iodo sancycline derivative (1) can be reacted with a substituted alkyne in the presence of palladium to synthesize the alkynyl derivative 17. Compound 17 may be converted to the acyl substituted compound 18 by any technique known in the art. The desired oxime product 19 can be obtained by reacting the acyl moiety with a primary hydroxylamine. Compounds I, O, and AN may be synthesized as shown in Scheme 7.

Scheme 7

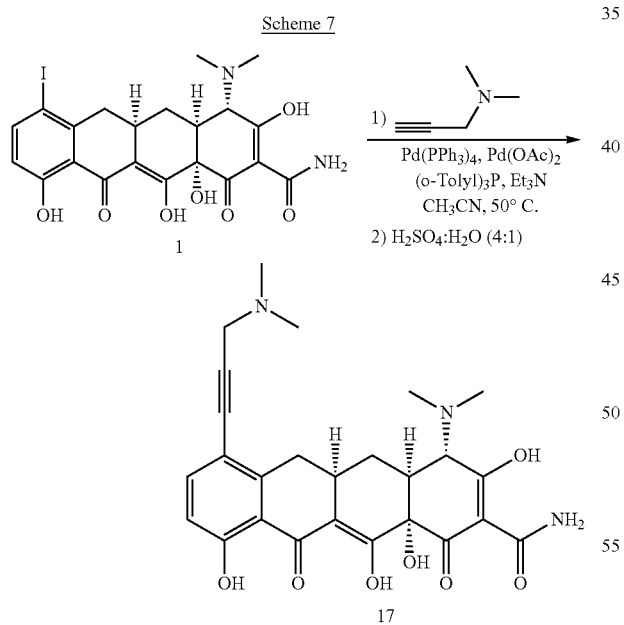

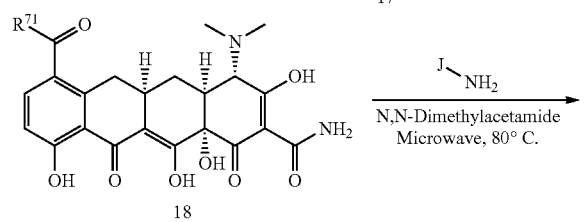

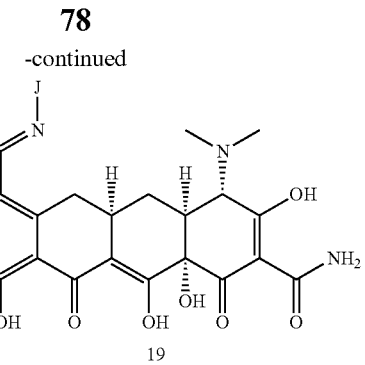

Scheme 8 is a general synthetic scheme showing the synthesis of 7-substituted hydrazone compounds. A 7-substituted aldehyde tetracycline derivative, prepared as described above in Scheme 4, is combined with a primary hydrazone to form the desired product 20. Compounds X and AC may be synthesized as shown in Scheme 8.

Scheme 8

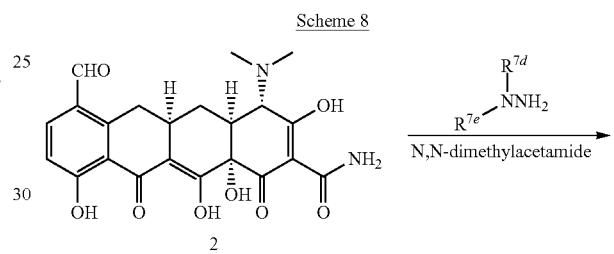

7-substituted hydrazines may also be synthesized as shown in Scheme 9. Starting with compound 2, synthesized as described in Scheme 4 above, may be reacted with a secondary hydrazine in the presence of a reducing agent to form compound 21. Compound Z may be synthesized as shown in Scheme 9.

Scheme 9

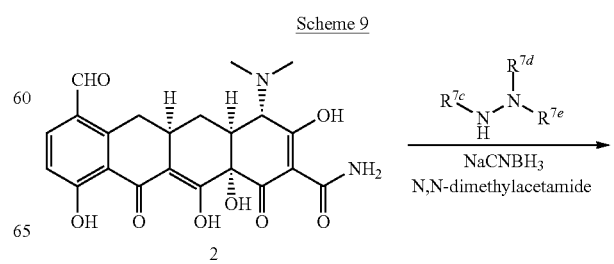

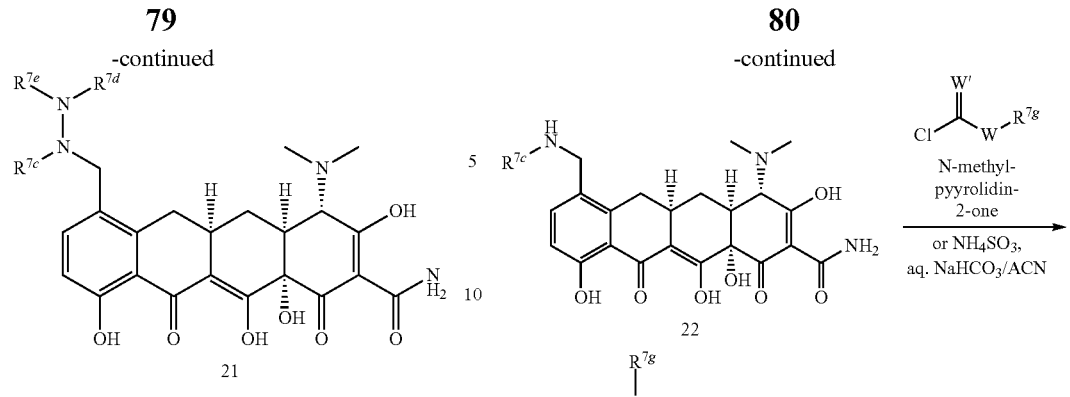

Scheme 10 further depicts a method of synthesizing a 7-substituted aminoalkyl tetracycline compound. Compound 2 is reacted with a primary amine in the presence of a reducing agent to form the secondary amine intermediate (22), which is then mixed with an acid chloride to form compound 23. Compounds F, H, CV and CW may be synthesized as illustrated in Scheme 10.

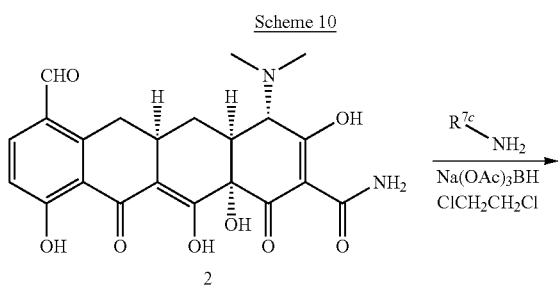

Scheme 11 describes a general method for preparing 9-substituted aminoalkyl substituted tetracycline compounds. Compound 24 may be reacted directly with a secondary amine to form compounds similar to 26. Alternatively, compound 24 may be mixed with a primary amine to yield the substituted imine 25, which may be further reduced to produce the aminoalkyl compound 26. Compounds V, AK and AH may be synthesized as shown in Scheme 11.

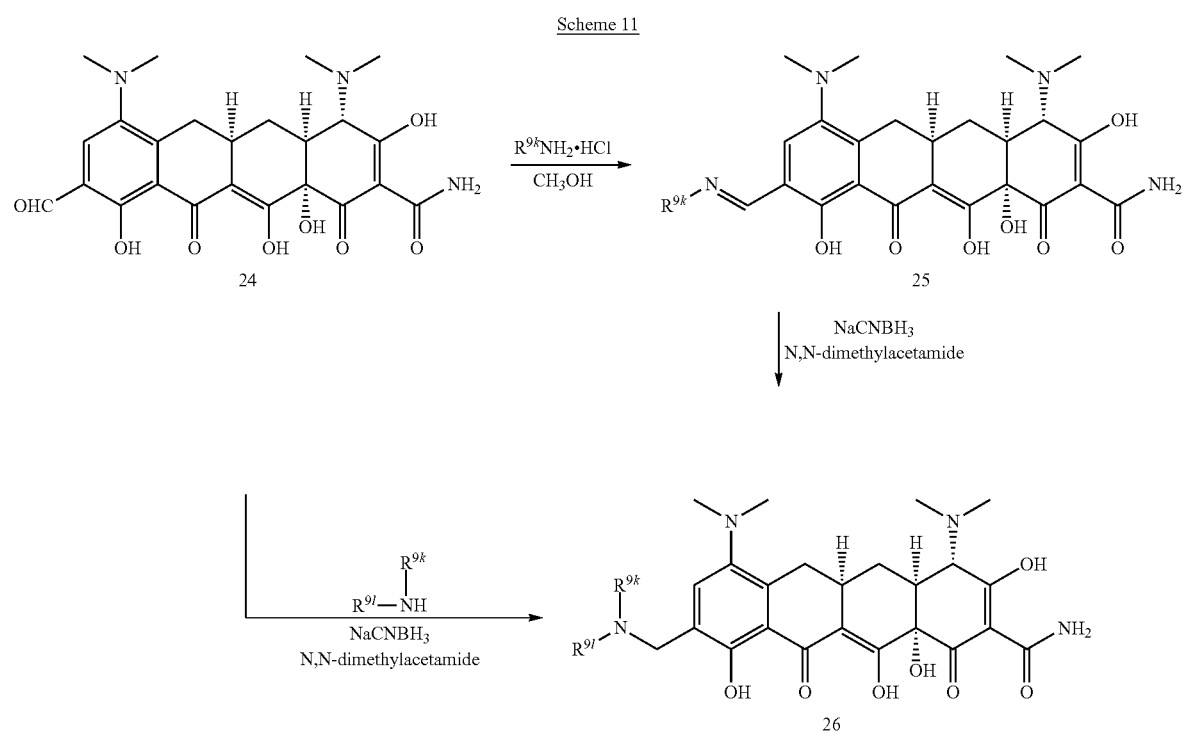

7-substituted tetracycline may also be prepared as shown in Scheme 12. Starting again with compound 2, reductive alkylation with a dioxalanyl secondary amine yields the intermediate 27. Subsequently exposing 27 to acidic conditions removes the protecting group to form intermediate 28, which may then be reacted with a primary amine to form product 29. Compound AL may be synthesized as shown in Scheme 12.

Scheme 12

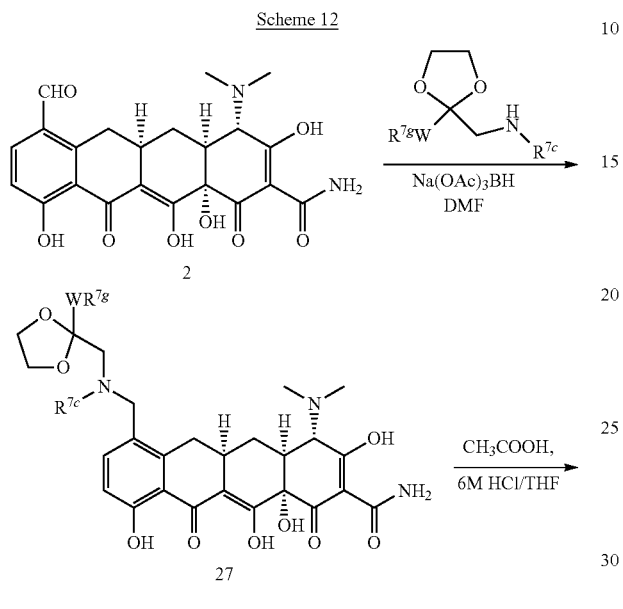

Scheme 13

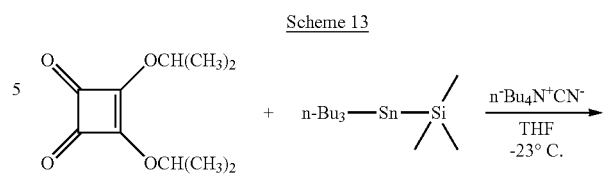

Scheme 14 continues to show the synthesis of cyclobutenedione 7-substituted tetracycline compounds, by reacting building block 31 with 7-iodo substituted sancycline (1) in a Stille coupling reaction to form 32. The amino substitution of product 33 is accomplished by reacting 32 with a primary amine in methanol. Compounds AD, AI and AJ may be synthesized as shown in Schemes 13 and 14.

Scheme 14

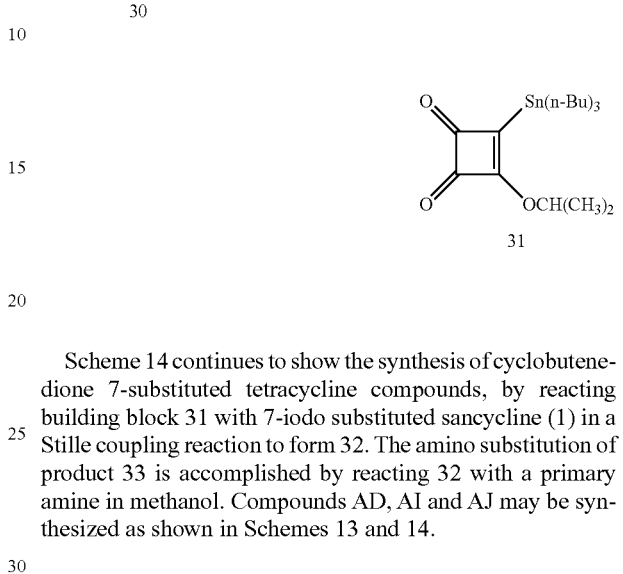

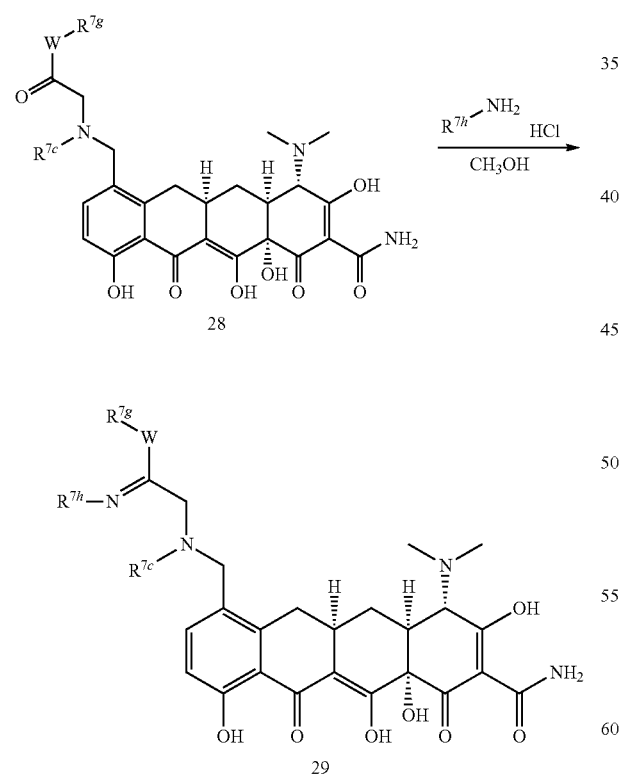

Schemes 13 and 14 illustrate the general synthesis of cyclobutene 7-substituted tetracycline compounds. Beginning with 30, tin reagent 31 is synthesized by reacting 30 with a trimethylsilyl substituted alkyltin derivative.

Scheme 15 depicts generally the synthesis of substituted aromatic 7-substituted tetracycline compounds. Beginning with 1 and performing a Suzuki coupling reaction in the presence of a boronic acid and a palladium catalyst, compounds of general formula 34 are formed. Compounds AO, AP, AQ, AR, AS, AT, AU, AV, AW, AX, AY, AZ, BA, BB, BN, DK, DL, DM, DN, DO and DP may be synthesized as shown in Scheme 15.

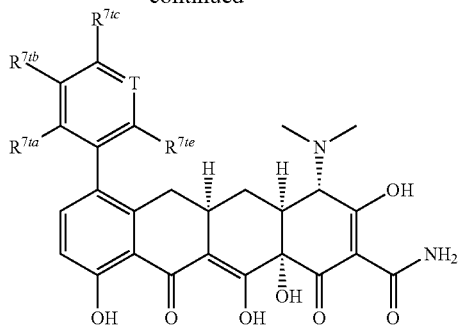

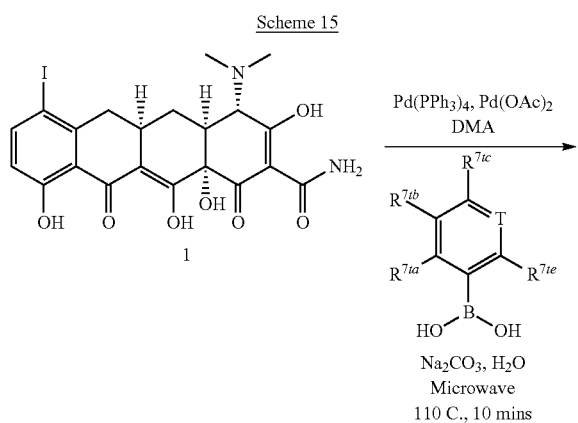

Scheme 16 also depicts the synthesis of substituted aromatic 7-substituted tetracycline compounds. Again, starting from 7-iodo substituted sancycline (1), a Suzuki coupling reaction is performed with a boronic acid in the presence of a palladium catalyst to provide intermediate 35 in which $R^{7tb}$ is either an amine or a carboxylic acid. If $R^{7tb}$ is a carboxylic acidic moiety, a coupling to a secondary amine in the presence of base and a typical coupling reagent to form 7-substituted tetracyclines similar to 36a. Compounds BC, BD, BE, BF, BG, BH, BI, BJ, BK and DQ may be synthesized as illustrated in this manner. If $R^{7tb}$ is an amino moiety, a coupling to an acid chloride or carboxylic acid in the presence of a base and a typical coupling reagent to form 7-substituted tetracyclines similar to 36b. Compounds BO and BP may be synthesized in this manner.

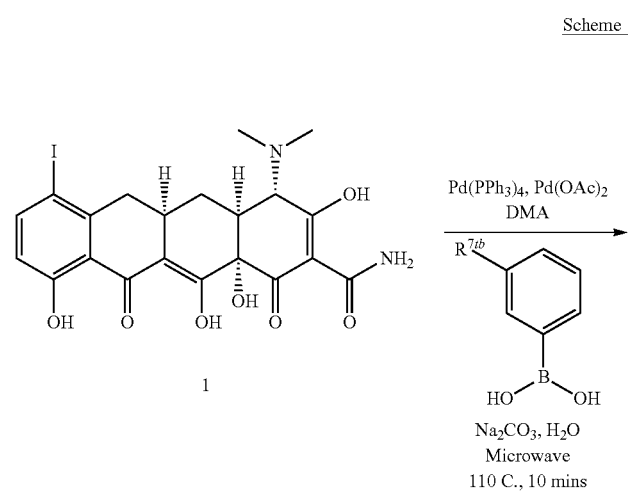

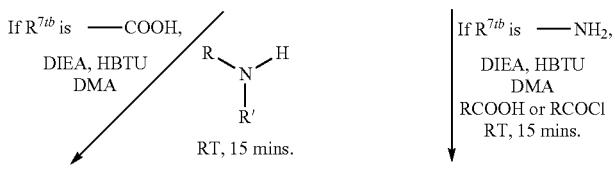

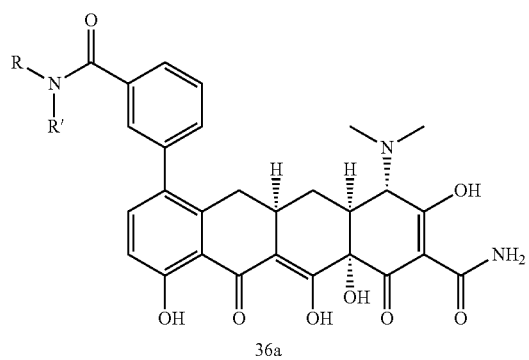

36a

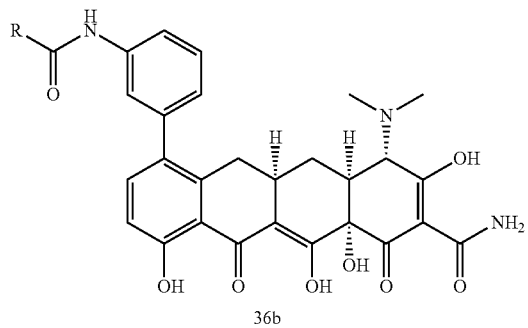

36b

Scheme 17 depicts a method for synthesizing aromatic substituted 9-substituted tetracycline compounds. A 9-iodo tetracycline derivative is reacted under Suzuki conditions by mixing with a boronic acid in the presence of the appropriate palladium catalyst to give compounds similar to compound 38. Compounds BL and BM may be synthesized as illustrated as in Scheme 17.

Scheme 17

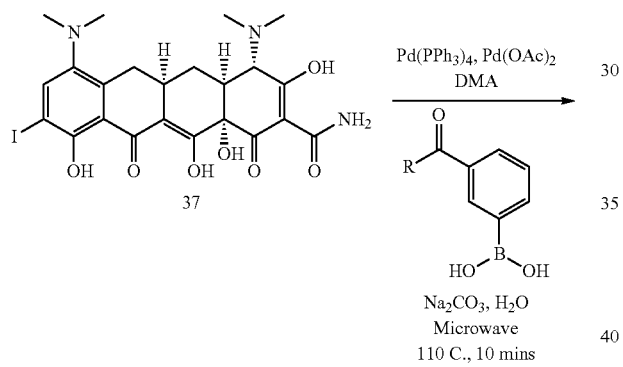

-continued

38

Scheme 18 also depicts a method for synthesizing 9-substituted tetracycline compounds by reacting 37 with a palladium catalyst and carbon monoxide in the presence of N-hydroxysuccinimide to generate an activated ester intermediate. Reaction of this intermediate with nucleophilic compounds such as alcohols, hydroxylamines or amines yields the desired ester, hydroxamic acid or amide, respectively, similar to 39. Compounds BQ, BR, BS, BT, BU, BV, BW, BX, BY and BZ were also synthesized in a similar manner.

Scheme 18

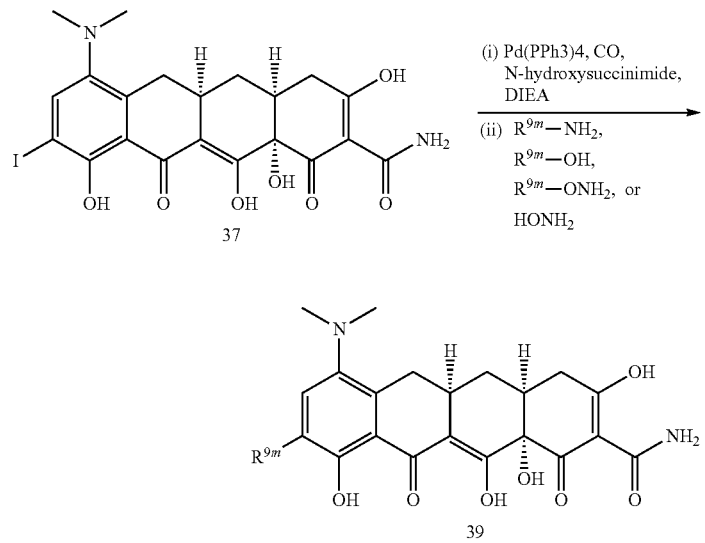

9-substituted oxime tetracycline compounds may be prepared as shown in Scheme 19. A 9-iodo substituted tetracycline derivative is subjected to Heck conditions to form an alkyne intermediate which is converted to 40 by acid hydrolysis. Intermediate 40 is subsequently reacted with an appropriate hydroxylamine to yield the desired product 41. Compounds CG and CH may be synthesized as shown in Scheme 19.

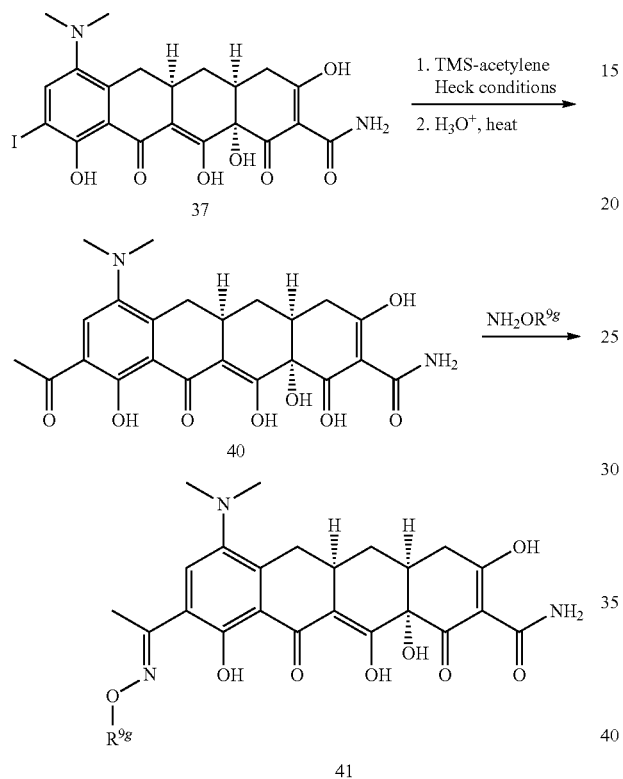

As shown in Scheme 20, 7-substituted tetracycline compounds can also be prepared by reacting the acyl intermediate 41 with hydrogen bromide to form the α-bromoketone substituted tetracycline 42. By reacting the brominated tetracycline with a secondary amine, followed by exposure to an acid chloride, the desired product 43 can be formed. Compounds CZ, DA and DB may be synthesized as illustrated in Scheme 20.

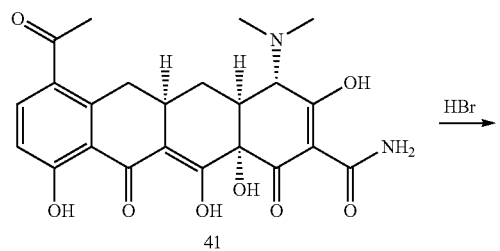

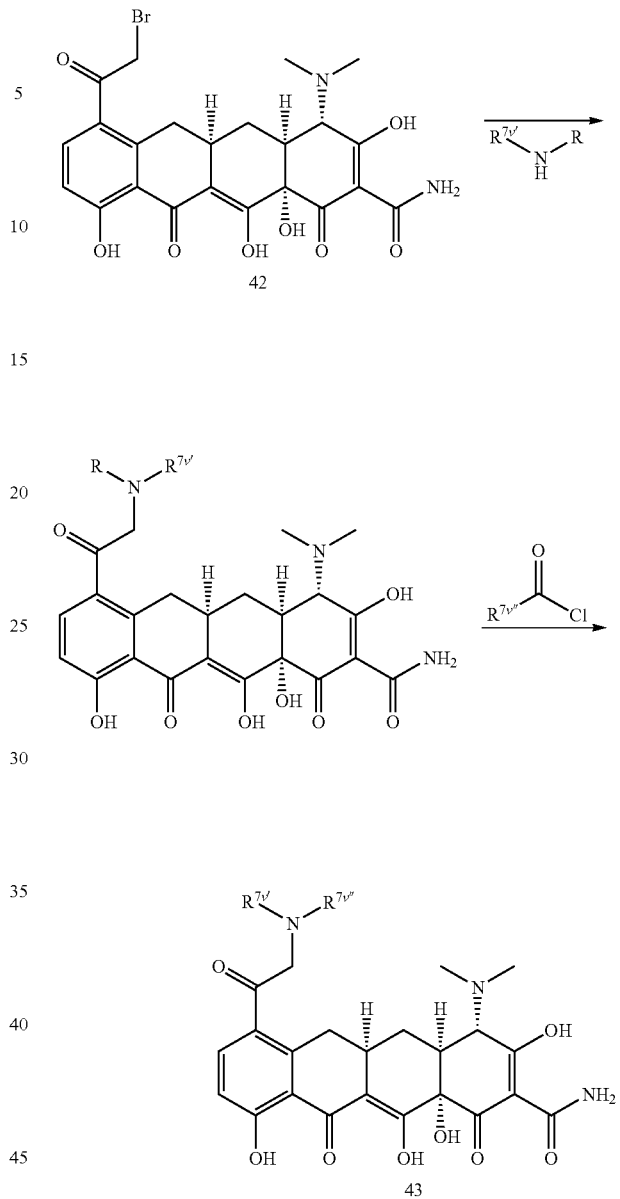

As shown in Scheme 21, 9-substituted-4-dedimethylamino tetracycline compounds may be synthesized starting from minocycline, which is exposed to the de-dimethylamino conditions of methyl iodide and zinc to form 4-dedimethylsancycline 44. Intermediate 44 is halogenated at the 9-position to form intermediate 45, and upon exposing 45 to the appropriate palladium conditions, compounds similar to 46 are formed. Compounds BQ, BR, BW, BX, BY, BZ, CA, CB, CC, CD, CE, CF, EI, EJ, EK, EL, EM, CI, CJ, CK, CL, EN, EO, EP, EQ, ER, ES, ET, EU, EV, EW, EX, FM and FN may be synthesized as shown in Scheme 21.

Scheme 21

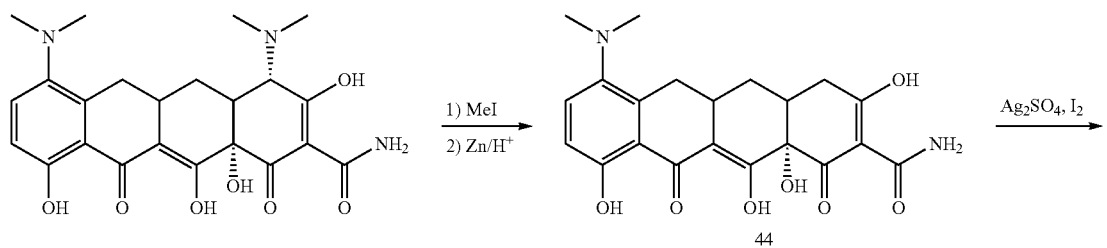

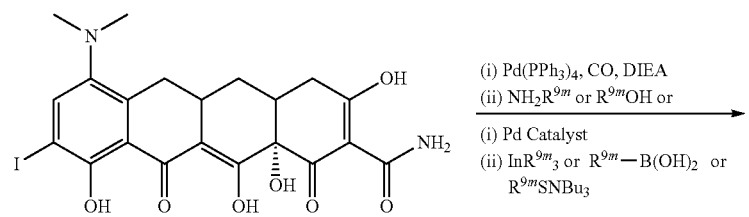

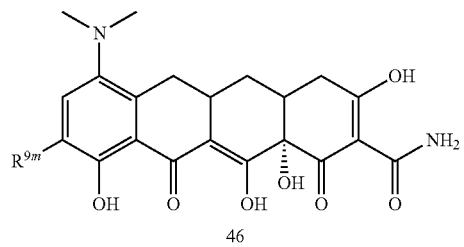

As shown in Scheme 22, 9-substituted-4-dedimethylamino doxycycline compounds may be synthesized starting from doxycycline, which is exposed to the de-dimethylamino conditions of methyl iodide and zinc to form 4-dedimethyldoxycycline 47. Intermediate 47 is halogenated at the 9-position to form intermediate 48, and upon exposing 48 to the appropriate palladium conditions, compounds similar to 49 are formed. Compound CP may be synthesized as shown in Scheme 22.

Scheme 23 illustrates the synthesis of 10-substituted tetracycline compounds. Starting with minocycline, the 10-position hydroxide is deprotonated in the presence of a strong base, followed by the addition of triflate to form intermediate 50, which then undergoes either Stille or Suzuki conditions or carbonylation conditions to form compounds similar to 10-substituted compounds 51. Compounds CM, CN, CO, EY, EZ, FA, FO, FP and FQ may be synthesized as illustrated in Scheme 23.

Scheme 22

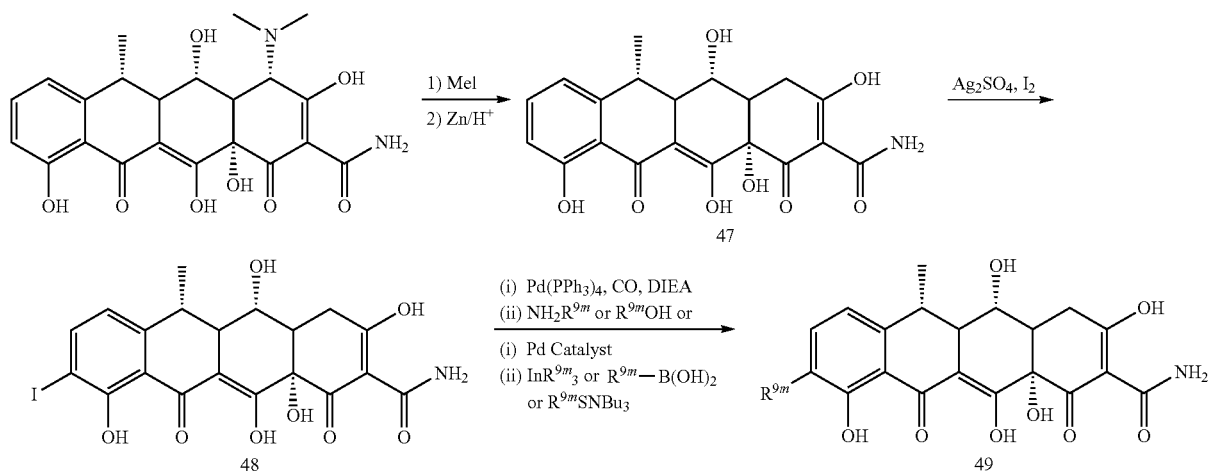

Scheme 23

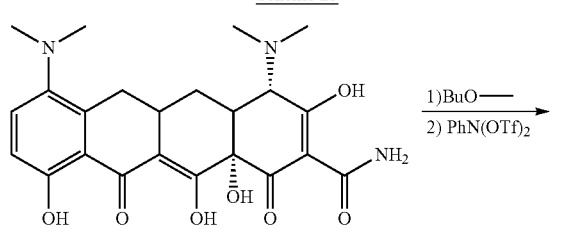

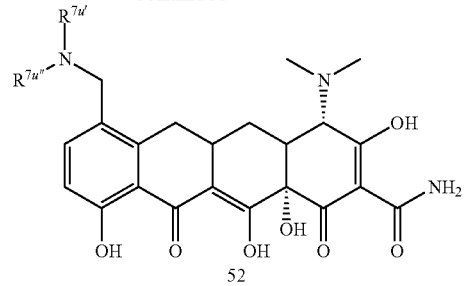

52

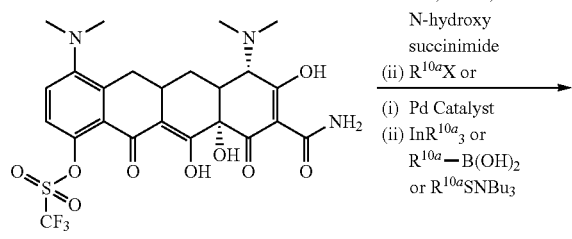

50

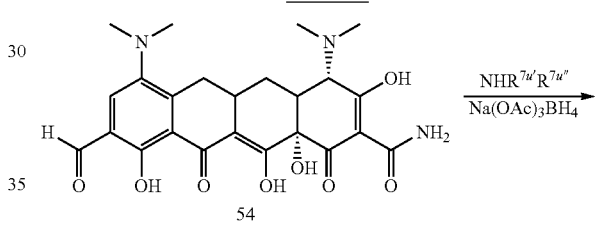

51

Scheme 24 illustrates the synthesis of 7-aminomethyl substituted tetracycline compounds. Compound 1 is exposed to a secondary amine in the presence of a reducing agent to from compounds similar to 52. Compounds DC, DD, DE, DF, DG, DH, DI, DJ and FC may be synthesized as illustrated in Scheme 24.

Scheme 24

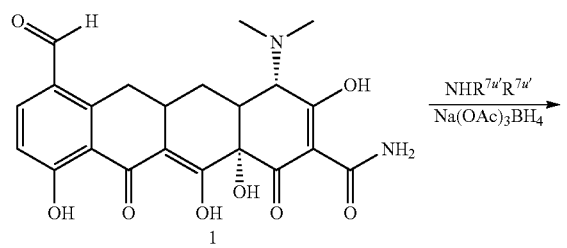

1

Scheme 25 provides a method for synthesizing 9-aminomethyl substituted tetracycline compounds. 9-formyl substituted compound 54 is reacted with a secondary amine in the presence of a reducing agent to provide the 9-aminomethyl substituted tetracycline compounds 55. Compounds FD, FE, FF, FG, FH, FI, FJ, FK and FL may be synthesized as illustrated in Scheme 25.

Scheme 25

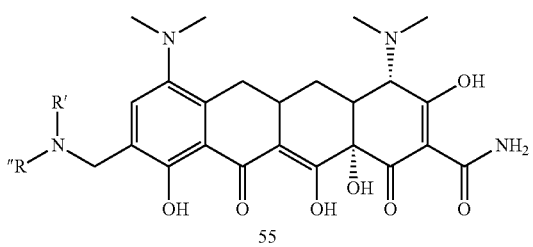

54

55

Scheme 26 illustrates the methods for synthesizing 9-alkyl or 9-carbonyl substituted tetracycline compounds starting with the 9-iodominocycline or 9-iodo-4-dedimethylminocycline compound 56, followed by palladium catalyzed alkynylation to form intermediate 57. Intermediate 57 may undergo either hydrogenolysis to form 9-alkyl substituted tetracycline compounds (58) or acid catalyzed hydrolysis to form 9-carbonyl substituted tetracycline compound (59). Compounds FR, FS, FT and FU may be prepared as illustrated in Scheme 26.

Scheme 26

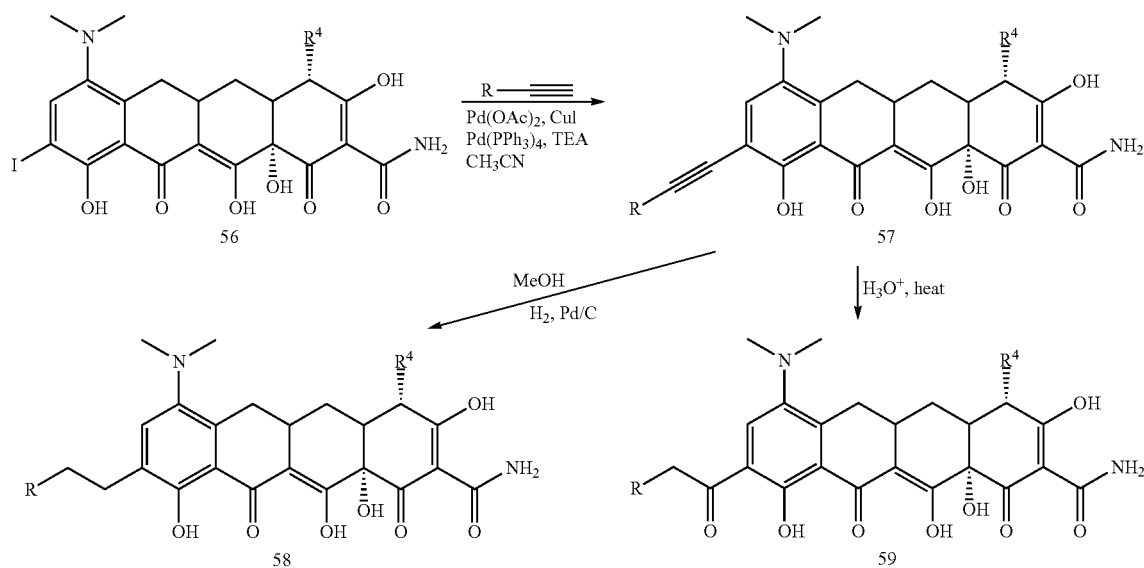

9-Alkyl substituted tetracycline compounds may also be synthesized as shown in Scheme 27. Again starting with 9-iodominocycline or 9-iodo-4-dedimethylminocycline compound 56, either Suzuki or Stille coupling conditions may produce the 9-alkyl substituted tetracycline compounds (60) or reaction with copper iodide with a fluorinated ester compound yields 9-trifluoroalkyl substituted compound 61. Compounds FV, FW, FX, FY, GA and GB may be synthesized as illustrated in Scheme 27.

7-Furanyl substituted tetracycline compounds may be synthesized as illustrated in Scheme 28. 7-Iodosancycline (1) is subjected to a formyl substituted furanyl boronic acid in the presence of palladium (II) acetate and sodium carbonate to yield intermediate 62. A reductive amination is then performed in the presence of an appropriate reducing agent and a secondary amine to convert the formyl moiety to a tertiary alkylamine (63). The substituents of the tertiary amine may be further derivitized, as shown by the reaction of compound 63

Scheme 27

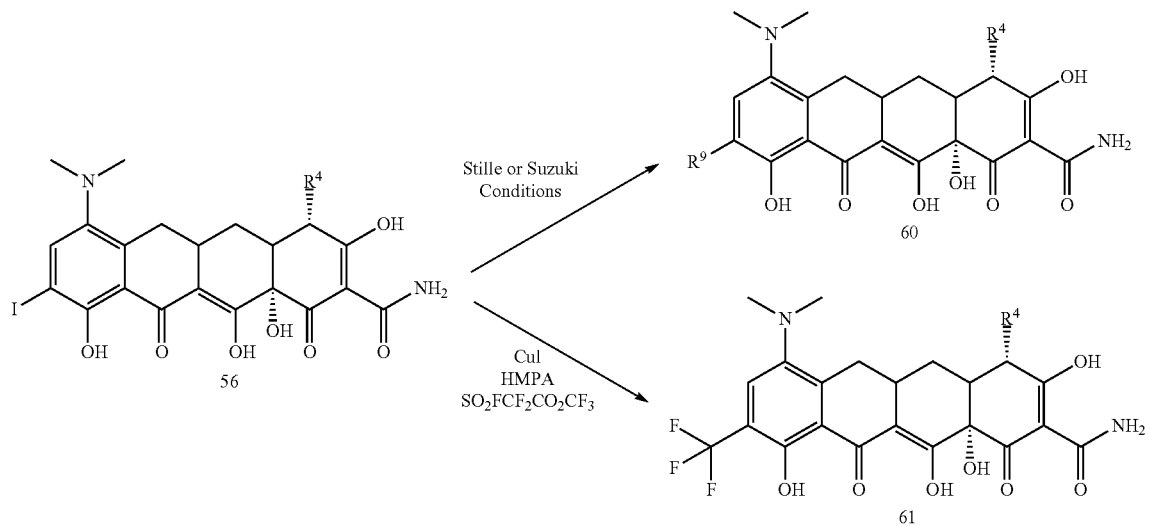

with methylchloroformate to form compound 64. Compounds FB, CQ, CR, CS and CT may be synthesized as shown in Scheme 28.

Scheme 28

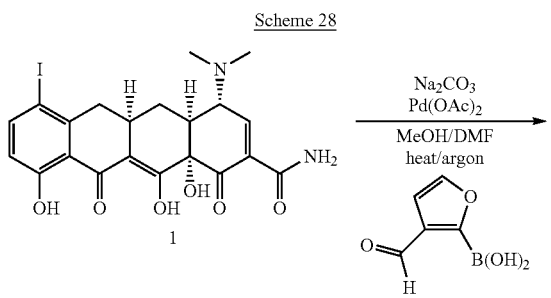

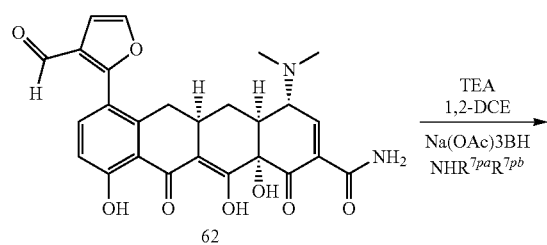

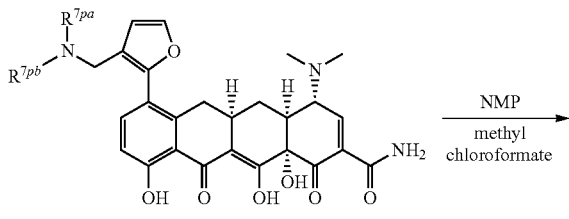

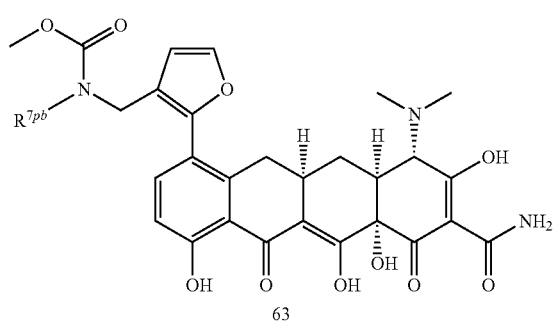

7-Pyridinyl-9-aminocarbonyl substituted tetracyclines may be synthesized as shown in Scheme 29. The 7-position of the 7-iodo-9-nitro tetracycline compound (8) is reacted under Stille conditions to form the 7-pyridinyl intermediate 64, which is then subjected to reducing conditions to form the 7-pyridinyl-9-amino tetracycline compound 65. The amino moiety of compound 65 is then reacted with a chloroformate to form the desired aminocarbonyl substituent in the 9 position (66). Compounds GS, GT, GU and GV may also be synthesized as shown in Scheme 29.

Scheme 29

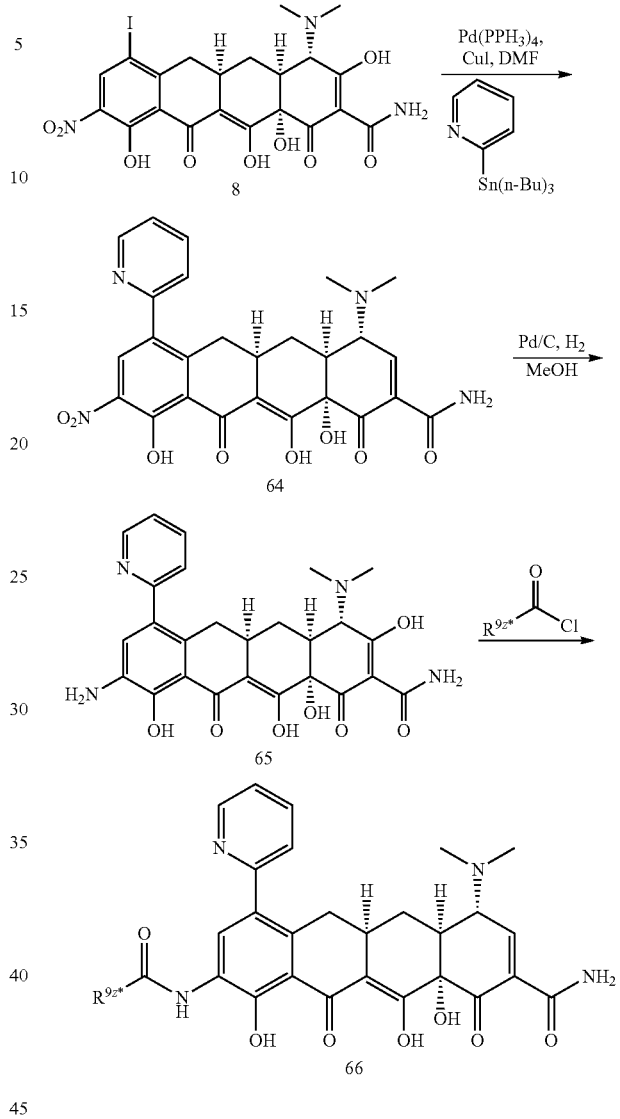

Scheme 30 illustrates methods for preparing both 9-aminomethyl substituted sancycline compounds and 7-substituted-9-aminomethyl tetracycline compounds. Sancycline is bromonated at the 7-position with N-bromosuccinimide and iodated at the 9-position with N-iodosuccinimide to form the dihalogenated reactive intermediate 67, which then undergoes formylation at the 9-position to yield a 7-bromo-9-formyl substituted tetracycline compound (68). Compound 68 may then undergo a reductive amination procedure in the presence of an appropriate secondary amine and a reducing agent to form compound 69. The bromo moiety at the 7-position may then be removed by exposing 69 to palladium on carbon in the presence of hydrogen gas to provide 9-aminomethyl sancycline compounds (71). Alternatively, the reactive intermediate 68 may first be exposed to reductive amination conditions as described above, followed by a pallium-indium cross coupling reaction to form 7-substituted-9-aminomethyl tetracycline compounds (70). Compounds GN, GO, GP and GQ may be synthesized as shown in Scheme 30.

Scheme 30

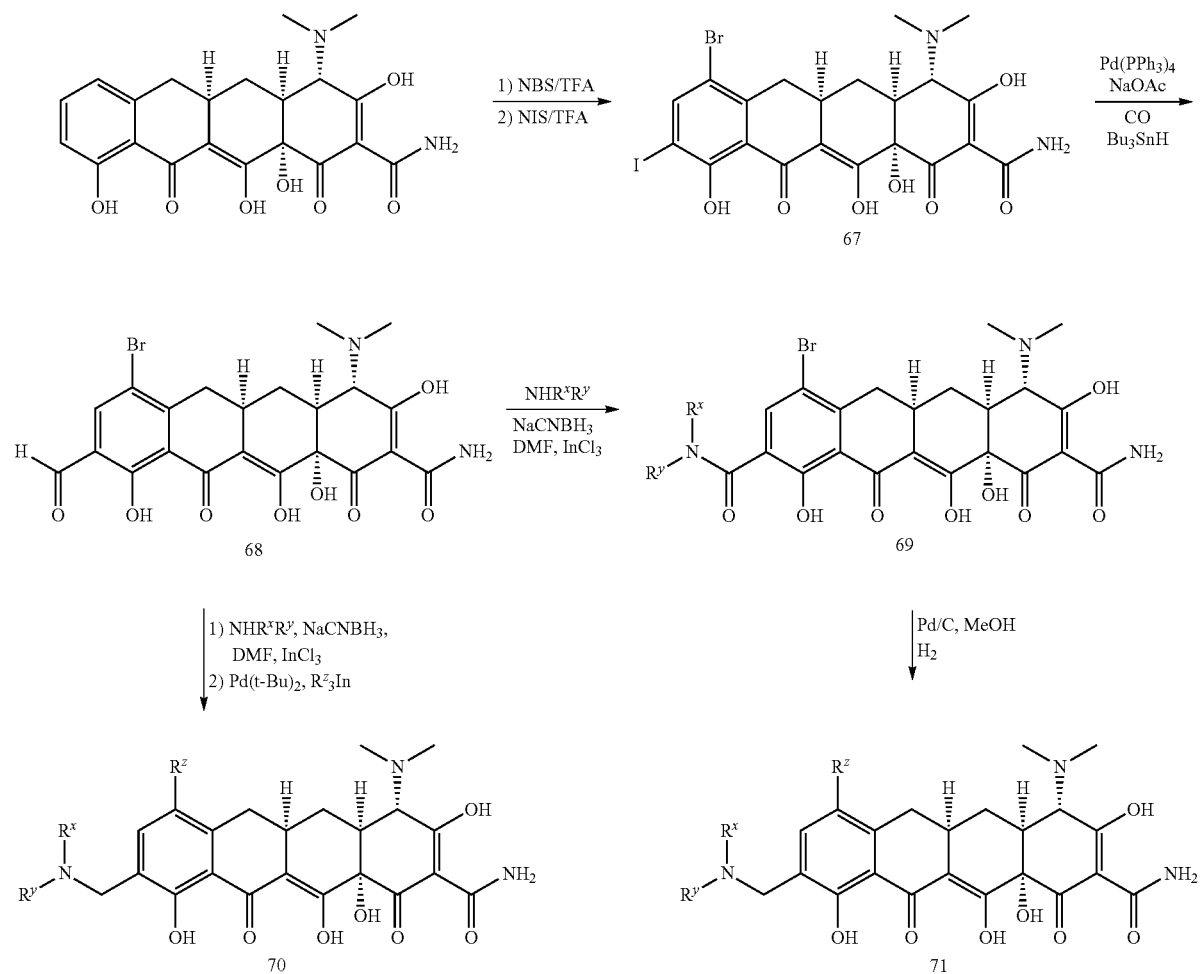

7-Substituted tetracycline compounds may be generally synthesized as shown in Scheme 31. A 7-iodo tetracycline compound (71) may be reacted under Suzuki, Stille or indium-palladium cross coupling reactions to form 7-substituted tetracycline compounds. Compounds GC, GD, GE, GF and GH may be synthesized as shown in Scheme 31.

Scheme 31

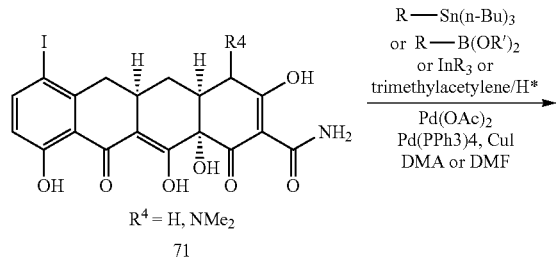

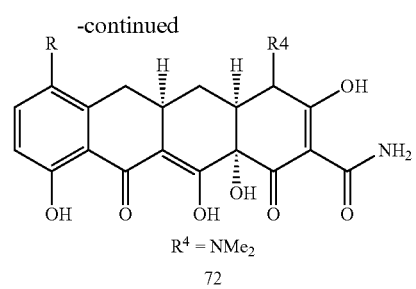

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ or straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls," the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical (CH₃CO—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl," "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts" *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

METHODS FOR TREATING TETRACYCLINE RESPONSIVE STATES

The invention also pertains to methods for treating a tetracycline responsive states in subjects, by administering to a subject an effective amount of a tetracycline compound of the invention (e.g., a compound of Formula I, II, III, IIIa, IV, IVa, V, Va, VI, VII, VIIa, VIII, VIIIa, IX, IXa, X, Xa, XI, XIa, XII, XIII, XIV, XV or XVI, or a compound listed in Table 2 or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention Tetracycline compound responsive states include bacterial, viral, parasitic, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, stroke, AMI, aortic aneurysm, neurodegenerative diseases and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.), are involved or are present in an area in aberrant amounts, e.g., in amounts which may be advantageous to alter, e.g., to benefit the subject. The term "inflammatory process associated state" also includes states in which there is an increase in acute phase proteins (e.g., C-reactive protein). The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

Tetracycline responsive states also include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; animal bites (e.g., spider bites, snake bites, insect bites and the like); burns (thermal, chemical, and electrical); inflammatory bowel disorder (IBD); common obstructive pulmonary disease (COPD); acute respiratory distress syndrome (ARDS); vasculitis; asthma; sepsis; nephritis; pancreatitis; hepatitis; lupus; viral infections; parasitic infections; and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of tetracycline compound responsive states include, but are not limited to, malaria, senescence, diabetes, vascular stroke, hemorrhagic stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention. Examples of other tetracycline compound responsive states include, but are not limited to, arteriosclerosis, angiogenesis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8; 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Other examples of tetracycline compound responsive states include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis (e.g., including but not limited to, relapsing and remitting multiple sclerosis, primary progressive multiple sclerosis, and secondary progressive multiple sclerosis), amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety. Other examples of tetracycline compound responsive states are described in WO 03/005971A2, U.S. Ser. No. 60/421,248, and U.S. Ser. No. 60/480,482, each incorporated herein by reference.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent that is known in the art to treat, prevent, or reduce the symptoms of a particular tetracycline responsive state. Furthermore, the other therapeutic agent may be any agent of benefit to the patient when administered in combination with the administration of a tetracycline compound. In one embodiment, the cancers treated by methods of the invention include those described in U.S. Pat. Nos. 6,100,248; 5,843,925; 5,837,696; or 5,668, 122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), postpump syndrome (PPS), adelectasis (e.g., collapsed lung) and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, chronic obstructive pulmonary disease (COPD), cystic fibrosis, and emphesema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, hemorrhagic stroke or ischemic stroke. The invention also pertains to a method for treating ischemia, stroke, hemorrhagic stroke or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. Some of the compounds of the invention are useful as antibiotics against organisms which are resistant and/or sensitive to other tetracycline compounds. The antibiotic activity of the tetracycline compounds of the invention may by using the in vitro standard broth dilution method described in Waitz, J. A., *CLSI, Document M7*-A2, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, or psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount." One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

PHARMACEUTICAL COMPOSITIONS OF THE INVENTION

The invention also pertains to pharmaceutical compositions comprising a therapeutically effective amount of a tetracycline compound (e.g., a compound of Formula I, II, III. IIIa, IV, IVa, V, Va, VI, VII, VIIa, VIII, VIIIa, IX, IXa, X, Xa, XI, Xa, XII, XIII, XIV, XV or XVI or a compound listed in Table 2 or any other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,11-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g., for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc.

Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g., 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of Formula I, II, III. IIIa, IV, IVa, V, Va, VI, VII, VIIa, VIII, VIIIa, IX, IXa, X, Xa, XI, Xa, XII, XIII, XIV, XV or XVI or a compound listed in Table 2, or any other compound described herein, for the preparation of a medicament. The medicament may include a pharmaceutically acceptable carrier and the tetracycline compound is an effective amount, e.g., an effective amount to treat a tetracycline responsive state.

In one embodiment, the substituted tetracycline compound is a compound of Table 2.

TABLE 2

| Code | Compound |
|------|----------|
| A | |
| B | |
| C | |
| D | |
| E | |
| F | |

TABLE 2-continued

| Code | Compound |
|---|---|
| G | |
| H | |
| I | |
| J | |
| K | |

TABLE 2-continued

| Code | Compound |
|---|---|
| L | |
| M | |
| N | |
| O | |
| P | |

TABLE 2-continued

| Code | Compound |
|------|----------|
| Q | (structure) |
| R | (structure) |
| S | (structure) |
| T | (structure) |
| U | (structure) |

TABLE 2-continued

| Code | Compound |
|---|---|
| V | |
| W | |
| X | |
| Y | |
| Z | |

TABLE 2-continued

| Code | Compound |
|------|----------|
| AA | (structure) |
| AB | (structure) |
| AC | (structure) |
| AD | (structure) |
| AE | (structure) |

TABLE 2-continued

| Code | Compound |
|------|----------|
| AF | |
| AG | |
| AH | |
| AI | |
| AJ | |

TABLE 2-continued

| Code | Compound |
|---|---|
| AK | |
| AL | |
| AM | |
| AN | |
| AO | |

TABLE 2-continued
| Code | Compound |
|---|---|
| AP | 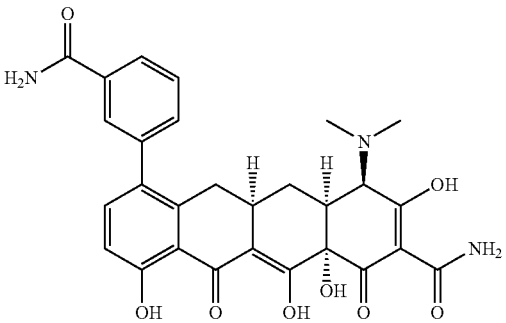 [SMILES: CN(C)[C@H]1C(O)=C(C(N)=O)C(=O)[C@@]2(O)C(O)=C3C(=O)c4c(O)ccc(-c5cccc(C(N)=O)c5)c4C[C@H]3C[C@@H]12] |
| AQ | 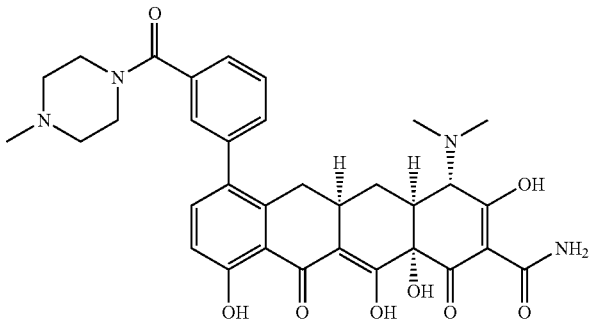 [SMILES: CN1CCN(C(=O)c2cccc(-c3ccc(O)c4c3C[C@H]3C[C@H]5[C@H](N(C)C)C(O)=C(C(N)=O)C(=O)[C@@]5(O)C(O)=C3C4=O)c2)CC1] |
| AR | 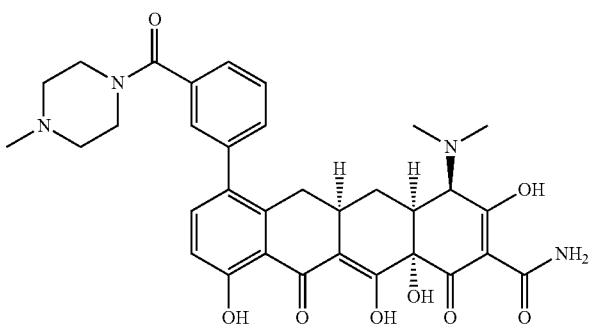 [SMILES: CN1CCN(C(=O)c2cccc(-c3ccc(O)c4c3C[C@H]3C[C@H]5[C@@H](N(C)C)C(O)=C(C(N)=O)C(=O)[C@@]5(O)C(O)=C3C4=O)c2)CC1] |
| AS | 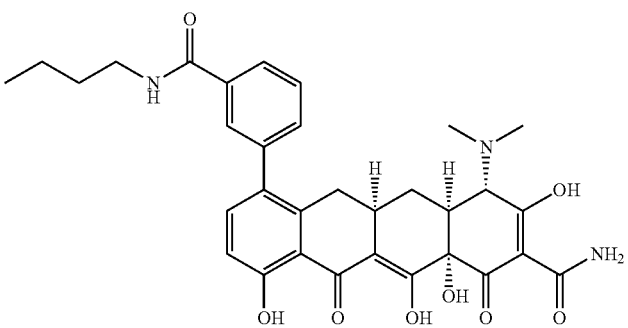 [SMILES: CCCCNC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] |

TABLE 2-continued
| Code | Compound |
|---|---|
| AT | 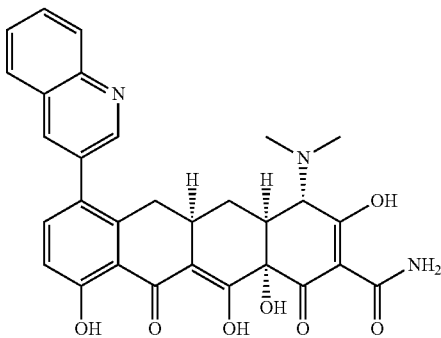 [SMILES: CN(C)[C@@H]1C(O)=C(C(N)=O)C(=O)[C@@]2(O)C(O)=C3C(=O)c4c(O)ccc(-c5cnc6ccccc6c5)c4C[C@H]3C[C@@H]12] |
| AU | 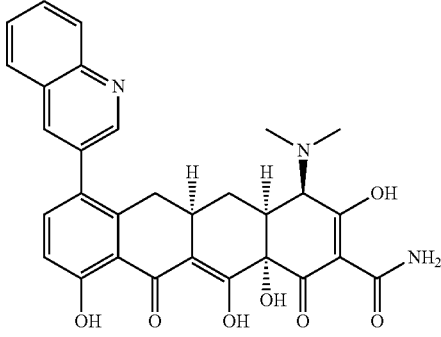 [SMILES: CN(C)[C@H]1C(O)=C(C(N)=O)C(=O)[C@@]2(O)C(O)=C3C(=O)c4c(O)ccc(-c5cnc6ccccc6c5)c4C[C@H]3C[C@@H]12] |
| AV | 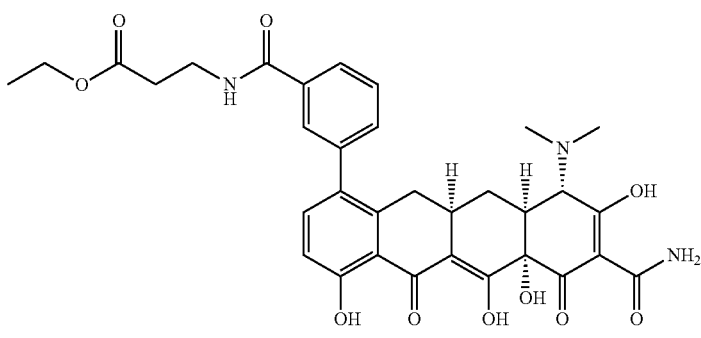 [SMILES: CCOC(=O)CCNC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] |
| AW | 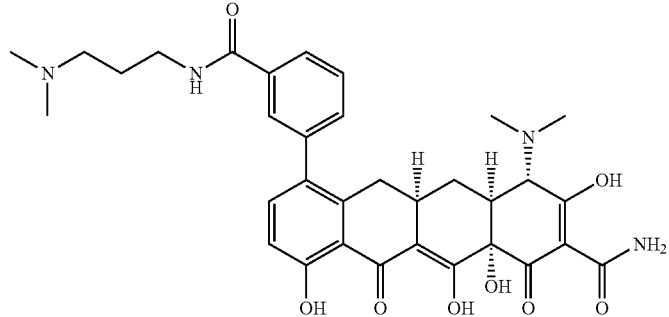 [SMILES: CN(C)CCCNC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] |

TABLE 2-continued

| Code | Compound |
|---|---|
| AX | |
| AY | |
| AZ | |
| BA | |

TABLE 2-continued

| Code | Compound |
|---|---|
| BB | |
| BC | |
| BD | |
| BE | |

TABLE 2-continued
| Code | Compound |
|---|---|
| BF | 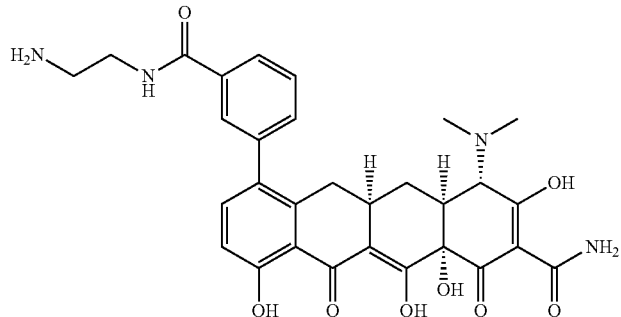 [SMILES: CN(C)[C@@H]1C(O)=C(C(N)=O)C(=O)[C@@]2(O)C(O)=C3C(=O)c4c(O)ccc(-c5cccc(C(=O)NCCN)c5)c4C[C@H]3C[C@@H]12] |
| BG | 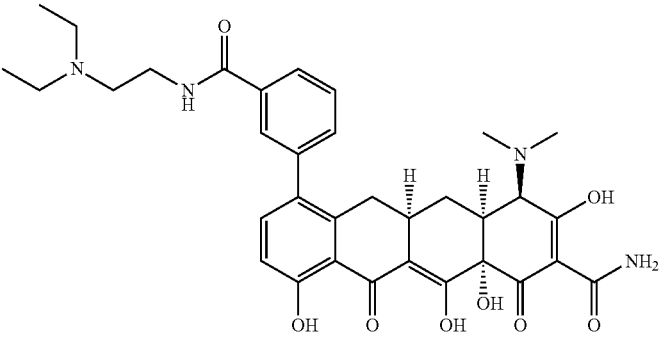 [SMILES: CCN(CC)CCNC(=O)c1cccc(-c2ccc(O)c3c2C[C@H]2C[C@H]4[C@@H](N(C)C)C(O)=C(C(N)=O)C(=O)[C@@]4(O)C(O)=C2C3=O)c1] |
| BH | 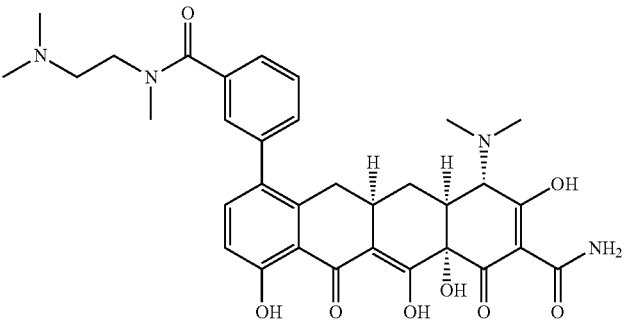 [SMILES: CN(C)CCN(C)C(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] |
| BI | 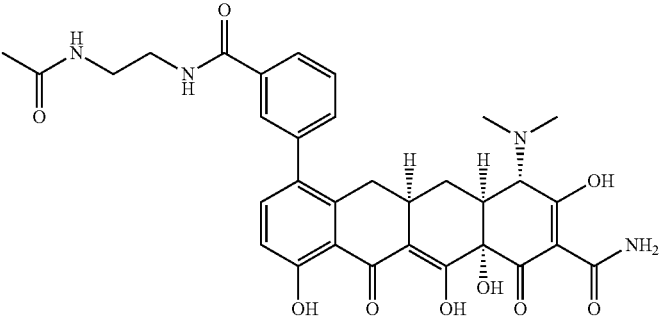 [SMILES: CC(=O)NCCNC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1] |

TABLE 2-continued

| Code | Compound |
|---|---|
| BJ | |
| BK | |
| BL | |
| BM | |
| BN | |

TABLE 2-continued

| Code | Compound |
|---|---|
| BO | (structure) |
| BP | (structure) |
| BQ | (structure) |
| BR | (structure) |
| BS | (structure) |
| BT | (structure) |

TABLE 2-continued

| Code | Compound |
|---|---|
| BU | |
| BV | |
| BW | |
| BX | |
| BY | |
| BZ | |
| CA | |

TABLE 2-continued

| Code | Compound |
|---|---|
| CB | (structure) |
| CC | (structure) |
| CD | (structure) |
| CE | (structure) |
| CF | (structure) |
| CG | (structure) |
| CH | (structure) |

TABLE 2-continued

| Code | Compound |
|---|---|
| CI | |
| CJ | |
| CK | |
| CL | |
| CM | |
| CN | |

TABLE 2-continued

| Code | Compound |
|------|----------|
| CO | |
| CP | |
| CQ | |
| CR | |
| CS | |
| CT | |

TABLE 2-continued

| Code | Compound |
|---|---|
| CU | (structure) |
| CV | (structure) |
| CW | (structure) |
| CX | (structure) |

TABLE 2-continued
| Code | Compound |
|---|---|
| CY | 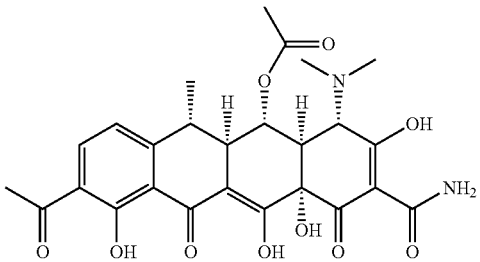 [SMILES: CC(=O)O[C@H]1[C@H]2C(=C(O)[C@]3(O)C(=O)C(C(N)=O)=C(O)[C@@H](N(C)C)[C@H]13)C(=O)c1c(ccc(C(C)=O)c1O)[C@@H]2C] |
| CZ | 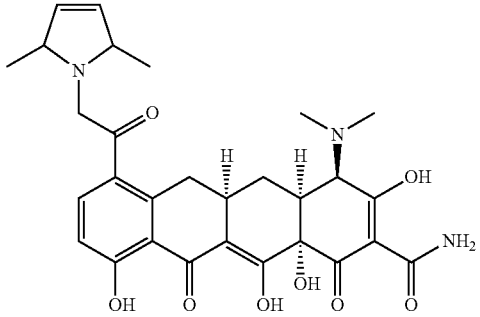 [SMILES: CC1C=CC(C)N1CC(=O)c1ccc(O)c2c1C[C@H]1C[C@H]3[C@@H](N(C)C)C(O)=C(C(N)=O)C(=O)[C@@]3(O)C(O)=C1C2=O] |
| DA | 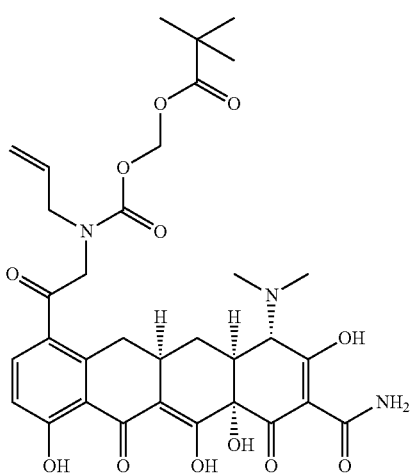 [SMILES: C=CCN(CC(=O)c1ccc(O)c2c1C[C@H]1C[C@H]3[C@H](N(C)C)C(O)=C(C(N)=O)C(=O)[C@@]3(O)C(O)=C1C2=O)C(=O)OCOC(=O)C(C)(C)C] |
| DB | 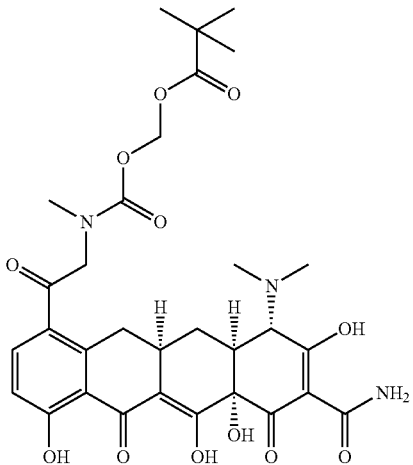 [SMILES: CN(CC(=O)c1ccc(O)c2c1C[C@H]1C[C@H]3[C@H](N(C)C)C(O)=C(C(N)=O)C(=O)[C@@]3(O)C(O)=C1C2=O)C(=O)OCOC(=O)C(C)(C)C] |

TABLE 2-continued

| Code | Compound |
|---|---|
| DC | |
| DD | |
| DE | |
| DF | |
| DG | |

TABLE 2-continued

| Code | Compound |
|---|---|
| DH | (structure) |
| DI | (structure) |
| DJ | (structure) |
| DK | (structure) |
| DL | (structure) |

TABLE 2-continued

| Code | Compound |
|------|----------|
| DM | *(chemical structure)* |
| DN | *(chemical structure)* |
| DO | *(chemical structure)* |
| DP | *(chemical structure)* |
| DQ | *(chemical structure)* |

TABLE 2-continued
| Code | Compound |
|---|---|
| DR | 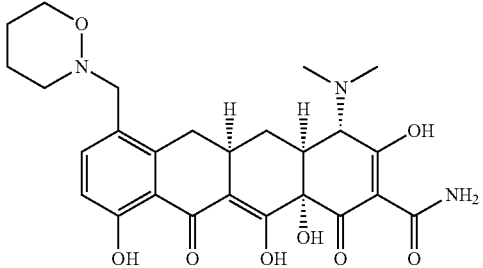 [SMILES: CN(C)[C@@H]1C(O)=C(C(N)=O)C(=O)[C@@]2(O)C(O)=C3C(=O)c4c(O)ccc(CN5CCCCO5)c4C[C@H]3C[C@@H]12] |
| DS | 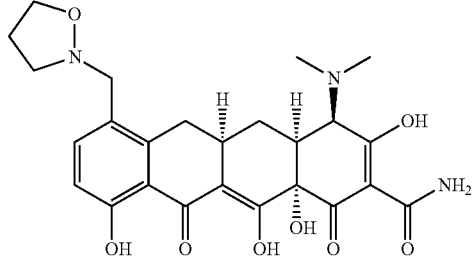 |
| DT | 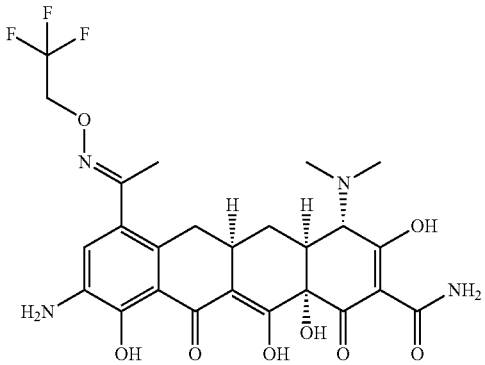 [SMILES: C/C(=N\OCC(F)(F)F)c1cc(N)c(O)c2c1C[C@H]1C[C@H]3[C@H](N(C)C)C(O)=C(C(N)=O)C(=O)[C@@]3(O)C(O)=C1C2=O] |
| DU | 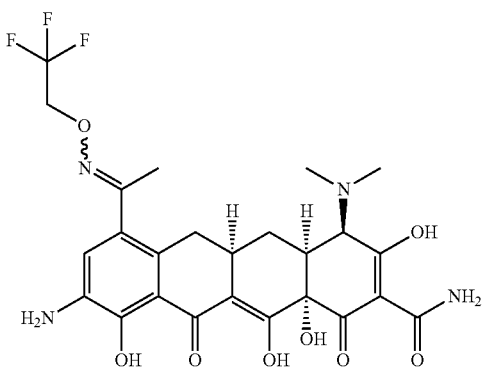 [SMILES: CC(=NOCC(F)(F)F)c1cc(N)c(O)c2c1C[C@H]1C[C@H]3[C@@H](N(C)C)C(O)=C(C(N)=O)C(=O)[C@@]3(O)C(O)=C1C2=O] |

TABLE 2-continued

| Code | Compound |
|------|----------|
| DV | (structure) |
| DW | (structure) |
| DX | (structure) |
| DY | (structure) |

TABLE 2-continued
| Code | Compound |
|---|---|
| DZ | 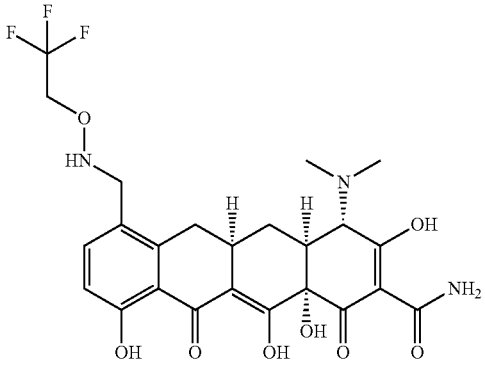 [SMILES: CN(C)[C@@H]1C(O)=C(C(N)=O)C(=O)[C@@]2(O)C(O)=C3C(=O)c4c(O)ccc(CNOCC(F)(F)F)c4C[C@H]3C[C@@H]12] |
| EA | 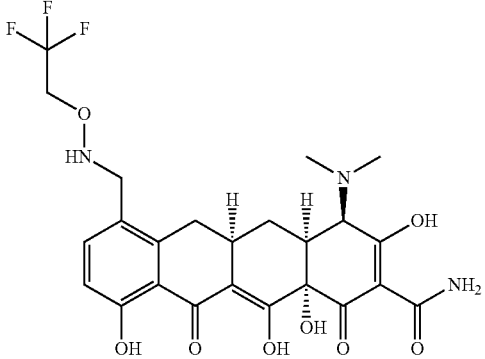 [SMILES: CN(C)[C@H]1C(O)=C(C(N)=O)C(=O)[C@@]2(O)C(O)=C3C(=O)c4c(O)ccc(CNOCC(F)(F)F)c4C[C@H]3C[C@@H]12] |
| EB | 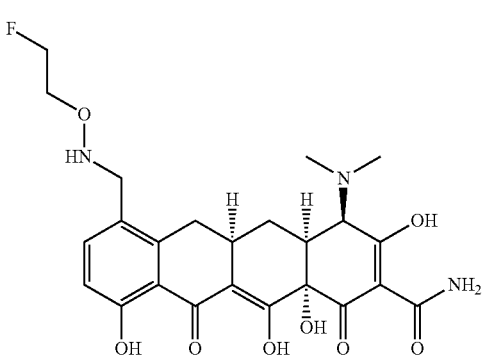 [SMILES: CN(C)[C@H]1C(O)=C(C(N)=O)C(=O)[C@@]2(O)C(O)=C3C(=O)c4c(O)ccc(CNOCCF)c4C[C@H]3C[C@@H]12] |
| EC | 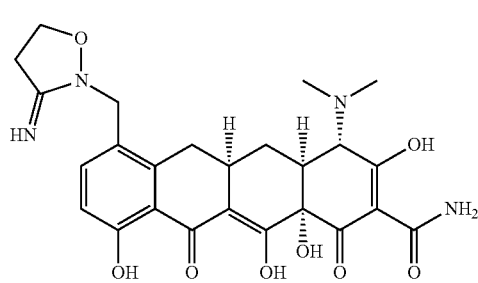 [SMILES: CN(C)[C@@H]1C(O)=C(C(N)=O)C(=O)[C@@]2(O)C(O)=C3C(=O)c4c(O)ccc(CN5OCCC5=N)c4C[C@H]3C[C@@H]12] |

TABLE 2-continued

| Code | Compound |
|------|----------|
| ED | (structure: tetracycline core with 7-position substituent —CH₂—NH—O—CH₂—C(=O)—O—CH₃) |
| EE | (structure: tetracycline core with 7-position substituent —CH₂—NH—O—CHF₂) |
| EF | (structure: tetracycline core with 7-position substituent —CH₂—NH—O—CH₂—C(=O)—OH) |
| EG | (structure: tetracycline core with 7-position substituent —CH₂—NH—O—CH₂—C(=O)—CH₃) |

TABLE 2-continued

| Code | Compound |
|---|---|
| EH | (structure) |
| EI | (structure) |
| EJ | (structure) |
| EK | (structure) |
| EL | (structure) |
| EM | (structure) |

TABLE 2-continued

| Code | Compound |
|---|---|
| EN | |
| EO | |
| EP | |
| EQ | |
| ER | |
| ES | |
| ET | |

TABLE 2-continued

| Code | Compound |
|------|----------|
| EU | |
| EV | |
| EW | |
| EX | |
| EY | |
| EZ | |

TABLE 2-continued
| Code | Compound |
|---|---|
| FA | 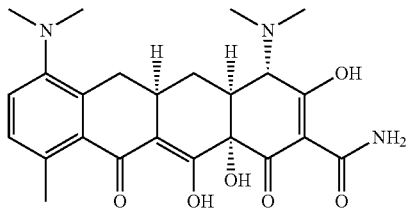 [SMILES: Cc1ccc(N(C)C)c2c1C(=O)C1=C(O)[C@]3(O)C(=O)C(C(N)=O)=C(O)[C@@H](N(C)C)[C@@H]3C[C@@H]1C2] |
| FB | 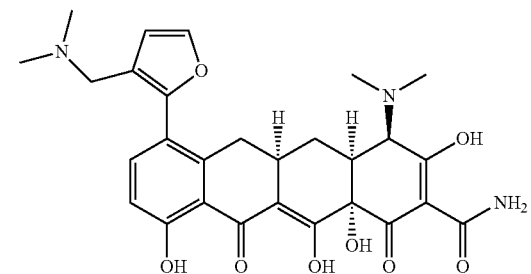 [SMILES: CN(C)Cc1ccoc1-c1ccc(O)c2c1C[C@H]1C[C@H]3[C@@H](N(C)C)C(O)=C(C(N)=O)C(=O)[C@@]3(O)C(O)=C1C2=O] |
| FC | 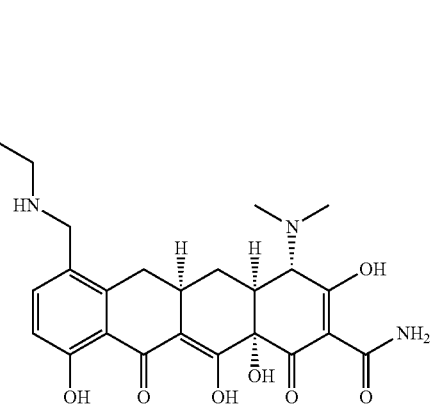 |
| FD | 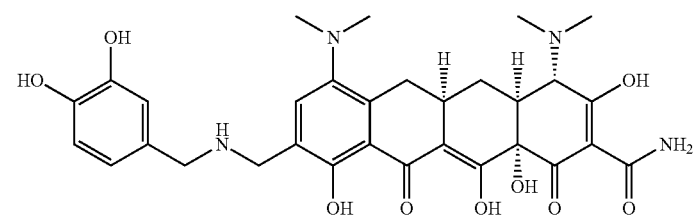 [SMILES: CN(C)c1cc(CNCc2ccc(O)c(O)c2)c(O)c2c1C[C@H]1C[C@H]3[C@H](N(C)C)C(O)=C(C(N)=O)C(=O)[C@@]3(O)C(O)=C1C2=O] |
| FE | 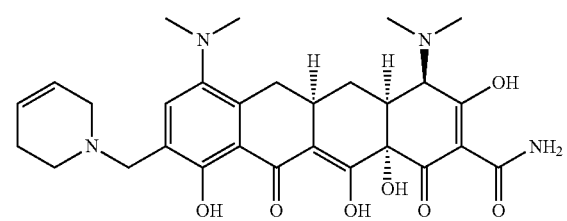 [SMILES: CN(C)c1cc(CN2CC=CCC2)c(O)c2c1C[C@H]1C[C@H]3[C@@H](N(C)C)C(O)=C(C(N)=O)C(=O)[C@@]3(O)C(O)=C1C2=O] |
| FF | 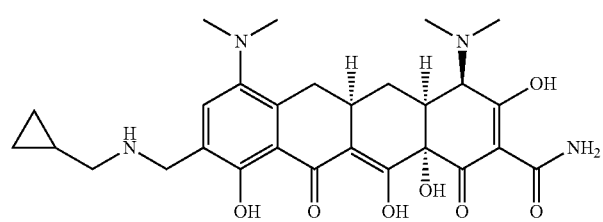 [SMILES: CN(C)c1cc(CNCC2CC2)c(O)c2c1C[C@H]1C[C@H]3[C@@H](N(C)C)C(O)=C(C(N)=O)C(=O)[C@@]3(O)C(O)=C1C2=O] |

TABLE 2-continued
| Code | Compound |
|---|---|
| FG | 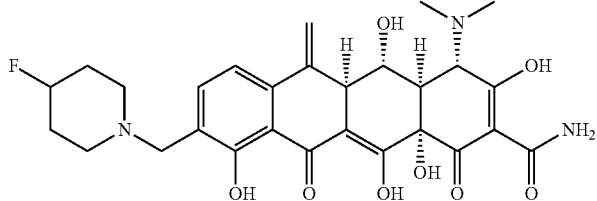 [SMILES: C=C1c2ccc(CN3CCC(F)CC3)c(O)c2C(=O)C2=C(O)[C@]3(O)C(=O)C(C(N)=O)=C(O)[C@@H](N(C)C)[C@@H]3[C@@H](O)[C@H]12] |
| FH | 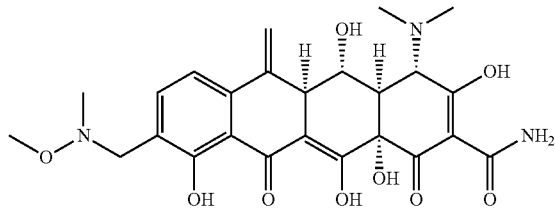 [SMILES: C=C1c2ccc(CN(C)OC)c(O)c2C(=O)C2=C(O)[C@]3(O)C(=O)C(C(N)=O)=C(O)[C@@H](N(C)C)[C@@H]3[C@@H](O)[C@H]12] |
| FI | 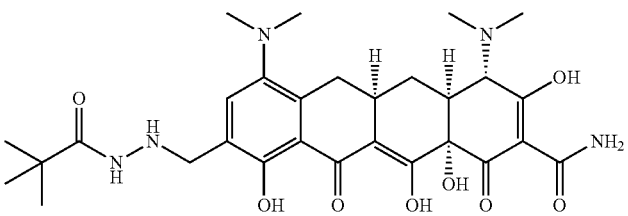 [SMILES: CN(C)c1cc(CNNC(=O)C(C)(C)C)c(O)c2c1C[C@H]1C[C@H]3[C@H](N(C)C)C(O)=C(C(N)=O)C(=O)[C@@]3(O)C(O)=C1C2=O] |
| FJ | 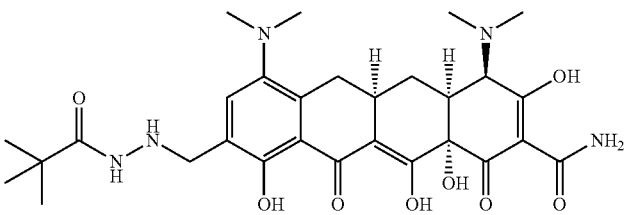 [SMILES: CN(C)c1cc(CNNC(=O)C(C)(C)C)c(O)c2c1C[C@H]1C[C@H]3[C@@H](N(C)C)C(O)=C(C(N)=O)C(=O)[C@@]3(O)C(O)=C1C2=O] |
| FK | 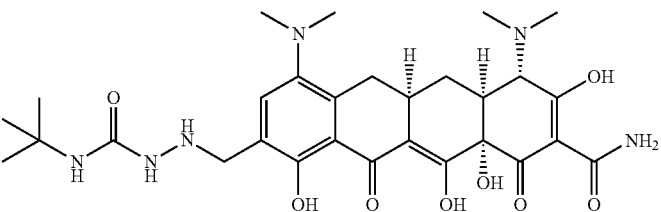 [SMILES: CN(C)c1cc(CNNC(=O)NC(C)(C)C)c(O)c2c1C[C@H]1C[C@H]3[C@H](N(C)C)C(O)=C(C(N)=O)C(=O)[C@@]3(O)C(O)=C1C2=O] |
| FL | 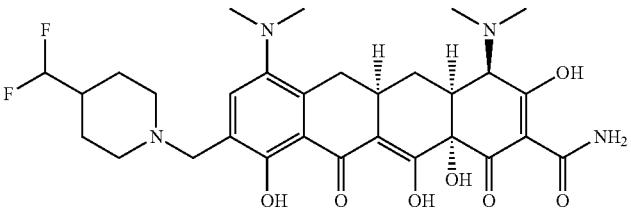 [SMILES: CN(C)c1cc(CN2CCC(C(F)F)CC2)c(O)c2c1C[C@H]1C[C@H]3[C@@H](N(C)C)C(O)=C(C(N)=O)C(=O)[C@@]3(O)C(O)=C1C2=O] |
| FM | 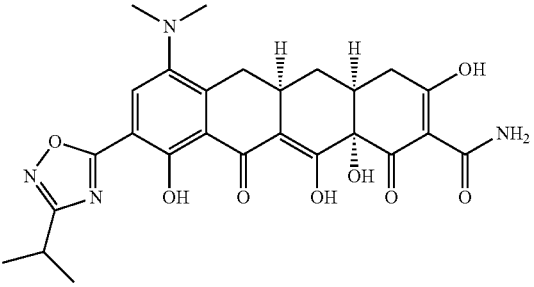 |

TABLE 2-continued

| Code | Compound |
|---|---|
| FN | (structure) |
| FO | (structure) |
| FP | (structure) |
| FQ | (structure) |
| FR | (structure) |
| FS | (structure) |

TABLE 2-continued

| Code | Compound |
|---|---|
| FT | (structure) |
| FU | (structure) |
| FV | (structure) |
| FW | (structure) |
| FX | (structure) |
| FY | (structure) |
| FZ | (structure) |

TABLE 2-continued
| Code | Compound |
|---|---|
| GA | 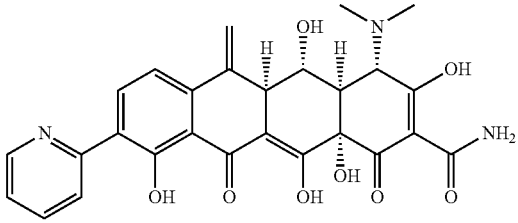 [SMILES: C=C1c2ccc(-c3ccccn3)c(O)c2C(=O)C2=C(O)[C@]3(O)C(=O)C(C(N)=O)=C(O)[C@@H](N(C)C)[C@@H]3[C@@H](O)[C@H]12] |
| GB | 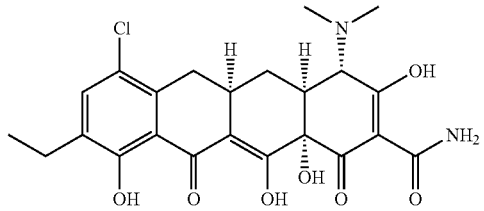 [SMILES: CCc1cc(Cl)c2c(c1O)C(=O)C1=C(O)[C@]3(O)C(=O)C(C(N)=O)=C(O)[C@@H](N(C)C)[C@@H]3C[C@@H]1C2] |
| GC | 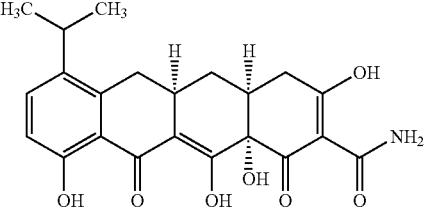 [SMILES: CC(C)c1ccc(O)c2c1C[C@H]1C[C@H]3CC(O)=C(C(N)=O)C(=O)[C@@]3(O)C(O)=C1C2=O] |
| GD | 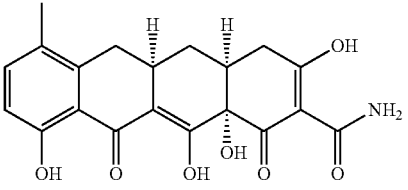 [SMILES: Cc1ccc(O)c2c1C[C@H]1C[C@H]3CC(O)=C(C(N)=O)C(=O)[C@@]3(O)C(O)=C1C2=O] |
| GE | 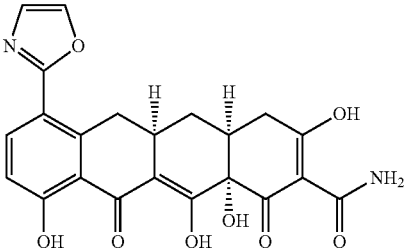 [SMILES: NC(=O)C1=C(O)C[C@@H]2C[C@@H]3Cc4c(-c5ncco5)ccc(O)c4C(=O)C3=C(O)[C@]2(O)C1=O] |
| GF | 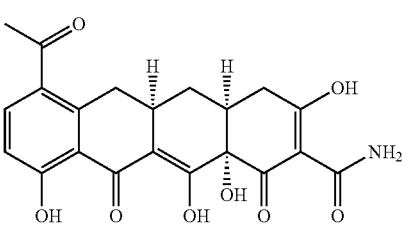 [SMILES: CC(=O)c1ccc(O)c2c1C[C@H]1C[C@H]3CC(O)=C(C(N)=O)C(=O)[C@@]3(O)C(O)=C1C2=O] |
| GH | 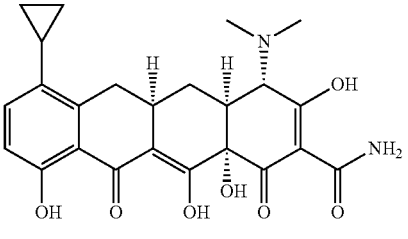 [SMILES: CN(C)[C@@H]1C(O)=C(C(N)=O)C(=O)[C@@]2(O)C(O)=C3C(=O)c4c(O)ccc(C5CC5)c4C[C@H]3C[C@@H]12] |

TABLE 2-continued

| Code | Compound |
|---|---|
| GI | (structure) |
| GK | (structure) |
| GL | (structure) |
| GM | (structure) |
| GN | (structure) |
| GO | (structure) |
| GP | (structure) |

TABLE 2-continued

| Code | Compound |
|------|----------|
| GQ | |
| GR | |
| GS | |
| GT | |
| GU | |

TABLE 2-continued

| Code | Compound |
|---|---|
| GV | |

EXEMPLIFICATION OF THE INVENTION

Example 1

Synthesis of Select Compounds of the Invention

3-[3-((6aS,10S,10aS,11aR)-8-Carbamoyl-10-dimethylamino-4,6,6a,9-tetrahydroxy-5,7-dioxo-5,6a,7,10,10a,11,11a,12-octahydro-naphthacen-1-yl)-benzoylamino]-propionic acid ethyl ester (Compound AV)

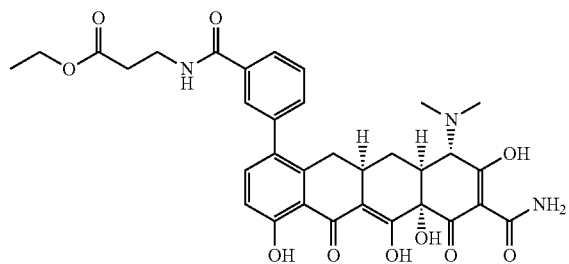 [SMILES: CCOC(=O)CCNC(=O)c1cccc(-c2ccc(O)c3c2C[C@H]2C[C@H]4[C@H](N(C)C)C(O)=C(C(N)=O)C(=O)[C@@]4(O)C(O)=C2C3=O)c1]

An amount 1.00 g of 7-iodosancycline trifluoroacetic acid salt, 177 mg of palladium (0) tetrakistriphenylphosphine, 35 mg of palladium (II) acetate and 457 mg of ethyl 3-(3-borobenzoylamino)propionate, 98% were loaded in a dry 20 mL microwave reaction vessel equipped with a magnetic stir bar. Dry dimethylacetamide (DMA, 10 mL) was added and argon was bubbled through the solution for 5 minutes. In a separate vial, sodium acetate (487 mg) was dissolved in distilled water (5 mL) and argon was bubbled through the solution for 5 minutes. The sodium acetate solution was added to the microwave reaction vessel which was sealed with a crimper. The reaction mixture was then subjected to microwave irradiation for 10 minutes at 110° C., and the reaction was monitored by LC/MS. The reaction mixture was filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to a minimum volume. The residue was then purified by preparative HPLC chromatography (C18, linear gradient 27-32% acetonitrile in water with 0.2% formic acid). The fractions were evaporated and the resulting residue was purified again by preparative HPLC chromatography (C18, linear gradient 20-35% acetonitrile in 20 mM aqueous triethanolamine, pH 7.4) in order to separate the 4-epimers. The fractions were collected and the organic solvent was evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 634 (MH+). $^1$H-NMR (300 MHz, tetramethylsilane (TMS) as internal standard at 0 ppm): δ 7.78 (dm, 1H), 7.70 (m, 1H), 7.51 (t, 1H), 7.45 (d, 2H), 6.92 (d, 1H), 4.13 (q, 2H), 4.00 (s, 1H), 3.63 (t, 2H), 2.97-2.80 (m, 8H), 2.77 (dd, 1H), 2.64 (t, 2H), 2.52 (t, 1H), 2.08-1.95 (m, 1H), 1.53 (q, 1H), 1.23 (t, 3H). Compounds AO, AP, AQ, AR, AS, AT, AU, AW, AX, AY, AZ, BA, BB, DK, DL, DM, DN, DO and DP were prepared in a similar manner.

(4S,4aS,5aR,12aS)-7-[3-(2-Diethylamino-ethylcarbamoyl)-phenyl]-4-dimethylamino-3,10,12,12a-tetrahydroxy-1,11-dioxo-1,4,4a,5,5a,6,11,12a-octahydro-naphthacene-2-carboxylic acid amide (Compound BC)

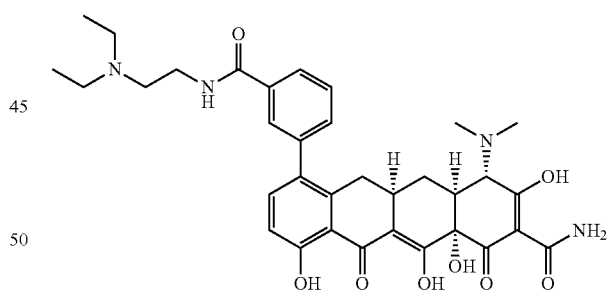

An amount of 2.5 g of 7-iodosancycline trifluoroacetic acid salt, 221 mg of palladium (0) tetrakistriphenylphosphine, 43 mg of palladium (II) acetate and 777 mg of 3-carboxy-phenylboronic acid were loaded in a dry 20 mL microwave reaction vessel equipped with a magnetic stir bar. Dry DMA (13 mL) was added and argon was bubbled through the solution for 5 minutes. In a separate vial, sodium acetate (105.99 g/mol, 1.215 g, 11.46 mmol, 3.0 eq.) was dissolved in distilled water (7 mL) and argon was bubbled through the solution for 5 minutes. The sodium acetate solution was added to the microwave reaction vessel, which was sealed with a crimper. The reaction mixture was then subjected to microwave irradiation for 10 minutes at 110° C., and the reaction was monitored by LC/MS. The reaction mixture was filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to dryness to yield an orange solid, which was used in the next step without further purification.

An amount of 340 mg of 7-(3-carboxy-phenyl)-sancycline TFA salt and 212 mg of O-benzotriazol-1-yl-N,N,N'N'-tetramethyluronium hexafluoro-phosphate were loaded in a dry 10 mL vial equipped with a magnetic stir bar. Dry DMA (2.5 mL) was added, followed by diisopropylethylamine (180 μL). After 5 minutes of stirring at room temperature, N,N-diethylethylenediamine, 98% (150 μL) was added, the reaction mixture was stirred at room temperature for 15 minutes and the reaction was monitored by LC/MS. The mixture was filtered through celite, evaporated in a rotary evaporator, and the residue was purified by preparative HPLC chromatography (C18, linear gradient 25-35% acetonitrile in water with 0.2% formic acid). The fractions were combined, evaporated, and the resulting residue was purified again by preparative HPLC chromatography (C18, linear gradient 20-35% acetonitrile in 20 mM aqueous triethanolamine, pH 7.4) in order to separate the 4-epimers. The fractions were collected and the organic solvent evaporated. The resulting aqueous solution was loaded on a DVB column, washed with DI water, and then washed with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 633 (MH+). $^1$H-NMR (300 MHz, tetramethylsilane (TMS) as internal standard at 0 ppm): δ 7.87 (dm, 1H), 7.79 (m, 1H), 7.60-7.47 (m, 2H), 7.44 (d, 1H), 6.93 (d, 1H), 4.02 (s, 1H), 3.76 (t, 2H), 3.45-3.30 (m, 6H), 3.02-2.85 (m, 8H), 2.78 (dd, 1H), 2.54 (t, 1H), 2.10-1.95 (m, 1H), 1.53 (q, 1H), 1.35 (t, 6H). Compounds BD, BE, BF, BG, BH, BI, BJ, BK and DQ were prepared in a similar manner.

(4S,4aS,5aR,12aS)-4,7-Bis-dimethylamino-9-[3-(2-dimethylamino-ethylcarbamoyl)-phenyl]-3,10,12,12a-tetrahydroxy-1,11-dioxo-1,4,4a,5,5a,6,11,12a-octahydro-naphthacene-2-carboxylic acid amide (Compound BL)

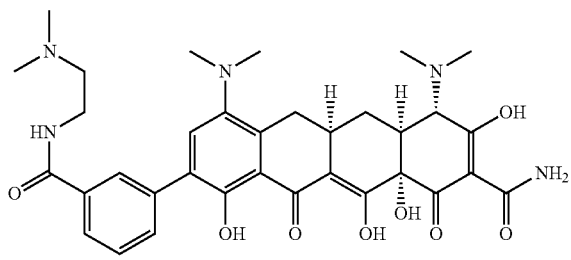 [SMILES: CN(C)CCNC(=O)c1cccc(-c2cc(N(C)C)c3c(c2O)C(=O)C2=C(O)[C@]4(O)C(=O)C(C(N)=O)=C(O)[C@@H](N(C)C)[C@@H]4C[C@@H]2C3)c1]

An amount of 500 mg of 9-iodo-minocycline free base, 100 mg of palladium (0) tetrakis triphenylphosphine, 20 mg of palladium (II) acetate and 234 mg of [3-(3-N,N-dimethylaminoetylaminocarbonyl)-phenyl]-boronic acid were loaded in a dry 20 mL microwave reaction vessel equipped with a magnetic stir bar. Dry DMA (4 mL) was added and argon is bubbled through the solution for 5 minutes. In a separate vial, sodium acetate (274 mg) was dissolved in DI water (2 mL) and argon was bubbled through the solution for 5 minutes. The sodium acetate solution was added to the microwave reaction vessel, which was sealed with a crimper. The reaction mixture was then subjected to microwave irradiation for 10 minutes at 110° C., and the reaction was monitored by LC/MS. The reaction mixture was filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to a minimum volume. The residue was then purified by HPLC chromatography (C18, linear gradient 10-20% acetonitrile in water with 0.2% formic acid). The fractions were combined, evaporated, and the resulting residue was purified again by preparative HPLC chromatography (C18, linear gradient 10-20% acetonitrile in 20 mM aqueous triethanolamine, pH 7.4) in order to separate the 4-epimers. The fractions were collected and the organic solvent evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 648 (MH+). $^1$H-NMR (300 MHz, tetramethylsilane (TMS) as internal standard at 0 ppm): δ 8.26 (t, 1H), 8.16 (s, 1H), 7.94 (m, 2H), 7.59 (t, 1H), 4.19 (s, 1H), 3.82 (t, 2H), 3.50-3.30 (m, 9H), 3.30-3.10 (m, 2H), 3.10-2.90 (m, 9H), 2.62 (t, 1H), 2.42-2.30 (m, 1H), 1.71 (q, 1H). Compound BM was prepared in a similar manner.

4aS,5aR,12aS)-7-[3-(2-Dimethylamino-ethylcarbamoyl)-phenyl]-3,10,12,12a-tetrahydroxy-1,11-dioxo-1,4,4a,5,5a,6,11,12a-octahydro-naphthacene-2-carboxylic acid amide (Compound BN)

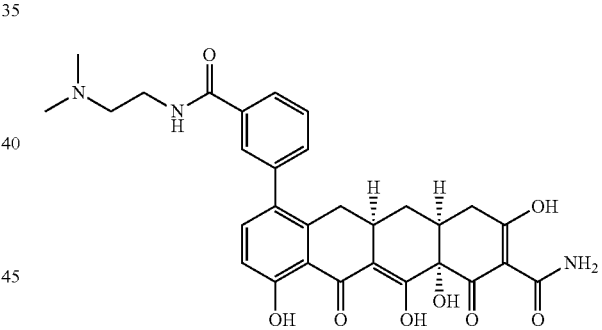

An amount of 1.00 g of 7-iodo-4-dedimethyl-sancycline free base, 233 mg of palladium (0) tetrakis triphenylphosphine, 45 mg of palladium (II) acetate and 544 mg of [3-(3-N,N-dimethylaminoethylaminocarbonyl)-phenyl]-boronic acid were loaded in a dry 20 mL microwave reaction vessel equipped with a magnetic stir bar. Dry DMA (8 mL) was added and argon was bubbled through the solution for 5 minutes. In a separate vial, sodium acetate (640 mg) was dissolved in distilled water (4 mL) and argon was bubbled through the solution for 5 minutes. The sodium acetate solution was added to the microwave reaction vessel, which was sealed with a crimper. The reaction mixture was then subjected to microwave irradiation for 10 minutes at 110° C. and the reaction was monitored by LC/MS. The reaction mixture was filtered through a pad of celite and washed with methanol. After evaporation of organic solvents, the aqueous solution was purified on a fluorinated DVB (DiVinylBenzene) column with gradients of a 50/50 methanol/acetonitrile, 0.1% TFA solution into a 0.1% TFA water solution. The fractions were collected and evaporated to a minimum volume. The residue was then purified by preparative HPLC chromatography (C18, linear gradient 20-35% acetonitrile in water with 0.2% formic acid). The fractions were combined, evaporated, and the resulting residue was purified again by preparative HPLC chromatography (C18, linear gradient 15-35% acetonitrile in 20 mM aqueous triethanolamine, pH 7.4) in order to separate the 4-epimers. The fractions were collected and the organic solvent evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 562 (MH+). 1H-NMR (300 MHz, tetramethylsilane (TMS) as internal standard at 0 ppm): δ 7.87 (dm, 1H), 7.78 (s, 1H), 7.60-7.45 (m, 2H), 7.41 (d, 1H), 6.90 (d, 1H), 3.76 (m, 2H), 3.38 (t, 2H), 3.21 (dd, 1H), 2.98 (s, 6H), 2.85-2.62 (m, 2H), 2.57-2.22 (m, 3H), 1.90-1.80 (m, 1H), 1.48 (q, 1H).

(4S,4aS,5aR,12aS)-4-Dimethylamino-7-[3-(2-dimethylamino-acetylamino)-phenyl]-3,10,12,12a-tetrahydroxy-1,11-dioxo-1,4,4a,5,5a,6,11,12a-octahydro-naphthacene-2-carboxylic acid amide (Compound BO)

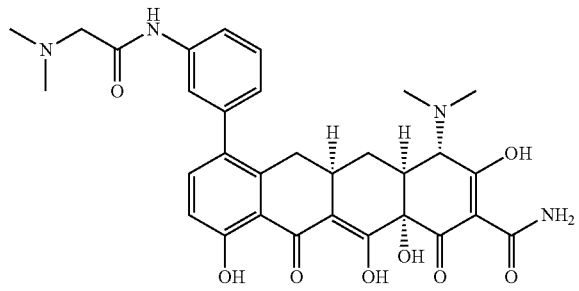 [SMILES: CN(C)CC(=O)Nc1cccc(-c2ccc(O)c3c2C[C@H]2C[C@H]4[C@H](N(C)C)C(O)=C(C(N)=O)C(=O)[C@@]4(O)C(O)=C2C3=O)c1]

An amount of 2.50 g of 7-iodosancycline trifluoroacetic acid salt, 221 mg palladium (0) tetrakis triphenylphosphine, 42 mg of palladium (II) acetate, and 812 mg of 3-aminophenylboronic acid were loaded in a dry 20 mL microwave reaction vessel equipped with a magnetic stir bar. Dry DMA (13 mL) was added and argon was bubbled through the solution for 5 minutes. In a separate vial, sodium acetate (1.22 g) was dissolved in distilled water (7 mL) and argon was bubbled through the solution for 5 minutes. The sodium acetate solution was added to the microwave reaction vessel, which was sealed with a crimper. The reaction mixture was then subjected to microwave irradiation for 20 minutes at 120° C., and the reaction was monitored by LC/MS. The reaction mixture was then filtered through a pad of celite and washed with methanol. After evaporation of organic solvents, the aqueous solution was purified on a fluorinated DVB (Di-VinylBenzene) column with gradients of a 50/50 methanol/acetonitrile, 0.1% TFA solution into a 0.1% TFA water solution. The fractions were collected and evaporated to dryness to yield a brown solid which is used in the next step without further purification.

An amount of 250 mg of 7-(3-amino-phenyl)-sancycline TFA salt and 250 µL of diisopropylethylamine were loaded into a dry 5 mL microwave reaction vessel equipped with a magnetic stir bar. After 5 minutes of stirring, dimethylamino acetyl chloride, 85% (667 mg) was added, the reaction vessel was sealed, the reaction mixture was subjected to microwave irradiation for 5 minutes at 100° C. and the reaction was monitored by LC/MS. The mixture was filtered through celite, evaporated in a rotary evaporator, and the residue was purified by preparative HPLC chromatography (C18, linear gradient 10-30% acetonitrile in water with 0.2% formic acid). The fractions were combined, evaporated, and the resulting residue was purified again by preparative HPLC chromatography (C18, linear gradient 15-25% acetonitrile in 20 mM aqueous triethanolamine, pH 7.4) in order to separate the 4-epimers. The fractions were collected and the organic solvent evaporated. The resulting aqueous solution was loaded on a DVB column, washed with distilled water, and then with a 0.1% hydrochloric acid solution. After eluting with a 50/50 mixture of methanol and acetonitrile, the solution was evaporated and the residue dried under high vacuum and $P_2O_5$ overnight to yield a yellow solid as an HCl salt. ESIMS: m/z 591 (MH+). 1H-NMR (300 MHz, tetramethylsilane (TMS) as internal standard at 0 ppm): δ 7.56 (m, 2H), 7.45-7.32 (m, 2H), 7.07 (d, 1H), 6.91 (d, 2H), 4.15 (s, 2H), 4.04 (s, 1H), 3.20-2.70 (m, 15H), 2.48 (t, 1H), 2.04 (m, 1H), 1.51, (m, 1H). Compound BP was prepared in a similar manner.

(4S,4aS,5aR,12aS)-4-Dimethylamino-3,10,12,12a-tetrahydroxy-7-[methoxy-methyl-amino)-methyl]-1,11-dioxo-1,4,4a,5,5a,6,11,12a-octahydro-naphthacene-2-carboxylic acid amide (Compound P)

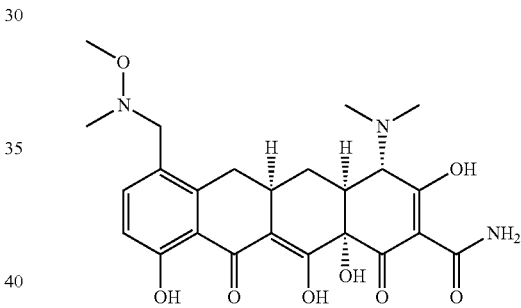

A solution of 7-formylsanscycline TFA salt (2.23 g) and N,O-dimethylhydroxylamine hydrochloride (780 mg) in N,N-dimethylacetamide (15 mL) was stirred for 10 minutes at room temperature under argon atmosphere. To this solution was added sodium cyanoborohydride (302 mg). The solution was stirred for 5 minutes and monitored by LC-MS. The reaction mixture was poured into diethyl ether, and the resulting precipitates were collected by filtration under vacuum. The crude product was purified by preparative HPLC (C18 column, linear gradient 10-40% acetonitrile in 20 mM aqueous triethanolamine, pH 7.4). The prep-HPLC fractions were collected, and the organic solvent (acetonitrile) was evaporated in vacuo. The resulting aqueous solution was loaded onto a clean PDVB SPE column, washed with distilled water, then with a 0.1 M sodium acetate solution followed by distilled water. The product was eluted with 0.1% TFA in acetonitrile. After concentrating under vacuum, 565 mg was obtained as a TFA salt. The TFA salt was converted to the hydrochloride salt by adding methanolic HCl followed by in vacuo evaporation. This process was repeated twice to give a yellow solid. ESIMS: m/z 488 (MH+). $^1$H NMR (300 MHz, $CD_3OD$) δ 7.46 (1H, J=8.6 Hz), 6.81 (d, 1H, J=8.6 Hz), 4.09 (d, 1H, J=1.0 Hz), 3.79 (d, 1H, J=13.1 Hz), 3.73 (d, 1H, J=13.1 Hz), 3.36 (m, 1H), 3.27 (s, 3H), 3.08-2.95 (8H), 2.61 (s, 3H), 2.38 (t, 1H, J=14.8), 2.22 (m, 1H), 1.64 (m, 1H).

Compounds Y, U and DR were prepared in a similar manner, and compound DS may be synthesized in a similar manner.

4S,4aS 5aR,12aS)-4Dimethylamino-9-[(2,2-dimethyl-propylamino)-methyl]-7-1-ethoxyimino-ethyl-3,10,12,12a-tetrahydroxy-1,11-dioxo-1,4,4a,5,5a,6,11,12a-octahydro-naphthacene-2-carboxylic acid amide (Compound N)

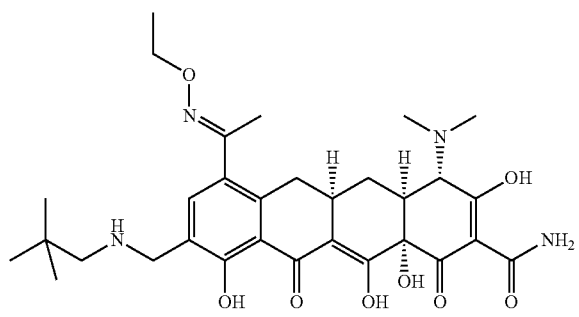 [SMILES: CCO/N=C(\C)c1cc(CNCC(C)(C)C)c(O)c2c1C[C@H]1C[C@H]3[C@H](N(C)C)C(O)=C(C(N)=O)C(=O)[C@@]3(O)C(O)=C1C2=O]

A solution of 7-acetyl-9-[(2,2-dimethylpropylamino)-methyl]-sancycline (0.383 mmol) and O-ethylhydroxylamine hydrochloride (2.30 mmol) in methanol (15 mL) was stirred overnight. The solvent was evaporated and purified by prep-HPLC (C18 column (linear gradient 15-30% acetonitrile in water with 0.1% TFA) to give a yellow solid. ESIMS: m/z 599 (MH+); $^1$H NMR (300 MHz, CD$_3$OD) δ 7.60 (s, 1H), 4.33 (s, 2H), 5.06 (m, 2H), 4.16 (2H, q, J=7.0 Hz), 4.08 (s, 1H), 3.11-2.90 (11H), 2.52 (m, 1H), 2.18 (m, 1H), 2.15 (s, 3H), 1.28 (3H, t, J=7.0 Hz), 1.06 (s, 9H).

(4S,4aS,5aR,12aS)-9-Amino-7-(1-tert-butoxyimino-ethyl)-4-dimethylamino-3,10,12,12a-tetrahydroxy-1,11-dioxo-1,4,4a,5,5a,6,11,12a-octahydro-naphthacene-2-carboxylic acid amide (Compound Q)

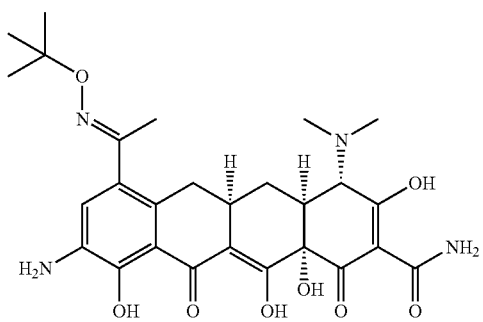 [SMILES: C/C(=N\OC(C)(C)C)c1cc(N)c(O)c2c1C[C@H]1C[C@H]3[C@H](N(C)C)C(O)=C(C(N)=O)C(=O)[C@@]3(O)C(O)=C1C2=O]

A solution of 7-acetyl-9-aminosancycline hydrochloride (0.79 mmol) and O-tert-butylhydroxylamine hydrochloride (4.74 mmol) in methanol (10 mL) was stirred overnight. The methanol was evaporated and the resulting compound purified by prep-HPLC using C18 column (linear gradient 15-35% acetonitrile in water with 0.1% TFA) to give a yellow solid: ESIMS m/z 543 (MH+); $^1$HNMR (300 MHz, CD$_3$OD) ε☐7.54 (s, 1H), 4.14 (s, 1H), 3.14-2.99 (9H), 2.52 (m, 1H), 2.20 (m, 1H), 2.16 (s, 3H), 1.32 (s, 9H). Compounds M and R were prepared in a similar manner and compound DU may be prepared in a similar manner.

(4S,4aS,5aR,12aS)-9-Amino-4-dimethylamino-3,10,12,12a-tetrahydroxy-1,1,1-dioxo-7-[1-(2,2,2-trifluoro-ethoxyimino)-ethyl]-1,4,4a,5,5a,6,11,12a-octahydro-naphthacene-2-carboxylic acid amide (Compound DT)

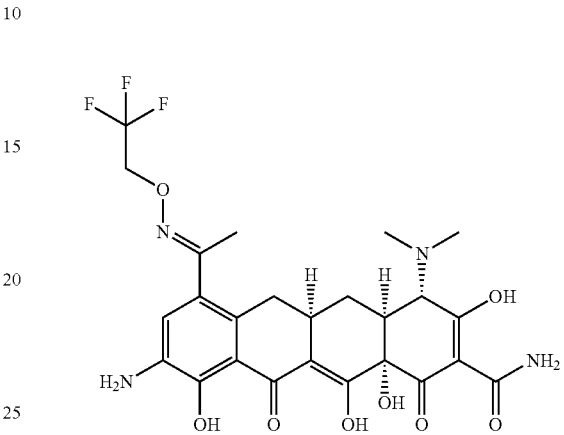

A solution of 7-acetyl-9-amino-sancycline (1.5 mmol) and 2,2,2-trifluoroethylhydroxylamine hydrochloride (3 mmol) in methanol (20 mL) was stirred overnight. The methanol was reduced and the crude product was purified by prep-HPLC using C18 column (linear gradient 10-35% acetonitrile in water with 0.1% TFA) to give a yellow solid: MS (Mz+1=569); $^1$H NMR (300 MHz, CD$_3$OD) δ 7.48 (s, 1H), 4.63 (d, 1H, J=8.9 Hz), 4.57 (d, 1H, J=8.9 Hz), 4.12 (☐☐d, 1H, J=0.9 Hz), 3.10-2.96 (9H), 2.50 (m, 1H), 2.22 (s, 3H), 2.18 (m, 1H), 1.62 (m, 1H). Compounds M and R were prepared in a similar manner and compound DU may be prepared in a similar manner.

(4S,4aS,5aR,12aS)-4-Dimethylamino-7-(ethoxyamino-methyl)-3,10,12,12a-tetrahydroxy-1,11-dioxo-1,4,4a,5,5a,6,11,12a-octahydro-naphthacene-2-carboxylic acid amide (Compound AA)

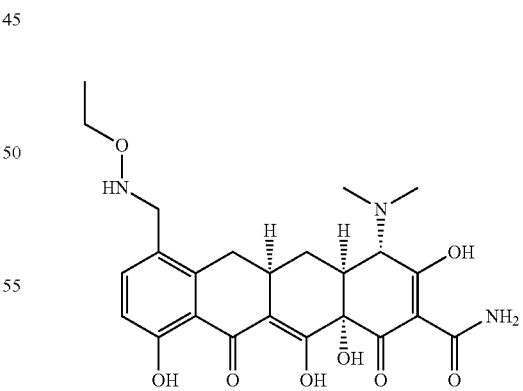

An amount of 7-formyl-sancycline (1.5 g) was combined with methanol (30 mL) and O-(ethoxy)methylamine (1.5 g). The reaction solution was stirred at room temperature for 3 hours under a blanket of argon and was monitored by HPLC and LC/MS. The solvent was evaporated in vacuo and a yellow solid (2.3 g) was isolated as an oxime. ESIMS: m/z 485 (MH+).

The oxime (2.3 g) was suspended in methanol saturated with HCl (45 mL) and cooled in an ice bath. An amount of 585 mg of NaCNBH₃ was added in small batches followed by a few drops of methanol saturated with HCl via syringe. The reducing agent was added over the course of 2 hours and the reaction was monitored by HPLC and LC/MS. The solvent was evaporated in vacuo and was purified. The compound purified by HPLC (C18, linear gradient 10-45% acetonitrile in 20 mM aqueous triethanolamine, pH 7.4). The purified compound was dried in vacuo and redissolved in methanol (20 mL) saturated with HCl to exchange the salt. The compound was dried overnight over P₂O₅ to yield the product (0.21 mg, 13%) as a yellow powder. ESIMS: m/z 488 (MH+). ¹H NMR (300 MHz, CD₃OD) δ 7.63 (1H, d, J=9 Hz), 6.93 (1H, d, J=9 Hz), 4.53 (s, 1H), 4.17 (m, 3H), 3.25 (m, 1H), 3.07 (m, 8H), 2.44 (m, 1H), 2.31 (m, 1H), 1.62 (m, 1H), 1.29 (3H, t, J=7 Hz). Compounds AM, AB, AE, AF and AG were prepared in a similar manner.

(4S,4aS,5aR,12aS-4-Dimethylamino-3,10,12,12a-tetrahydroxy-7-isopropoxyamino-methyl)-1,11-dioxo-1,4,4a,5,5a,6,11,12a-octahydro-naphthacene-2-carboxylic acid amide (Compound DV)

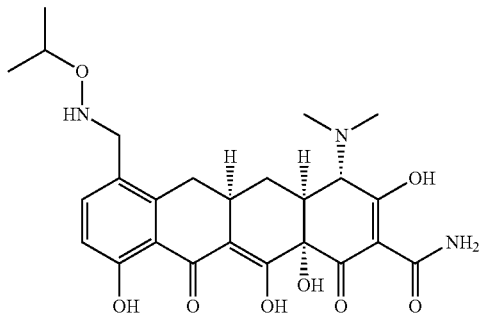 [SMILES: CC(C)ONCc1ccc(O)c2c1C[C@H]1C[C@H]3[C@H](N(C)C)C(O)=C(C(N)=O)C(=O)[C@@]3(O)C(O)=C1C2=O]

A solution of 7-formylsancycline (1.8 mmol) and O-isopropylhydroxylamine hydrochloride (9 mmol) in methanol (25 mL) was stirred overnight. The solvent was reduced and the crude product was used for the next reaction without further purification. A solution of 7-(isopropoxyimino-methyl)-sancycline (2 mmol) in methanol saturated with HCl was cooled in an ice-bath and NaCNBH₃ was added portion-wise while stirring at the same temperature. The solvent was evaporated and the crude product was purified by prep-HPLC using C18 column (linear gradient 15-30% acetonitrile in 20 mM aqueous triethanolamine, pH 7.4) to give a yellow solid: MS (Mz+1=502); ¹H NMR (300 MHz, CD₃OD) δ 7.63 (d, 1H, J=8.7 Hz), 6.92 (d, 1H, J=8.7 Hz), 4.44 (m, 1H), 4.14 (d, 1H, J=1.2 Hz), 3.27-2.97 (9H), 2.43 (t, 1H, J=14.4), 2.27 (m, 1H), 1.29 (m, 6H). Compounds AM, AB, AE, AF, AG, DX, DZ, EA, EB and ED were prepared in a similar manner and compounds EE and EF may be synthesized in a similar manner.

(4S,4aS,5aR,12aS)-4-Dimethylamino-7-[(2-fluoro-ethoxyamino)-methyl]-3,10,12,12a-tetrahydroxy-1,11-dioxo-1,4,4a,5,5a,6,11,12a-octahydro-naphthacene-2-carboxylic acid amide (Compound DW)

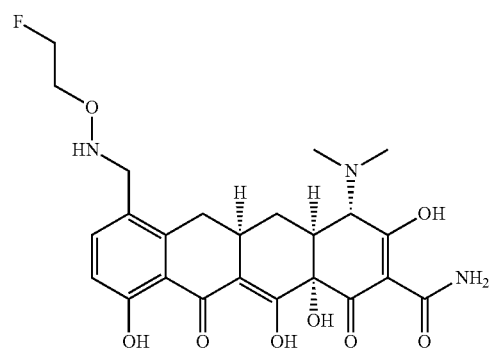 [SMILES: CN(C)[C@@H]1C(O)=C(C(N)=O)C(=O)[C@@]2(O)C(O)=C3C(=O)c4c(O)ccc(CNOCCF)c4C[C@H]3C[C@@H]12]

A solution of 7-formylsancyline (4 mmol) and 2-fluoroethylhydroxylamine hydrochloride (10 mmol) in methanol (50 mL) was stirred overnight, after which LC-MS showed completion of the reaction. The solvent was reduced and the crude product was used for the next reaction without further purification. To a cooled solution of 7-(2'-fluoro-ethoxyimino-methyl)-sancycline (2 mmol) in methanol saturated with HCl was added portion-wise NaCNBH₃ (8 mmol) over 8 hours while stirring at the same temperature. The solvent was reduced and the crude product was purified by prep-HPLC using C18 column (linear gradient 10-40% acetonitrile in 20 mM aqueous triethanolamine, pH 7.4) to give a yellow solid: MS (Mz+1=506); ¹H NMR (300 MHz, CD₃OD) δ 7.65 (d, 1H, J=8.8 Hz), 6.93 (d, 1H, J=8.8 Hz), 4.75 (m, 1H), 4.61-4.55 (3H), 4.46 (m, 1H), 4.36 (m, 1H), 4.16 (d, 1H, J=1.2 Hz), 3.26-2.97 (9H), 2.45 (t, 1H, J=14.4), 2.31 (m, 1H), 1.63 (m, 1H). Compounds AM, AB, AE, AF, AG, DX, DZ, EA, EB and ED were prepared in a similar manner and compounds EE and EF may be synthesized in a similar manner.

4S,4aS,5aR,12aS)-4-Dimethylamino-3,10,12,12a-tetrahydroxy-7-(3-imino-isoxazolidin-2-ylmethyl)-1,11-dioxo-1,4,4a,5,5a,6,11,12a-octahydro-naphthacene-2-carboxylic acid amide (Compound EC)

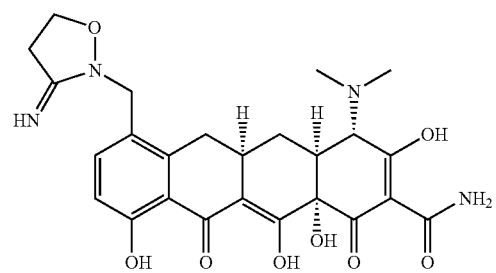 [SMILES: CN(C)[C@@H]1C(O)=C(C(N)=O)C(=O)[C@@]2(O)C(O)=C3C(=O)c4c(O)ccc(CN5OCCC5=N)c4C[C@H]3C[C@@H]12]

A solution of 7-formylsancycline (2 mmol) and 3-aminooxy-propionnitrile (4 mmol) in methanol (30 mL) was stirred overnight. The solvent was reduced and the crude product was used for the next reaction without further purification. A solution of 7-(2'-cyanoethoxyimmuno-methyl)-sancycline in methanol and HCl was cooled with an ice-bath and NaCNBH$_3$ was added portion-wise and stirred for 1.5 hours. The solvent was evaporated and the compound was purified by prep-HPLC using C-18 column (linear gradient 10-40% acetonitrile in 20 mM aqueous triethanolamine, pH 7.4) to give a yellow solid: MS (Mz+1=513); $^1$H NMR (300 MHz, CD$_3$OD) δ 7.47 (d, 1H, J=8.8 Hz), 6.86 (d, 1H, J=8.8 Hz), 5.11 (d, 1H, J=15.9 Hz), 4.96 (d, 1H, J=15.9 Hz), 4.41 (m, 2H), 4.11 (s, 1H), 3.50 (t, 2H, J=8.4 Hz), 3.20-2.94 (9H), 2.38 (t, 1H, J=15.3 Hz), 2.28 (m, 1H), 1.60 (m, 1H). Compounds AM, AB, AE, AF, AG, DX, DZ, EA, EB and ED were prepared in a similar manner and compounds EE and EF may be synthesized in a similar manner.

(4S,4aS,5aR,12aS)-4-Dimethylamino-3,12,12a-trihydroxy-1,11-dioxo-7-pyrazin-2-yl-1,4,4a,5,5a,6,11,12a-octahydro-naphthacene-2-carboxylic acid amide (Compound W)

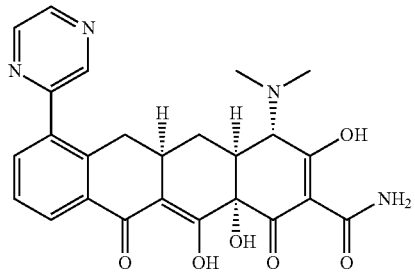 [SMILES: CN(C)[C@@H]1C(O)=C(C(N)=O)C(=O)[C@@]2(O)C(O)=C3C(=O)c4cccc(-c5cnccn5)c4C[C@H]3C[C@@H]12]

An amount of 7-iodo-sancycline (1 g) was combined with CuI (0.029 g), Pd$_2$(dba)$_3$ (0.140 g), tri-2-furylphosphine (0.284 g), 2-tributylstannylpyrazine (0.677 g), and DMF (6 mL) in a 20 mL glass microwave vial. The reaction mixture was subjected to microwave irradiation for 10 minutes at 100° C. on high absorbance, and was monitored by HPLC and LC/MS. The solvent was evaporated in vacuo and the free-base of the above compound was made by pouring 8 g of product into 1.8 L water (0.1% TFA). Celite was added, and material was filtered through a celite plug. The water filtrate was loaded onto a prepared DVB column, and washed with water (0.1% TFA), 0.25 M NaOAc until a basic pH was obtained. The DVB column was then washed with distilled water until a neutral pH was obtained, and the compound was then eluted as the free-base with CH$_3$CN.

The resulting 7-pyrazine-sancycline-free base (1 g) was combined with dry THF (15 mL) and the reaction solution was cooled in an ice bath under a blanket of argon. Potassium t-butoxide (1.17 g) was added in one addition. The resulting heterogeneous mixture was stirred in an ice bath for 45 minutes. An amount of N-phenylbis(trifluoromethanesulfonamide) (1.49 g) was added in one addition. The resulting solution was stirred in an ice bath for 45 minutes, then was warmed to room temperature and stirred another 1 hour. The reaction monitored by HPLC and LC/MS. The reaction mixture was poured into 200 mL 0.5M HCl, celite was added, and mixture was filtered through a celite plug. The water filtrate was loaded onto a prepared DVB column, washed with 0.5M HCl, water, then eluted with CH$_3$CN (0.1% TFA). The product was evaporated to dryness and purified by HPLC (C18, linear gradient 5-45% acetonitrile in water with 0.1% TFA). Clean fractions were evaporated to dryness.

The resulting 7-pyrazine-10-triflate-sancycline (0.220 g) was combined with ammonium formate (0.112 g), lithium chloride (0.074 g), Pd$_2$(dppf)$_2$Cl$_2$ (0.052 g) DMA (1.5 mL) and water (1.5 mL) in a glass microwave vial, which was then purged with argon and microwave irradiated for 10 minutes at 100° C. on high absorbance. The reaction was monitored by HPLC and LC/MS and was poured into 100 mL water (0.1% TFA), and filtered through celite. The yellow eluent was loaded onto a prepared 2 g DVB cartridge and eluted with CH$_3$CN (0.1% TFA). The solvent was evaporated and purified by HPLC (C18, linear gradient 5-45% acetonitrile in water with 0.1% TFA). The purified compound was dried in vacuo, redissolved in methanol (20 mL) saturated with HCl and dried overnight over P$_2$O$_5$ to yield the product (0.035 g, 16%) as a yellow powder. ESIMS: m/z 477 (MH+). $^1$HNMR (300 MHz, CD$_3$OD) δ 8.77 (m, 1H), 8.71 (m, 1H), 8.63 (m, 1H), 8.14 (m, 1H), 7.71 (m, 1H), 7.57 (m, 1H), 3.99 (m, 1H), 2.97 (m, 9H), 2.63 (m, 1H), 2.04 (m, 1H), 1.62 (m, 1H). Compounds D, E, F, G and S were prepared in a similar manner.

(4S,4aS,5aR,12aS)-4-Dimethylamino-3,10,12,12a-tetrahydroxy-1,11-dioxo-7-(1H-pyrrol-2-yl)-1,4,4a,5,5a,6,11,12a-octahydro-naphthacene-2-carboxylic acid amide (Compound T)

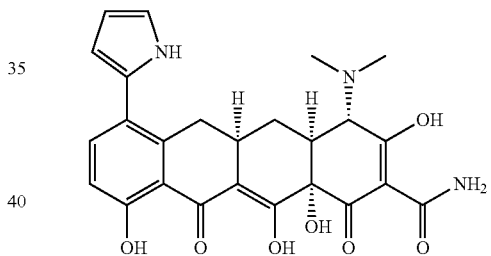

An amount of 7-iodo-sancycline (1 g) was combined with Pd(OAc)$_2$ (0.034 g), methanol (1 mL), and DMF (2 mL) in a glass microwave vial and the reaction mixture was purged with argon. An amount of Na$_2$CO$_3$ (0.482 g) was dissolved in water (1 mL) and was added to the reaction vessel. An amount of 1-N-Boc-pyrrole-2-boronic acid (0.645 g) was dissolved in DMF (1 mL) and added to the reaction vessel. The resulting mixture was microwave irradiated for 10 minutes at 100° C. and the reaction was monitored by HPLC and LC/MS. The reaction mixture was filtered through celite, and solvent was reduced in vacuo. The crude reaction mixture was then precipitated in 500 mL diethyl ether to yield a yellow precipitate, which was then filtered, rinsed with fresh diethyl ether, and dried under vacuum, to yield 700 mg of a yellow solid. The yellow solid was added to TFA (10 mL) and stirred at room temperature 5 minutes, followed by evaporation of the solvent. The resulting material was purified by HPLC (C18, linear gradient 15-50% acetonitrile in water with 0.1% TFA), dried in vacuo, redissolved in methanol (20 mL) saturated with HCl and dried overnight over P$_2$O$_5$ to yield the product (0.020 g, 3%) as a yellow powder. ESIMS: m/z 480 (MH+). $^1$H NMR (300 MHz, CD$_3$OD) δ 7.53 (1H, d, J=9 Hz), 6.87 (1H, d, J=9 Hz), 6.80 (m, 1H), 6.16 (m, 1H), 6.08 (m, 1H), 4.06 (s, 1H), 3.18 (m, 1H), 2.98 (m, 9H), 2.49 (m, 1H), 2.09 (m, 1H), 1.61 (m, 1H). Compounds J, K and L were prepared in a similar manner.

(4R,4aS,5aR,12aS)-4-Dimethylamino-7-(3-dimethylamino-1-ethoxyimino-propyl)-3,10,12,12a-tetrahydroxy-1,11-dioxo-1,4,4a,5,5a,6,11,12a-octahydro-naphthacene-2-carboxylic acid amide (Compound AN)

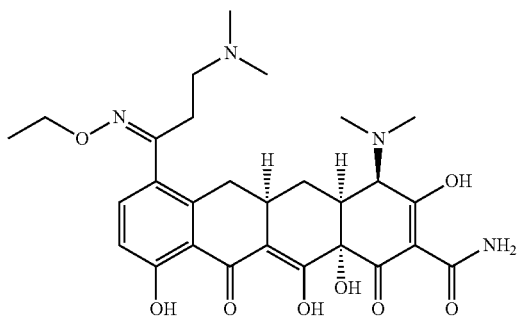 [SMILES: CCO/N=C(/CCN(C)C)c1ccc(O)c2c1C[C@H]1C[C@H]3[C@@H](N(C)C)C(O)=C(C(N)=O)C(=O)[C@@]3(O)C(O)=C1C2=O]

A solution of 7-(3'-dimethylamino-propionyl)-sancycline (5.12 mmol) and O-ethoxylamine hydrochloride (41 mmol) in N,N-dimethylacetamide was stirred at 80° C. under microwave conditions for 70 minutes. The product was purified by prep-HPLC using a C18 column (linear gradient 10-40% acetonitrile in water with 0.1% TFA) to give a yellow solid: ESIMS: m/z 557 (MH+); $^1$HNMR (300 MHz, CD$_3$OD) δ 7.39 (m, 1H), 6.91 (m, 1H), 4.86 (1H, d, J=3.9 Hz), 4.26-4.08 (m, 2H), 3.5 (m, 1H), 3.30-2.87 (18H), 2.50 (m, 1H), 2.20 (m, 1H), 1.56 (m, 1H), 1.36-1.19 (m, 3H). Compound O was also prepared in this manner.

(4S,4aS,5aR,12aS)-4-Dimethylamino-3,10,12,12a-tetrahydroxy-1,11-dioxo-7-(pyrrol-1-yliminomethyl)-1,4,4a,5,5a,6,11,12a-octahydro-naphthacene-2-carboxylic acid amide (Compound AC)

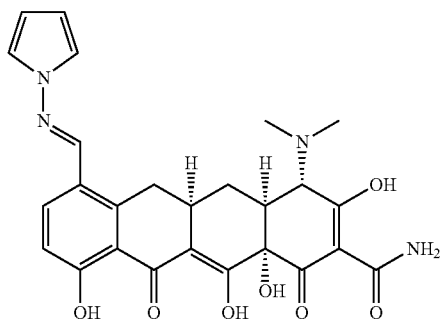 [SMILES: CN(C)[C@@H]1C(O)=C(C(N)=O)C(=O)[C@@]2(O)C(O)=C3C(=O)c4c(O)ccc(/C=N/n5cccc5)c4C[C@H]3C[C@@H]12]

An amount of 7-formyl sancycline (0.4 g) was combined with 1-amino pyrrole (0.223 g) and DMA (8 mL) and was stirred at room temperature under a blanket of argon for 30 minutes. The reaction was monitored by HPLC and LC/MS. The crude reaction mixture was poured into water (0.1% TFA) (100 mL) and loaded onto a prepared 5 g DVB cartridge. The loaded cartridge was washed with water, then eluted with CH$_3$CN (0.1% TFA) and the product was purified by HPLC (C18, linear gradient 10-70% acetonitrile in 20 mM aqueous triethanolamine, pH 7.4). The purified compound was dried in vacuo, redissolved in methanol (20 mL) saturated with HCl and was dried overnight over P$_2$O$_5$ to yield the product (0.035 g, 8%) as a yellow powder. ESIMS: m/z 507 (MH+). $^1$H NMR (300 MHz, CD$_3$OD) δ 8.78 (s, 1H), 8.12 (1H, d, J=9 Hz), 7.23 (2H, t, J=3 Hz), 6.93 (1H, d, J=9 Hz), 6.17 (2H, t, J=3 Hz), 4.08 (s, 1H), 3.54 (m, 1H), 2.97 (m, 9H), 2.47 (m, 1H), 2.24 (m, 1H), 1.65 (m, 1H). Compound X was also prepared in this manner.

(4S,4aS,5aR,12aS)-7-(N,N"-Diethyl-hydrazinomethyl)-4-dimethylamino-3,10,12,12a-tetrahydroxy-1,11-dioxo-1,4,4a,5,5a,6,11,12a-octahydro-naphthacene-2-carboxylic acid amide (Compound Z)

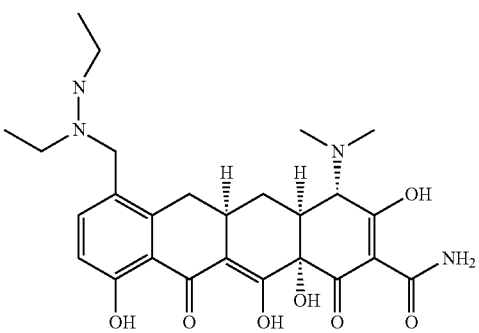 [SMILES: CCNN(CC)Cc1ccc(O)c2c1C[C@H]1C[C@H]3[C@H](N(C)C)C(O)=C(C(N)=O)C(=O)[C@@]3(O)C(O)=C1C2=O]

An amount of 7-formyl sancycline (0.5 g) was combined with 1,2-diethylhydrazine (0.546 g), triethylamine (0.472 g) and DMA (10 mL) and was stirred at room temperature under a blanket of argon 45 minutes. An amount of NaCNBH$_3$ (0.084 g) was added to reaction mixture and stirred overnight at room temperature. Reaction monitored by HPLC and LC/MS and complete by morning. Poured reaction mixture into water (0.1% TFA), loaded onto a prepared 5 g DVB cartridge, and eluted with CH$_3$CN (0.1% TFA). Compound purified by HPLC (C18, linear gradient 5-60% acetonitrile in 20 mM aqueous triethanolamine, pH 7.4). Purified compound was dried in vacuo and redissolved in methanol (20 mL) saturated with HCl to exchange the salt. The compound was dried overnight over P$_2$O$_5$ to yield the product (0.030 g, 6%) as a yellow powder. ESIMS: m/z 515 (MH+). $^1$H NMR (300 MHz, CD$_3$OD) δ 7.53 (1H, d, J=9 Hz), 6.87 (1H, d, J=9 Hz), 4.18 (m, 1H), 4.06 (s, 2H), 3.19 (m, 1H), 3.00 (m, 10H), 2.40 (m, 1H), 2.20 (m, 1H), 1.64 (m, 1H), 1.24 (3H, t, J=9 Hz), 1.13 (m, 3H).

Allyl-(6aS,10S,10aS,11aR)-8-carbamoyl-10-dimethylamino-4,6,6a,9-tetrahydroxy-5,7-dioxo-5,6a,7,10,10a,11,11a,12-octahydro-naphthacen-1-ylmethyl)-carbamic acid methyl ester (Compound F)

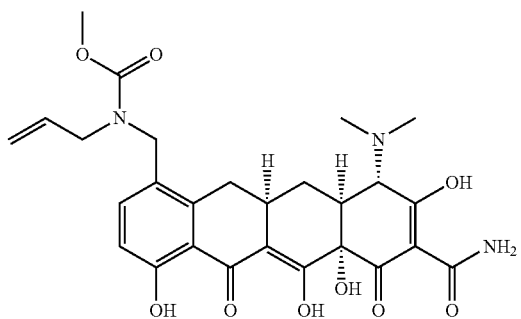 [SMILES: C=CCN(Cc1ccc(O)c2c1C[C@H]1C[C@H]3[C@H](N(C)C)C(O)=C(C(N)=O)C(=O)[C@@]3(O)C(O)=C1C2=O)C(=O)OC]

A solution of 7-formylsancycline (1.5 mmol) and allylamine (4.5 mmol) in 1,2-dichloroethane (50 mL) was stirred for 30 minutes. Sodium triacetoxyborohydride was added and stirred for additional 3 hours. The solvent and excess reagent was evaporated and the crude material was purified by prep-HPLC using C18 column (linear gradient 15-30 acetonitrile in water with 0.2% formic acid) to give 7-allylaminomethyl-sancycline as a yellow solid: ESIMS: m/z 484 (MH+).

To a solution of 7-allylaminomethyl-sancycline (0.78 mmol) in N,N-dimethylacetamide (7 mL) was added methylchloroformate (1.6 mmol) dropwise and the reaction mixture was stirred for 1 hour. An additional amount of methylchloroformate (1.6 mmol) was added and stirred for additional 3 hours. The resulting product was purified by prep prep-HPLC using C18 column (linear gradient 15-30 acetonitrile in water with 0.2% formic acid) to give a yellow solid: ESIMS: m/z 542 (MH+); $^1$H NMR (300 MHz, CD$_3$OD) δ 7.34 (1H, d, J=8.5 Hz), 6.82 (1H, d, J=8.5 Hz), 5.71 (m, 1H), 5.06 (m, 2H), 4.47 (m, 2H), 4.08 (1H, d, J=0.9 Hz), 3.84-3.65 (m, 2H), 3.71 (s, 3H), 3.21-2.92 (9H), 2.30-1.94 (2H), 1.59 (m, 1H).

(4S,4aS,5aR,12aS)-4,7-Bis-dimethylamino-3,10,12,12a-tetrahydroxy-9-(methoxyimino-methyl)-1,11-dioxo-1,4,4a,5,5a,6,11,12a-octahydro-naphthacene-2-carboxylic acid amide (Compound V)

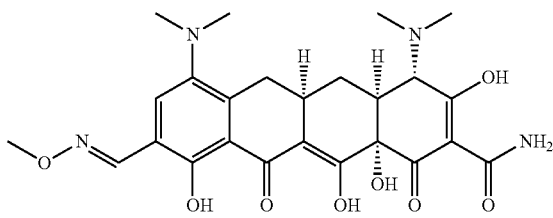 [SMILES: CO/N=C/c1cc(N(C)C)c2c(c1O)C(=O)C1=C(O)[C@]3(O)C(=O)C(C(N)=O)=C(O)[C@@H](N(C)C)[C@@H]3C[C@@H]1C2]

A solution of 9-formylminocycline (1.19 mmol) and O-methylhydroxylamine hydrochloride (5.96 mmol) in methanol (15 mL) was stirred for 1.5 hours. The solvent was evaporated and purified by prep-HPLC using C18 column (linear gradient 10-50% acetonitrile in 20 mM aqueous triethanolamine, pH 7.4) to give a yellow solid: ESIMS m/z 515 (MH+); $^1$H NMR (300 MHz, CD$_3$OD) δ 8.42 (s, 1H), 8.09 (s, 1H), 4.13 (1H, d, J=1.2 Hz), 3.99 (s, 3H), 3.35 (m, 1H), 3.09-2.98 (14H), 2.43 (m, 1H), 2.24 (m, 1H), 1.69 (m, 1H). Compounds AK and AH may be prepared as described above.

(4S,4aS,5aR,12aS)-4-Dimethylamino-3,10,12,12a-tetrahydroxy-7-(2-methylamino-3,4-dioxo-cyclobut-1-enyl)-1,11-dioxo-1,4,4a,5,5a,6,11,12a-octahydro-naphthacene-2-carboxylic acid amide (Compound AD)

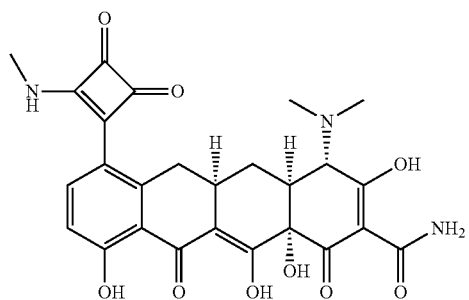 [SMILES: CNc1c(-c2ccc(O)c3c2C[C@H]2C[C@H]4[C@H](N(C)C)C(O)=C(C(N)=O)C(=O)[C@@]4(O)C(O)=C2C3=O)c(=O)c1=O]

A mixture of 7-iodosancycline (2 mmol), 3-isopropooxy-4-tributylstannanyl-cyclobut-3-ene-1,2-dione (4.4 mmol), tetrakis(triphenylphosphine)palladium (0.4 mmol) and CuI (0.4 mmol) in N,N-dimethylacetamide was microwave irradiated for 50 minutes at 80° C. The resulting compound was purified using a DVB column to give 7-(2'-isopropoxy-3',4'-dioxo-cyclobut-1'-enyl)-sancycline as a yellow solid::ESIMS m/z 553 (MH+).

To a solution of 7-(2'-isopropoxy-3',4'-dioxo-cyclobut-1'-enyl)-sancycline (0.9 mmol) in methanol (20 mL) was added 1 mL of 33% methylamine in absolute ethanol and the reaction mixture was stirred for 40 minutes. The resulting product was purified prep-HPLC using C18 column (linear gradient 10-40% acetonitrile in 20 mM aqueous triethanolamine, pH 7.4) to give a yellow solid: ESIMS m/z 524 (MH+); $^1$H NMR (300 MHz, CD$_3$OD) δ 7.46 (1H, d, J=8.7 Hz), 6.88 (1H, d, J=8.7 Hz), 4.01 (s, 1H), 3.27 (s, 3H), 3.07-2.82 (9H), 2.45 (m, 1H), 2.10 (m, 1H), 1.52 (m, 1H). Compounds AI and AJ may be prepared in this manner.

(4S,4aS,5aR,12aS)-4-Dimethylamino-7-[(2-ethoxy-imino-propyl)-methyl-amino]-methyl-3,10,12,12a-tetrahydroxy-1,11-dioxo-1,4,4a,5,5a,6,11,12a-octahydro-naphthacene-2-carboxylic acid amide (Compound AL)

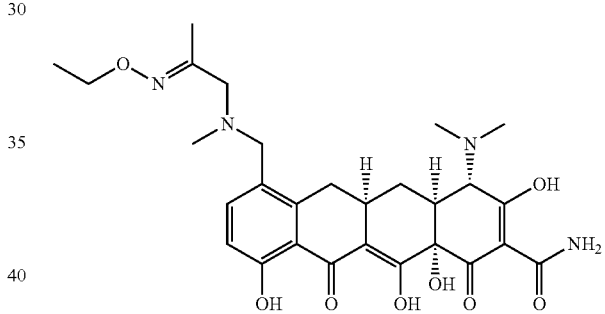

A solution of 7-formylsancycline (2 mmol) and methyl-(2-methyl-[1,3]dioxolan-2-ylmethyl)-amine (6 mmol) in N,N-dimethylformamide (30 mL) was stirred for 40 minutes. Sodium triacetoxyborohydride (6 mmol) was added and the reaction was stirred for 6 hours. The solvent was evaporated and the crude material was dissolved in a mixture of tetrahydrofuran (10 mL), acetic acid (10 mL) and 6M HCl (10 mL). This solution was stirred at 60° C. for 6 hours. Upon completion, the solvent and excess reagents were evaporated and the crude material was purified by prep-HPLC using C18 column (linear gradient 20-50% acetonitrile in 20 mM aqueous triethanolamine, pH 7.4) to give 7-{[(methyl-2'-oxo-propyl)-methyl-amino]-methyl}-sancycline as a yellow solid: ESIMS m/z 514 (MH+).

A solution of 7-{[methyl-(2'-oxo-propyl)-amino]-methyl}-sancycline (0.63 mmol) and O-ethylhydroxyamine hydrochloride (3.15 mmol) in methanol (15 mL) was stirred for 8 hours. The solvent was evaporated and purified by prep-HPLC using C18 column (linear gradient 20-50% acetonitrile in 20 mM aqueous triethanolamine, pH 7.4) to give a yellow solid: ESIMS m/z 557 (MH+); $^1$H NMR (300 MHz, CD$_3$OD) δ 7.69 (1H, d, J=8.7 Hz), 6.99 (1H, d, J=8.7 Hz), 4.65 (m, 1H), 4.35 (m, 1H), 4.24 (2H, q, J=7.1 Hz), 4.15

(s, 1H), 4.07 (brs, 2H), 3.24-2.85 (12H), 2.50 (m, 1H), 2.30 (m, 1H), 1.95 (s, 3H), 1.52 (m, 1H), 1.31 (3H, t, J=7.1 Hz).

(4aS,5aR,12aS)-7-Dimethylamino-3,10,12,12a-tetrahydroxy-1,11-dioxo-1,4,4a,5,5a,6,11,12a-octahydro-naphthacene-2,9-dicarboxylic acid 2-amide 9-(hydroxy-methyl-amide) 4-dedimethylamino-minocycline-9-N-methylhydroxamic acid (Compound CC)

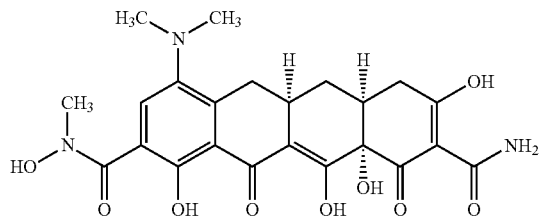 [SMILES: CN(O)C(=O)c1cc(N(C)C)c2c(c1O)C(=O)C1=C(O)[C@]3(O)C(=O)C(C(N)=O)=C(O)C[C@@H]3C[C@@H]1C2]

Minocycline/HCl salt (200 g, 0.406 mol) was suspended in 3 L water and an amount of NaHCO₃ (34 g, 0.406 mol) was added in 3 portions and the pH was adjusted to 6.5-7.0. The solution was then extracted with 2×1.5 L CH₂Cl₂. The solution was concentrated to dryness to give minocycline as the freebase, then redissolved in THF (1.6 L) and was charged in a 3 L 3-necked flask equipped with an over-head stirrer and a temperature probe while under argon. An amount of methyl iodide (289 g, 2.03 mol) was added and the solution was heated at 40-45° C. for approximately 16 hours, at which point it was verified by HPLC that no minocycline was left in solution. The solution was then poured into 6 L of heptane while on ice bath and stirred for at least 20 minutes at <5° C. The precipitate was filtered and washed with hexane (400 mL). The solid was dried under reduced pressure to a constant weight. An amount of 186 g methylammonium salt of minocycline was isolated.

In a 3 L, 3-necked RBF equipped with overhead stirrer and a temperature probe a mixture of 200 ml DMF, 50 ml TFA, and 15 ml water was cooled on an ice bath to <5° C. An amount of 4-methylammonium minocycline (100 g) was added to the flask. Upon dissolution, Zn powder (14 g, 100 mesh) was added in 6 portions approximately every 30 minutes (~2.33 g each addition). The reaction was monitored by HPLC. When less than approximately 10% of 4-trimethyammonium minocycline remained, the solution was filtered through a bed of Celite and was washed with 500 mL water. The solution was then poured into 2 L of water and the pH was adjusted with aqueous ammonia to a pH of 3.5. The aqueous solution was extracted first with 1 L dichloromethane (two times) and the combined organic layers were back-washed with 1 L water, dried on sodium sulfate, filtered and concentrated under reduced pressure down to an oil, to yield 4-dedimethylamino minocycline (48 g).

An amount of 4-dedimethyl minocycline (48 g, 0.115 mol) was charged in a flask under argon atmosphere and methanesulfonic acid (350 mL) was added. Ag₂SO₄ (75 g, 0.24 mol) and iodine (61.5 g, 0.24 mol) were added and the mixture was stirred for 3 hours. Upon HPLC confirming completion of the reaction, the mixture was poured into 4% aqueous sodium sulfite (3.5 L) and was stirred for at least one hour. The solution was filtered through a bed of Celite, then washed with 200 ml of water. The aqueous layer was loaded onto a column containing divinylbenzyl resin. A gradient of 20-60% organic (1:1 methanol:acetonitrile) in water with an overall trifluoroacetic acid of 1.0% was used to elute compound 4-dedimethylamine-9-iodo minocycline. The combined fractions were reduced of organic, the pH adjusted with aqueous NaHCO₃ to a pH of 7 and extracted with methylene chloride to give 20 g of 4-dedimethylamine-9-iodo minocycline as the freebase.

To a 500 mL flask was added (2.00 g) 4-dedimethylamino-9-iodo minocycline free base and NMP (37 mL), N-hydroxysuccinimide (3.9 g). To remove residual water from the above reactants, toluene was added (37 mL), the flask was placed on the rotary evaporator (35 mm Hg, 45° C.) until all the toluene was evaporated. The flask was backfilled with argon and the contents were then transferred via cannula to a dry 500 L flask. To the 500 mL flask was added tetrakis-(triphenylphosphine)palladium(0) (2.00 g) and DIEA (2.60 mL). The flask was placed under vacuum (20 mm Hg) and purged 3 times with carbon monoxide. The flask was then heated to 60° C. under 1.0 atm of carbon monoxide and let stir for 1 hour. Subsequently, methylhydroxylamine (1.7 mL) and DIEA (0.5 mL) was added and the reaction was heated in a microwave reactor for 1 minute at 100° C. The reaction was added to water (1.0 L) and the pH was lowered to 2 using trifluoroacetic acid. The solution was then filtered through celite, loaded onto a reverse phase column and the crude product was purified by reverse phase HPLC (C18, linear gradient 10-30% MeCN in water with 0.1% TFA). The fractions containing the final product were loaded onto DVB plug, washed with aqueous HCl (1.0 L, 0.01 N) and eluted with acetonitrile to give the HCl salt of 4-dedimethylamino-9-N-methylhydroxamic acid minocycline (1000 mg, 44%). ¹H-NMR (300 MHz, chemical shifts in ppm with TMS as internal reference at 0 ppm) δ 1.5-1.7 (m, 1H), 2.1-2.25 (m, 1H), 2.35-2.7 (m, 3H), 2.9-3.1 (m, 1H), 3.2-3.3 (brs, 7H), 3.35 (s, 2H), 3.45 (s, 2H), 7.91 (s, 1H). MW calcd for C₂₃H₂₅N₃O₉ 487.46, ESIMS obs. m/z 488.25 (MH+). Compounds BQ, BR, BS, BT, BU, BV, BW, BX, BY, BZ, CA, CB, CD, CE, CF, EJ, EK and EM were prepared as described above.

(4aS,5aR,12aS)-7-Dimethylamino-3,10,12,12a-tetrahydroxy-1,11-dioxo-1,4,4a,5,5a,6,11,12a-octahydro-naphthacene-2,9-dicarboxylic acid 2-amide 9-tert-butylamide (Compound EI)

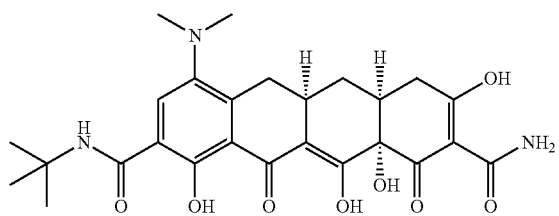 [SMILES: CN(C)c1cc(C(=O)NC(C)(C)C)c(O)c2c1C[C@H]1C[C@H]3CC(O)=C(C(N)=O)C(=O)[C@@]3(O)C(O)=C1C2=O]

To a 500 mL flask was added (2.00 g, 4.30 mmol) 4-dedimethylamine-9-iodo minocycline free base (see synthesis of compound CC), NMP (37 mL), N-hydroxysuccinimide (3.9 g, 38 mmol). To remove residual water from the above reactants toluene was added (37 mL), the flask was placed on the rotary evaporator (5 mm Hg, 45° C.) until all the toluene was evaporated. The flask was backfilled with argon and the contents were then transferred via cannula to a dry 500 L flask. To the 0.5 L flask was added tetrakis(triphenylphosphine)palladium(0) (2.00 g, 1.67 mmol) and DIEA (2.60 mL, 1.48 mmol). The flask was placed under vacuum (20 mm Hg) and purged 3 times with carbon monoxide. The flask was then heated to 60° C. under 1.0 atm of carbon monoxide and let stir for 1 hour until all 4-dedimethlyamino-9-iodo minocycline was consumed and a peak for the corresponding NHS-ester intermediate (M+1) of 556 M/Z was formed as determined via LCMS. Subsequently, tert-butylamine (4.0 mL, 38 mmol) and DIEA (4.0 mL, 38 mmol) was added and the reaction was heated in a microwave reactor for 1 minute at 100 C. The reaction was added to acetonitrile (150 mL) followed by water (0.8 L) and the pH was lowered to pH 2 using trifluoroacetic acid. The solution was then filtered through celite to remove the catalyst, loaded onto a reverse phase column and the crude product was purified by HPLC (C18, linear gradient 30-45% acetonitrile in water with 0.2% Formic acid). The fractions containing the final product were loaded onto DVB plug, washed with aqueous HCl (1.0 L, 0.01 N) and eluted with methanol to give the HCl salt of 4-dedimethyl-9-tertbutylcarboxamido minocycline (500 mg, 0.91 mmol, 20%). $^1$H-NMR (300 MHz, chemical shifts in ppm with TMS as internal reference at 0 ppm) δ 1.4 (s, 9H), 1.6-1.8 (m, 1H), 2.1-2.25 (m, 1H), 2.35-2.7 (m, 3H), 2.9-3.1 (m, 1H), 3.15-3.3 (m, 1H), 3.38 (s, 1H), 8.45 (s, 1H). MS (electron spray) calcd for $C_{26}H_{31}N_3O_8$ 513.54. found (MH$^+$) 514.25. Compounds BQ, BR, BS, BT, BU, BV, BW, BX, BY, BZ, CA, CB, CD, CE, CF, EJ, EK and EM were prepared as described above.

(5aR,6aS,10aS)-9-Carbamoyl-4-dimethylamino-1,8,10a,11-tetrahydroxy-10,12-dioxo-5,5a,6,6a,7,10,10a,12-octahydro-naphthacene-2-carboxylic acid 2,2-dimethyl-propyl ester (Compound EL)

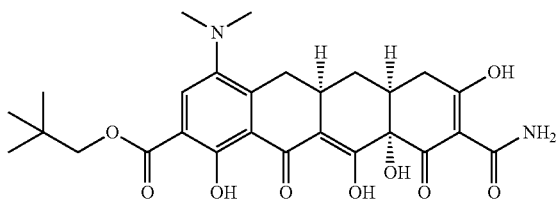 [SMILES: CN(C)c1cc(C(=O)OCC(C)(C)C)c(O)c2c1C[C@H]1C[C@H]3CC(O)=C(C(N)=O)C(=O)[C@@]3(O)C(O)=C1C2=O]

To a 250 mL flask was added (1.50 g, 2.78 mmol) 4-dedimethylamine-9-iodo minocycline free base (see synthesis of compound CC) and NMP (12 mL). To remove residual water from the above reactants, toluene was added (25 mL), the flask was placed on the rotary evaporator (5 mm Hg, 45° C.) until all the toluene was evaporated. The flask was backfilled with argon and the contents were then transferred via cannula to a dry 50 mL flask. To the 50 mL flask was added tetrakis(triphenylphosphine)palladium(0) (0.70 g, 0.56 mmol) and DIEA (1.30 mL, 8.33 mmol). The flask was placed under vacuum (30 mm Hg) and purged 3 times with carbon monoxide. The flask was then heated to 60° C. under 1.0 atm of carbon monoxide. An amount of neopentyl alcohol (7.5 mL, 68 mmol) was added and the reaction was stirred overnight until all 4-dedimethlyamino-9-iodo minocycline was consumed and the product was formed as determined via LCMS. The reaction was added to acetonitrile (300 mL) followed by the addition of water (0.7 L) and lastly the pH was lowered to pH 2 using trifluoroacetic acid. The solution was then filtered through celite to remove the catalyst, loaded onto a reverse phase column and the crude product was purified by HPLC (C18, linear gradient 50-60% acetonitrile in water with 0.2% Formic acid). The fractions containing the final product were loaded onto DVB plug, washed with aqueous HCl (1.0 L, 0.01 N) and eluted with methanol to give the HCl salt of 4-dedimethyl-9-neopentylcarboxyester minocycline (450 mg, 0.97 mmol, 35%). $^1$H-NMR (300 MHz, chemical shifts in ppm with TMS as internal reference at 0 ppm) δ 1.08 (s, 9H), 1.6-1.8 (m, 1H), 2.1-2.25 (m, 1H), 2.35-2.7 (m, 3H), 2.9-3.15 (m, 1H), 3.15-3.0 (m, 1H), 4.05-4.2 (m, 2H), 8.4 (s, 1H). MS (electron spray) calcd for $C_{27}H_{32}N_2O_9$ 528.54. found (M+1) 529.25. Compounds BQ, BR, BS, BT, BU, BV, BW, BX, BY, BZ, CA, CB, CD, CE, CF, EJ, EK and EM were prepared as described above.

(4S,4aS,5aR,12aS)-4,7-Bis-dimethylamino-9-(1-ethoxyimino-ethyl)-3,10,12,12a-tetrahydroxy-1,11-dioxo-1,4,4a,5,5a,6,11,12a-octahydro-naphthacene-2-carboxylic acid amide (Compound CG)

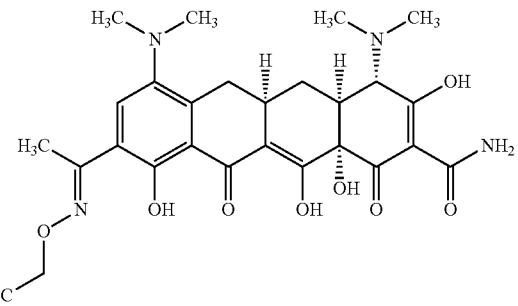

A 100 mL round-bottom flask was charged with a stir bar, 9-acetylminocycline (1.75 g), O-ethylhydroxylamine (1.548 g), and 30 mL of methanol. The reaction mixture was stirred at room temperature for 3 hours, while the reaction progress was monitored with HPLC/LCMS. Upon completion, the reaction mixture was poured in water (500 mL) and purified by preparative HPLC (C18, linear gradient 15-55% acetonitrile in 20 mM aqueous triethanolamine and TFA, pH 7.4). The product fractions were diluted with water, loaded onto a DVB plug (0.5"×3" diam), and washed thoroughly with water. The product was then eluted with methanol and the solution was evaporated to dryness. An amount of 0.454 g of compound was isolated. ESIMS: m/z 543.4 (MH+) obs. $^1$H NMR (300 MHz, CD$_3$OD) δ 7.34 (s, 1H), 4.18 (q, 2H), 3.68 (t, 1H), 3.36 (m, 1H), 2.90 (m, 2H), 2.87 (s, 6H), 2.59 (s, 6H), 2.20 (s, 3H), 2.19 (m, 2H), 2.61 (q, 1H), 1.30 (t, 3H).

(4aS,5aR,12aS)-7-Dimethylamino-3,10,12,12a-tetrahydroxy-9-(1-methoxyimino-ethyl)-1,11-dioxo-1,4,4a,5,5a 6,11,12a-octahydro-naphthacene-2-carboxylic acid amide (Compound CH)

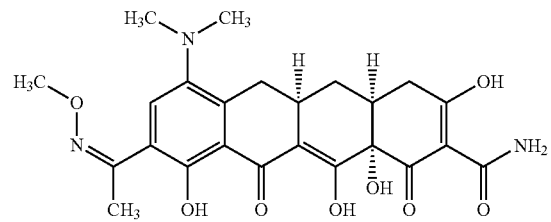 [SMILES: CO/N=C(/C)c1cc(N(C)C)c2c(c1O)C(=O)C1=C(O)[C@]3(O)C(=O)C(C(N)=O)=C(O)C[C@@H]3C[C@@H]1C2]

To a mixture of 9-acetyl-4-dedimethylaminominocycline (2.02 g) and MeONH$_2$ (1.56 g) was added methanol (30 mL) and the reaction was stirred at room temperature for 2.4 hours. Upon completion of the reaction (monitored via LCMS), the reaction mixture was poured into water and was purified by preparative HPLC (C18, linear gradient 15-55% acetonitrile in 20 mM aqueous triethanolamine and TFA, pH 7.4). Isolated 0.667 g. ESIMS m/z 486.25 (MH+) $^1$H NMR (300 MHz, CD$_3$OD) δ 7.34 (s, 1H), 3.93 (s, 3H), 3.38 (dd, 1H), 3.26 (m, 1H), 2.75 (m, 1H), 2.58 (s, 6H), 2.47 (m, 2H), 2.19 (s, 3H), 2.06 (m, 2H), 1.60 (q, 1H).

(4aS,5aR,12aS)-7-Dimethylamino-3,10,12,12a-tetrahydroxy-9-isoxazol-4-yl-1,11-dioxo-1,4,4a,5,5a,6,11,12a-octahydro-naphthacene-2-carboxylic acid (Compound CJ)

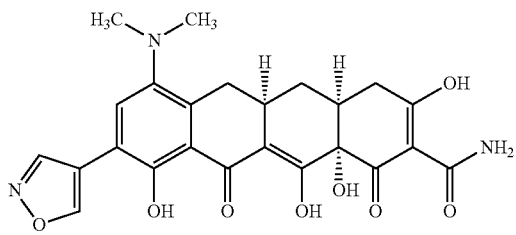 [SMILES: CN(C)c1cc(-c2cnoc2)c(O)c2c1C[C@H]1C[C@H]3CC(O)=C(C(N)=O)C(=O)[C@@]3(O)C(O)=C1C2=O]

To 9-iodo-4-dedimethylaminominocycline (2.0 g) was added a DMF (15 mL) previously purged with argon to remove any oxygen, a previously prepared solution of $Na_2CO_3$ (784 mg) in water (5.0 mL), dichloro(1,1' bis-diphenylphosphine)(Ferrocene)Pd(0) complexed with DCM (541 mg) and 4-isoxazoleboronic acid pinacol ester (1.08 g). The reaction was subject to microwave irradiation for duration of 1 minute at temperature of 100 C. Following, the reaction was added to an aqueous solution containing acetonitrile (20%) and TFA (0.2%). The solution was then filtered through celite to remove the catalyst, loaded onto a C18 reverse phase column and the crude product was purified by reverse phase HPLC (C18, linear gradient 20-40% MeCN in water with 0.1% TFA). The fractions containing the final product were loaded onto DVB plug, washed with aqueous HCl (1.0 L, 0.01 N) and eluted with methanol to give the HCl salt of 4-dedimethylamino-9-(isoxazol-4-yl)-minocycline (1000 mg, 1.93 mmol, 51%). $^1$H-NMR (Bruker DPX300 300 MHz spectrometer, chemical shifts in ppm with TMS as internal reference at 0 ppm) δ 1.6-1.8 (m, 1H), 2.1-2.25 (m, 1H), 2.35-2.7 (m, 3H), 2.9-3.1 (m, 1H), 3.18-3.3 (m, 2H), 3.35-3.45 (m, 6H), 8.3 (s, 1H), 9.15 (s, 1H), 9.35 (s, 1H). MW calcd for $C_{24}H_{23}N_3O_8$ 481.47, ESIMS found m/z 482 (MH+). Compounds CI, CK, EP, EQ, ER, ES, ET, EU, EV, EW and EX were prepared in this manner.

(4aS,5aR,12aS)-7-Dimethylamino-3,10,12,12a-tetrahydroxy-1,11-dioxo-9-pyridin-3-yl-1,4,4a,5,5a,6,11,12a-octahydro-naphthacene-2-carboxylic acid amide (Compound CL)

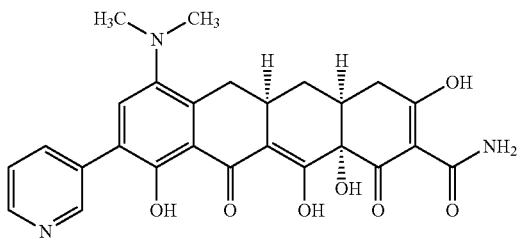 [SMILES: CN(C)c1cc(-c2cccnc2)c(O)c2c1C[C@H]1C[C@H]3CC(O)=C(C(N)=O)C(=O)[C@@]3(O)C(O)=C1C2=O]

To a 500 mL round bottom flask was added 9-iodo-4-dedimethylaminominocycline (2.0 g), NMP (10 mL) and toluene (10 mL). The toluene and residual water of stock solution containing 9-iodo-4-dedimethylaminominocycline was then removed by rotary evaporation (5.0 mm Hg, 45° C.) and backfilled with argon to give 10 mL of a 0.37 M stock solution of 9-iodo-4-dedimethylaminominocycline in NMP. To a microwave vial was added tris(dibenzyldieneacetone)-dipalladium(0) (339 mg), tri-2-furylphosphine (858 mg), CuI (70 mg), stock solution 9-iodo-4-dedimethylaminominocycline followed by 3-(tri-n-butylstannyl)-pyridine (3 mL). The microwave vial was capped, heated to and maintained at a temperature of 100° C. for 10 minute using a microwave reactor. The reaction mixture was then cooled to room temperature, added to water (1.0 L) and the pH was lowered to 2 using trifluoroacetic acid. The solution was then filtered through celite to remove the catalyst, loaded onto a reverse phase column and the crude product was purified by reverse phase HPLC (C18, linear gradient 20-40% MeCN in water with 0.1% TFA). The fractions containing the final product were loaded onto a DVB plug, washed with aqueous HCl (1.0 L, 0.01 N) and eluted with acetonitrile to give the HCl salt (350 mg, 0.66 mmol, 18%). $^1$H-NMR (Bruker DPX300 300 MHz spectrometer, chemical shifts in ppm with TMS as internal reference at 0 ppm) δ 1.6-1.8 (m, 1H), 2.1-2.25 (m, 1H), 2.4-2.7 (m, 3H), 2.95-3.15 (m, 1H), 3.18-3.3 (m, 2H), 3.35-3.45 (m, 9H), 8.20-8.29 (m, 1H), 8.3 (s, 1H), 8.91-8.93 (d, 1H, J=5 Hz), 9.01-9.09 (m, 1 H), 9.3 (s, 1 H), MW calcd for $C_{26}H_{25}N_3O_7$ is 491.50. ESIMS: found m/z 492.00 (MH+). Compounds CI, CK, EP, EQ, ER, ES, ET, EU, EV, EW and EX were prepared in this manner.

(4aS,5aR,12aS)-7-Dimethylamino-3,10,12,12a-tetrahydroxy-9-(2-methyl-2H-pyrazol-3-yl)-1,11-dioxo-1,4,4a,5,5a,6,11,12a-octahydro-naphthacene-2-carboxylic acid amide (Compound EN)

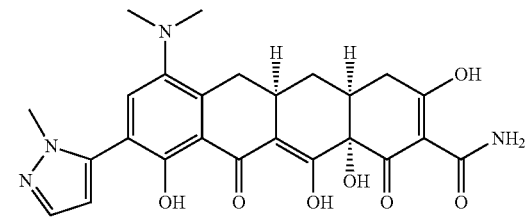 [SMILES: CN(C)c1cc(-c2ccnn2C)c(O)c2c1C[C@H]1C[C@H]3CC(O)=C(C(N)=O)C(=O)[C@@]3(O)C(O)=C1C2=O]

To 9-iodo-4-dedimethyl minocycline (1.5 g, 2.78 mmol, see synthesis of compound CC) was added N-methylpyrrolidone (10 mL, previously purged with argon to remove any oxygen), a previously prepared solution of $NaCO_3$ (584 mg, 5.56 mmol) in water (4.0 mL, also previously purged with argon), 1,1'-Bis(diphenylphosphino)-ferrocene)dichloropalladium(II)complex with dichloromethane 1:1 (400 mg, 0.556 mmol) and 1-methyl-4-(4,4,5,5-tetramethyl-1,3,2-dioxaborolan-2-yl)-1H-pyrazole (867 mg, 4.17 mmol). The reaction was subject to microwave irradiation for duration of 2 minutes at temperature of 100° C. Following, the reaction was added to an aqueous solution containing acetonitrile (10%) and TFA (0.2%). The solution was then filtered through celite to remove the catalyst, loaded onto a reverse phase column and purified by HPLC (C18, linear gradient 15-25% acetonitrile in water with 0.1% TFA). The fractions containing the final product were loaded onto DVB plug, washed with aqueous HCl (1.0 L, 0.01 N) and eluted with methanol to give the HCl salt of 4-dedimethyl-9-(1-methylpyrazole) minocycline (510 mg, 0.96 mmol, 35%). $^1$H-NMR (Bruker DPX300 300 MHz spectrometer, chemical shifts in ppm with TMS as internal reference at 0 ppm) δ 1.6-1.8 (m, 1H), 2.1-2.25 (m, 1H), 2.35-2.65 (m, 3H), 2.8-3.2 (m, 6H), 3.2-3.3 (m, 1H), 3.79 (s, 3H), 6.4 (s, 1H), 7.55 (s, 1H), 7.75 (bis, 1H). MS (electron spray) calcd for $C_{25}H_{26}N_4O_7$ 494.50. found (M+1) 495.20. Compounds CI, CK, EP, EQ, ER, ES, ET, EU, EV, EW and EX were prepared in this manner.

(4aS,5aR,12aS)-7-Dimethylamino-3,10,12,12a-tetrahydroxy-9-(3-methyl-3H-imidazol-4-yl)-1,11-dioxo-1,4,4a,5,5a,6,11,12a-octahydro-naphthacene-2-carboxylic acid amide (Compound EO)

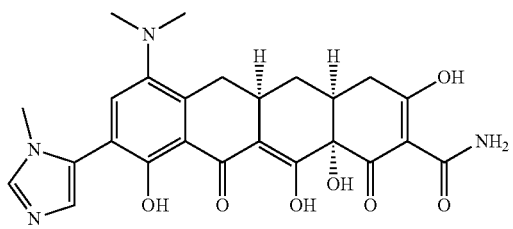 [SMILES: CN(C)c1cc(-c2cncn2C)c(O)c2c1C[C@H]1C[C@H]3CC(O)=C(C(N)=O)C(=O)[C@@]3(O)C(O)=C1C2=O]

To a 100 mL round bottom flask was added 9-iodo 4-dedimethyl minocycline (1.5 g, 2.78 mmol, see synthesis of compound CC), N-methylpyrrolidone (10 mL) and toluene (10 mL). The toluene and residual water of the stock solution containing the 9-iodo 4-dedimethyl minocycline was then removed by rotary evaporation (5.0 mm Hg, 45° C.) and backfilled with argon to give 10 mL of a 0.28 M stock solution of 9-iodo 4-dedimethyl minocycline in NMP. To a 20 mL microwave vial was added tris(dibenzyldieneacetone)dipalladium(0) (250 mg, 0.28 mmol), tri-2-furylphosphine (645 mg, 2.8 mmol), CuI (53 mg, 0.28 mmol), and the stock solution of 9-iodo-4-dedimethyl minocycline followed by 1-methyl-5-tributylstannanyl-1H-imidazole (2.0 g, 5.56 mmol). The microwave vial was capped, heated to 100° C. for 15 minutes using a microwave reactor. The reaction mixture was then cooled to room temperature, added to water (1.0 L) and the pH was lowered to pH 2 using trifluoroacetic acid. The solution was then filtered through celite to remove the catalyst, loaded onto a reverse phase column and the crude product was purified by HPLC (C18, linear gradient 10-25% acetonitrile in water with 0.1% TFA). The fractions containing the final product were loaded onto a DVB plug, washed with aqueous HCl (1.0 L, 0.01 N) and eluted with acetonitrile to give the HCl salt (510 mg, 0.96 mmol, 35%). $^1$H-NMR (300 MHz spectrometer, chemical shifts in ppm with TMS as internal reference at 0 ppm) δ 1.6-1.8 (m, 1H), 2.1-2.25 (m, 1H), 2.3-2.65 (m, 3H), 2.8-3.0 (m, 7H), 3.4-3.5 (m, 2H), 3.89 (s, 3H), 7.7 (d, J=7.4 Hz, 2H), 9.1 (s, 1H). MS (electron spray) calcd for $C_{26}H_{25}N_3O_7$ 494.50. found (M+1) 495.20. Compounds CI, CK, EP, EQ, ER, ES, ET, EU, EV, EW and EX were prepared in this manner.

(4aS,5aR,12aS)-9-Cyclopropyl-7-dimethylamino-3,10,12,12a-tetrahydroxy-1,11-dioxo-1,4,4a,5,5a,6,11,12a-octahydro-naphthacene-2-carboxylic acid amide (Compound ER)

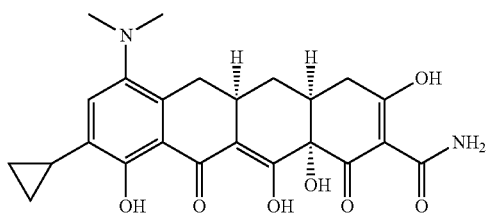 [SMILES: CN(C)c1cc(C2CC2)c(O)c2c1C[C@H]1C[C@H]3CC(O)=C(C(N)=O)C(=O)[C@@]3(O)C(O)=C1C2=O]

To a 200 mL round bottom flask was added tetrahydrofuran (THF, 20 mL), a stir bar and indium trichloride (InCl$_3$, 2.21 g, 10.0 mmol). The flask was then cooled to −78° C. by placing it in a dry ice bath. A solution of cyclopropylmagnesiumbromide in THF (60 mL, 0.5 N, 30 mmol) was slowly added to the stirred reaction over 5 minutes to generate a tricyclopropyl-indium intermediate stock solution. Next, the reaction was allowed to warm to room temperature. To 9-iodo-4-dedimethyl minocycline (2.0 g, 1.2 mmol, see the synthesis of compound CC) was added NMP (18 mL) and toluene (18 mL). The toluene and residual water of stock the stock solution containing 9-iodo-4-dedimethyl minocycline was then removed by rotary evaporation (5.0 mm Hg, 45° C.) and backfilled with argon to give 10 mL of a 0.2 M stock solution of 9-Iodo 4-dedimethyl minocycline in NMP. Next, trans-(PdCl$_2$(PPh$_3$)$_2$) (0.378, 0.74 mmol) was added to the reaction as well as the above tricyclopropyll-indium intermediate stock solution (29 mL). The reaction was heated to 60° C. for 3 hours. The reaction was then added to an aqueous solution (2.0 L) containing acetonitrile (20%) and TFA was added until a pH of 2 was reached. The solution was then filtered through celite to remove the catalyst, loaded onto a reverse phase column and purified by HPLC (C18, linear gradient 20-35% acetonitrile in water with 0.1% TFA). The fractions containing the final product were loaded onto DVB plug, washed with aqueous HCl (1.0 L, 0.01 N) and eluted with acetonitrile to give the HCl salt of 9-cyclopropyl minocycline (450 mg, 0.92 mmol, 76%). $^1$H-NMR (300 MHz, chemical shifts in ppm with TMS as internal reference at 0 ppm) δ 0.70-0.90)m, 1H), 0.91-1.15 (m, 1H), 1.58-1.80 (m, 1H), 2.00-2.40 (m, 2H), 2.40-2.65 (m, 3H), 2.80-3.10 (s, 1H), 3.10-3.40 (brm, 8H), 7.45 (s, 1H). MS (electron spray) calcd for $C_{24}H_{26}N_2O_7$ 454.48. found (M+1) 455.20. Compounds CI, CK, EP, EQ, ER, ES, ET, EU, EV, EW and EX were prepared in this manner.

(4aS,5aR,12aS)-7-Dimethylamino-9-furan-2-yl-3,10,12,12a-tetrahydroxy-1,11-dioxo-1,4,4a,5,5a,6,11,12a-octahydro-naphthacene-2-carboxylic acid amide (Compound EU)

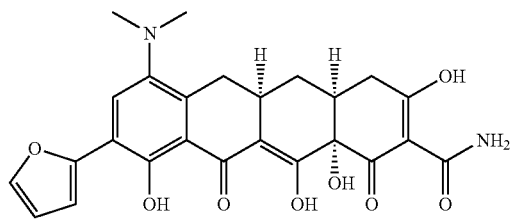 [SMILES: CN(C)c1cc(-c2ccco2)c(O)c2c1C[C@H]1C[C@H]3CC(O)=C(C(N)=O)C(=O)[C@@]3(O)C(O)=C1C2=O]

MS (ESI+) m/z Theor. Calc. 480.47, Obs. 481.2 (MH$^+$). $^1$H NMR (300 MHz, CD$_3$OD) δ 8.29 (s, 1H), 7.65 (t, 1H), 7.20 (d, 1H), 6.61 (m, 1H), 3.24 (d, 1H), 3.14 (dd, 1H), 2.98 (m, 1H), 2.49 (m, 3H), 2.13 (dm, 1H), 1.65 (m, 1H).

(4aS,5aR,12aS)-7-Dimethylamino-3,10,12,12a-tetrahydroxy-1,11-dioxo-9-phenyl-1,4,4a,5,5a,6,11,12a-octahydro-naphthacene-2-carboxylic acid amide (Compound EV)

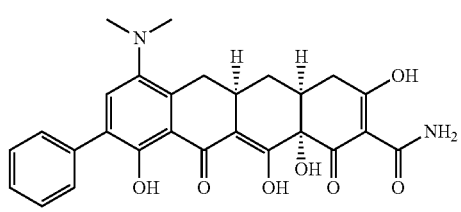 [SMILES: CN(C)c1cc(-c2ccccc2)c(O)c2c1C[C@H]1C[C@H]3CC(O)=C(C(N)=O)C(=O)[C@@]3(O)C(O)=C1C2=O]

MS (ESI+) m/z Theor. Calc. 490.509, Obs. 491.20 (MO. ¹H NMR (300 MHz, CD₃OD) δ 7.91 (s, 1H), 7.61 (m, 2H), 7.42 (m, 3H), 3.19 (m, 2H), 2.98 (m, 1H), 2.45 (m, 3H), 2.14 (dm, 1H), 1.65 (m, 1H).

(4aS,5aR,12aS)-9-(4-Carbamoyl-phenyl)-7-dimethylamino-3,10,12,12a-tetrahydroxy-1,11-dioxo-1,4,4a,5,5a,6,11,12a-octahydro-naphthacene-2-carboxylic acid amide (Compound EW)

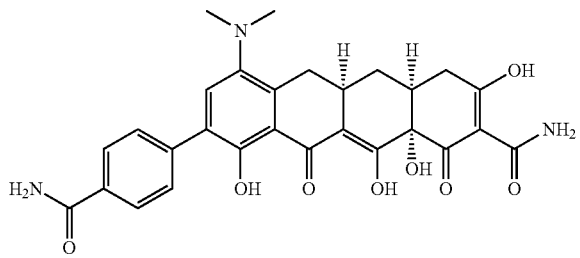 [SMILES: CN(C)c1cc(-c2ccc(C(N)=O)cc2)c(O)c2c1C[C@H]1C[C@H]3CC(O)=C(C(N)=O)C(=O)[C@@]3(O)C(O)=C1C2=O]

MS (ESI+) m/z Theor. Calc. 533.53, Obs. 534.20 (MH⁺). ¹H NMR (300 MHz, CD₃OD) δ 7.96 (m, 3H), 7.75 (m, 2H), 3.16 (m, 2H), 3.01 (m, 1H), 2.52 (m, 3H), 2.16 (dm, 1H), 1.67 (m, 1H).

(4aS,5aR,12aS)-9-(5,6-Dihydro-4H-pyran-2-yl)-7-dimethylamino-3,10,12,12a-tetrahydroxy-1,11-dioxo-1,4,4a,5,5a,6,11,12a-octahydro-naphthacene-2-carboxylic acid amide (Compound EX)

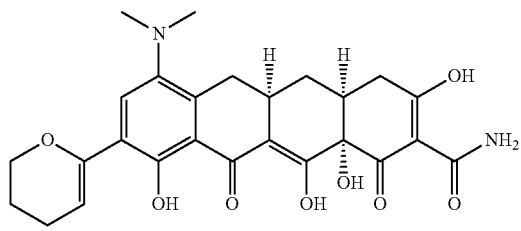 [SMILES: CN(C)c1cc(C2=CCCCO2)c(O)c2c1C[C@H]1C[C@H]3CC(O)=C(C(N)=O)C(=O)[C@@]3(O)C(O)=C1C2=O]

MS (ESI+) m/z Theor. Calc. 496.51, Obs. 497.20 (MH⁺). ¹H NMR (300 MHz, CD₃OD) δ 7.56 (s, 1H), 5.70 (t, 1H), 4.12 (m, 2H), 3.01 (m, 1H), 2.72 (m, 1H), 2.56 (s, 6H), 2.36 (m, 2H), 1.99-2.3 (m, 5H), 1.94 (m, 2H), 1.5-1.85 (m, 2H).

(4S,4aS,5aR,12aS)-4,7-Bis-dimethylamino-3,12,12a-trihydroxy-10-oxazol-2-yl-1,11-dioxo-1,4,4a,5,5a,6,11,12a-octahydro-naphthacene-2-carboxylic acid amide (Compound CM)

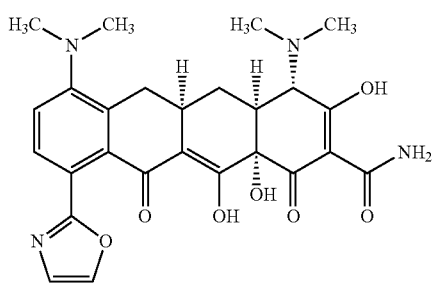

To a solution of anhydrous freebase minocycline (11.4 g) in anhydrous THF under argon (163 mL) at 0° C. was added a 1 M solution of potassium tert-butoxide (87.5 mL) dropwise. After 45 min, N-phenylbis(trifluoromethanesulfonimide) (18.8 g) was added at once. After 1 hour, the solution was allowed to slowly warm to room temperature. After another 2 hours, the solution was slowly poured into a vigorously stirring solution of 0.1 M HCl and Celite. After 15 minutes, the solution was filtered through a large plug of Celite rinsing with 0.1M HCl. The water layer was loaded onto a DVB resin for purification. After the solution was loaded, a 0.1 M HCl solution was eluted, then CH₃CN with 1 mL conc. HCl. The yellow eluent was collected until it became colorless. The solution was concentrated under reduced pressure and further dried high vacuum to afford 13.2 g of minocycline 10-triflate as a brown solid in 90% yield.

To minocycline 10-triflate (1.0 g) was added DMF (10 mL) dichloro(1,1'bis)(diphenylphosphine)-(ferrocene)Pd (II) complexed with DCM (1.0 g), DIEA (0.50 mL,) and 2-tributylstanyl oxazole. The reaction was heated to 110° C. for 5 minutes using a microwave reactor. The reaction mixture was then cooled to room temperature, added to water (0.5 L) and the pH was lowered to 2 using trifluoroacetic acid. The solution was then filtered through celite to remove the catalyst, loaded onto a reverse phase column and the crude product was purified by reverse phase HPLC (C18, linear gradient 20-40% MeCN in water with 0.1% TFA). The fractions containing the final product were loaded onto a DVB plug, washed with aqueous HCl (1.0 L, 0.01 N) and eluted with acetonitrile to give the HCl salt of the product (100 mg, 0.71 mmol). ESIMS: m/z 509 (MH+); ¹H-NMR (Bruker DPX300 300 MHz spectrometer, chemical shifts in ppm with TMS as internal reference at 0 ppm) δ 1.6-1.8 (m, 1H), 2.3-2.5 (m, 1H), 2.55-2.7 (m, 1H), 2.95-3.15 (m, 7H), 3.25-3.3 (m, 6H), 3.35-3.45 (m, 1H), 7.5 (s, 1H), 7.85 (d, J=7.4 Hz, 1H), 7.95 (d, J=7.4 Hz, 1H), 8.15 (s, 1H).

(5aR,6aS,7S,10aS)-9-Carbamoyl-4,7-bis-dimethylamino-8,10a,11-trihydroxy-10,12-dioxo-5,5a,6,6a,7,10,10a,12-octahydro-naphthacene-1-carboxylic acid methyl ester (Compound CN)

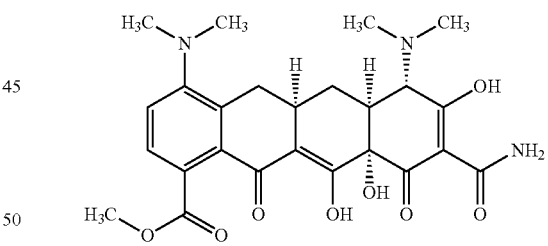

To a 500 mL flask was added (2.00 g) minocycline-10-triflate and NMP (37 mL). To remove residual water from the above reactants, toluene was added (37 mL), the flask was placed on the rotary evaporator (35 mm Hg, 45° C.) until all the toluene was evaporated. The flask was backfilled with argon and the contents were then transferred via cannula to a dry 250 mL flask. To the 250 mL flask was added dichloromethane adduct of dichloro(1,1' bis-diphenylphosphine)(Ferrocene)Pd(II) (1.0 g), DIEA (0.50 mL) and DIEA (2.60 mL). The flask was placed under vacuum (20 mm Hg) and purged three times with carbon monoxide. The flask was then heated to 60° C. under 1.0 atm of carbon monoxide and let stir for 1 hour. After 1 hour, methanol was added (50 mL) and the reaction was allowed to stir for an additional 1 hour. The reaction mixture was then cooled to room temperature, added to water (0.5 L) and the pH was lowered to 2 using trifluoroacetic acid. The solution was then filtered through celite to remove the catalyst, loaded onto a reverse phase column and the crude product was purified by reverse phase HPLC (C18, linear gradient 15-35% MeCN in water with 0.1% TFA). The fractions containing the final product were loaded onto a DVB plug, washed with aqueous HCl (1.0 L, 0.01 N) and eluted with acetonitrile to give the HCl salt of the product (400 mg, 0.70 mmol). ESIMS m/z 500 (MH+). $^1$H-NMR (Bruker DPX300 300 MHz spectrometer, chemical shifts in ppm with TMS as internal reference at 0 ppm) δ 1.6-1.8 (m, 1H), 2.25-2.35 (m, 1H), 2.35-2.7 (m, 1H), 2.95-3.25 (m, 14H), 3.25-3.3 (m, 7H), 3.85 (3, 3H), 4.15 (s, 1H), 7.55 (d, J=7.4 Hz, 1H), 7.75 (d, J=7.4 Hz, 1H). Compound CO was prepared in this manner.

(4S,4aS,5aR,12aS)-4,7-Bis-dimethylamino-3,12,12a-trihydroxy-1,11-dioxo-10-(2H-pyrazol-3-yl)-1,4,4a,5,5a,6,11,12a-octahydro-naphthacene-2-carboxylic acid amide (Compound EY)

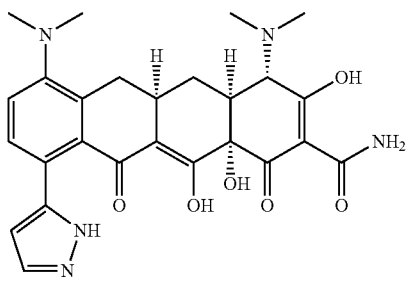 [SMILES: CN(C)c1ccc(-c2ccn[nH]2)c2c1C[C@H]1C[C@H]3[C@H](N(C)C)C(O)=C(C(N)=O)C(=O)[C@@]3(O)C(O)=C1C2=O]

To minocycline-10-triflate (2.0 g, 2.45 mmol, see synthesis of compound CM) was added NMP (15 mL, previously purged with argon to remove any oxygen), a previously prepared solution of Na$_2$CO$_3$ (1.5 mg, 14 mmol) in water (5.0 mL, also previously purged with argon) and 4-(4,4,5,5-tetramethyl-1,3,2-dioxaborolan-2-yl)-1H-pyrazole (1.0 mg, 9.0 mmol). The reaction was subject to microwave irradiation for 4 minute at temperature of 125° C. The reaction mixture was then added to an aqueous solution (2.0 L) containing acetonitrile (10%) and TFA was added until a pH of 2 was reached. The solution was then filtered through celite to remove the catalyst, loaded onto a reverse phase column and purified by HPLC (C18, linear gradient 15-25% acetonitrile in water with 0.1% TFA). The fractions containing the final product were loaded onto DVB plug, washed with aqueous HCl (1.0 L, 0.01 N) and eluted with methanol to give the HCl salt of 10-pyrazole minocycline (150 mg, 0.24 mmol, 10%). $^1$H-NMR (300 MHz, chemical shifts in ppm with TMS as internal reference at 0 ppm) δ 1.6-1.8 (m, 1H), 2.29-2.41 (m, 1H), 2.42-2.60 (m, 1H), 3.01 (s, 3H), 3.1 (brs, 4H), 3.18 (brs, 7H), 3.35-3.45 (m, 2H), 4.18 (s, 1H), 6.7 (s, 1H), 7.59 (d, J=7.4 Hz, 1H), 7.85 (d, J=7.4 Hz, 1H), 8.15 (s, 1H). MS (electron spray) calcd for C$_{26}$H$_{29}$N$_5$O$_6$ 507.54. found (M+2) 254.8 (the found mass represents the doubly charged species, hence the molecular weight found is half the actual molecular weight).

(4S,4aS,5aR,12aS)-10-Cyano-4,7-bis-dimethylamino-3,12,12a-trihydroxy-1,11-dioxo-1,4,4a,5,5a,6,11,12a-octahydro-naphthacene-2-carboxylic acid amide (Compound EZ)

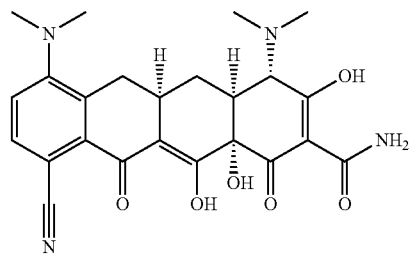 [SMILES: CN(C)c1ccc(C#N)c2c1C[C@H]1C[C@H]3[C@H](N(C)C)C(O)=C(C(N)=O)C(=O)[C@@]3(O)C(O)=C1C2=O]

To minocycline-10-triflate (4.0 g, 2.45 mmol, see the synthesis of compound CM) was added NMP (30 mL, previously purged with argon to remove any oxygen), Zn(CN)$_2$ (2.3 g, 19.6 mmol) and tetrakis-(triphenylphosphine)palladium(0) (1.9 g, 1.6 mmol). The reaction was subject to microwave irradiation for 10 minute at a temperature of 110° C. The reaction mixture was then added to an aqueous solution (2.0 L) containing acetonitrile (10%) and TFA was added until a pH of 2 was reached. The solution was then filtered through celite to remove the catalyst, loaded onto a reverse phase column and purified by HPLC (C18, linear gradient 20-40% acetonitrile in water with 0.1% TFA). The fractions containing the final product were loaded onto DVB plug, washed with aqueous NaOAc (1.0 L, 0.01 N) and eluted with methanol to give the free base of 10-cyano minocycline (250 mg, 0.24 mmol, 10%). $^1$H-NMR (300 MHz, chemical shifts in ppm with TMS as internal reference at 0 ppm) δ 1.6-1.8 (m, 1H), 2.05-2.21 (m, 1H), 2.30-2.50 (m, 1H), 2.65 (s, 6H), 2.8 (bis, 7H), 3.00-3.20 (m, 1H), 3.25-3.35 (m, 1H), 7.20-7.35 (m, 1H), 7.05-7.20 (m, 1H). MS (electron spray) calcd for C$_{24}$H$_{26}$N$_4$O$_6$ 466.49. found (M+1) 467.20.

(4S,4aS,5aR,12aS)-4,7-Bis-dimethylamino-3,12,12a-trihydroxy-10-methyl-1,11-dioxo-1,4,4a,5,5a,6,11,12a-octahydro-naphthacene-2-carboxylic acid amide (Compound FA

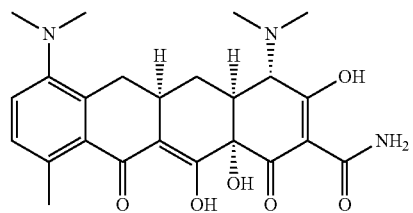 [SMILES: Cc1ccc(N(C)C)c2c1C(=O)C1=C(O)[C@]3(O)C(=O)C(C(N)=O)=C(O)[C@@H](N(C)C)[C@@H]3C[C@@H]1C2]

To a 200 mL round bottom flask was added tetrahydrafuran (THF, 40 mL), a stir bar and indium trichloride (InCl$_3$, 4.4 g, 20.0 mmol). The flask was then cooled to −78° C. by placing it in a dry ice bath. A solution of methylmagnesiumchloride in THF (20 mL, 3.0 N, 60 mmol) was slowly added to the stirred reaction over 5 minutes to generate a trimethyl-indium intermediate stock solution. The reaction was then allowed to warm to room temperature. To minocycline-10-triflate (1.0 g, 0.61 mmol, see the synthesis of compound CM) was added NMP (10 mL), trans-PdCl$_2$(PPh$_3$)$_2$ (1.0 g, 1.4 mmol) and the above trimethyl-indium intermediate stock solution (15 mL). The reaction was subject to microwave irradiation for 4 minutes at a temperature of 110° C. Next, the reaction was added to an aqueous solution (2.0 L) containing acetonitrile (10%) and TFA was added until a pH of 2 was reached. The solution was then filtered through celite to remove the catalyst, loaded onto a reverse phase column and purified by HPLC (C18, linear gradient 15-30% acetonitrile in water with 0.1% TFA). The fractions containing the final product were loaded onto DVB plug, washed with aqueous NaOAc (1.0 L, 0.01 N) and eluted with methanol to give the free base of 10-methyl minocycline (200 mg, 0.44 mmol, 67%). $^1$H-NMR (300 MHz spectrometer, chemical shifts in ppm with TMS as internal reference at 0 ppm) δ 1.58-1.8 (m, 1H), 2.30-2.50 (m, 1H), 2.45-2.60 (m, 1H), 2.75 (s, 3H), 2.90-3.20 (brm, 8H), 4.19 (s, 1H), 7.48 (d, J=7.5 Hz, 1H), 7.89 (d, J=7.5 Hz, 1H). MS (electron spray) calcd for C$_{24}$H$_{29}$N$_3$O$_6$ 455.51. found (M+1) 456.25.

(4aR,5S,5aR,6R,12aS)-3,5,10,12,12a-Pentahydroxy-6-methyl-9-oxazol-2-yl-1,11-dioxo-1,4,4a,5,5a,6,11,12a-octahydro-naphthacene-2-carboxylic acid amide (Compound CP)

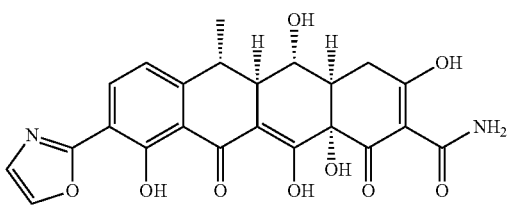 [SMILES: C[C@H]1c2ccc(-c3ncco3)c(O)c2C(=O)C2=C(O)[C@]3(O)C(=O)C(C(N)=O)=C(O)C[C@@H]3[C@@H](O)[C@@H]21]

To a 500 mL round bottom flask was added 9-iodo-4-dedimethylaminodoxycycline (3.7 mmol), NMP (10 mL) and toluene (10 mL). The toluene and residual water of stock solution containing 9-iodo-4-dedimethylaminodoxycycline was then removed by rotary evaporation (5.0 mm Hg, 45° C.) and backfilled with argon to give 10 mL of a 0.37 M stock solution of 9-iodo-4-dedimethylaminodoxycycline in NMP. To a microwave vial was added tetrakis-(triphenylphosphine) palladium(0) (0.37 mmol), the stock solution 9-iodo-4-dedimethylaminodoxycycline followed by oxazol-2-ylzinc in THF at 0.36M (10 mmol). The microwave vial was capped, heated to and maintained at a temperature of 100° C. for 10 minute using a microwave reactor. The reaction mixture was then cooled to room temperature, added to water (1.0 L) and the pH was lowered to 2 using trifluoroacetic acid. The solution was then filtered through celite to remove the catalyst, loaded onto a reverse phase column and the crude product was purified by reverse phase HPLC (C18, linear gradient 10-25% MeCN in water with 0.1% TFA). The fractions containing the final product were loaded onto a DVB plug, washed with aqueous HCl (1.0 L, 0.01 N) and eluted with acetonitrile to give the HCl salt. $^1$H-NMR (Bruker DPX300 300 MHz spectrometer, chemical shifts in ppm with TMS as internal reference at 0 ppm) δ 1.56-1.58 (d, 3H, J=6.9 Hz), 2.30-2.55 (m, 2H), 2.7-2.85 (m, 1H), 2.9-3.15 (m, 2H), 3.36 (s, 6H), 3.62-3.72 (m, 1H), 7.12-7.14 (d, 1H, J=8.3 Hz), 7.37 (s, 1H), 8.03 (s, 1H), 8.10-8.13 (d, 1H, J=8.3 Hz), MW calcd for C$_{23}$H$_{20}$N$_2$O$_9$ 468.42, ESIMS found m/z 469.10 (MH+).

(4S,4aS,5aR,12aS)-4-Dimethylamino-3,10,12,12a-tetrahydroxy-7-(3-methylaminomethyl-furan-2-yl)-1,11-dioxo-1,4,4a,5,5a,6,11,12a-octahydro-naphthacene-2-carboxylic acid amide (Compound CQ)

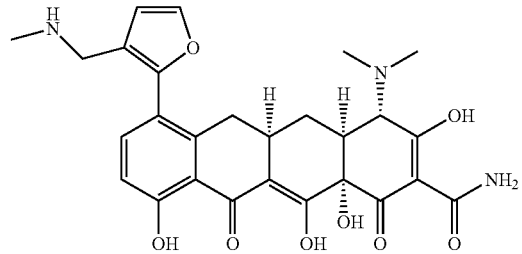 [SMILES: CNCc1ccoc1-c1ccc(O)c2c1C[C@H]1C[C@H]3[C@H](N(C)C)C(O)=C(C(N)=O)C(=O)[C@@]3(O)C(O)=C1C2=O]

7-iodo-sancycline•TFA (2 g) was combined with palladium (II) acetate (83 mg) in methanol (150 mL) in a 2-neck round bottom flask equipped with an argon line. The contents were purged with argon while heating to 70° C. (oil bath temp) for 10 minutes. Separately, sodium carbonate (1.17 g in 40 mL water) was purged with argon for 5 minutes prior to addition into the reaction solution. This was followed by the addition of an argon degassed solution of 3-formyl-furan-2-yl boronic acid (1.0 g in 40 mL DMF). The reaction mixture was stirred at 70° C. in an argon atmosphere for 1-2 hours. Upon completion of reaction (monitored by LC-MS), reaction solution was gravity filtered through celite to remove catalyst, and solvent removed in vacuo. The solid material was dissolved in methanol, and precipitated using 300 mL of diethyl ether. The solid obtained after filtration was dried overnight in vacuum oven and used as such for the next step.

A mixture of 7-(3'-formyl-furan-2'-yl)-sancycline (1.02 g), methylamine hydrochloride (0.216 g) and triethylamine (404 µL) in DMF (30 mL) was stirred for 0.5 hours. Sodium triacetoxyborohydride (1.26 g) was added and the reaction mixture was stirred for 5 hours. Completion of the reaction was monitored by HPLC/LC-MS. The solvent was then evaporated, and the crude material obtained was redissolved in 5 mL of methanol and precipitated using 400 mL of diethyl ether. The solid obtained after filtration was purified by prep-HPLC (C18, linear gradient 5-35% acetonitrile in water with 0.1% TFA to give a yellow solid, which was converted to its HCl salt using saturated MeOH/HCl. ESIMS: m/z 524 (MH+). $^1$H NMR (300 MHz, CD$_3$OD): δ 7.67-7.62 (m, 1H), 7.50-7.41 (m, 1H), 6.98-6.90 (m, 1H), 6.72-6.69 (m, 1H), 4.08 (s, 1H), 3.96-3.88 (m, 2H), 3.20-2.88 (m, 8H), 2.71-2.59 (m, 4H), 2.52-2.39 (m, 1H), 2.15-1.94 (m, 1H), 1.60-1.44 (m, 1H). Compounds CS, CT and FB were synthesized in a similar manner.

2-((6aS,10S,10aS,11aR)-8-Carbamoyl-10-dimethylamino-4,6,6a,9-tetrahydroxy-5,7-dioxo-5,6a,7,10,10a,11,11a,12-octahydro-naphthacen-1-yl)-furan-3-ylmethyl]-methyl-carbamic acid methyl ester (Compound CR)

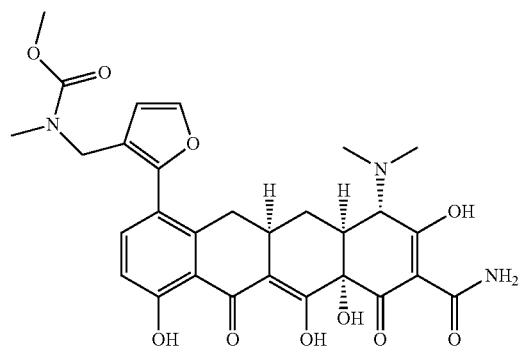 [SMILES: COC(=O)N(C)Cc1ccoc1-c1ccc(O)c2c1C[C@H]1C[C@H]3[C@H](N(C)C)C(O)=C(C(N)=O)C(=O)[C@@]3(O)C(O)=C1C2=O]

An amount of 7-(3-methylaminomethyl-furan-2-yl)-sancycline (523 mg) was dissolved in 10 mL of NMP and methylchloroformate (187 µL) was added to the solution. The reaction mixture was stirred at room temperature for 20 minutes. Upon completion, the product was then precipitated using 250 mL of diethyl ether. The solid obtained after filteration was purified using preparative HPLC (C18, linear gradient 10-45% acetonitrile in water with 0.1% TFA). Fractions were evaporated and the solid obtained was then converted to its HCL salt using saturated MeOH/HCl. ESIMS: (m/z) 582 (MH+). $^1$H NMR (300 MHz, CD$_3$OD): δ 7.55-7.50 (m, 1H), 7.48-7.40 (d, 1H), 6.94-6.88 (d, 1H), 6.50-6.46 (m, 1H), 4.40-4.11 (m, 2H), 4.06 (s, 1H), 3.65-3.52 (m, 3H), 3.20-2.90 (m, 8H), 2.74-2.60 (m, 4H), 2.52-2.38 (m, 1H), 2.12-1.88 (m, 1H), 1.62-1.48 (m, 1H). Compounds CS, CT and FB were synthesized in a similar manner.

(4S,12aS)-7-(Bis-trideutromethyl-amino)-4-dimethylamino-9-[(2,2-dimethyl-propylamino)-methyl]-3,10,12,12a-tetrahydroxy-1,11-dioxo-1,4,4a,5,5a,6,11,12a-octahydro-naphthacene-2-carboxylic acid amide (Compound CU)

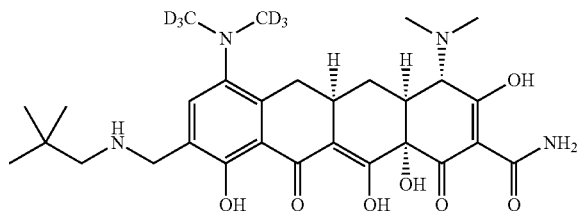 [SMILES: [2H]C([2H])([2H])N(c1cc(CNCC(C)(C)C)c(O)c2c1C[C@H]1C[C@H]3[C@H](N(C)C)C(O)=C(C(N)=O)C(=O)[C@@]3(O)C(O)=C1C2=O)C([2H])([2H])[2H]]

Dibenzyl azodicarboxylate (132 mmol) was added to trifluoroacetic acid (400 mL) at 5-10° C. and stirred to give a solution. Sancycline (88 mmol) was added portionwise while maintaining the temperature below 10° C. The reaction mixture was stirred at 5-10° C. for 7 hours and the mixture was concentrated. The residue was dissolved in methanol and hydrogenated at 40 psi H$_2$ in the presence of 5% Pd/C (20 g) for 3 hours. After completion of reaction, the catalyst was filtered and the methanol was removed.

The crude 7-aminosancycline was dissolved in methanol. To this solution, deuterated-formaldehyde and 5% Pd/C were added. The reaction mixture was subjected to hydrogenation with deuterated gas. After the completion of the reaction, the crude material was extracted by dichloromethane at pH2 and then extracted at pH7. The organic extracts at pH7 were combined and the solvent was removed. The residue was dissolved in 1N HCl and purified by prep.HPLC (~5 g).

Triflic acid (160 mL) was charged into a three-necked round bottom flask under nitrogen. The 7-(bis-trideuteromethyl-amino)-sancycline mono-hydrochloride (0.065 mol) was added portion-wise to the acid, keeping the temperature between 20-25° C. N-hydroxymethylphthalimide was added (25.5 g), keeping the temperature between 20-25° C. The reaction mixture was stirred for 1-2 hours and a second portion of N-hydroxymethylphthalimide was added (6.5 g), still maintaining the temperature between 20-25° C. Upon completion of the reaction, the acid solution is added to an ice/water mixture slowly, such that the water temperature does not rise above 25° C. After stirring for 10 minutes, the product was filtered and washed with water. The solid was dissolved in acetone (~0.3 L) and stirred for 5 minutes. Subsequently, the material was neutralized to pH 6.0-6.5 with triethylamine. After observing a stable pH for ~10 minutes, 6L of water was added to the acetone solution and the yellow solid was fully precipitated out. The solid was collected by filtration and washed with water and isopropanol. Upon removal of the solvent, the residue was dried further under reduced pressure at ≤30° C. for 2 days. The product was isolated as a mixture of the bis- and tris-alkylated product in an approximately 60:40 ratio based on HPLC analysis.

A 1 L, three-necked round bottom flask was charged with the intermediate (40 g) under argon. Ethyl alcohol (2 L, anhydrous, 200 proof) was added with stirring, and the resulting suspension was cooled to 0-8° C. A solution of methylamine in ethanol (160 mL, 33%, ~8 M) was added gradually such that the reaction temperature remained below 15° C. The reaction was stirred under an argon atmosphere at 18-28° C. for 15 to 23 hours. Upon completion, Celite (16 g) was added; the reaction mixture was then cooled to 0-5° C. and stirred for 1-2 hours. The resulting suspension of the phthalamide byproduct and Celite was filtered and washed with absolute ethanol. The filtrate was charged into a 12 L, three-necked round bottom flask under argon with ice-bath and t-butyl methyl ether (600 L) is added rapidly with stirring, resulting in a yellow suspension. The suspension was stirred for 2 to 3 hours, then filtered and washed with THF. The solvent was then removed and the product was dried under reduced pressure (under a latex film) and dried overnight under high vacuum at room temperature to obtain 21.8 g of the product as a yellow solid.

Methanol (120 mL) was charged in a 1 L pressure bottle under argon, followed by the addition of triethylamine (15 mL). The product from the previous reaction (20 g) was suspended in this solvent mixture and stirred for 10 minutes. Trimethylacetaldehyde (20 mL) was added to the suspension over 10 minutes. After stirring the resulting solution for 10-15 minutes, 5% Pd/C (10 g) was added. The reaction mixture was purged twice with argon, then three times with H$_2$. The reaction was stirred under 40-50 psi of hydrogen pressure for 2-4 hours. Upon completion of the reaction, the solution was filtered through a celite bed under an argon flow, and washed with methanol (3×10 mL). prep. HPLC. ESIMS: m/z 563 (MH+).

2,2-Dimethyl-propionic acid (6aS,10S,10aS,11aR)-8-carbamoyl-10-dimethylamino-4,6,6a,9-tetrahydroxy-5,7-dioxo-5,6a,7,10,10a,11,11a,12-octahydro-naphthacen-1-ylmethylcarbamoyloxymethyl ester (Compound CV)

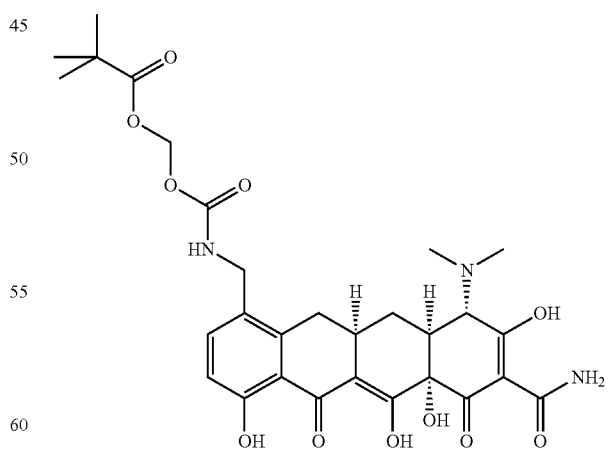

A mixture of 7-aminomethylsancycline TFA salt (1.5 g) and ammonium sulfite (100 mg) in a mixture of 40 mL of acetonitrile and 40 mL of saturated sodium hydrogen carbonate was purged with argon for 15 minutes. A solution of the chloroformate in dry acetonitrile was slowly added to the reaction mixture. The reaction mixture was then stirred for additional 1 hour. The desired material was extracted with several portions of ethyl acetate. The combined ethyl acetate solution was washed once with brine and solvent evaporated. The product was obtained via C18 column (linear gradient 5-30% acetonitrile in water with 0.1% TFA). ESIMS: m/z 602 (MH+). $^1$H NMR (300 MHz, CD$_3$OD) δ ☐7.46 (d, 1H), 6.82 (d, 1H), 5.72-5.67 (m, 2H), 4.15-4.40 (m, 2H), 4.07 (s, 1H,), 3.2-2.90 (m, 9H), 2.40-2.15 (m, 2H), 1.68-1.50 (m, 1H), 1.10 (s, 9H). Compound CW was also prepared as described above.

(4R,4aS,5aR,12aS)-4-Cyclopentylamino-7-dimethylamino-3,10,12,12a-tetrahydroxy-1,11-dioxo-1,4,4a,5,5a,6,11,12a-octahydro-naphthacene-2-carboxylic acid amide (Compound CX)

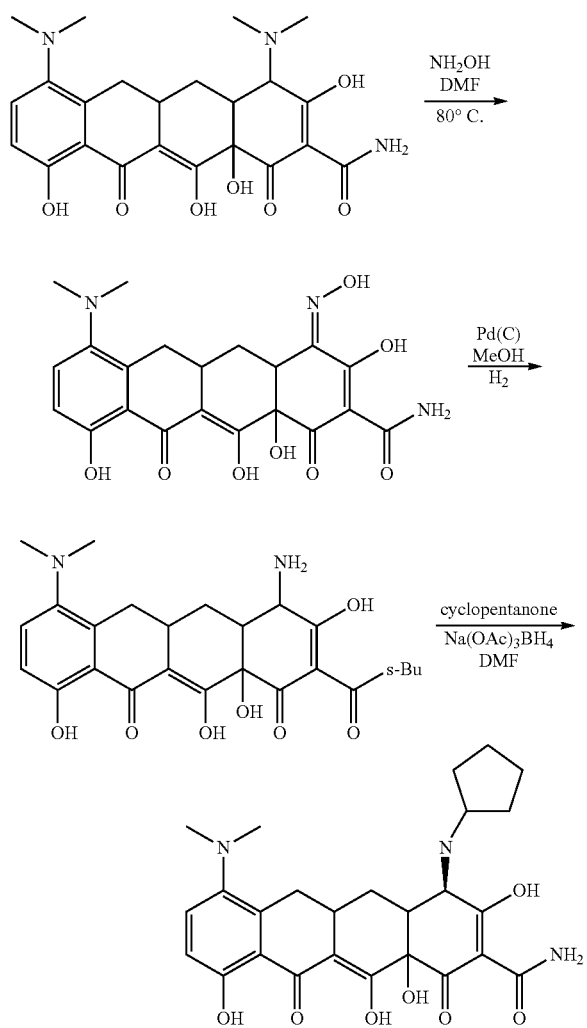

To a solution of minocycline 2HCl (29.3 g) in DMF (300 mL) was added a solution of hydroxylamine 50% in H$_2$O (7.98 mL). The solution was heated to 80° C. for 2 hours while exposed to the air. After cooling to room temperature, the solution was diluted with water. The water solution was filtered through a plug of DVB resin eluting with a 500 mL gradient of acetonitrile and water (5%-10%-20%-50%). At the 50% gradient, the product eluted as a yellow solution. The solution was concentrated under reduced pressure and further dried under vacuum to afford 12 g as a yellow/orange solid in 45% yield.

To a solution of 4-oximinominocycline (11.1 g) in MeOH (250 mL) and AcOH (7.22 mL), was added 5% Pd on carbon and flushed with H$_2$. The solution was placed under vacuum for three successive cycles. After the final cycle, the flask was placed under 50 psi of H$_2$ for 16 hours. After flushing the flask with nitrogen, the solution was filtered through a plug of celite, while rinsing with MeOH. The solution was concentrated under reduced pressure to afford a thick oil. The oil was poured into isopropanol (1 L) with vigorous stirring and the resulting suspension was collected on a sintered funnel while rinsing with cold isopropanol. The 4-amino-minocycline product was further dried under high vacuum overnight to afford 7.6 g as a light brown solid in 71% yield. 1.2 g (1.8 mmol) of 4-amino-minocycline TFA salt was reductively coupled with excess cyclopentanone (~10 eq) in the presence of 3 eq. of sodium triacetoxyborohydride in 10 ml of DMF. The reaction mixture was stirred at RT for several hrs. The reaction was monitored by analytical HPLC. The final product was isolated via preparative HPLC. ESIMS m/z 498 (MH+); $^1$H NMR (300 MHz, CD$_3$OD) δ ☐7.91 (d, 1H), 7.09 (d, 1H), 4.78 (d, 1H), 3.92-3.87 (m, 1H), 3.43 (m, 1H), 3.27 (s, 6H), 3.04-2.94 (m, 2H), 2.61-2.51 (m, 1H), 2.25-2.22 (m, 3H), 1.91-1.82 (m, 6H), 1.78-1.74 (m, 1H).

(4R,4aS,5aR,12aS)-4-Dimethylamino-7-[2-(2,5-dimethyl-2,5-dihydro-pyrrol-1-yl)-acetyl]-3,10,12,12a-tetrahydroxy-1,11-dioxo-1,4,4a,5,5a,6,11,12a-octahydro-naphthacene-2-carboxylic acid amide (Compound CZ)

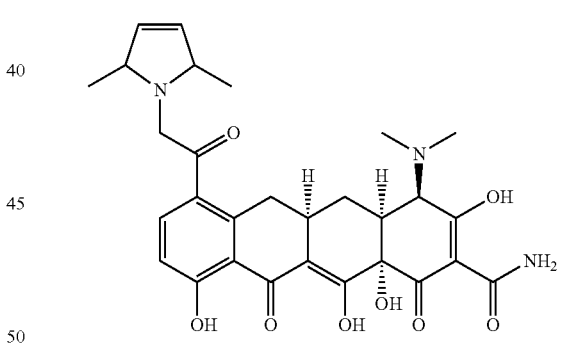

To a solution of 7-acetylsancycline (2 mmol) in acetic acid and water was added hydrogen bromide followed by bromine. The reaction mixture was stirred for 10 minutes and poured into ether. The solid intermediate was collected by filtration. The crude product, α-bromoketone, was dissolved in N-methyl-pyrrolidin-2-one and K$_2$CO$_3$, Na$_2$SO$_3$ and 2,5-dimethylpyrrolidine (1 mL) were added and stirred for 45 minutes. The crude material was purified by prep-HPLC using C18 column (linear gradient 5-30% acetonitrile in water with 0.1% TFA) to give the product as a yellow solid: ESIMS m/z 552 (MH+); $^1$H NMR (300 MHz, CD$_3$OD) δ 8.05 (m, 1H), 6.99 (m, 1H), 5.96 (2H, d, J=0.8 Hz), 5.20 (m, 1H), 4.54 (m, 2H), 3.78 (m, 1H), 3.23-2.88 (8H), 2.53 (m, 1H), 2.16 (m, 1H), 1.67-1.41 (7H). Compound DB was prepared in a similar manner.

Acetic acid (4S,4aR,5S,5aR,6R,12aS)-9-acetyl-2-carbamoyl-4-dimethylamino-3,10,12,12a-tetrahydroxy-6-methyl-1,11-dioxo-1,4,4a,5,5a,6,11,12a-octahydro-naphthacen-5-yl ester (Compound CY)

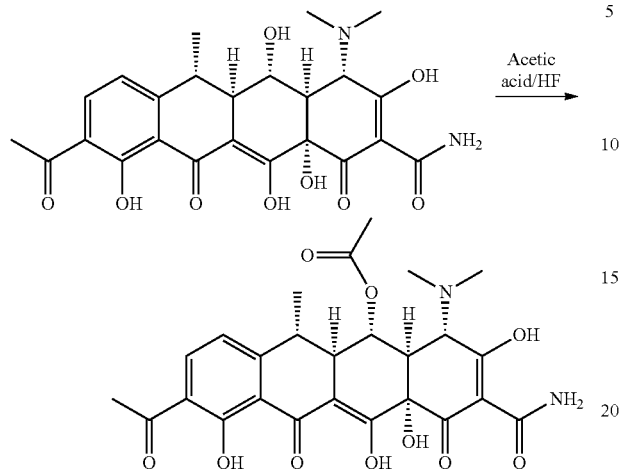

To 10 ml of HF condensed in a polypropylene tube in dry ice, was added in one portion 1 g of 9-acetyl-doxycycline followed by 10 mL of glacial acetic acid. The reaction mixture was left standing at room temperature for overnight. The excess HF was gently removed by slow stream of argon. The residue was then taken by methanol and evaporated to dryness. The crude material was directly purified by C18 column (linear gradient 1-100% acetonitrile in water with 0.1% TFA). The final product was isolated as a yellow solid. ESIMS: m/z 529 (MH+); $^1$H NMR (300 MHz, CD$_3$OD) δ □8.08 (1H, d), 7.1 (1H, d), 5.25 (m, 1H), 3.79 (s, 1H), 3.01 (s, 6H), 2.90 (m, 2H), 2.65 (s, 3H), 2.22 (s, 3H), 1.36 (d, 3H).

2,2-Dimethyl-propionic acid {allyl-[2-((6aS,10S,10aS,11aR)-8-carbamoyl-10-dimethylamino-4,6,6a,9-tetrahydroxy-5,7-dioxo-5,6a,7,10,10a,11,11a,12-octahydro-naphthacen-1-yl)-2-oxo-ethyl]-carbamoyloxy}-methyl ester (Compound DA)

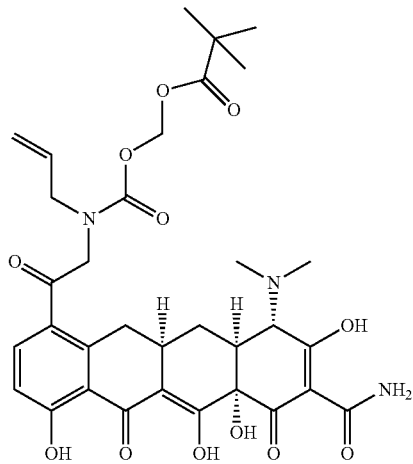 [SMILES: C=CCN(CC(=O)c1ccc(O)c2c1C[C@H]1C[C@H]3[C@H](N(C)C)C(O)=C(C(N)=O)C(=O)[C@@]3(O)C(O)=C1C2=O)C(=O)OCOC(=O)C(C)(C)C]

7-Acetylsancycline (2 mmol) was dissolved in acetic acid and water. Hydrogen bromide followed by bromine were added and stirred for 10 minutes. The intermediate was precipitated from ether and the crude intermediate, α-bromoketone, was dissolved in N-methyl-pyrrolidin-2-one, and K$_2$CO$_3$, Na$_2$SO$_3$ and allylamine (0.8 mL) were added and the reaction mixture was stirred for 10 minutes. The solution was precipitated from ether and further purified to give 7-(2'-allylamino-acetyl)-sancycline as a yellow solid: MS (Mz+1=512).

To a suspension of 7-(2'-allylamino-acetyl)-sancycline (1.2 mmol) and Na$_2$SO$_3$ in a mixture of saturated solution of sodium bicarbonate and acetonitrile was added slowly a solution of 2,2-dimethylpropionylmethylchloroformate in acetonitrile. The reaction mixture was stirred for 10 minutes. The product was extracted with ethyacetate and further purified by prep-HPLC using C18 column (linear gradient 35-45% acetonitrile in water with 0.1% TFA) to give the final product as a yellow solid: ESIMS m/z 670 (MH+); $^1$H NMR (300 MHz, CD$_3$OD) δ 7.92 (m, 1H), 6.94 (m, 1H), 5.84-5.68 (3H), 5.20 (m, 2H), 4.69 (m, 1H), 4.43 (m, 1H), 4.11-3.97 (3H), 3.49 (m, 1H), 3.10-2.84 (8H), 2.46 (m, 1H), 2.21 (m, 1H), 1.65 (m, 1H), 1.17 (m, 9H). Compound DB was prepared in a similar manner.

(4S,4aS,5aR,12aS)-7-Cyclopropylaminomethyl-4-dimethylamino-3,10,12,12a-tetrahydroxy-1,11-dioxo-1,4,4a,5,5a,6,11,12a-octahydro-naphthacene-2-carboxylic acid amide (Compound DC)

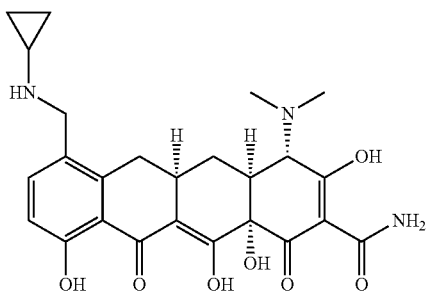 [SMILES: CN(C)[C@@H]1C(O)=C(C(N)=O)C(=O)[C@@]2(O)C(O)=C3C(=O)c4c(O)ccc(CNC5CC5)c4C[C@H]3C[C@@H]12]

An amount of 1.5 g (2.69 mmol) of 7-formyl-sancycline TFA salt was reductively aminated with 562 mL of cyclopropylamine in the presence of sodium triacetoxyborohydride in 10 mL of DMF. The reaction mixture was stirred at room temperature for several hours. The reaction was followed by C18 column (linear gradient 1-100% acetonitrile in water with 0.1% TFA). ESIMS: (m/z) 484 (MH+). $^1$H NMR (300 MHz, CD$_3$OD) δ □7.64-760 (m, 1H), 6.95-6.91 (m, 1H), 4.36 (s, 2H), 4.14 (s, 1H), 3.23 (m, 1H), 3.07-3.00 (m, 8H), 2.87 (m, 1H), 2.50 (m, 1H), 2.4 (m, 1H), 1.55 (m, 1H), 0.95 (m, 4H). Compounds DD, DE, DG, DH, DI, DJ and FC were prepared in a similar manner.

(4S,4aS,5aR,12aS)-7-(tert-Butylamino-methyl)-4-dimethylamino-3,10,12,12a-tetrahydroxy-1,11-dioxo-1,4,4a,5,5a,6,11,12a-octahydro-naphthacene-2-carboxylic acid amide (Compound DF)

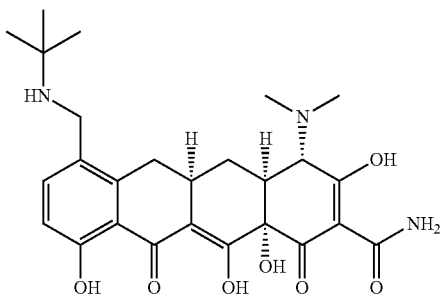 [SMILES: CN(C)[C@@H]1C(O)=C(C(N)=O)C(=O)[C@@]2(O)C(O)=C3C(=O)c4c(O)ccc(CNC(C)(C)C)c4C[C@H]3C[C@@H]12]

A mixture of 7-formylsancycline (1 mmol), tert-butylamine (3 mmol), and indium trichloride (0.1 mmol) in DMF was stirred for 1 hour. Sodium triacetoxyborohydride (3 mmol) was added and stirred for additional 7 hours. The product was purified by C18 column (linear gradient 5-30% acetonitrile in water with 0.1% TFA) to give a yellow solid: ESIMS m/z 500 (MH+); $^1$H NMR (300 MHz, CD$_3$OD) δ 7.64 (1H, d, J=8.5 Hz), 6.95 (1H, d, J=8.5 Hz), 4.22 (s, 2H), 4.15 (s, 1H), 3.23-3.01 (9H), 2.49 (m, 1H), 2.32 (m, 1H), 1.61 (m, 1H), 1.51 (s, 9H). Compounds DD, DE, DG, DH, DI, DJ and FC were prepared in a similar manner.

(4R,4aS,5aR,12aS)-9-(3,6-Dihydro-2H-pyridin-1-ylmethyl)-4,7-bis-dimethylamino-3,10,12,12a-tetrahydroxy-1,11-dioxo-1,4,4a,5,5a,6,11,12a-octahydro-naphthacene-2-carboxylic acid amide
(Compound FE)

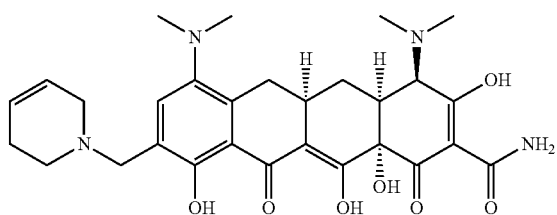 [SMILES: CN(C)c1cc(CN2CC=CCC2)c(O)c2c1C[C@H]1C[C@H]3[C@@H](N(C)C)C(O)=C(C(N)=O)C(=O)[C@@]3(O)C(O)=C1C2=O]

A solution of 9-formylminocycline (9 mmol) and 1,2,3,6-tetrahydropyridine (27 mmol) in 1,2-dichloroethane (120 mL) was stirred for 40 min. Sodium triacetoxyborohydride (18 mmol) was added portionwise over 1 hour. The resulting mixture was stirred for additional 2 hour. The solvent was subsequently reduced and the product was purified by HPLC using C18 column (linear gradient 10-40 acetonitrile in 20 mM aqueous triethanolamine, pH 7.4) to give a yellow solid: MS (Mz+1=553); $^1$H NMR (300 MHz, CD$_3$OD) δ 8.42 (s, 1H), 6.00 (m, 1H), 5.75 (m, 1H), 4.86 (d, 1H, J=3.9 Hz), 4.53 (s, 2H), 3.84 (s, 2H), 3.66 (m, 1H), 3.47-3.34 (8H), 3.22-2.98 (8H), 2.61 (m, 2H), 2.45 (m, 1H), 2.25 (m, 1H), 1.39 (m, 1H). Compounds FF and FJ were prepared in a similar manner and compound FL may be prepared in this manner.

(4S,4aS,5aR,12aS)-9-[(3,4-Dihydroxy-benzylamino)-methyl]-4,7-bis-dimethylamino-3,10,12,12a-tetrahydroxy-1,11-dioxo-1,4,4a,5,5a,6,11,12a-octahydro-naphthacene-2-carboxylic acid amide
(Compound FD)

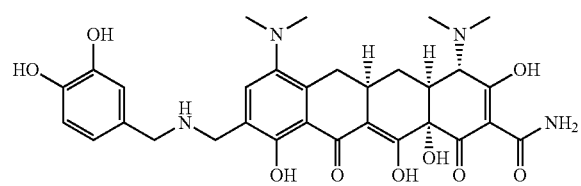 [SMILES: CN(C)c1cc(CNCc2ccc(O)c(O)c2)c(O)c2c1C[C@H]1C[C@H]3[C@H](N(C)C)C(O)=C(C(N)=O)C(=O)[C@@]3(O)C(O)=C1C2=O]

M–H=607; $^1$H NMR (300 MHz, CD$_3$OD) δ 7.51 (s, 1H), 6.82-6.9 (m, 3H), 4.4-4.4 (m, 4H), 3.06 (s, 6H), 2.75 (s, 6H) 2.63 (sm 2H), 2.43-2.49 (m, 4H) 1.8 (m, 2H).

(4S,4aR,5S,5aR,12aS)-4-Dimethylamino-9-(4-fluoro-piperidin-1-ylmethyl)-3,5,10,12,12a-pentahydroxy-6-methylene-1,11-dioxo-1,4,4a,5,5a,6,11,12a-octahydro-naphthacene-2-carboxylic acid amide
(Compound FG)

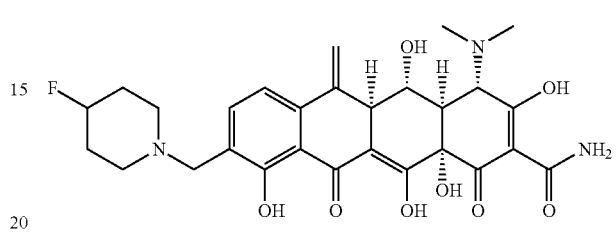

A mixture 9-formylmethacycline (0.56 g, 1 mmol), and 4-fluoropiperidine HCl (0.28 g, 2 mmol) in DMF (7 mL) was stirred under argon at room temperature. To this, triethylamine (202 µL, 2 mmol) was added and the reaction mixture was stirred at room temperature for 1 hour. Sodium cyanoborohydride (0.19 g, 3 mmol) was then added and the reaction mixture was stirred at room temperature for another 2 hours. The DMF was removed and the crude material was purified using preparative HPLC (C18, linear gradient 10-40% acetonitrile in water with 0.1% TFA). The yellow solid obtained after evaporation was converted to its HCl salt using saturated solution of methanol-HCl MS (ESI+) m/z 557.57, obs. 558.30 (MH$^+$); $^1$H NMR (300 MHz, CD$_3$OD) δ 7.70 (d, J=7.2 Hz, 1H), 7.24 (d, J=7.2 Hz, 1H), 5.65 (d, J=3.5 Hz, 1H), 5.50 (d, J=3.5 Hz, 1H) 4.55 (s, 1H), 4.40 (s, 2H), 3.88 (m, 1H), 3.67 (m, 1H), 3.55-3.32 (m, 3H), 3.02-2.78 (m, 7H), 2.40-1.91 (m, 4H). Compounds FF and FJ were prepared in a similar manner and compound FL may be prepared in this manner.

(4S,4aR,5S,5aR,12aS)-4-Dimethylamino-3,5,10,12,12a-pentahydroxy-9-[(methoxy-methyl-amino)-methyl]-6-methylene-1,11-dioxo-1,4,4a,5,5a,6,11,12a-octahydro-naphthacene-2-carboxylic acid amide
(Compound FH)

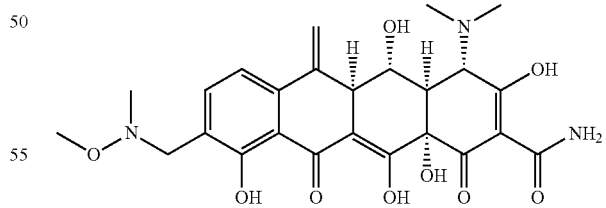

A mixture 9-formylmethacycline (0.56 g, 1 mmol), and N,O-dimethylhydroxylamine HCl (0.19 g, 2 mmol) in DMF (10 mL) was stirred under argon at room temperature for 1 hour. Sodium cyanoborohydride (0.09 g, 1.5 mmol) was then added and the reaction mixture was stirred at room temperature for another 1 minute. The DMF was removed and the crude material was purified using preparative HPLC (C18, linear gradient 15-40% acetonitrile in water with 0.1% TFA). The yellow solid obtained after evaporation was converted to its HCl salt using saturated solution of methanol-HCl MS (ESI+) m/z 515.51, obs. 516.25 (MH$^+$); $^1$H NMR (300 MHz, CD$_3$OD) δ 7.69 (d, J=7.2 Hz, 1H), 7.18 (d, J=7.2 Hz, 1H), 5.65 (d, J=3.5 Hz, 1H), 5.48 (d, J=3.5 Hz, 1H) 4.60 (s, 1H), 4.10 (s, 2H), 3.91 (m, 1H), 3.70 (m, 1H), 3.58 (s, 3H), 3.12-2.94 (m, 6H), 2.81 (s, 3H), 2.10 (s, 1H). Compounds FF and FJ were prepared in a similar manner and compound FL may be prepared in this manner.

(4S,4aS,5aR,12aS)-4,7-Bis-dimethylamino-9-[N"-(2, 2-dimethyl-propionyl)-hydrazinomethyl]-3,10,12, 12a-tetrahydroxy-1,11-dioxo-1,4,4a,5,5a,6,11,12a-octahydro-naphthacene-2-carboxylic acid amide (Compound FI)

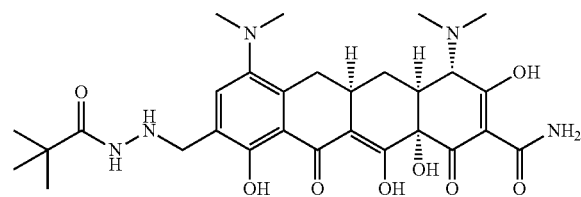 [SMILES: CN(C)c1cc(CNNC(=O)C(C)(C)C)c(O)c2c1C[C@H]1C[C@H]3[C@H](N(C)C)C(O)=C(C(N)=O)C(=O)[C@@]3(O)C(O)=C1C2=O]

To solution of 9-formylminocycline (1.21 g, 2.50 mmol) in anhydrous dichloroethane (25 mL) at room temperature was added pivaloylhydrazide (0.465 g, 4.00 mmol). After 16 hours, the solution was concentrated under reduced pressure. The crude product was redissolved in acetic acid at room temperature and borane trimethylamine complex (0.191 g, 2.63 mmol) was added. After 12 hours, the solution was poured into 2% TFA water. The water solution was loaded onto a DVB column for solid phase extraction and the product was isolated by eluting with 1% TFA/CH$_3$CN. The crude product was further purified by preparatory HPLC (C18, linear gradient 10-60% acetonitrile in water with 0.1% TFA) to afford 0.47 g in 32% yield as a yellow solid. $^1$H NMR (300 MHz, CD$_3$OD) δ 8.15 (s, 1 H), 4.49-4.44 (m, 2 H), 4.12 (s, 1 H), 3.48-3.35 (m, 1H), 3.23-2.90 (m, 16 H), 2.57-2.46 (m, 1 H), 2.33-2.25 (m, 1 H), 1.70-1.53 (m, 1 H), 1.12 (s, 9H). LC/MS (MH$^+$) 586. Compounds FF and FJ were synthesized in a similar manner and compound FL may be synthesized in a similar manner.

(4S,4aS,5aR,12aS)-4,7-Bis-dimethylamino-3,10,12, 12a-tetrahydroxy-9-(4"-tert-butyl-semicarbazido-1"-methyl)-1,11-dioxo-1,4,4a,5,5a,6,11,12a-octahydro-naphthacene-2-carboxylic acid amide (Compound FK)

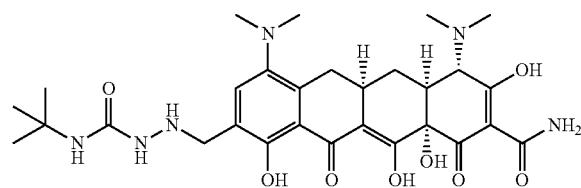 [SMILES: CN(C)c1cc(CNNC(=O)NC(C)(C)C)c(O)c2c1C[C@H]1C[C@H]3[C@H](N(C)C)C(O)=C(C(N)=O)C(=O)[C@@]3(O)C(O)=C1C2=O]

To solution of 9-formylminocycline (1.21 g, 2.50 mmol) in anhydrous dichloroethane (25 mL) at room temperature was added t-butylsemicarbazide (0.391 g, 3.00 mmol). After 16 hours, the solution was concentrated under reduced pressure. The crude product was redissolved in acetic acid (8.3 mL) at room temperature and borane trimethylamine complex (0.191 g, 2.63 mmol) was added. After 12 hours, the solution was poured into 2% TFA water. The water solution was loaded onto a DVB column for solid phase extraction and the product was isolated by eluting with 1% TFA/CH$_3$CN. The crude product was further purified by preparatory HPLC (C18, linear gradient 10-60% acetonitrile in water with 0.1% TFA) to afford 0.53 g in 35% yield as a yellow solid. $^1$H NMR (300 MHz, CD$_3$OD) δ 8.06 (s, 1 H), 4.42-4.39 (m, 2 H), 4.11 (s, 1 H), 3.32-3.14 (m, 4 H), 3.07-2.91 (m, 7 H), 2.56-2.43 (m, 1 H), 2.37-2.28 (m, 1 H), 1.72-1.57 (m, 1 H), 1.20 (s, 9 H). LC/MS (MH$^+$) 601. Compounds FF and FJ were synthesized in a similar manner and compound FL may be synthesized in a similar manner.

(4aS,5aR,12aS)-7-Dimethylamino-3,10,12,12a-tetrahydroxy-9-(3-isopropyl-[1,2,4]oxadiazol-5-yl)-1, 11-dioxo-1,4,4a,5,5a,6,11,12a-octahydro-naphthacene-2-carboxylic acid amide (Compound FM)

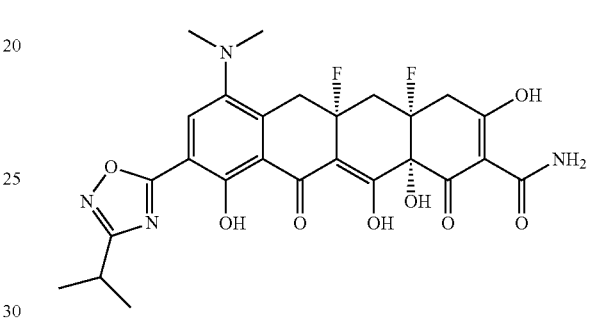

To a 500 mL flask was added (4.00 g, 8.60 mmol) 4-dedimethylamine-9-iodo minocycline free base (see the synthesis of compound CC), NMP (50 mL), N-hydroxysuccinimide (3.9 g, 38 mmol). To the reaction flask was added a stir bar, tetrakis(triphenylphosphine)palladium(0) (2.00 g, 1.67 mmol) and DIEA (3.0 mL, 1.7 mmol). The flask was placed under vacuum (20 mm Hg) and purged 3 times with carbon monoxide. The flask was then heated to 60° C. under 1.0 atm of carbon monoxide and was stirred for 1 hour until the 4-dedimethlyamine-9-iodo minocycline was consumed and a peak for the corresponding 9-NHS-ester 4-dedimethylamino minocycline intermediate [(M+1) of 556 M/Z] was formed as observed by LCMS. The NHS-ester intermediate was then reacted with N'-hydroxy-2-methylpropanimidamide (2.0 g, 19.6 mmol) at room temperature for 2 hours to give the noncyclized intermediate [(M+1) of 543 M/Z] as determined by LCMS. The noncyclized intermediate was isolated by adding it to 50 mL acetonitrile followed by dilution of the reaction mixture with water to a total volume of 2.0 L. Subsequently, the water was adjusted to a pH of 2 using trifluoroacetic acid. The aqueous solution was then filtered and loaded onto a plug of divinylbenzene resin and purified (10-60% MeCN, 0.1% TFA) to give 1 g of crude noncyclized intermediate. To noncyclized-intermediate (2.0 g, 3.7 mmol) in a 500 mL round bottom flask was added NMP (80 mL) and toluene (80 mL). To prevent hydrolysis during the subsequent cyclization step, residual water was removed from the noncyclized intermediate by subjecting it to rotary evaporator (5 mm Hg, 45° C.) until all the toluene/water was evaporated. Next, the flask was backfilled with argon and diisopropylamine (2 mL, 1.13 mmol) was added. To facilitate cyclization the contents were heated to 125° C. for 8 minutes via microwave irradiation. The reaction was then added to acetonitrile, diluted with water to a final volume of two liters and trifluoroacetic acid was added to a final pH of 2. The solution was then filtered through celite to remove the catalyst, loaded onto a reverse phase column and the crude product was purified by HPLC (C18, linear gradient 30-40% acetonitrile in water with 0.1% TFA). The fractions containing the final product were loaded onto a DVB plug, washed with aqueous HCl (1.0 L, 0.01 N) and eluted with methanol to give the HCl salt of 9-(3-isopropyl-1,2,4-Oxadiazoyl)-4-dedimethylamino minocycline (280 mg, 0.53 mmol, 12%). ¹H-NMR (300 MHz, chemical shifts in ppm with TMS as internal reference at 0 ppm) δ 1.47 (d, J=7.5 Hz, 6H), 1.55-1.75 (m, 1H), 2.0-2.2 (m, 1H), 2.15-2.6 (m, 3H), 2.6-2.9 (m, 7H), 3.05-3.19 (m, 1H), 3.20-3.45 (m, 3H), 8.00 (s, 1H). ESI-MS (electron spray) calcd. for $C_{26}H_{28}N_4O_8$ 524.54. found (M+1), 525.25. Compound FN was also synthesized in a similar manner.

(4aS,5aR,12aS)-7-Dimethylamino-3,10,12,12a-tetrahydroxy-1,11-dioxo-9-propionyl-1,4,4a,5,5a,6,11,12a-octahydro-naphthacene-2-carboxylic acid amide (Compound FR)

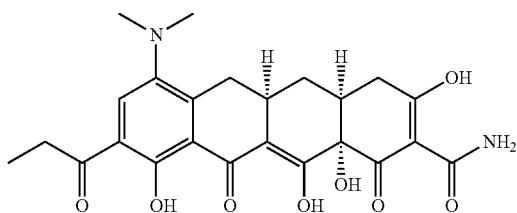

A reaction flask (in case of propyne, a pressure reactor was used for reaction) was charged with, 9-iodo-4-dedimethylaminominocycline (10 g, 18.51 mmol, see the synthesis of compound CC), palladium (II) acetate (0.415 g, 1.85 mmol), CuI (0.705 g, 3.70 mmol), and Pd(PPh₃)₄ (2.14 g, 1.85 mmol) and the acetylene (4 equiv). The solvent was added to the reaction mixture, followed by the acetylene reagent and the Et₃N and the reaction flask was purged with argon for 1 minute. The reaction flask was heated to 75° C. and allowed to stir until the starting material has been consumed (typical reaction time is between 5 minutes and 1 hour), as indicated by sampling the reaction at regular intervals via LCMS. The reaction mixture was then filtered warm, through a bed of Celite and washed with 4×50 mL of MeCN. The combined filtrate was evaporated to dryness, which was further dried under high vacuum for 18 hours to afford the crude acetylene-substituted product. It was used without purification for the next step.

To the flask containing the dried product from the previous step was added the TFA solution (100 mL) and stirred at room temperature for 5 minutes, followed by stirring at 80° C. for 5 min. An 80% solution of H₂SO₄ (100 mL) was freshly prepared and added (while hot) to the reaction mixture over approximately 60 seconds. The reaction turned into a solution, after a momentary appearance of some precipitate. The reaction mixture was stirred at 75° C. until the reaction was confirmed to be complete by LCMS monitoring. The reaction mixture was poured into 800 mL of ice-water and allowed to stir for 20 minutes. The suspension was filtered over a bed of Celite and the precipitate was washed with 6×100 mL portions of dilute HCl (ca. 2-3%) and/or dilute formic acid (ca. 2-3%). The yellow filtrate was filtered again through a 0.22μ frit and purified by prep-HPLC (C18, linear gradient 25-55% acetonitrile in water with 0.2% formic acid, 280 nm) carefully to remove a closely eluting impurity (detected only by MS, obs. m/z 557.2). The combined pure fractions were diluted three times with water and the solution was loaded onto a clean DVB column, washed with water containing approximately 1% HCl (ca. 2 L) and eluted into methanol. The methanol solution was evaporated to dryness and further dried under high vacuum for 18 hours to afford 3.17 g of the desired product as an HCl salt. MS (ESI+) m/z Theor. Calc. 470.47, obs. 471.20 (MH⁺). ¹H NMR (300 MHz, CD₃OD) δ 8.25 (s, 1H), 3.13 (m, 3H), 2.98 (m, 1H), 2.50 (m, 3H), 2.12 (dm, 1H), 1.68 (m, 1H), 1.17 (t, 3H).

(4aS,5aR,12aS)-7-Dimethylamino-9-(3,3-dimethylbutyryl)-3,10,12,12a-tetrahydroxy-1,11-dioxo-1,4,4a,5,5a,6,11,12a-octahydro-naphthacene-2-carboxylic acid amide (Compound FS)

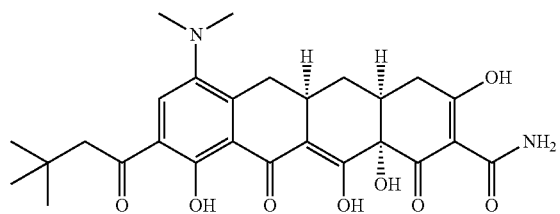 [SMILES: CN(C)c1cc(C(=O)CC(C)(C)C)c(O)c2c1C[C@H]1C[C@H]3CC(O)=C(C(N)=O)C(=O)[C@@]3(O)C(O)=C1C2=O]

MS (ESI+) m/z Theor. Calc. 512.55, Obs. 513.25 (MH⁺). ¹H NMR (300 MHz, CD₃OD) δ 8.16 (s, 1H), 3.18 (m, 1H), 3.07 (s, 2H), 2.97 (m, 1H), 2.50 (m, 3H), 2.12 (dm, 1H), 1.66 (m, 1H), 1.06 (s, 9H).

(4aS,5aR,12aS)-7-Dimethylamino-9-(3-dimethylamino-propionyl)-3,10,12,12a-tetrahydroxy-1,11-dioxo-1,4,4a,5,5a,6,11,12a-octahydro-naphthacene-2-carboxylic acid amide (Compound FT)

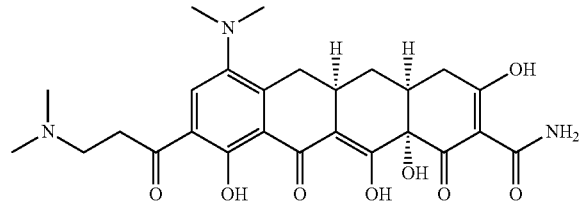 [SMILES: CN(C)CCC(=O)c1cc(N(C)C)c2c(c1O)C(=O)C1=C(O)[C@]3(O)C(=O)C(C(N)=O)=C(O)C[C@@H]3C[C@@H]1C2]

MS (ESI+) m/z Theor. Calc. 513.54, Obs. 514.30 (MH⁺). 1H NMR (300 MHz, CD₃OD) δ 8.38 (s, 1H), 3.69 (m, 2H), 3.55 (m, 2H), 3.22 (m, 1H), 3.00 (m, 7H), 2.51 (m, 3H), 2.14 (dm, 1H), 1.69 (m, 1H).

(4aS,5aR,12aS)-7-Dimethylamino-9-(3-dimethylamino-propyl)-3,10,12,12a-tetrahydroxy-1,11-dioxo-1,4,4a,5,5a,6,11,12a-octahydro-naphthacene-2-carboxylic acid amide (Compound FU)

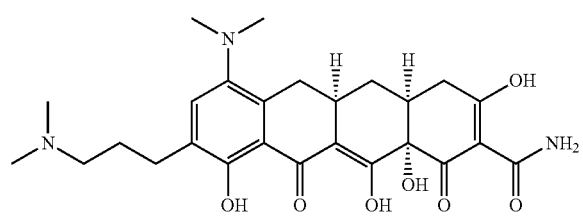 [SMILES: CN(C)CCCc1cc(N(C)C)c2c(c1O)C(=O)C1=C(O)[C@]3(O)C(=O)C(C(N)=O)=C(O)C[C@@H]3C[C@@H]1C2]

The 9-acetylene minocycline intermediate (0.870 g) prepared from N,N-dimethyl-propargylamine was dissolved in MeOH (20 mL) and stirred under a hydrogen atmosphere (50 psi) in presence of 10% Pd/C (0.092 g) for 3 hours, when LCMS monitoring of the reaction confirmed completion of the reaction. The reaction mixture was filtered over a bed of Celite, washed with 2×10 mL of MeOH and the combined filtrate was evaporated to dryness. The product was purified using preparative HPLC (C18, linear gradient 15-55% acetonitrile in water with 0.2% formic acid, 280 nm). The pure product fractions were concentrated on a DVB column, converted into HCl salt, and eluted in pure methanol. The methanol solution was evaporated to dryness, and further dried under high vacuum for 12 hours to afford the desired product as its HCl salt (0.180 g). MS (ESI+) m/z 499.56, obs. 500.30 (MH+). $^1$H NMR (300 MHz, CD$_3$OD) δ 7.93 (s, 1H), 3.18 (m, 4H), 2.98 (m, 1H), 2.90 (s, 6H), 2.82 (t, 2H), 2.48 (m, 3H), 2.11 (m, 3H), 1.65 (m, 1H).

(4aS,5aR,12aS)-7-Dimethylamino-9-ethyl-3,10,12,12a-tetrahydroxy-1,11-dioxo-1,4,4a,5,5a,6,11,12a-octahydro-naphthacene-2-carboxylic acid amide (Compound FV)

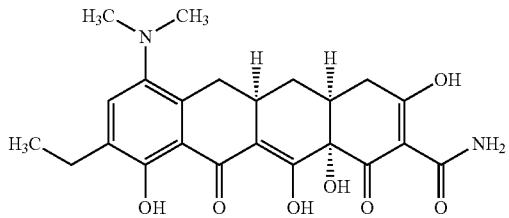 [SMILES: CCc1cc(N(C)C)c2c(c1O)C(=O)C1=C(O)[C@]3(O)C(=O)C(C(N)=O)=C(O)C[C@@H]3C[C@@H]1C2]

In a 2-necked, 100 mL flask, 9-iodo-4-dedimethylamino-minocycline freebase (3.0 g, 5.56 mmol, see synthesis of compound CC) and Pd(PPh$_3$)$_4$ (0.291 g, 0.569 mmol) were charged and the flask was degassed by vacuum followed by argon three times. To the flask, 30 mL of THF was added and the solution/suspension was allowed to stir for 2-3 minutes. A 0.24 M solution of Et$_3$In (prepared from the reaction of ethylmagnesium chloride (3 equiv) and InCl$_3$) (23.1 mL, 5.55 mmol) was added to the reaction mixture. The flask was equipped with a reflux condenser and the reaction mixture was allowed to reflux (oil bath temp=85° C.). After 1 hour, a reaction aliquot showed (by LCMS) the consumption of the starting material. The reaction flask was removed from the oil bath and allowed to cool to room temperature. The reaction mixture was diluted with 60 mL of water and treated with TFA to adjust the pH to 2. The organic solvent was reduced by rotary evaporation. The residual mixture was then diluted with 25 mL of water containing 1% TFA and filtered through Celite. The Celite layer was washed with 3×20 mL portions of 1% TFA/water. The resulting yellow solution was purified using preparative HPLC (C18, linear gradient 20%-50% acetonitrile in water with 0.1% TFA, 280 nm). The main fractions were diluted 4 x with water, loaded onto a DVB column, washed first with 1% HCl in water and then eluted in MeOH. The yellow MeOH solution was then evaporated to dryness, dissolved again in MeOH/dil HCl and evaporated to dryness. It was further dried under high vacuum for 16 hours to afford 1.272 g of pure material. MS (ESI+) m/z Theor. Calc. 442.46, obs. 443.20 (MH+). $^1$H NMR (300 MHz, CD$_3$OD) δ 7.78 (s, 1H), 3.18 (m, 4H), 2.95 (m, 1H), 2.73 (q, 2H), 2.43 (m, 3H), 2.11 (dm, 1H), 1.64 (m, 1H), 1.24 (t, 3H).

4aS,5aR,12aS-7-Dimethylamino-3,10,12,12a-tetrahydroxy-9-isopropyl-1,11-dioxo-1,4,4a,5,5a,6,11,12a-octahydro-naphthacene-2-carboxylic acid amide (Compound FW)

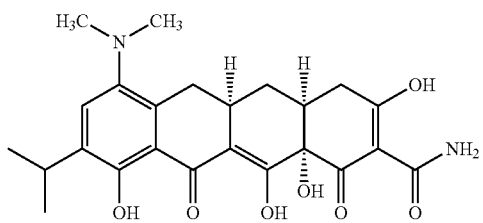 [SMILES: CC(C)c1cc(N(C)C)c2c(c1O)C(=O)C1=C(O)[C@]3(O)C(=O)C(C(N)=O)=C(O)C[C@@H]3C[C@@H]1C2]

MS (ESI+) m/z Theor. Calc. 456.49, obs. 457.20 (MH+). $^1$H NMR (300 MHz, CD$_3$OD) δ 7.73 (1H), 3.11 (m, 1H), 2.94 (m, 1H), 2.43 (m, 3H), 2.11 (dm, 1H), 1.63 (m, 1H), 1.26 (m, 6H).

4aS,5aR,12aS-7-Dimethylamino-9-(2,2-dimethyl-propyl)-3,10,12,12a-tetrahydroxy-1,11-dioxo-1,4,4a,5,5a,6,11,12a-octahydro-naphthacene-2-carboxylic acid amide (Compound FX)

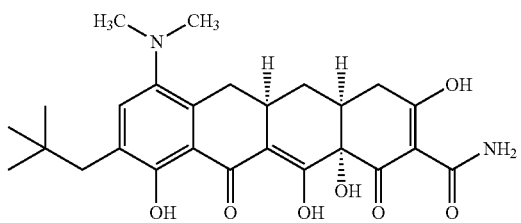 [SMILES: CN(C)c1cc(CC(C)(C)C)c(O)c2c1C[C@H]1C[C@H]3CC(O)=C(C(N)=O)C(=O)[C@@]3(O)C(O)=C1C2=O]

MS (ESI+) m/z Theor. Calc. 484.54, obs. 485.25 (MH+). $^1$H NMR (300 MHz, CD$_3$OD) δ 7.69 (s, 1H), 3.11 (dd, 1H), 2.96 (m, 1H), 2.66 (m, 2H), 2.45 (m, 3H), 2.12 (dm, 1H), 1.65 (m, 1H), 0.96 (s, 9H).

(4aS,5aR,12aS)-7-Dimethylamino-3,10,12,12a-tetrahydroxy-1,11-dioxo-9-trifluoromethyl-1,4,4a,5,5a,6,11,12a-octahydro-naphthacene-2-carboxylic acid amide (Compound FY)

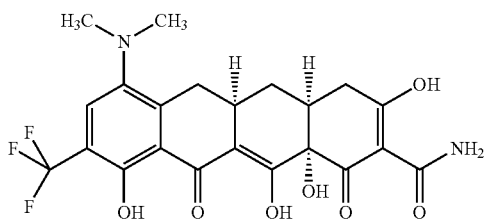 [SMILES: CN(C)c1cc(C(F)(F)F)c(O)c2c1C[C@H]1C[C@H]3CC(O)=C(C(N)=O)C(=O)[C@@]3(O)C(O)=C1C2=O]

A 100 mL 2-necked flask was charged with a stir bar, 9-iodo-4-dedimethylamino-minocycline (1.86 g, 3.43 mmol, see the synthesis of compound CC), CuI (0.721 g, 3.78 mmol), HMPA (10 mL) and methyl-2,2-difluoro-2-(sulfonyl)-acetate (1.2 mL, 9.43 mmol). The reaction mixture was purged with argon, and stirred at 80° C. with frequent monitoring of the reaction mixture with LCMS. After 30 minutes, another 1.2 mL of methyl-2,2-difluoro-2-(sulfonyl)-acetate was added to the reaction mixture and allowed to stir at that temperature. Upon the consumption of the starting material as indicated by LCMS, the reaction mixture was cooled to room temperature and poured into 200 mL of water. The suspension was stirred for 2 hours, filtered, washed with 5×20 mL portions of water, and air dried. The crude material was dissolved in MeCN (containing 2% TFA), diluted with water 5 times and purified by preparative HPLC (C18, linear gradient 20%-55% acetonitrile in water with 0.1% TFA, 280 nm). The pure product fractions were concentrated on a DVB column, converted into HCl salt, eluted with MeOH and the methanolic solution was evaporated to dryness. It was further dried under high vacuum for 16 hours to afford 0.241 g of the desired product. MS (ESI+) m/z Theor. Calc. 482.41, obs. 483.35 (MH+) $^1$H NMR (300 MHz, CD$_3$OD) δ 8.16 (s, 1H), 3.00 (m, 1H), 2.5 (m, 3H), 2.13 (dm, 1H), 1.66 (m, 1H).

(4R,4aS,5aR,12aS)-4,7-Bis-dimethylamino-9-ethyl-,
10,12,12a-tetrahydroxy-1,11-dioxo-1,4,4a,5,5a,6,11,
12a-octahydro-naphthacene-2-carboxylic acid amide
(Compound FZ)

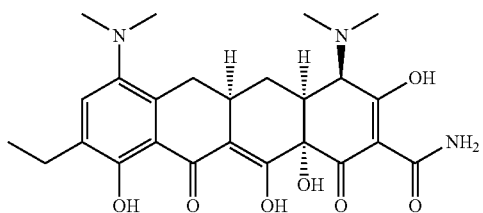 [SMILES: CCc1cc(N(C)C)c2c(c1O)C(=O)C1=C(O)[C@]3(O)C(=O)C(C(N)=O)=C(O)[C@H](N(C)C)[C@@H]3C[C@@H]1C2]

$^1$H NMR (300 MHz, CD$_3$OD) δ7.30 (s, 1H), 3.78 (d, 1H), 3.44 (m, 1H), 3.01 (br.s, 6H), 2.99-2.85 (m, 2H), 2.68 (q, 2H), 2.62 (s, 6H), 2.28-2.02 (m, 1H), 1.63 (q, 1H), 1.21 (t, 3H). LCMS (m/z): 486 (MH$^+$).

(4S,4aR,5S,5aR,12aS)-4-Dimethylamino-3,5,10,12,
12a-pentahydroxy-6-methylene-1,11-dioxo-9-pyri-
din-2-yl-1,4,4a,5,5a,6,11,12a-octahydro-naph-
thacene-2-carboxylic acid amide (Compound GA)

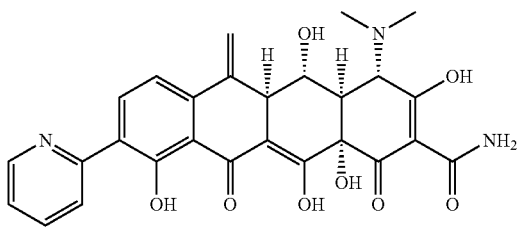 [SMILES: C=C1c2ccc(-c3ccccn3)c(O)c2C(=O)C2=C(O)[C@]3(O)C(=O)C(C(N)=O)=C(O)[C@@H](N(C)C)[C@@H]3[C@@H](O)[C@H]12]

An amount of 9-iodo-methacycline (569 mg, 1 mmol), Pd(PPh$_3$)$_4$ (115 mg, 0.1 mmol), and copper iodide (38 mg) were taken in 20 mL of DMF. To this pyridin-2-yl tributyl stannane (441 mg, 1.2 mmol) was added and the reaction mixture was stirred at room temperature for 3 hours. Completion of the reaction was monitored using LCMS. The solvent was then removed under vacuum and the crude material was purified using preparative HPLC (C18, linear gradient 10-40% acetonitrile in water with 0.1% TFA). The yellow solid obtained after evaporation was converted to its HCl salt using saturated solution of methanol-HCl MS (ESI+) m/z 519.50, obs. 520.25 (MH$^+$); $^1$H NMR (300 MHz, CD$_3$OD) δ 8.80 (d, J=3.4 Hz, 1H), 8.51 (t, 1H), 8.28 (d, J=7.2 Hz, 1H), 7.99 (d, J=7.2 Hz, 1H), 7.89 (t, 1H), 7.35 (d, J=7.2 Hz, 1H), 5.71 (s, 1H), 1H), 5.15 (s, 1H) 4.55 (s, 1H), 3.89 (m, 1H), 3.70 (m, 1H), 3.06-2.88 (m, 7H).

(4S,4aS,5aR,12aS)-7-Chloro-4-dimethylamino-9-
ethyl-3,10,12,12a-tetrahydroxy-1,11-dioxo-1,4,4a
5,5a,6,11,12a-octahydro-naphthacene-2-carboxylic
acid amide (Compound GB)

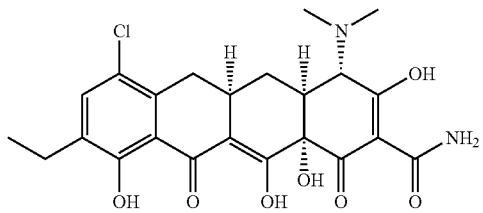 [SMILES: CCc1cc(Cl)c2c(c1O)C(=O)C1=C(O)[C@]3(O)C(=O)C(C(N)=O)=C(O)[C@@H](N(C)C)[C@@H]3C[C@@H]1C2]

A 100 mL 2 or 3 neck round-bottom flask with reflux condenser was charged with anhydrous InCl$_3$ (1.21 g, 4.05 mmol) and dried under vacuum with a heat gun. After the flask cooled to ambient temperature and flushed with argon, anhydrous THF (24.0 mL) was added. The solution was cooled to −78° C. and EtMgBr (12.2 mL, 12.2 mmol) as a 1 M solution in THF was added. After 15 minutes, the solution was allowed to slowly warm to room temperature to form a clear heterogeneous solution. The reaction flask was added 7-chloro-9-iodosancycline (2.07 g, 3.60 mmol) and Pd(t-Bu$_3$)$_2$ (0.092 g, 0.180 mmol). The solution was heated to reflux under argon until complete (approximately 1 hour). After cooling to ambient temperature, the solution was quenched with MeOH (0.5 mL) and poured into a stirring cold solution of 1M HCl (0.3 L). After 1 hour, the solution was filtered through a pad of Celite rinsing with water. The water solution was loaded onto a DVB column for solid phase extraction and the product was isolated by eluting with 1% TFA/CH$_3$CN. The crude product was further purified by preparatory HPLC (C18, linear gradient 15-65% acetonitrile in water with 0.1% TFA, to afford 1.31 g in 76% yield as a yellow solid. $^1$H NMR (300 MHz, CD$_3$OD) δ 7.38 (s, 1 H), 4.05 (s, 1 H), 3.29-3.20 (m, 1 H), 3.06-2.93 (m, 8 H), 2.69-2.50 (m, 2 H), 2.34-2.18 (m, 2 H), 1.72-1.57 (m, 1 H), 1.16 (t, J=7.1 Hz, 3 H). LC/MS (MH$^+$) 477.

(4aS,5aR,12aS)-3,10,12,12a-Tetrahydroxy-7-isopro-
pyl-1,11-dioxo-1,4,4a,5,5a,6,11,12a-octahydro-naph-
thacene-2-carboxylic acid amide (Compound GC)

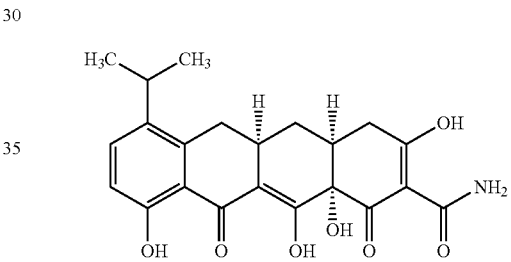

A 100 mL 2-necked flask was charged with a stir bar, 7-iodo-4-dedimethylamino-sancycline (1.5 g, 3.02 mmol), palladium (II) acetate (0.068 g, 0.31 mmol), Pd(PPh$_3$)$_4$(0.349 g, 0.31 mmol), and methanol (20 mL). The reaction mixture was then purged with argon. The suspension was first treated with an aqueous solution of Na$_2$CO$_3$ (0.962 g, 0.91 mmol), and then with a DMF solution of 2-propenyl-boronic acid (prepared from a modified procedure from *Tet. Lett.* 2001, 42, 4083-4085) (0.391 g, 4.55 mmol in 3 mL DMF). The reaction mixture was stirred at 70° C. for 2 hours and monitored with LCMS. Upon the completion of reaction, it was precipitated with water (200 mL), the resulting precipitate was filtered, washed with water and air-dried. The crude product was purified by preparative HPLC (C18, linear gradient 30%-75% acetonitrile in water with 0.1% TFA, 280 nm). The pure product fractions were evaporated to dryness and the resulting material was used as such for the next step.

The product from the previous step (0.670 g) was dissolved in methanol, treated with 0.080 g of 10% Pd/C, and stirred under a hydrogen atmosphere (50 psi) for 3 hours. Upon the consumption of the starting material, the reaction mixture was filtered through a bed of Celite, washed the filter with 2×20 mL methanol portions and the combined organic solution was evaporated to dryness. It was purified by preparative HPLC (C18, linear gradient 30%-75% acetonitrile in water with 0.1% TFA, 280 nm). The pure fractions were combined and evaporated to dryness. Upon further drying under high vacuum for 18 hours, 0.252 g of desired product was isolated. MS (ESI+) m/z Theor. Calc. 413.42, obs. 414.10 (MH+). $^1$H NMR (300 MHz, CD₃OD) δ 7.42 (d, 1H), 6.77 (d, 1H), 2.79 (m, 1H), 2.29 (m, 3H), 2.02 (m, 1H), 1.58 (m, 1H), 1.16 (dd, 6H).

(4aS,5aR,12aS)-3,10,12,12a-Tetrahydroxy-7-methyl-1,11-dioxo-1,4,4a,5,5a,6,11,12a-octahydro-naphthacene-2-carboxylic acid amide (Compound GD)

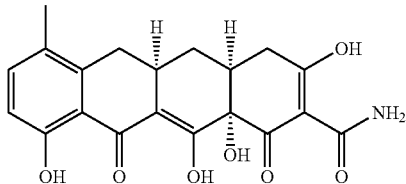 [SMILES: Cc1ccc(O)c2c1C[C@H]1C[C@H]3CC(O)=C(C(N)=O)C(=O)[C@@]3(O)C(O)=C1C2=O]

MS (ESI+) m/z Theor. Calc. 385.37, obs. 386.15 (MH⁺).
¹H NMR (300 MHz, CD₃OD) δ 7.26 (d, 1H), 6.67 (d, 1H), 2.98 (dd, 1H), 2.79 (m, 1H), 2.44 (m, 2H), 2.20 (m, 4H), 2.01 (m, 1H), 1.56 (m, 1H).

(4aS,5aR,12aS)-3,10,12,12a-Tetrahydroxy-7-oxazol-2-yl-1,11-dioxo-1,4,4a,5,5a,6,11,12a-octahydro-naphthacene-2-carboxylic acid amide (Compound GE)

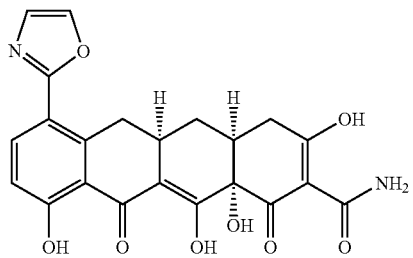 [SMILES: NC(=O)C1=C(O)C[C@@H]2C[C@@H]3Cc4c(-c5ncco5)ccc(O)c4C(=O)C3=C(O)[C@]2(O)C1=O]

MS (ESI+) m/z Theor. Calc. 438.39, obs. 439.20 (MH⁺).
¹H NMR (300 MHz, CD₃OD) δ 8.03 (s, 1H), 7.96 (d, 1H), 7.36 (s, 1H), 6.96 (d, 1H), 3.64 (m, 1H), 2.84 (m, 1H), 2.48 (m, 3H), 2.02 (m, 1H), 1.59 (m, 1H).

(4aS,5aR,12aS)-7-Acetyl-3,10,12,12a-tetrahydroxy-1,11-dioxo-1,4,4a,5,5a,6,11,12a-octahydro-naphthacene-2-carboxylic acid amide (Compound GF)

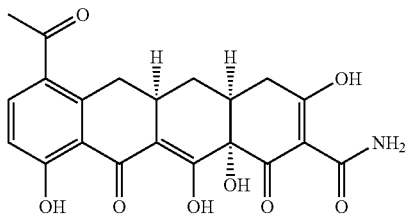 [SMILES: CC(=O)c1ccc(O)c2c1C[C@H]1C[C@H]3CC(O)=C(C(N)=O)C(=O)[C@@]3(O)C(O)=C1C2=O]

MS (ESI+) m/z Theor. Calc. 413.38, obs. 414.20 (MH⁺) ¹H NMR (300 MHz, CD₃OD) δ 7.96 (d, 1H), 6.87 (d, 1H), 3.45 (dd, 1H), 2.78 (m, 1H), 2.52 (s, 3H), 2.41 (m, 3H), 1.99 (dm, 1H), 1.55 (m, 1H).

(4S,4aS,5aR,12aS)-7-Cyclopropyl-4-dimethylamino-3,10,12,12a-tetrahydroxy-1,11-dioxo-1,4,4a,5,5a,6,11,12a-octahydro-naphthacene-2-carboxylic acid amide (Compound GH)

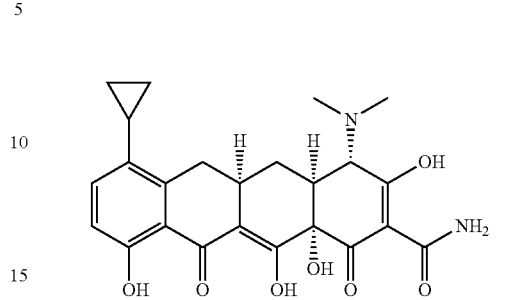

A 1000 mL 2 or 3 neck round-bottomed flask with reflux condenser was charged with anhydrous InCl₃ (12.1 g, 40.5 mmol) and dried under vacuum with a heat gun. After the flask cooled to ambient temperature and was flushed with argon, anhydrous THF (240 mL) was added. The solution was cooled to −78° C. and c-PrMgBr (244 mL, 122 mmol) as a 0.5 M solution in THF was added. After 15 minutes, the solution was allowed to slowly warm to room temperature to form a clear heterogeneous solution. To the reaction flask was added 7-iodosancycline (19.4 g, 36.0 mmol) and Pd(t-Bu₃)₂ (0.920 g, 1.80 mmol). The solution was heated to reflux under argon until complete (approximately 1 hour). After cooling to ambient temperature, the solution was quenched with MeOH (1 mL) and poured into a stirring cold solution of 1M HCl (3 L). After 1 hour, the solution was filtered through a pad of Celite, while rinsing with water. The water solution was loaded onto a DVB column for solid phase extraction and the product was isolated by eluting with 1% TFA/CH₃CN. The crude product was further purified by preparatory HPLC (C18, linear gradient 20-60% acetonitrile in water with 0.1% TFA, to afford 11.8 g in 72% yield as a yellow solid. ¹H NMR (CD₃OD) δ 7.18 (d, J=7.4 Hz, 1 H), 6.61 (d, J=7.4 Hz, 1 H), 3.99 (s, 1 H), 3.34 (dd, J=9.1, 2.8 Hz, 1 H), 3.05-2.84 (m, 10 H), 2.32-2.09 (m, 2 H), 0.86-0.75 (m, 2 H), 0.51-0.37 (m, 2 H). LC/MS (MH⁺) 455.

(4aS,5aR,12aS)-7-Dimethylamino-3,12,12a-trihydroxy-10-methoxy-1,11-dioxo-1,4,4a,5,5a,6,11,12a-octahydro-naphthacene-2-carboxylic acid amide (Compound GI)

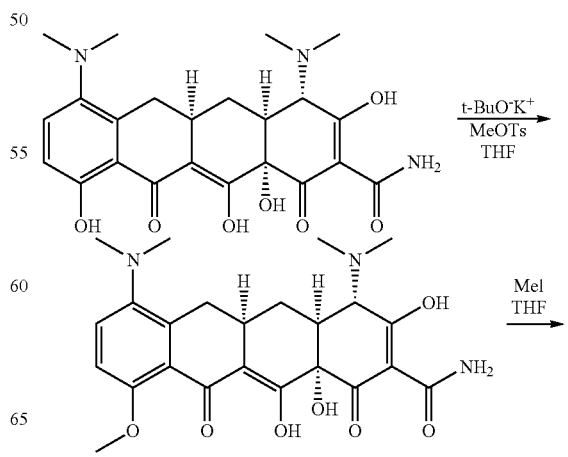

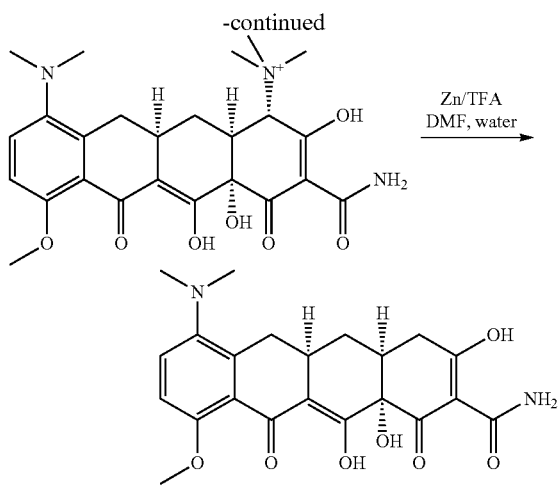

A solution of minocycline (6 g) in THF (80 mL) was cooled to −68° C. and treated with solid tert-BuO⁻K⁺ (5.37 g) and allowed to stir for 60 minutes. The suspension was allowed to warm to room temperature over a period of 1.5 hours. The reaction was cooled to 4° C., treated with MeOTs (5.5 mL) and allowed to stir to warm up slowly to room temperature. The reaction was approximately 75% complete after 5 hours, when it was poured into 0.75 L of ether, stirred for 1 hour at room temperature, filtered (slow filtration) and washed with ether (3×200 mL). Upon drying overnight under vacuum, 12.2 g of crude (dark green) solid was isolated. All the solid was dissolved first in 10% MeCN/water (ca. 500 mL) and the solution (dark green) was acidified with dilute HCl (pH=2). The solution was then diluted with triethanolamine-aqueous buffer (pH=7.4) and the pH was adjusted to 7.3-7.4 with aqueous NaHCO₃ solution and 3-4 mL of triethanolamine. The solution was filtered over Celite and the filtrate was diluted with water (2 L). The material was purified using preparative HPLC (C18, linear gradient 15-35% acetonitrile in 20 mM aqueous triethanolamine and TFA, pH 7.4). The product fractions were immediately acidified with TFA. The pure fractions were combined, the pH adjusted with aqueous NaHCO₃ solution to 7.3, and then diluted with triethanolamine/TFA buffer (pH=7.4). The triethanolamine was washed away with water after loading the product fractions (diluted 3 times with water) onto a DVB column. The product was eluted with pure methanol and the yellow solution evaporated to dryness. The product was further dried under high vacuum for 18 hours to afford 1.37 g (isolated) of yellow solid. It was used for the next step without further purification.

To a solution of 10-methoxyminocycline (1.3 g) in THF (15 mL, warmed briefly), was added MeI (1.5 mL, excess) and allowed to stir at room temperature. When the LC/MS monitoring of the reaction mixture indicated consumption of the starting material, the reaction mixture was treated with 160 mL of t-BME. The resulting yellow suspension was stirred for 2 hours, and the precipitate was filtered, washed with 3×100 mL of t-BME portions and dried under vacuum (air-aspirator). The solid was further dried for 3 h under high vacuum. Isolated 1.6 g of yellow powder.

The de-dimethyl-amination step was carried out using standard reduction conditions, described earlier for the synthesis of 4-dedimethylamino minocycline. The product was purified using preparative HPLC (C18, linear gradient 15-35% acetonitrile in water containing 0.2% formic acid) affording 0.245 g of product as its HCl salt. MS (ESI+) m/z Theor. Calc. 428.43, obs. 429.15 (MH⁺). ¹H NMR (300 MHz, CD₃OD) δ 7.91 (d, 1H), 7.27 (d, 1H), 3.94 (s, 3H), 3.04 (m, 1H), 2.83 (m, 1H), 2.44 (m, 3H), 2.15 (dm, 1H), 1.63 (m, 1H).

(4aS,5aR,12aS)-9-Benzoyl-7-dimethylamino-3,10,12,12a-tetrahydroxy-1,11-dioxo-1,4,4a,5,5a,6,11,12a-octahydro-naphthacene-2-carboxylic acid amide
(Compound GK)

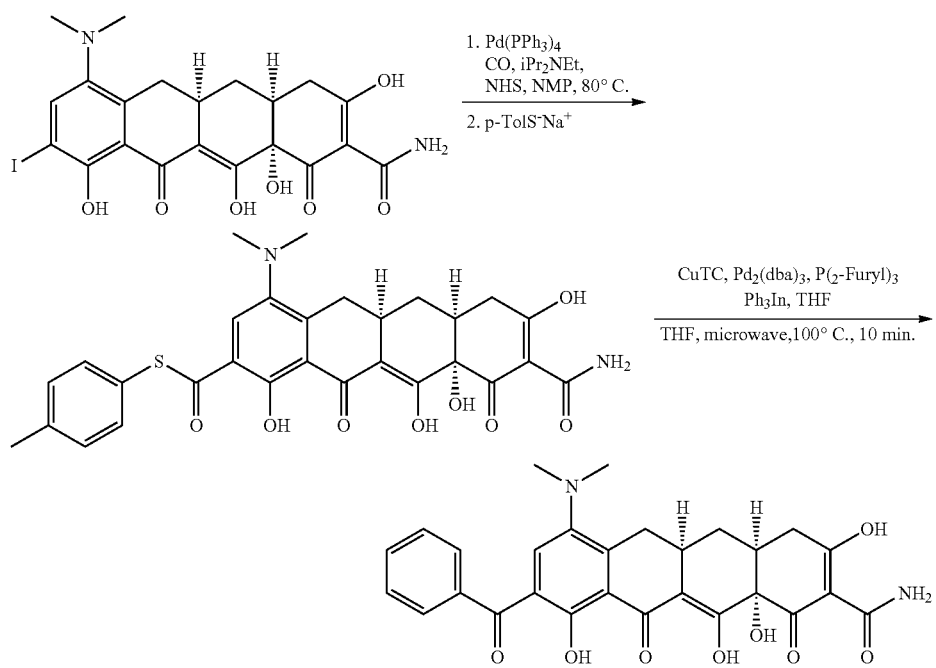

To suspension of 9-iodo-4-dedimethylamino-minocycline (DDAM, freebase, 6 g, 11.1 mmol), Pd(PPh$_3$)$_4$ (1.37 g, 1.185 mmol), N-hydroxysuccinimide (6.51 g, 56.56 mmol) in NMP (50 mL), was added di-isopropylethylamine (9 mL). The reaction mixture was degassed (vacuum/argoncycle) and then the reaction flask was heated to 80° C. in an oil bath. A butyl-rubber-balloon was filled with CO and connected to the reaction flask. The reaction mixture was then degassed and refilled with CO three times and allowed to stir under a CO atmosphere. The reaction was monitored with LC-MS and when >98% of the 9-I-4-DDAM was consumed (with the formation of 9-hydroxysuccinimide-ester of 4-dedimethylamino-minocycline, obs. m/z 556), the reaction mixture was transferred (using a cannula) into a dry 200 mL flask containing sodium 4-methylbenzenethiolate (3.78 g, 25.6 mmol) and a stir bar. This reaction mixture was stirred first at 80° C. for 1.5 hours and then at room temperature for 2 hours. The LC-MS indicated the formation of the desired 9-Tol-S-ester (obs m/z=565). The reaction mixture was then filtered through a bed of Celite and the filtrate was poured into water (500 mL). The resulting suspension was stirred for 30 minutes and then acidified with dilute HCl (pH=1). The product was extracted into EtOAc (3×350 mL) and the organic layer was washed with 3×400 mL portions of water, followed by brine (200 mL). The organic layer was dried over anhydrous Na$_2$SO$_4$ and evaporated to dryness to afford 8.3 g of crude thioester. The crude product was used in the next step.

To a suspension of crude 9-(4-methylphenyl)thiocarboxylacyl-4-dedimethylamino-minocycline (1.2 g, 2.12 mmol), copper(I)-thiophenecarboxylate (0.650 g, 3.4 mmol), Pd$_2$(dba)$_3$ (0.106 g, 0.116 mmol), and P(2-furyl)$_3$ (0.196 g, 0.84 mmol) in anhydrous THF (10 mL) under argon was added a solution of previously prepared Ph$_3$In (16 mL of 0.29 M solution in THF, prepared earlier). The reaction mixture was heated at 90° C. for 2 hours, while monitoring at regular intervals. If the reaction appeared stalled, fresh catalysts and reagent were added to the reaction mixture and continued to stir at 90° C. until the reaction was complete. The reaction mixture was filtered over a bed of Celite and the Celite bed was washed with 3×10 mL portions of THF. The combined filtrate and the washings were evaporated to dryness (a thick oil). The residue was dissolved in MeCN (100 mL) containing 5 mL of TFA and diluted with water (500 mL). The suspension was filtered over a bed of Celite and the filtrate was purified using preparative HPLC (C18, linear gradient 25%-45% acetonitrile in water containing 0.2% formic acid). The product fractions were combined, diluted with ca. 1.8 L of water and loaded onto a DVB column (0.5"×3" diam.). The product was first washed with 8-10% methanol/water (600 mL), and then with a solution containing ca. 1% HCl/20% MeOH/water (ca. 1200 mL, total volume). The product was eluted in MeOH. The yellow solution was collected, evaporated to dryness, suspended/dissolved in MeOH (20 mL)/5% HCl (2 mL) and evaporated to dryness again. The product was further dried overnight under high vacuum to afford 0.412 g of the product. MS (ESI+) m/z Theor. Calc. 518.519, obs. 519.25 (MH$^+$). $^1$H NMR (300 MHz, CD$_3$OD) δ 8.02 (s, 1H), 7.82 (m, 2H), 7.65 (m, 1H), 7.51 (m, 2H), 3.16 (dd, 1H), 3.06 (m, 1H), 2.51 (m, 3H), 2.15 (dm, 1H), 1.68 (m, 1H).

(4S,4aS,5aR,12aS)-4-Dimethylamino-9-[(methoxymethyl-amino)-methyl-3,10,12,12a-tetrahydroxy-1,11-dioxo-1,4,4a,5,5a,6,11,12a-octahydro-naphthacene-2-carboxylic acid amide (Compound GL)

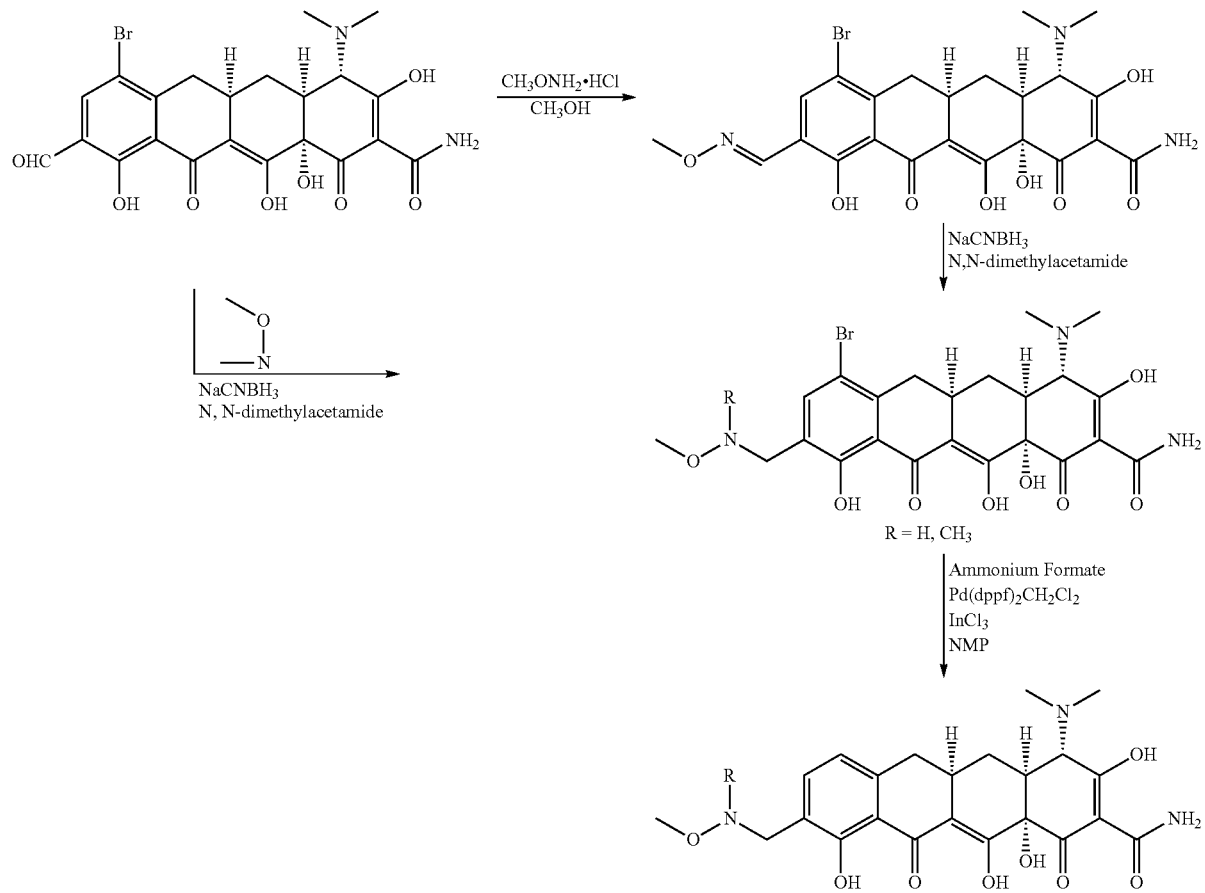

An amount of 7-bromo-9-formyl-sancycline (1.92 mmol) was combined with N,O-dimethyl-hydroxylamine HCl salt (3.84 mmol) and DMA (8 mL) and stirred under an argon atmosphere at room temperature for 1.5 hours. Sodium cyanoborohydride (2.3 mmol) was added and the reaction was monitored by LC/MS. Reaction was complete within 10 minutes. The reaction mixture was triturated in diethyl ether (300 mL), and filtered to give 1.3 g of 7-bromo-9-methoxyaminomethyl sancycline. An amount of 7-bromo-9-methoxyaminomethyl sancycline (0.88 mmol) was combined with ammonium formate (8.83 mmol), Pd(dppf)$_2$CH$_2$Cl$_2$ (0.0883 mmol), InCl$_3$ (0.442 mmol), and NMP (7 mL) in a microwave vial, and placed in the microwave on high absorbance for 5 minutes at 100° C. The reaction mixture was poured into water (400 mL with 0.1% TFA) and was filtered through celite. The crude product was purified by prep-HPLC using a C-18 column (linear gradient 10-40% acetonitrile in water with 0.1% TFA). ESI-MS: (MH+)=488. $^1$H NMR (300 MHz, CD$_3$OD) δ 7.64 (1H, d, J=9 Hz), 6.90 (1H, d, J=6 Hz), 4.67 (m, 2H), 4.11 (s, 1H), 3.98 (m, 3H), 3.17 (m, 4H), 2.97 (m, 9H), 2.61 (m, 1H), 2.23 (m, 1H), 1.61 (m, 1H).

Compound GM was also synthesized in a similar manner.

(4S,4aS,5aR,12aS)-7-Bromo-4-dimethylamino-3,10, 12,12a-tetrahydroxy-9-iodo-1,11-dioxo-1,4,4a,5,5a, 6,11,12a-octahydro-naphthacene-2-carboxylic acid amide (Compound GN)

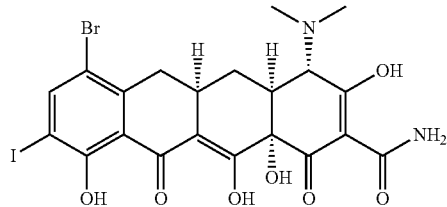 [SMILES: CN(C)[C@@H]1C(O)=C(C(N)=O)C(=O)[C@@]2(O)C(O)=C3C(=O)c4c(O)c(I)cc(Br)c4C[C@H]3C[C@@H]12]

To a solution of sancycline•TFA (53.2 g, 101 mmol) in TFA (400 mL) at 0° C. was added powdered NBS (85.4 g, 303 mmol) in portions over a 15 minutes period. After 2 hours, solid NIS (45.4 g, 202 mmol) was added and stirred for another 5 hours at 0° C. The solution was poured into a vigorously stirring solution of 10% Na$_2$SO$_3$ (500 mL) at 0° C. where the pH was adjusted pH=7.5 with solid NaOAc. After 30 minutes, the resulting suspended product was collected on a fine fritted funnel rinsing with water. The crude product was redissolved in a solution of THF (300 mL) with DVB (approx. 200 g) then poured into a vigorously stirring solution of 0.5 M HCl. The suspension was poured onto a prepared DVB column and after loading the product was eluted with MeOH with 1% HCl. The product in solution was concentrated under reduced pressure then dried under high vacuum to afford 57.5 g as a yellow solid in 92% yield. $^1$H NMR (CD$_3$OD) δ 8.02 (s, 1 H), 3.98 (s, 1 H), 3.17-2.78 (m, 9 H), 2.29-2.06 (m, 2 H), 1.62-1.46 (m, 1 H). LC/MS (MH$^+$) 620. Compound GQ was synthesized in a similar manner.

(4S,4aS,5aR,12aS)-7-Bromo-4-dimethylamino-9-formyl-3,10,12,12a-tetrahydroxy-1,11-dioxo-1,4,4a, 5,5a,6,11,12a-octahydro-naphthacene-2-carboxylic acid amide (Compound GO)

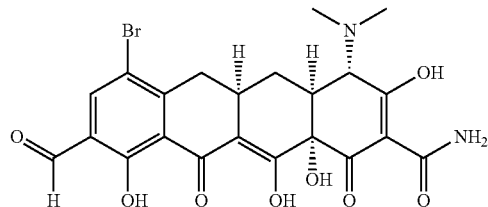 [SMILES: CN(C)[C@@H]1C(O)=C(C(N)=O)C(=O)[C@@]2(O)C(O)=C3C(=O)c4c(O)c(C=O)cc(Br)c4C[C@H]3C[C@@H]12]

An oven dried 500 mL 3-neck flask with internal thermometer was charged with 9-iodo-7-bromosancycline (18.9 g, 30.5 mmol), powdered anhydrous NaOAc (5.00 g, 61.0 mmol), Pd(PPh$_3$)$_4$ (3.52 g, 2.50 mmol) and anhydrous NMP at (102 mL). The flask was purged with carbon monoxide by bubbling the solution for 20 minutes, then a large balloon of carbon monoxide was affixed to the top of the flask to maintain a positive pressure. The reaction flask was heated to 70° C. At 30 minutes past obtained reaction temperature, Bu$_3$SnH (9.02 mL, 33.6 mmol) was added via syringe pump at a rate of 2.26 mL per hour for a total of 4 hours. After completion of reaction, the reaction was cooled to ambient temperature and then poured into a stirring solution of 2.5% TFA/H$_2$O (1000 mL) with Celite and potassium fluoride (17.7 g, 305 mmol). After 15 minutes, the solution was filtered through a plug of Celite rinsing with 1% TFA/H$_2$O. The combined water solution was loaded onto a previously prepared column of DVB resin (7×15 cm packed DVB column). After loading, a solution of 1% TFA/H$_2$O (approx. 1 L) was eluted then a gradient of CH$_3$CN/water with 1% TFA was eluted to obtain the desired product. The fractions containing product were concentrated under reduced pressure to afford 14 g in 71% yield as a TFA salt. $^1$H NMR (CD$_3$OD) (exists as methyl hemiacetal) d 7.74 (s, 1 H), 5.56 (s, 1 H), 4.03 (s, 1 H), 3.22-3.15 (m, 3 H), 3.02-2.85 (m, 3 H), 2.38-2.27 (m, 1 H), 2.19-2.08 (m, 1 H), 1.66-1.50 (m, 1 H). LC/MS (MH+) 523, 521 due to Br. Compound GQ was synthesized in a similar manner.

(4S,4aS,5aR,12aS)-4-Dimethylamino-9-(4-fluoropiperidin-1-ylmethyl)-3,10,12,12a-tetrahydroxy-1, 11-dioxo-1,4,4a,5,5a,6,11,12a-octahydro-naphthacene-2-carboxylic acid amide (Compound GP)

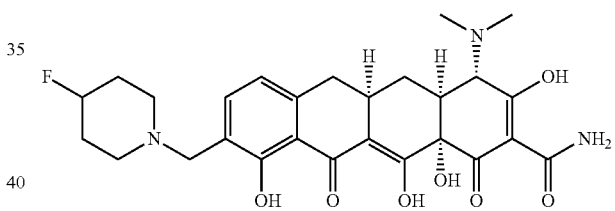

A mixture of 7-bromo-9-formyl sancycline (1.07 g, 2 mmol), InCl$_3$ (0.02 g, 0.2 mmol), and 4-fluoropiperidine HCl (0.84 g, 6 mmol) in DMF (20 mL) was stirred under argon at room temperature. To this triethylamine (8084, 6 mmol) was added and the reaction mixture was stirred at room temperature for 1 hour. Sodium cyanoborohydride (0.19 g, 3 mmol) was then added and the reaction mixture was stirred at room temperature for another 2 hours. The completion of the reaction was monitored by LCMS. The reaction was quenched by adding water/0.1% TFA (1L), the pH of the solution was adjusted to 2 by adding TFA. The resulting solution was then passed through celite and washed with 200 mL of water. The water layer was then loaded onto a DVB column, washed with water and the desired product was eluted with methanol. Solvent was evaporated to give a brown-yellow solid which was used without further purification for the next step.

An amount of 7-bromo-9-(4'-fluoropiperidinyl)-aminomethyl sancycline (1.07 g) was taken in 50 mL of methyl alcohol. To this Pd/C (5%, 250 mg) was added and the reaction mixture was hydrogenated at 45 psi for 6 hours. The reaction was filtered through celite and the yellow filtrate was evaporated to dryness to give a yellow solid, which was purified using preparative HPLC (C18, linear gradient 7-25% acetonitrile in water with 0.1% TFA). The organic solvent was reduced and the water layer was loaded onto a DVB column to remove water. The desired product was eluted with methanol. The yellow solid obtained was converted to its HCl salt using saturated solution of methanol-HCl. MS (ESI+) m/z 529.56, obs. 530.00 (MH+); $^1$H NMR (300 MHz, CD$_3$OD) δ 7.67 (d, J=8.6 Hz, 1H), 6.92 (d, J=8.5 Hz, 1H), 5.05 (m, 1H), 4.41 (s, 2H), 4.10 (s, 1H), 3.65-3.44 (m, 2H), 3.30-2.91 (m, 10H), 2.62 (t, 1H), 2.41-1.92 (m, 5H), 1.52 (m, 1H). Compound GQ was synthesized in a similar manner.

[4-((6aS,10R,10aS,11aR)-8-Carbamoyl-10-dimethylamino-4,6,6a,9-tetrahydroxy-5,7-dioxo-5,6a,7,10,10a,11,11a,12-octahydro-naphthacen-1-yl)-phenyl]-carbamic acid 2-fluoro-ethyl ester (Compound GR)

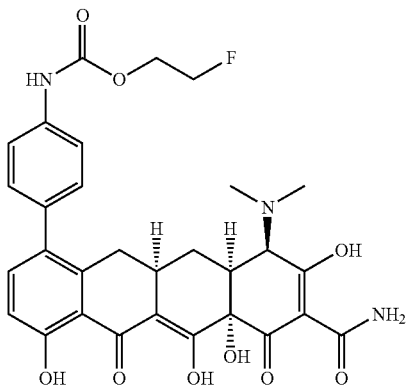 [SMILES: CN(C)[C@H]1C(O)=C(C(N)=O)C(=O)[C@@]2(O)C(O)=C3C(=O)c4c(O)ccc(-c5ccc(NC(=O)OCCF)cc5)c4C[C@H]3C[C@@H]12]

A solution of 7-iodosanscycline trifluoroacetate (654.43 mg, 1 mmol), Pd(PPh$_3$)$_4$ (115.6 mg, 0.1 mmol), and palladium (II) acetate (22.5, 0.1 mmol) in 20 mL methanol was purged with argon for 10 minutes. A solution of sodium carbonate (424 mg, 4 mmol) in 5 mL water was added and the mixture was purged for additional 5 minutes. A solution of 4-nitrophenyl boronic acid (0.33 g, 2 mmol) in DMF (5 mL) was purged with argon and added to the mixture. The reaction mixture was heated to 65° C. and stirred at the same temperature for 3 hours. The reaction mixture was cooled and filtered through celite pad. The filtrate was taken, solvent evaporated and the crude product was precipitated from ether, which was used for the next step without any purification.

An amount of 7-(4'-Nitro-phenyl)-sancycline (1.0 g) was taken in 50 mL of methyl alcohol. To this Pd/C (5%, 250 mg) was added and the reaction mixture was hydrogenated at 45 psi for 3 hours. The reaction was filtered through celite and the yellow filtrate was evaporated to dryness to give a yellow solid, which was used for the next step without any purification.

An amount of 7-(4'-amino-phenyl)-sancycline (2.02 g, 2 mmol), was taken in 25 mL of NMP. To this solution 2-fluoroethyl chloroformate (1.01 g, 8 mmol) was added and the reaction mixture was stirred at room temperature for 1 hour. The reaction mixture was then poured into 2 L of water with 0.1% TFA and was then filtered through celite to give a clear yellow solution, which was then purified using preparative HPLC (C18, linear gradient 10-50% acetonitrile in 20 mM aqueous triethanolamine, pH 7.4). The organic solvent was reduced and the water layer was loaded onto a DVB column, which was washed with 6 L of water. The desired product was then eluted with methanol. The yellow solid obtained was converted to its HCl salt using saturated solution of methanol-HCl. MS (ESI+) m/z 595.57, obs. 596.35 (MH+); $^1$H NMR (300 MHz, CD$_3$OD) δ 7.49 (d, J=7.2 Hz, 2H) 7.38 (d, J=8.5 Hz, 1H), 7.15 (d, J=7.2 Hz, 2H), 6.87 (d, J=8.5 Hz, 1H), 4.81 (m, 1H), 4.72 (m, 1H), 4.56 (m, 1H), 4.46 (m, 1H), 4.32 (m, 1H), 3.17 (s, 3H), 3.00-2.73 (m, 6H), 2.50 (t, 1H), 1.89 (m, 1H), 1.51 (m, 1H).

(4S,4aS,5aR,12aS)-4-Dimethylamino-9-(2-dimethylamino-acetylamino)-3,10,12,12a-tetrahydroxy-1,11-dioxo-7-pyridin-2-yl-1,4,4a,5,5a,6,11,12a-octahydro-naphthacene-2-carboxylic acid amide (Compound GU)

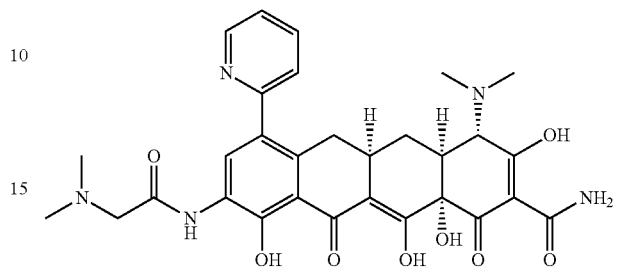

An amount of 7-iodo-9-nitrosancycline (0.58 g, 1 mmol), Pd(PPh$_3$)$_4$ (0.11 g, 0.1 mmol), CuI (0.038 g, 0.2 mmol) were taken in anhydrous DMF (20 mL), and purged with argon for 5 minutes. To this solution 2-pyridinyl-stannane (0.44 g, 1.2 mmol) was added and the reaction mixture was stirred at room temperature for 2 hours. The reaction was then poured into 1 L of water/0.1% TFA solution and was filtered through celite and washed with water/0.1% TFA (100 mL). The water layer was then loaded to a DVB column. The product was isolated at 15-20% acetonitrile and the solvent was evaporated to give a yellow-brown powder, which was used for the next step without further purification.

An amount of 7-pyridin-2-yl-9-nitrosancycline (200 mg) was taken in 20 mL of methyl alcohol. To this Pd/C (5%, 20 mg) was added and the reaction mixture was hydrogenated at 40 psi for 2 hours. The reaction was filtered through celite and the yellow filtrate was evaporated to dryness to give a yellow solid, which was used for the final step without further purification.

An amount of 7-pyridin-2-yl-9-aminosancycline (0.50 g, 1 mmol) was taken in 7 mL of NMP. To this solution N,N-dimethylglycyl chloride (2 mmol) was added and the reaction mixture was stirred at room temperature for 10-60 minutes. The reaction mixture was poured into 1 L of water with 0.1% TFA and then filtered through celite to give a clear yellow solution, which was then purified using preparative HPLC (C18, linear gradient 10-25% acetonitrile in 20 mM aqueous triethanolamine, pH 7.4). MS (ESI+) m/z 591.61, obs. 592.35 (MH+); $^1$H NMR (300 MHz, CD$_3$OD) δ 8.92 (d, J=4.5 Hz, 1H), 8.70 (t, 1H), 8.51 (s, 1H), 8.13 (m, 2H), 4.30 (s, 2H), 4.11 (s, 1H), 3.21-2.90 (m, 14H), 2.68 (m, 2H), 2.13 (m, 1H), 1.55 (m, 1H). Compounds GT and GV were also synthesized in a similar manner.

((5aR,6aS,7S,10aS)-9-Carbamoyl-7-dimethylamino-1,8,10a,11-tetrahydroxy-10,12-dioxo-4-pyridin-2-yl-5,5a,6,6a,7,10,10a,12-octahydro-naphthacen-2-ylcarbamoyl)-methyl]-trimethyl-ammonium (Compound GS)

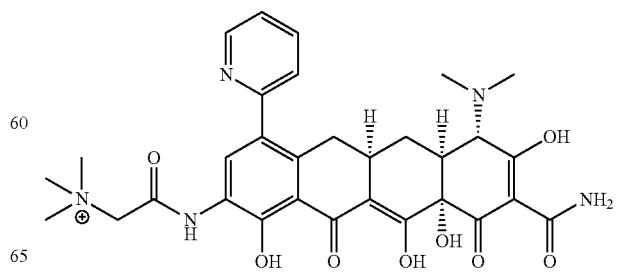

MS (ESI+) m/z 606.65, obs. 606.35 (M+); ¹H NMR (300 MHz, CD₃OD) δ 8.90 (d, J=4.5 Hz, 1H), 8.69 (t, 1H), 8.46 (s, 1H), 8.12 (m, 2H), 4.49 (s, 2H), 4.09 (s, 1H), 3.40 (s, 9H), 3.21-2.90 (m, 7H), 2.67 (m, 2H), 2.12 (m, 1H), 1.52 (m, 1H).

Example 2

Anti-Bacterial Activity

In this example, the gram (+) and gram (−) antibacterial activities of the tetracycline compounds used in the methods of the invention were assessed.

Gram (−) and gram (+) antibacterial minimum inhibitory concentration (MIC) values (μg/mL) were obtained using CLSI methodology for anti-bacterial susceptibility testing. On each day of testing, serial dilutions of compounds were prepared in microdilution plates using a Tecan robotic workstation. Mueller Hinton broth cultures of representative sensitive and resistant gram negative strains were grown or adjusted to match the turbidity of a 0.5 McFarland standard. 1:200 dilutions were made in an appropriate broth (cation supplemented Mueller Hinton broth) to allow a final inoculum of 1×10⁵ cfu. Plates were incubated at 35° C. in ambient air for 18-24 hours, were read spectrophotometrically and checked manually for evidence of bacterial growth. The lowest dilution of compound that inhibited growth was recorded as the MIC. Lysed horse blood was used to supplement broth for testing *S. pneumoniae*. The MIC's for each compound were assessed against *S. aureus, S. pneumoniae, P. acnes, E. coli* and *B. theta*. The results are shown in Table 3. Good antibacterial activity (e.g., less than about 4 μg/mL) is indicated by "***," modest antibacterial activity (between about 4 and 8 μg/mL) is indicated by "* *," or weak or no antibacterial activity (greater than about 8 μg/mL) is indicated by "*." The symbol "-" indicates that no data was obtained.

TABLE 3

| Compound Code | S. aureus RN450 | S. pneumoniae 157E - Strep | P. acnes ATCC 6919 | P. acnes ATCC 11827 | E. coli ATCC 25922 | E. coli MG 1655 | B. thetaiotaomicron ATCC 29741 |
|---|---|---|---|---|---|---|---|
| A | *** | *** | *** | *** | *** | ** | * |
| B | *** | *** | *** | *** | * | * | ** |
| C | *** | *** | *** | *** | * | * | * |
| D | *** | *** | ** | ** | * | * | * |
| E | *** | *** | *** | *** | ** | * | * |
| F | *** | *** | *** | *** | * | * | ** |
| G | *** | *** | ** | ** | ** | * | * |
| H | *** | *** | ** | ** | * | * | * |
| J | *** | *** | *** | *** | *** | *** | *** |
| K | *** | *** | *** | *** | *** | *** | *** |
| L | *** | *** | *** | *** | *** | *** | *** |
| M | *** | *** | *** | *** | *** | ** | ** |
| N | *** | *** | *** | *** | *** | ** | *** |
| O | *** | *** | *** | *** | *** | *** | *** |
| P | *** | *** | *** | *** | ** | ** | ** |
| Q | *** | *** | *** | *** | ** | ** | ** |
| R | *** | *** | *** | *** | * | * | ** |
| S | *** | *** | ** | ** | * | * | * |
| T | *** | *** | *** | *** | *** | *** | ** |
| U | *** | *** | *** | *** | *** | ** | ** |
| V | *** | *** | *** | *** | * | * | ** |
| W | *** | *** | *** | *** | * | * | * |
| X | *** | *** | *** | *** | *** | *** | *** |
| Y | *** | ** | *** | *** | * | * | * |
| Z | *** | *** | *** | *** | ** | ** | * |
| AA | *** | *** | *** | *** | ** | ** | ** |
| AB | *** | *** | *** | *** | ** | * | ** |
| AC | *** | *** | *** | *** | ** | * | ** |
| AD | *** | *** | *** | *** | ** | ** | * |
| AE | *** | *** | *** | *** | ** | * | ** |
| AF | *** | *** | *** | *** | ** | ** | *** |
| AL | *** | *** | *** | *** | ** | ** | ** |
| AM | ** | ** | *** | *** | * | * | ** |
| AN | *** | *** | *** | *** | *** | *** | ** |
| DR | *** | *** | *** | *** | ** | * | ** |
| DT | *** | *** | *** | *** | ** | ** | ** |
| DV | *** | *** | *** | *** | ** | * | ** |
| DW | *** | *** | *** | *** | *** | * | ** |
| DX | *** | *** | *** | *** | ** | ** | *** |
| DY | *** | ** | *** | *** | * | * | ** |
| DZ | *** | *** | *** | *** | ** | * | *** |
| EA | *** | ** | *** | *** | * | * | ** |
| EB | *** | ** | *** | *** | * | * | ** |
| EC | *** | *** | — | — | * | * | — |
| ED | *** | *** | *** | *** | ** | ** | *** |
| GL | ** | ** | ** | ** | * | * | ** |
| GM | *** | *** | *** | ** | * | * | ** |
| Doxycycline | *** | *** | *** | *** | *** | *** | ** |
| Minocycline | *** | *** | *** | *** | *** | *** | ** |

Example 3

Toxicity Profile

In this example, the cytotoxicity of the tetracycline compounds used in the methods of the invention were assessed.

Mammalian cell cytotoxicity was assessed to evaluate potential in vivo risks associated with the tetracycline compounds of the invention. A soluble, non-toxic redox dye ("Resazurin"; Alamar Blue) was used to assess a tetracycline compound's effect on cellular metabolism. At the onset of the experiment, cultures of mammalian COS-1 or CHO cells were washed, trypsinized, and harvested. Cell suspensions were prepared, seeded into 96-well black-walled microtiter plates, and incubated overnight at 37° C., in 5% $CO_2$ and approximately 95% humidity. On the next day, serial dilutions of test drug were prepared under sterile conditions and transferred to cell plates. Plates were then incubated under the above conditions for 24 hours. Following the incubation period, the media/drug was aspirated, and 50 μL of resazurin was added. Plates were then incubated under the above conditions for 2 hours and then in the dark at room temperature for an additional 30 minutes. Fluorescence measurements were taken (excitation 535 nm, emission 590 nm) and toxic effects in treated versus control cells were compared based on the degree of fluorescence in each well. The results are shown in Table 4. Minocycline and doxycycline toxicity scores are shown for comparison. Compounds which showed cytotoxicity at concentrations of less than about 35 μg/mL are indicated by "*," compounds which showed cytotoxicity at concentrations between about 35 and 75 μg/mL are indicated by "," and compounds that showed minimal or no cytotoxicity are indicated by "*" (e.g., at concentrations greater than about 75 μg/mL).

TABLE 4

| Compound | COS-1 Cytotoxicity $IC_{50}$ (μg/mL) | CHO Cytotoxicity $IC_{50}$ (μg/mL) |
|---|---|---|
| Minocycline | * | * |
| Doxycycline | * | * |
| A | *** | *** |
| B | *** | *** |
| C | * | * |
| D | * | * |
| E | * | * |
| F | *** | *** |
| G | * | * |
| H | * | * |
| J | * | * |
| K | * | * |
| L | *** | *** |
| M | * | * |
| N | * | * |
| O | ** | *** |
| P | * | * |
| Q | *** | *** |
| R | * | * |
| S | * | * |
| T | *** | *** |
| U | * | ** |
| V | *** | *** |
| W | * | * |
| X | *** | *** |
| Y | * | * |
| Z | * | * |
| AA | * | * |
| AB | *** | *** |
| AC | *** | *** |
| AD | * | * |
| AE | * | *** |
| AF | ** | ** |
| AL | *** | *** |
| AM | * | * |
| AN | * | * |
| DR | ** | ** |
| DV | *** | *** |
| DW | * | * |
| DX | *** | ** |
| DY | * | * |
| DZ | *** | *** |
| EA | * | * |
| ED | * | * |
| GL | ** | ** |
| GM | *** | *** |

Example 4

Phototoxic Potential

In this example, the phototoxic potential of the tetracycline compounds used in the methods of the invention was assessed. In particular, 3T3 fibroblast cells were harvested and plated at a concentration of $1 \times 10^5$ cells/mL and the plates were incubated overnight at 37° C., in 5% $CO_2$ and approximately 95% humidity. On the following day the medium was removed from the plates and replaced with Hanks' Balanced Salt Solution (HBSS). Drug dilutions were made in HBSS and added to the plates. For each compound tested, a duplicate plate was prepared that was not exposed to light as a control for compound toxicity. Plates were then incubated in a dark drawer (for controls), or under UV light (meter reading of 1.6-1.8 $mW/cm^2$) for 50 minutes. Cells were then washed with HBSS, fresh medium was added, and plates were incubated overnight as described above. The following day neutral red was added as an indicator of cell viability. The plates were then incubated for an additional 3 hours. Cells were then washed with HBSS and blotted on absorbent paper to remove excess liquid. A solution of 50% EtOH, 10% glacial acetic acid was added and after 20 minutes incubation, and the plate's absorbance at 535 nm was read using a Wallace Victor 5 spectrophotometer. The phototoxicity reflected the difference between the light-treated and control cultures. The results are given in Table 5. Results for the tetracycline derivative COL-3, as well doxycycline and minocycline are shown for comparison. Compounds which showed phototoxicity are indicated by "****" (e.g., less than 5 μg/mL), compounds which showed moderate phototoxicity are indicated by "* * *" (e.g., greater than about 5 μg/mL and less than about 25 μg/mL), compounds which showed some phototoxicity are indicated by "**" (e.g., greater than about 25 μg/mL and less than about 75 μg/mL) and compounds that showed minimal or no phototoxicity are indicated by "*" (e.g., greater than about 75 μg/mL).

TABLE 5

| Compound Code | Dark Tox50 (uM) | UV Tox50 (uM) |
|---|---|---|
| Minocycline | * | * |
| Doxycycline | * | *** |
| COL-3 | ** | **** |
| A | * | *** |
| B | * | * |
| C | * | ** |
| D | * | ** |
| E | * | ** |
| F | * | ** |

TABLE 5-continued

| Compound Code | Dark Tox50 (uM) | UV Tox50 (uM) |
|---|---|---|
| G | * | ** |
| H | * | * |
| J | * | * |
| K | * | * |
| L | * | **** |
| M | * | * |
| N | * | * |
| O | * | ** |
| P | * | ** |
| Q | * | * |
| R | * | * |
| S | * | ** |
| T | * | * |
| U | * | * |
| V | * | * |
| W | * | ** |
| X | * | *** |
| Y | * | * |
| Z | * | * |
| AA | * | * |
| AB | * | *** |
| AC | * | * |
| AD | * | * |
| AE | * | ** |
| AF | * | * |
| AL | * | *** |
| AM | * | * |
| AN | * | * |
| DR | * | * |
| DV | * | ** |
| DW | * | * |
| DX | * | ** |
| DY | * | * |
| DZ | * | *** |
| EA | * | * |
| ED | * | * |
| GM | * | ** |

Example 5

Half-Life Determination of the Oxidation

In this example, the half-life of minocycline and a tetracycline compound of the invention were assessed under oxidative conditions, as described in Nilges, et al. (Nilges M, Enochs W, Swartz H. *J. Org. Chem.* 1991, 56, 5623-30). Not to be limited by theory, it is believed that the tissue staining may be caused oxidative instability. The tetracycline compounds were subjected to accelerated oxidation in a continuous-flow microreactor using a 15 molar excess of sodium periodate at pH 11 and 22° C. Aliquots of each reaction mixture were quenched at various time points with ascorbic acid and the disappearance of each compound was determined by RP-HPLC. Pseudo first-order rate constants and $t_{1/2}$ values were obtained from the plots of log (Ao-At/Ao) versus time, where Ao is the HPLC area determined for each compound at time=0 and At is the HPLC area at time=t. The results indicated that minocycline had a half-life for oxidation of 8.2 seconds, while compound B had a half-life for oxidation of 495 seconds.

Example 6

In vivo Anti-bacterial Activity with *S. aureus* Model

In this example, the in vivo anti-bacterial activity of the tetracycline compounds used in the methods of the invention were assessed.

Groups of five mice were injected intraperitoneally with a lethal dose of *S. aureus* RN450 in a medium of mucin. Mice were evaluated at 24 hours to determine survival. Untreated animals experienced 100% mortality. Subcutaneous treatment with a single dose of minocycline, doxycycline or the test compound resulted in 100% survival. In some instances, a dose response study was performed with the compound such that a $PD_{50}$ (a dose of compound that protects 50% of the animals) could be calculated. The results are shown in Table 6.

TABLE 6

| Compound | Dose (mg/kg) | Percent Survival | PD50 (mg/kg) |
|---|---|---|---|
| Untreated | — | 0 (0/5) | — |
| Minocycline | 5 | 100 (5/5) | 0.72 |
| Doxycycline | 5 | 100 (5/5) | 0.13 |
| A | 5 | 100 (5/5) | — |
| C | 5 | 100 (5/5) | — |
| P | 5 | 100 (5/5) | 0.13 |
| Q | 5 | 100 (5/5) | 0.45 |
| V | | | 1.4 |
| W | | | 1.08 |
| AA | 5 | 100 (5/5) | — |
| AD | | | 4.54 |
| AF | | | 0.23 |
| DV | | | 1.1 |
| DW | | | 0.48 |
| DX | | 0.58 | 0.58 |
| DZ | | | 1.11 |

Example 7

Figure 1:
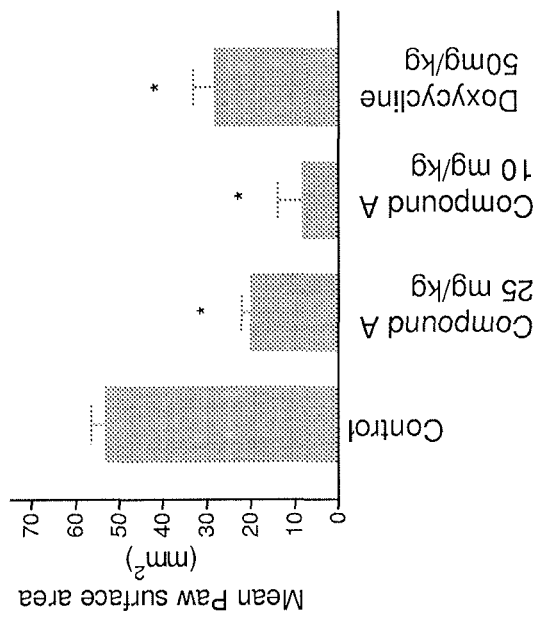
FIG. 1 is a graphical comparison of the modulation of carregeenan induced inflammation in the rat paw edema model between doxycycline and compound A.

In Vivo Anti-Inflammatory Activity with Rat Carrageenan-Induced Paw Edema Inflammatory Model To asses the anti-inflammatory potential of the tetracycline compounds used in the methods of the invention, the tetracycline compounds were assessed in a model of carrageenan induced rat paw inflammation. The model used a sub-plantar injection of carrageenan in the rat to induce an inflammatory response. The test compound or saline (control) was administered IP 30 minutes before a subplantar injection of carrageenan (1.5 mg/0.1 mL). Paw volume was measured (mm²) before subplantar injection and again 3 hours after the injection of carrageenan using a plethysmometer. The results are shown in FIGS. 1 and 2. Significant differences as determined by a Kruskal-Wallis One Way ANOVA are noted between the inflammation of the untreated controls versus treated animals (p=0.5)

FIG. 1 compares the modulation of carregeenan induced inflammation of doxycycline with various doses of compound A. Doxycycline exhibited a 50% effective concentration ($EC_{50}$) at approximately 50 mg/kg, while compound A exhibited improved activity.

FIG. 2 compares the modulation of carregeenan induced inflammation of minocycline compared with various doses of compound P. Minocycline exhibited an $EC_{50}$ at approximately 50 mg/kg, while compound P exhibited similar or improved activity.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A tetracycline compound of formula (VIIa):

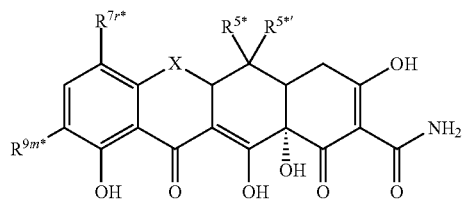

wherein
X is $CR^{6*}CR^{6*'}$;
$R^{5*}$ is hydrogen;
$R^{5*'}$ is hydrogen hydroxyl;
$R^{6*'}$ is hydrogen or alkyl;
$R^{6*}$ is hydrogen;
$R^{7r*}$ alkylamino; and
$R^{9m*}$ is oxazolyl or isoxazolyl, or a pharmaceutically acceptable salt thereof.

2. The tetracycline compound of claim 1, wherein oxazolyl is substituted with methyl or isopropyl.

3. The tetracycline compound of claim 1, wherein $R^{7r*}$ is dialkylamino.

4. The tetracycline compound of claim 1, wherein $R^{7r*}$ is dimethylamino.

5. The tetracycline compound of claim 1, wherein each of $R^{5*}$, $R^{5*'}$, $R^{6*}$, and $R^{6*'}$ is hydrogen.

6. The tetracycline compound of claim 5, wherein $R^{7r*}$ is dialkylamino.

7. The tetracycline compound of claim 6, wherein $R^{7r*}$ is dimethylamino.

8. The tetracycline compound of claim 1, wherein said compound is:

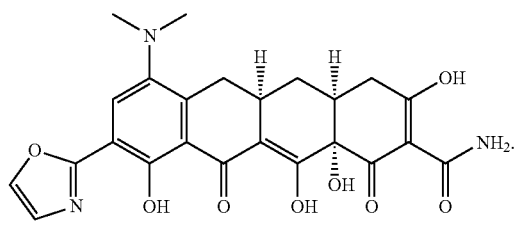 [SMILES: CN(C)c1cc(-c2ncco2)c(O)c2c1C[C@H]1C[C@H]3CC(O)=C(C(N)=O)C(=O)[C@@]3(O)C(O)=C1C2=O]

or a pharmaceutically acceptable salt thereof.

9. A pharmaceutical composition comprising a tetracycline compound of claim 1 and a pharmaceutical acceptable carrier.

10. The compound of claim 1, wherein the compound is:

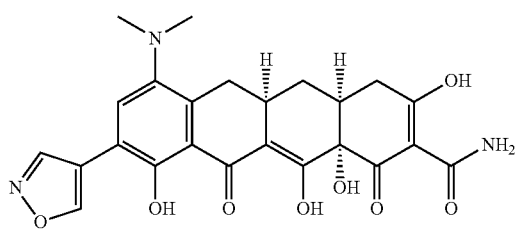 [SMILES: CN(C)c1cc(-c2cnoc2)c(O)c2c1C[C@H]1C[C@H]3CC(O)=C(C(N)=O)C(=O)[C@@]3(O)C(O)=C1C2=O]

or a pharmaceutically acceptable salt thereof.

11. A method for treating multiple sclerosis in a subject, comprising administering to said subject an effective amount of a tetracycline compound of any one of claims 1, 2, 3 to 7, 8 or 10, such that said subject is treated.

* * * * *

UNITED STATES PATENT AND TRADEMARK OFFICE
CERTIFICATE OF CORRECTION

PATENT NO. : 9,012,433 B2  
APPLICATION NO. : 13/686639  
DATED : April 21, 2015  
INVENTOR(S) : Paul Abato et al.

Page 1 of 1

It is certified that error appears in the above-identified patent and that said Letters Patent is hereby corrected as shown below:

In the Claims

At column 251, claim number 1, line number 18, delete "$CR^{6*}CR^{6*}$" and replace with --$CR^{6*}CR^{6*'}$--;

At column 251, claim number 1, line number 20, delete "hydrogen hydroxyl" and replace with --hydrogen or hydroxyl--.

Signed and Sealed this  
Eighteenth Day of August, 2015

Michelle K. Lee  
*Director of the United States Patent and Trademark Office*